US012617867B2

(12) United States Patent
Xu et al.

(10) Patent No.: US 12,617,867 B2
(45) Date of Patent: *May 5, 2026

(54) LIGAND-DRUG CONJUGATE OF EXATECAN ANALOGUE, PREPARATION METHOD THEREFOR AND APPLICATION THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Jianyan Xu, Shanghai (CN); Ying Zhang, Shanghai (CN); Xiaofeng Cai, Shanghai (CN); Bolei Qu, Shanghai (CN); Jindong Liang, Shanghai (CN); Lianshan Zhang, Shanghai (CN); Feng He, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1010 days.

This patent is subject to a terminal disclaimer.

(21) Appl. No.: 17/280,129

(22) PCT Filed: Sep. 25, 2019

(86) PCT No.: PCT/CN2019/107873

§ 371 (c)(1),
(2) Date: Mar. 25, 2021

(87) PCT Pub. No.: WO2020/063676

PCT Pub. Date: Apr. 2, 2020

(65) Prior Publication Data

US 2021/0353764 A1 Nov. 18, 2021

(30) Foreign Application Priority Data

Sep. 26, 2018 (CN) ........................ 201811123833.1

(51) Int. Cl.
*A61K 47/68* (2017.01)
*A61K 47/54* (2017.01)
(Continued)

(52) U.S. Cl.
CPC .............. *C07K 16/32* (2013.01); *A61K 47/54* (2017.08); *A61K 47/65* (2017.08); *A61K 47/68* (2017.08);
(Continued)

(58) Field of Classification Search
None
See application file for complete search history.

(56) References Cited

U.S. PATENT DOCUMENTS 4,970,198 A 11/1990 Lee et al.
5,079,233 A 1/1992 Lee
(Continued)

FOREIGN PATENT DOCUMENTS

EP 2910573 A1 8/2015
WO 2004010957 A2 2/2004
(Continued)

OTHER PUBLICATIONS

Herceptin (trastuzumab) Label information (2010), downloaded Jun. 17, 2024 from https://www.accessdata.fda.gov/drugsatfda_docs/label/2010/103792s5250lbl.pdf (Year: 2010).*
(Continued)

*Primary Examiner* — Karl J Puttlitz
(74) *Attorney, Agent, or Firm* — Goodwin Procter LLP

(57) ABSTRACT

The present invention relates to a ligand-drug conjugate of an exatecan analogue, a preparation method therefor and an
(Continued)

application thereof. Specifically, the present invention provides a ligand-drug conjugate having a structure shown in formula (-D), a preparation method therefor, a pharmaceutical composition containing same, and use thereof in preparation of drugs for treating cancers by means of receptor regulation. The definition of each substituent in formula (-D) is the same as that in the description.

(-D)

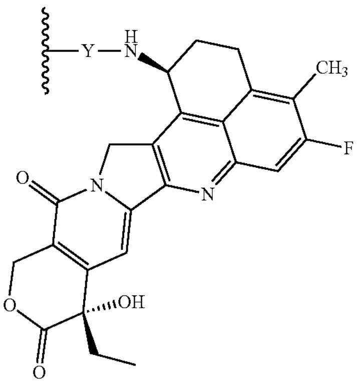

22 Claims, 4 Drawing Sheets

Specification includes a Sequence Listing.

(51) Int. Cl.
*A61K 47/65* (2017.01)
*C07K 16/18* (2006.01)
*C07K 16/32* (2006.01)

(52) U.S. Cl.
CPC ........ *A61K 47/68037* (2023.08); *C07K 16/18* (2013.01)

(56) References Cited

U.S. PATENT DOCUMENTS 5,585,089 A 12/1996 Queen et al.
5,606,040 A 2/1997 McGahren et al.
5,693,762 A 12/1997 Queen et al.
5,739,116 A 4/1998 Hamann et al.
5,767,285 A 6/1998 Hamann et al.
5,773,001 A 6/1998 Hamann et al.
6,221,335 B1 * 4/2001 Foster .................. C07B 59/002 424/1.81
6,440,710 B1 * 8/2002 Keinan .................. C12P 13/02 435/188.5
6,603,008 B1 * 8/2003 Ando .................. A61P 7/04 546/271.4
7,090,843 B1 8/2006 Francisco et al.
7,517,990 B2 * 4/2009 Ito .................. C07D 233/56 546/184
7,659,241 B2 2/2010 Senter et al.
8,088,387 B2 1/2012 Steeves et al.
2007/0082929 A1 * 4/2007 Gant .................. A61P 43/00 546/273.7
2007/0197695 A1 * 8/2007 Potyen .................. C08K 5/55 524/110
2017/0035906 A1 * 2/2017 Naito .................. C07K 16/3061
2021/0347894 A1 * 11/2021 Ying .................. A61K 47/68037
2023/0072897 A1 * 3/2023 Hua .................. A61K 47/6803

FOREIGN PATENT DOCUMENTS

WO 2005001038 A2 1/2005
WO 2005037992 A2 4/2005
WO 2008025020 A2 2/2008
WO 2014057687 A1 4/2014
WO 2014092804 A1 6/2014
WO 2015/155998 A1 10/2015
WO 2015146132 A1 10/2015
WO 2016057398 A1 4/2016
WO 2017139623 A1 8/2017

OTHER PUBLICATIONS

Kushner et al., Canadian Journal of Physiology and Pharmacology (1999), 77(2), 79-88 (Year: 1999).*

Tonn, Biological Mass Spectrometry vol. 22 Issue 11, pp. 633-642 (1993) (Year: 1993).*

Haskins, Biomedical Spectrometry vol. 9 Issue 7, pp. 269-277 (1982) (Year: 1982).*

Wolen, Journal of Clinical Pharmacology 1986; 26: 419-424 (Year: 1986).*

Browne, Journal of Clinical Pharmacology 1998; 38: 213-220 (Year: 1998).*

Baillie, Pharmacology Rev. 1981; 33: 81-132; (Year: 1981).*

Gouyette, Biomedical and Environmental Mass Spectrometry, vol. 15, 243-247 (1988) (Year: 1988).*

Shiose et al., "Relationship between drug release of DE-310, macromolecular prodrug of DX-8951f, and cathepsins activity in several tumors," Biol Pharm Bull 30 (12): 2365-2370 (2007).

Nakada et al., "Novel antibody drug conjugates containing exatecan derivative-based cytotoxic payloads," Bioorganic & Medicinal Chemistry Letters, 26 (6):1542-1545 (2016).

Ogitani et al., "Wide application of a novel topoisomerase I inhibitor-based drug conjugation technology," Bioorganic & Medicinal Chemistry Letters, 26(20):5069-5072 (2016).

Agatsuma, "Development of New ADC Technology with Topoisomerase I Inhibitor," The Pharmaceutical Society of Japan, Yakugaku Zasshi, 137(5):545-550. (2017) (see English abstract).

Yusuke Ogitani et al., "DS-8201a, A Novel HER2-Targeting ADC with a Novel DNA Topoisomerase I Inhibitor, Demonstrates a Promising Antitumor Efficacy with Differentiation from T-DM1" Clinical Cancer Research, vol. 22, No. 20, Mar. 29, 2016 (Mar. 29, 2016), © 2016 American Association for Cancer Research, pp. 5097-5108.

Agatsuma Toshinori, "Development of New ADC Technology with Topoisomerase I Inhibitor" Yakugaku Zasshi, vol. 137, No. 5, Dec. 31, 2017 (Dec. 31, 2017), © 2017 The Pharmaceutical Society of Japan, pp. 545-550.

Asher Mullard, "Maturing antibody-drug conjugate pipeline hits 30" Nature Reviews Drug Discovery, vol. 12, May 2013, © 2013 Macmillan Publishers Limited, pp. 329-332.

John F. Dijoseph, "Antibody-targeted chemotherapy with CMC-544: a CD22-targeted immunoconjugate of calicheamicin for the treatment of B-lymphoid malignancies" Blood, vol. 103, No. 5, Mar. 1, 2004 (Mar. 1, 2004), © 2004 by The American Society of Hematology, pp. 1807-1814.

Svetlana O. Doronina et al., "Development of potent monoclonal antibody auristatin conjugates for cancer therapy" Nature Biotechnology, vol. 21, No. 7, Jul. 2003, © 2003 Nature Publishing Group, pp. 778-784.

Yusuke Ogitani et al., "Bystander killing effect of DS-8201a, a novel anti-human epidermal growth factor receptor 2 antibody—drug conjugate, in tumors with human epidermal growth factor receptor 2 heterogeneity" Cancer Science, vol. 107, No. 7, © 2016 The Authors. Cancer Science published by John Wiley & Sons Australia, Ltd on behalf of Japanese Cancer Association, pp. 1039-1046.

* cited by examiner

LIGAND-DRUG CONJUGATE OF EXATECAN ANALOGUE, PREPARATION METHOD THEREFOR AND APPLICATION THEREOF

CROSS-REFERENCE TO RELATED APPLICATIONS

This application is the national stage of International Patent Application No. PCT/CN2019/107873, filed Sep. 25, 2019, which claims the benefit of and priority to Chinese Patent Application No. 201811123833.1, filed Sep. 26, 2018, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 25, 2019, is named "719074CPUS_126268-5013-US_Sequence_Listing.TXT" and is 18 kilobytes in size.

FIELD OF THE INVENTION

The present disclosure relates to a ligand-drug conjugate of exatecan analogue with a novel structure. Specifically, the present disclosure relates to a ligand-drug conjugate of exatecan analogue with a structural unit Y, a method for preparing the same, a pharmaceutical composition comprising the conjugate, and a use of the conjugate or the pharmaceutical composition.

BACKGROUND OF THE INVENTION

Chemotherapy remains one of the most important anticancer therapy along with surgery, radiotherapy and targeted therapy. Although there are many types of highly efficient cytotoxins, the difference between tumor cells and normal cells is very small, which limits the broad clinical application of these anti-cancer compounds due to the toxic side effect. Antibody drugs have become the frontline drugs for anti-tumor therapy because of the specificity of anti-tumor monoclonal antibody for tumor cell surface antigen. However, when the antibody is used alone as the anti-tumor drug, the efficacy is often unsatisfactory.

Antibody drug conjugates (ADCs) enable the combination a monoclonal antibody or an antibody fragment with a biologically active cytotoxin through a chemically stable linker, taking full advantage of the specificity of antibody binding to the surface antigens of normal cells or tumor cells and the high efficiency of the cytotoxin, while avoiding low efficacy of the antibody and the toxic side effect of the cytotoxin. That means, comparing with conventional chemotherapy drugs, antibody drug conjugates can accurately bind to tumor cells and reduce the affect to normal cells (Mullard A, (2013) *Nature Reviews Drug Discovery,* 12:329-332; DiJoseph J F, Armellino D C, (2004) *Blood,* 103:1807-1814).

In 2000, the first antibody drug conjugate Mylotarg (gemtuzumab ozogamicin, Wyeth Pharmaceuticals) was approved by the US Food and Drug Administration (FDA) for the treatment of acute myeloid leukemia (*Drugs of the Future* (2000) 25(7):686; U.S. Pat. Nos. 4,970,198; 5,079,233; 5,585,089; 5,606,040; 5,693,762; 5,739,116; 5,767,285; 5,773,001).

In August 2011, Adcetris (brentuximab vedotin, Seattle Genetics Inc.) was approved through the US FDA Fast Track for the treatment of Hodgkin lymphoma and relapsed anaplastic large cell lymphoma (*Nat. Biotechnol* (2003) 21(7):778-784; WO2004010957; WO2005001038; U.S. Pat. Nos. 7,090,843A; 7,659,241; WO2008025020). Adcetris® is a novel target ADC drug, which enables the drug to act directly on the target CD30 of lymphoma cell, trigger endocytosis and consequently induce tumor cell apoptosis.

Both Mylotarg and Adcetris are target therapies for hematologic tumors, the organizational structure of which is relatively simple compared with that of solid tumors. In February 2013, Kadcyla (ado-trastuzumab emtansine, T-DM1) was approved by FDA for the treatment of advanced or metastatic breast cancer patients who are HER2-positive with Trastuzumab (trade name: Herceptin)-resistant and paclitaxel-resistant (WO2005037992; U.S. Pat. No. 8,088,387). Kadcyla is the first ADC drug approved by FDA for the treatment of solid tumors.

There are several types of cytotoxic small molecules used in antibody drug conjugate, one of which is camptothecin derivatives, which show anti-tumor effect by inhibiting topoisomerase I. Documents reporting the use of the camptothecin derivative, exatecan (chemical name: (1S,9S)-1-amino-9-ethyl-5-fluoro-2,3-dihydro-9-hydroxy-4-methyl-1H,12H-benzo[de]pyrano[3',4':6,7]imidazo[1,2-b]quinoline-10,13(9H,15H)-dione) in antibody drug conjugate (ADC) comprise WO2014057687, Clinical Cancer Research (2016) 22 (20): 5097-5108, and *Cancer Sci* (2016) 107: 1039-1046. However, further development of ADC drugs with better efficacy is still needed.

SUMMARY OF THE INVENTION

In order to improve the ligand, especially the coupling effect between antibody and drug, the present disclosure provides a ligand-drug conjugate or a pharmaceutically acceptable salt or solvate thereof, wherein the ligand-drug conjugate comprises a structure of formula (-D):

(-D)

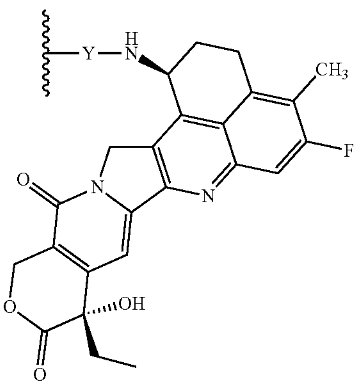

wherein:

Y is selected from the group consisting of —O—$(CR^aR^b)$m-$CR^1R^2$—C(O)—, —O—$CR^1R^2$—$(CR^aR^b)$m-, —O—CR'$R^2$—, —NH—$(CR^aR^b)$m-$CR^1R^2$—C(O)— and —S—$(CR^aR^b)$m-$CR^1R^2$—C(O)—;

$R^a$ and $R^b$ are identical or different and are each independently selected from the group consisting of hydrogen atom, deuterium atom, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$ together with the carbon atom to which they are attached form a cycloalkyl or heterocyclyl;

$R^1$ is selected from the group consisting of halogen, deuterated alkyl, cycloalkyl, cycloalkylalkyl, heterocyclyl, aryl and heteroaryl;

$R^2$ is selected from the group consisting of hydrogen atom, halogen, haloalkyl, deuterated alkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

or, $R^a$ and $R^2$ together with the carbon atom to which they are attached form a cycloalkyl or heterocyclyl;

wherein, the wavy line in -D represents a hydrogen atom, or a covalent binding to a linker unit or an antibody that binds to the antigen expressed by the target cell;

m is an integer from 0 to 4.

In some embodiments of the present disclosure, the provided ligand-drug conjugate or the pharmaceutically acceptable salt or solvate thereof is a compound with formula (-$D_1$) or a ligand-drug conjugate thereof or a pharmaceutically acceptable salt or solvate thereof:

(-$D_1$)

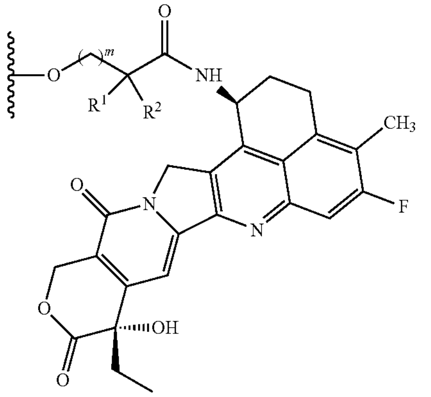

wherein:

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

the wavy line in formula -$D_1$ represents a hydrogen atom, or a covalent binding to a linker unit or an antibody that binds to the antigen expressed by the target cell;

m is 0 or 1.

In some embodiments of the present disclosure, the provided ligand-drug conjugate or the pharmaceutically acceptable salt or solvate thereof is a ligand-drug conjugate of formula (Pc-L-Y-Dr) or a pharmaceutically acceptable salt or solvate thereof:

(Pc-L-Y-Dr)

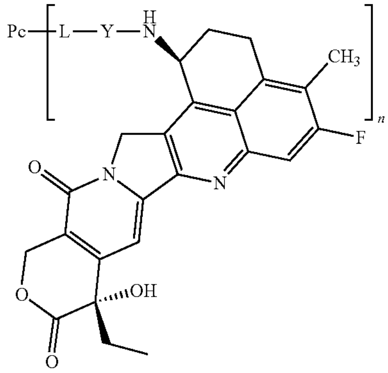

wherein:

Y is selected from the group consisting of —O—$(CR^aR^b)_m$—$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen atom, deuterium atom, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$ together with the carbon atom to which they are attached form a cycloalkyl or heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl;

$R^2$ is selected from the group consisting of hydrogen atom, halogen, haloalkyl, deuterated alkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

or, $R^a$ and $R^2$ together with the carbon atom to which they are attached form a cycloalkyl or heterocyclyl;

m is an integer from 0 to 4;

n is 1 to 10, which can be an integer or a decimal;

Pc is a ligand; and L is a linker unit.

In some embodiments of the present disclosure, in the provided ligand-drug conjugate or the pharmaceutically acceptable salt or solvate thereof, —Y— is —O—$(CR^aR^b)$m-$CR^1R^2$—C(O)—;

$R^a$ and $R^b$ are identical or different and are each independently selected from the group consisting of hydrogen atom, deuterium atom, halogen and alkyl;

$R^1$ is a $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

m is 0 or 1.

In some embodiments of the present disclosure, in the provided ligand-drug conjugate or the pharmaceutically acceptable salt or solvate thereof, the structural unit —Y— is —O—$(CH_2)$m-$CR^1R^2$—C(O)—;

$R^1$ is a $C_{3-6}$ cycloalkylalkyl or $C_{3-6}$ cycloalkyl;

$R^2$ is selected from the group consisting of hydrogen atom, haloalkyl and $C_{3-6}$ cycloalkyl;

or, $R^1$ and $R^2$ together with the carbon atom to which they are attached form a $C_{3-6}$ cycloalkyl;

m is 0 or 1.

In some embodiments of the present disclosure, in the provided ligand-drug conjugate or the pharmaceutically acceptable salt or solvate thereof, the structural unit —Y— is —O—$(CH_2)$m-$CR^1R^2$—C(O)—;

$R^1$ is a $C_{3-6}$ cycloalkylalkyl or $C_{3-6}$ cycloalkyl;

$R^2$ is a hydrogen atom;

or, $R^1$ and $R^2$ together with the carbon atom to which they are attached form a $C_{3-6}$ cycloalkyl;

m is 0 or 1.

In some embodiments of the present disclosure, in the provided ligand-drug conjugate or the pharmaceutically acceptable salt or solvate thereof, the structural unit —Y— is —O—$(CH_2)$m-$CR^1R^2$—C(O)—;

$R^1$ is a $C_{3-6}$ cycloalkylalkyl or $C_{3-6}$ cycloalkyl;

$R^2$ is a hydrogen atom;

or, $R^1$ and $R^2$ together with the carbon atom to which they are attached form a $C_{3-6}$ cycloalkyl;

m is 0.

In some other embodiments of the present disclosure, in the provided ligand-drug conjugate or the pharmaceutically acceptable salt or solvate thereof, the structural unit —Y— is selected from the group consisting of:

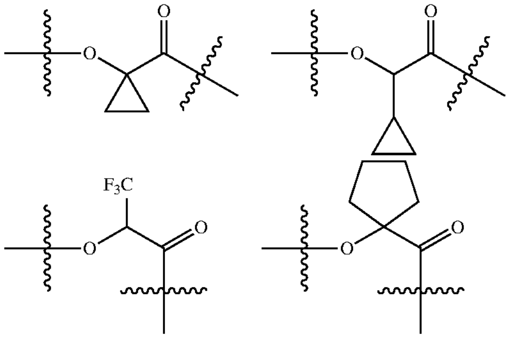

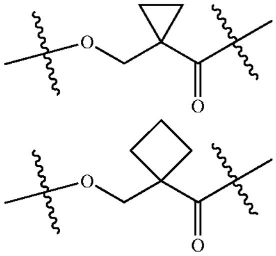

and

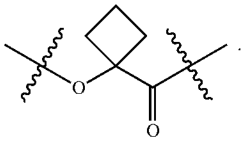

In some other embodiments of the present disclosure, in the provided ligand-drug conjugate or the pharmaceutically acceptable salt or solvate thereof, the O terminal of —Y— is connected to the linker unit L.

In some other embodiments of the present disclosure, the provided ligand-drug conjugate or the pharmaceutically acceptable salt or solvate thereof is a ligand-drug conjugate of formula (Pc-L-D1) or a pharmaceutically acceptable salt or solvate thereof:

($Pc-L-D_1$)

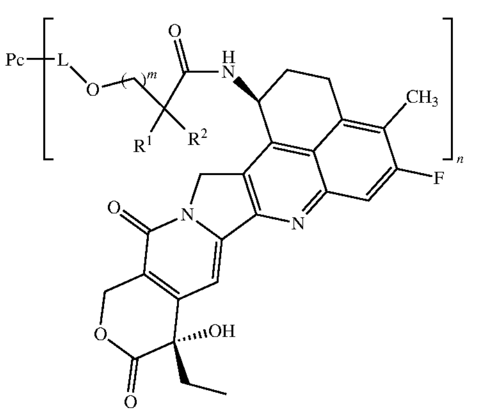

wherein:

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

m is 0 or 1;

n is 1 to 10, which can be an integer or a decimal;

Pc is a ligand; and L is a linker unit.

In another preferred embodiment of the present invention, in the ligand-drug conjugate or the pharmaceutically acceptable salt or solvate thereof according to the present invention, n is 2 to 8, which can be an integer or a decimal; and preferably n is 3 to 8, which can be an integer or a decimal.

In another preferred embodiment of the present invention, in the ligand-drug conjugate or the pharmaceutically acceptable salt or solvate thereof according to the present invention, the linker unit L is $$-L^1-L^2-L^3-L^4-,$$

$L^1$ is selected from the group consisting of -(succinimide-3-yl-N)—W—C(O)—, —$CH_2$—C(O)—$NR^3$—W—C(O)— and —C(O)—W—C(O)—, wherein W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20; and $L^2$ is preferably a chemical bond;

$L^3$ is a peptide residue composed of 2 to 7 amino acids, wherein the amino acids are optionally further substituted by one or more substituent(s) selected from the group consisting of halogen, hydroxy, cyano, amino, alkyl, chloroalkyl, deuterated alkyl, alkoxy and cycloalkyl;

$L^4$ is selected from the group consisting of $—NR^5(CR^6R^7)_t—$, $—C(O)NR^5$, $—C(O)NR^5(CH_2)_t—$ and a chemical bond, wherein t is an integer from 1 to 6; and $L^4$ is preferably $—NR^5(CR^6R^7)t-$;

$R^3$, $R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl.

In some other embodiments of the present disclosure, in the ligand-drug conjugate or the pharmaceutically acceptable salt or solvate thereof, the linker unit $L^1$ is selected from the group consisting of -(succinimide-3-yl-N)—$(CH_2)s^1$-C(O)—, -(succinimide-3-yl-N)—$CH_2$-cyclohexyl-C(O)—, -(succinimide-3-yl-N)—$(CH_2CH_2O)s^2$-$CH_2CH_2$—C(O)—, —$CH_2$—C(O)—$NR^3$—$(CH_2)s^3$-C(O)— and —C(O)—$(CH_2)s^4$C(O)—, wherein $s^1$ is an integer from 2 to 8, $s^2$ is an integer from 1 to 3, $s^3$ is an integer from 1 to 8, and $s^4$ is an integer from 1 to 8; and $s^1$ is preferably 5.

In some other embodiments of the present disclosure, in the ligand-drug conjugate or the pharmaceutically acceptable salt or solvate thereof, the linker unit $L^2$ is selected from the group consisting of —$NR^4(CH_2CH_2O)p^1CH_2C(O)$— and a chemical bond, wherein $p^1$ is an integer from 6 to 12.

In some other embodiments of the present disclosure, in the provided ligand-drug conjugate or the pharmaceutically acceptable salt or solvate thereof, $L^4$ is selected from —$NR^5(CR^6R^7)t$-, $R^5$ is selected from the group consisting of hydrogen atom and alkyl, $R^6$ and $R^7$ are identical or different and are each independently selected from the group consisting of hydrogen atom and alkyl, t is 1 or 2, and preferably 2; $L^4$ is preferably —$NR^5CR^6R^7$—; and $L^4$ is more preferably —$NHCH_2$—.

In some other embodiments of the present disclosure, in the provided ligand-drug conjugate or the pharmaceutically acceptable salt or solvate thereof, the linker unit $$-L^1-L^2-L^3-L^4-,$$

$L^1$ is

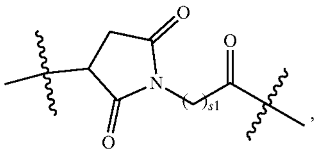

and $s^1$ is an integer from 2 to 8;

$L^2$ is a chemical bond;

$L^3$ is a tetrapeptide residue;

$L^4$ is —$NR^5(CR^6R^7)t$-, $R^5$ is selected from the group consisting of hydrogen atom and alkyl, $R^6$ and $R^7$ are identical or different and are each independently selected from the group consisting of hydrogen atom and alkyl, and t is 1 or 2.

In some other embodiments of the present disclosure, in the provided ligand-drug conjugate or the pharmaceutically acceptable salt or solvate thereof, the linker unit -L- is $$-L^1-L^2-L^3-L^4-,$$

$L^1$ is -(succinimide-3-yl-N)—$CH_2$-cyclohexyl-C(O)—;

$L^2$ is —$NR^4(CH_2CH_2O)_9CH_2C(O)$—;

$L^3$ is a tetrapeptide residue;

$L^4$ is —$NR^5(CR^6R^7)t$-, $R^5$ is selected from the group consisting of hydrogen atom and alkyl, $R^6$ and $R^7$ are identical or different and are each independently selected from the group consisting of hydrogen atom and alkyl, and t is 1 or 2.

In some other embodiments of the present disclosure, in the provided ligand-drug conjugate or the pharmaceutically acceptable salt or solvate thereof, the peptide residue of $L^3$ is an amino acid residue composed of one, two or more amino acid(s) selected from the group consisting of phenylalanine (E), glycine (G), valine (V), lysine (K), citrulline, serine (S), glutamic acid (E) and aspartic acid (N), preferably an amino acid residue composed of one, two or more amino acid(s) selected from the group consisting of phenylalanine and glycine, more preferably a tetrapeptide residue, and most preferably a tetrapeptide residue of GGFG (glycine-glycine-phenylalanine-glycine).

In some other embodiments of the present disclosure, in the provided ligand-drug conjugate or the pharmaceutically acceptable salt or solvate thereof, the $L^1$ terminal of the linker unit -L- is connected to the ligand, and the $L^4$ terminal of the linker unit -L- is connected to Y.

In some other embodiments of the present disclosure, in the provided ligand-drug conjugate or the pharmaceutically acceptable salt or solvate thereof, -L-Y— is:

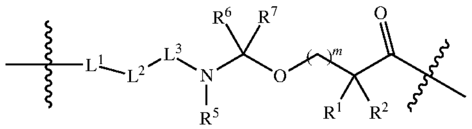

$L^1$ is selected from the group consisting of -(succinimide-3-yl-N)—$(CH_2)s^1$-C(O)— and -(succinimide-3-yl-N)—$CH_2$-cyclohexyl-C(O)—;

$L^2$ is —$NR^4(CH_2CH_2O)p^1CH_2C(O)$— or a chemical bond, and $p^1$ is an integer from 6 to 12;

$L^3$ is a tetrapeptide residue of GGFG;

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

$R^5$ is selected from the group consisting of hydrogen atom and alkyl, and $R^6$ and $R^7$ are identical or different and are each independently selected from the group consisting of hydrogen atom and alkyl;

$s^1$ is an integer from 2 to 8, and preferably 5;

m is an integer from 0 to 4.

In some other embodiments of the present disclosure, in the provided ligand-drug conjugate or the pharmaceutically acceptable salt or solvate thereof, -L-Y— is:

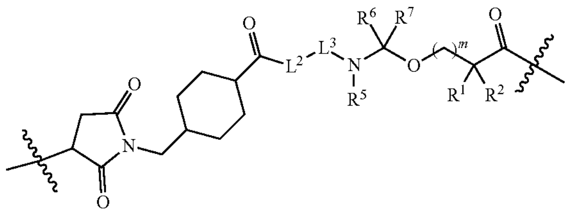

and preferably is:

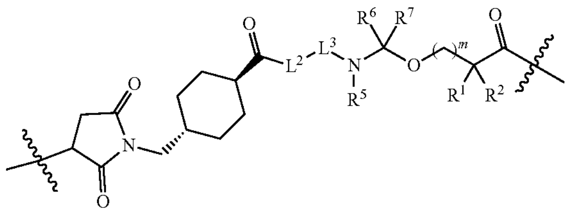

$L^2$ is —$NR^4(CH_2CH_2O)_9CH_2C(O)$—;

$L^3$ is a tetrapeptide residue of GGFG;

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

$R^5$ is selected from the group consisting of hydrogen atom and alkyl, and $R^6$ and $R^7$ are identical or different and are each independently selected from the group consisting of hydrogen atom and alkyl;

m is an integer from 0 to 4.

In some other embodiments of the present disclosure, in the provided ligand-drug conjugate of formula (Pc-L-Y-Dr) or the pharmaceutically acceptable salt or solvate thereof, -L-Y— is

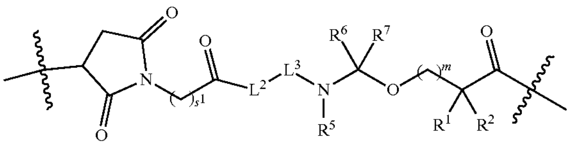

$L^2$ is a chemical bond;

$L^3$ is a tetrapeptide residue of GGFG;

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

$R^5$ is selected from the group consisting of hydrogen atom and alkyl, and $R^6$ and $R^7$ are identical or different and are each independently selected from the group consisting of hydrogen atom and alkyl;

$s^1$ is an integer from 2 to 8, and preferably 5;

m is an integer from 0 to 4.

Another aspect of the present disclosure provides a ligand-drug conjugate or a pharmaceutically acceptable salt or solvate thereof, wherein the ligand-drug conjugate contains a structure of formula (-L-Y—):

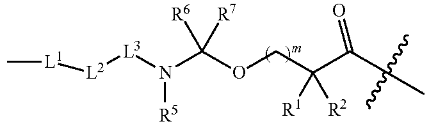

which can be used to form a ligand-drug conjugate by connecting the drug and the ligand via a linker fragment;

wherein:

$L^1$ is selected from the group consisting of -(succinimide-3-yl-N)—$(CH_2)s^1$-C(O)— and -(succinimide-3-yl-N)—$CH_2$-cyclohexyl-C(O)—;

$L^2$ is —$NR^4(CH_2CH_2O)p^1CH_2C(O)$— or a chemical bond, and $p^1$ is an integer from 1 to 20;

$L^3$ is a tetrapeptide residue of GGFG;

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

$R^5$, $R^6$ and $R^7$ are identical or different and are each independently selected from the group consisting of hydrogen atom and alkyl;

$s^1$ is an integer from 2 to 8;

m is an integer from 0 to 4.

Another aspect of the present disclosure provides a ligand-drug conjugate or a pharmaceutically acceptable salt or solvate thereof, wherein the ligand-drug conjugate comprises contains a structure of formula (-L-Y—):

(-L-Y-)

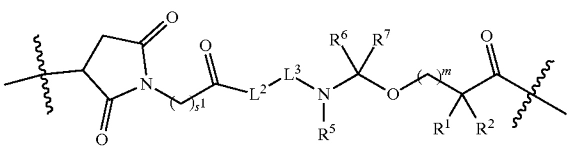

wherein:

$L^2$ is a chemical bond;

$L^3$ is a tetrapeptide residue of GGFG;

$R^1$ is a cycloalkylalkyl or cycloalkyl, and preferably $C_{3-6}$ cycloalkylalkyl or $C_{3-6}$ cycloalkyl;

$R^2$ is selected from the group consisting of hydrogen atom, haloalkyl and $C_{3-6}$ cycloalkyl, and preferably hydrogen atom;

or, $R^1$ and $R^2$ together with the carbon atom to which they are attached form a $C_{3-6}$ cycloalkyl;

$R^5$ is selected from the group consisting of hydrogen atom and alkyl, and $R^6$ and $R^7$ are identical or different and are each independently selected from the group consisting of hydrogen atom and alkyl;

$s^1$ is an integer from 2 to 8;

m is an integer from 0 to 4.

In some other embodiments of the present disclosure, the provided ligand-drug conjugate of formula (Pc-L-Y-Dr) or the pharmaceutically acceptable salt or solvate thereof is a ligand-drug conjugate of formula (Pc-$L_a$-Y-Dr) or a pharmaceutically acceptable salt or solvate thereof:

(Pc-$L_a$-Y-Dr)

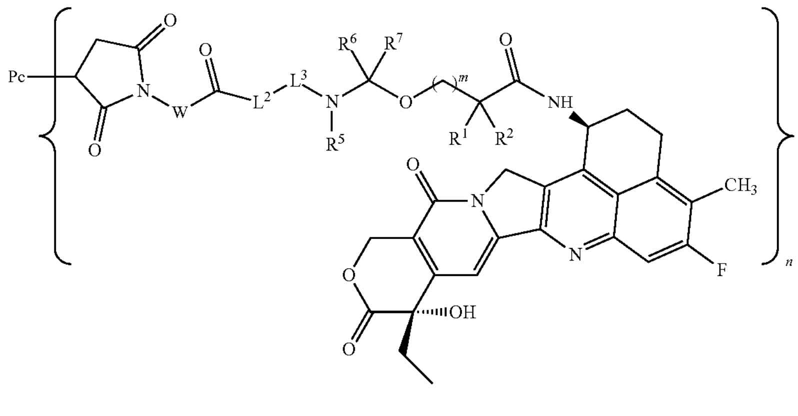

wherein:

W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue composed of 2 to 7 amino acids, the amino acid can be substituted or unsubstituted, when substituted, the substituent group(s) can be substituted at any available connection point, the substituent group(s) is one or more group(s) independently selected from the group consisting of halogen, hydroxy, cyano, amino, alkyl, chloroalkyl, deuterated alkyl, alkoxy and cycloalkyl;

$R^1$ is selected from the group consisting of halogen, cycloalkylalkyl, deuterated alkyl, cycloalkyl, heterocyclyl, aryl and heteroaryl, preferably cycloalkylalkyl or cycloalkyl, and more preferably $C_{3-6}$ cycloalkylalkyl or $C_{3-6}$ cycloalkyl;

$R^2$ is selected from the group consisting of hydrogen atom, halogen, haloalkyl, deuterated alkyl, cycloalkyl, heterocyclyl, aryl and heteroaryl, and preferably hydrogen atom; or, $R^1$ and $R^2$ together with the carbon atom to which they are attached form a cycloalkyl or heterocyclyl;

$R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

m is an integer from 0 to 4;

n is a non-zero integer or decimal from 0 to 10, preferably an integer or decimal from 1 to 10;

Pc is a ligand.

In some other embodiments of the present disclosure, the provided ligand-drug conjugate of formula (Pc-La-Y-Dr) or the pharmaceutically acceptable salt or solvate thereof is a ligand-drug conjugate of formula (Pc-$L_b$-Y-Dr) or a pharmaceutically acceptable salt or solvate thereof:

(Pc-$L_b$-Y-Dr)

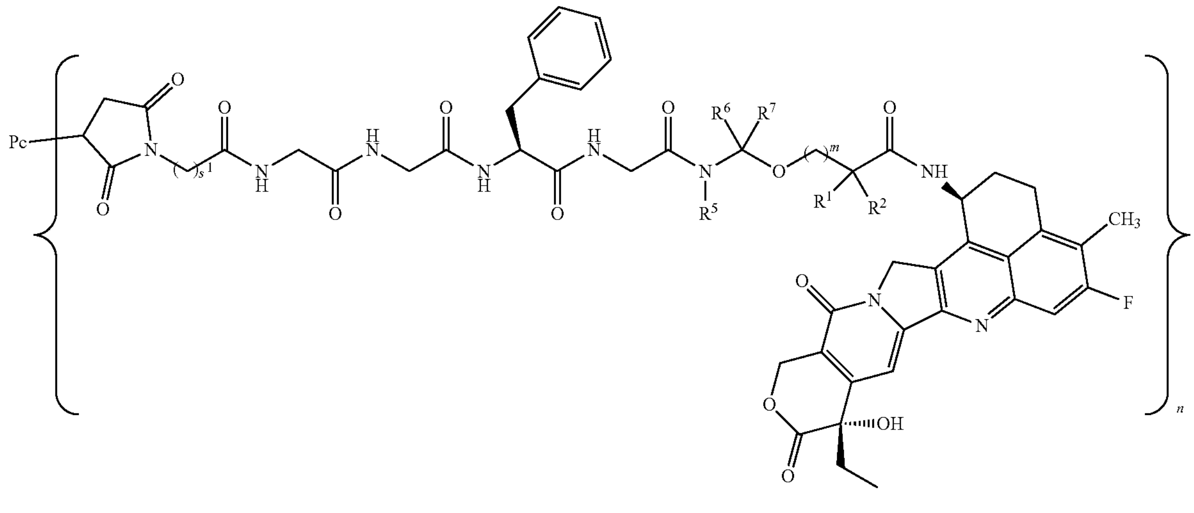

wherein:
$s^1$ is an integer from 2 to 8, and preferably 5;
Pc, $R^1$, $R^2$, $R^5$~$R^7$, m and n are as defined in formula (Pc-La-Y-Dr).
The linker unit -L-Y— of the ligand-drug conjugate of the present disclosure includes, but is not limited to:
| No. | Structure |
|---|---|
| —L—$Y^2$— | 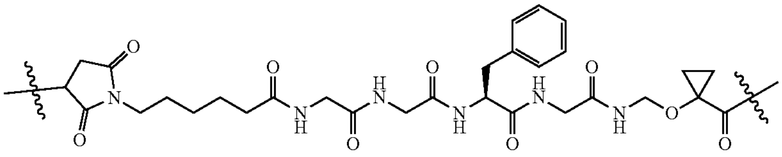 [SMILES: *C(=O)C1(OCNC(=O)CNC(=O)[C@H](Cc2ccccc2)NC(=O)CNC(=O)CNC(=O)CCCCCN2C(=O)CC(*)C2=O)CC1] |
| —L—$Y^3$— | 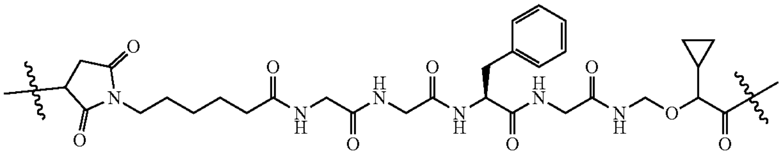 [SMILES: *C(=O)C(OCNC(=O)CNC(=O)[C@H](Cc1ccccc1)NC(=O)CNC(=O)CNC(=O)CCCCCN1C(=O)CC(*)C1=O)C1CC1] |
| —L—$Y^{3-A}$— | 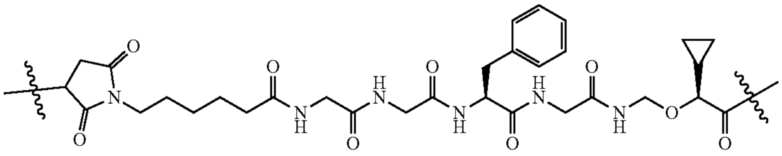 [SMILES: *C(=O)[C@@H](OCNC(=O)CNC(=O)[C@H](Cc1ccccc1)NC(=O)CNC(=O)CNC(=O)CCCCCN1C(=O)CC(*)C1=O)C1CC1] |
| —L—$Y^{3-B}$— | 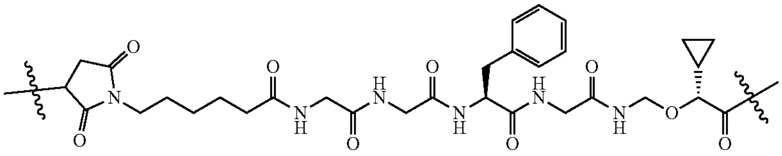 [SMILES: *C(=O)[C@H](OCNC(=O)CNC(=O)[C@H](Cc1ccccc1)NC(=O)CNC(=O)CNC(=O)CCCCCN1C(=O)CC(*)C1=O)C1CC1] |
| —L—$Y^6$— | 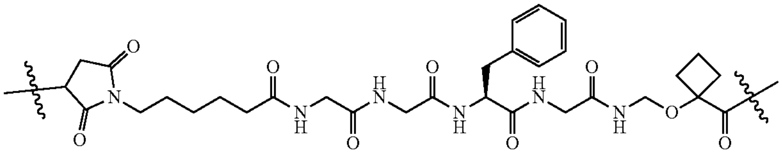 [SMILES: *C(=O)C1(OCNC(=O)CNC(=O)[C@H](Cc2ccccc2)NC(=O)CNC(=O)CNC(=O)CCCCCN2C(=O)CC(*)C2=O)CCC1] |
| —L—$Y^7$— | 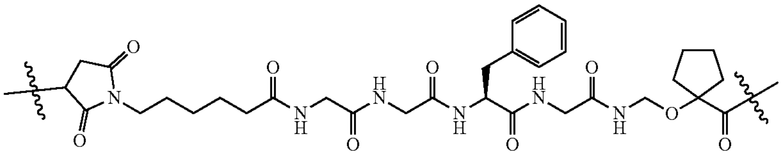 [SMILES: *C(=O)C1(OCNC(=O)CNC(=O)[C@H](Cc2ccccc2)NC(=O)CNC(=O)CNC(=O)CCCCCN2C(=O)CC(*)C2=O)CCCC1] |
| —L—$Y^8$— | 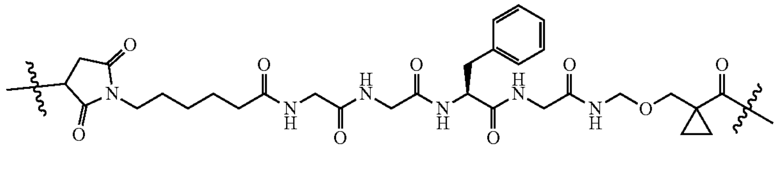 [SMILES: *C(=O)C1(COCNC(=O)CNC(=O)[C@H](Cc2ccccc2)NC(=O)CNC(=O)CNC(=O)CCCCCN2C(=O)CC(*)C2=O)CC1] |
| —L—$Y^9$— | 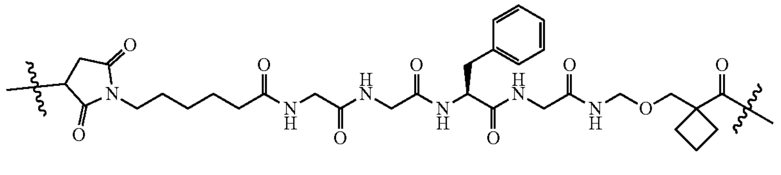 [SMILES: *C(=O)C1(COCNC(=O)CNC(=O)[C@H](Cc2ccccc2)NC(=O)CNC(=O)CNC(=O)CCCCCN2C(=O)CC(*)C2=O)CCC1] |

-continued
| No. | Structure |
|---|---|
| —L—$Y^{10}$— | 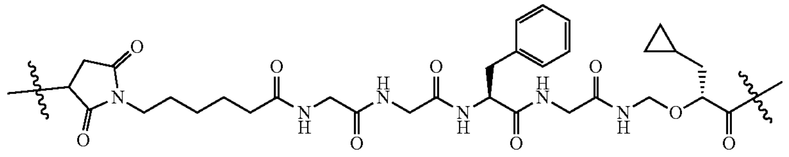 [SMILES: *C(=O)[C@@H](CC1CC1)OCNC(=O)CNC(=O)[C@H](Cc1ccccc1)NC(=O)CNC(=O)CNC(=O)CCCCCN1C(=O)CC(*)C1=O] |
| —L—$Y^{11}$— | 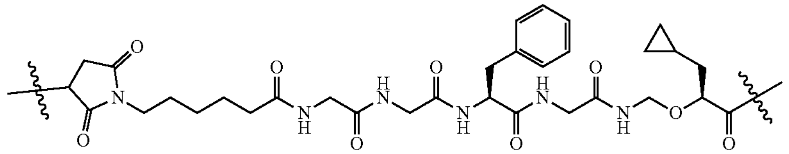 [SMILES: *C(=O)[C@H](CC1CC1)OCNC(=O)CNC(=O)[C@H](Cc1ccccc1)NC(=O)CNC(=O)CNC(=O)CCCCCN1C(=O)CC(*)C1=O] |
| —L—$Y^{12}$— | 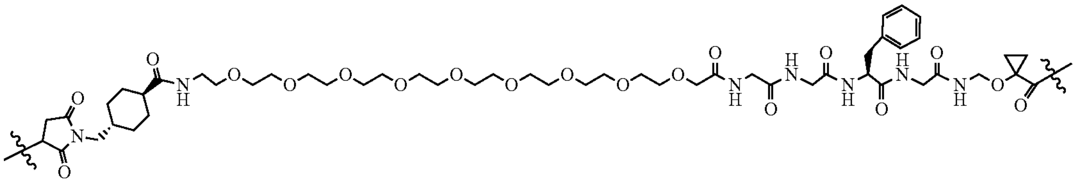 [SMILES: *C(=O)C1(OCNC(=O)CNC(=O)[C@H](Cc2ccccc2)NC(=O)CNC(=O)CNC(=O)COCCOCCOCCOCCOCCOCCOCCOCCOCCNC(=O)[C@H]2CC[C@H](CN3C(=O)CC(*)C3=O)CC2)CC1] |
| —L—$Y^{13}$— | 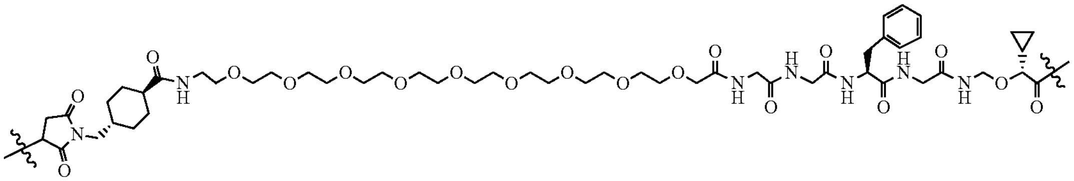 [SMILES: *C(=O)[C@H](OCNC(=O)CNC(=O)[C@H](Cc1ccccc1)NC(=O)CNC(=O)CNC(=O)COCCOCCOCCOCCOCCOCCOCCOCCOCCNC(=O)[C@H]1CC[C@H](CN2C(=O)CC(*)C2=O)CC1)C1CC1] |
| —L—$Y^{14}$— | 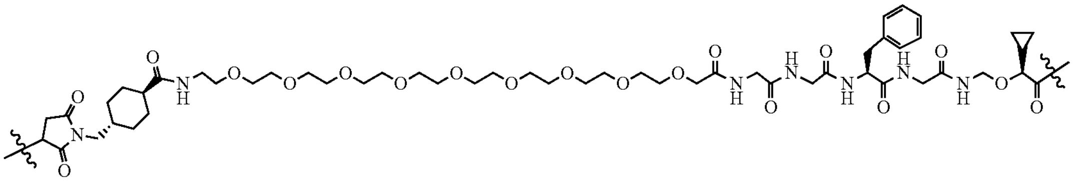 [SMILES: *C(=O)[C@@H](OCNC(=O)CNC(=O)[C@H](Cc1ccccc1)NC(=O)CNC(=O)CNC(=O)COCCOCCOCCOCCOCCOCCOCCOCCOCCNC(=O)[C@H]1CC[C@H](CN2C(=O)CC(*)C2=O)CC1)C1CC1] |
The ligand-drug conjugates of formula (Pc-L-Y-Dr) of the present disclosure include, but are not limited to:
| Structure |
|---|
| 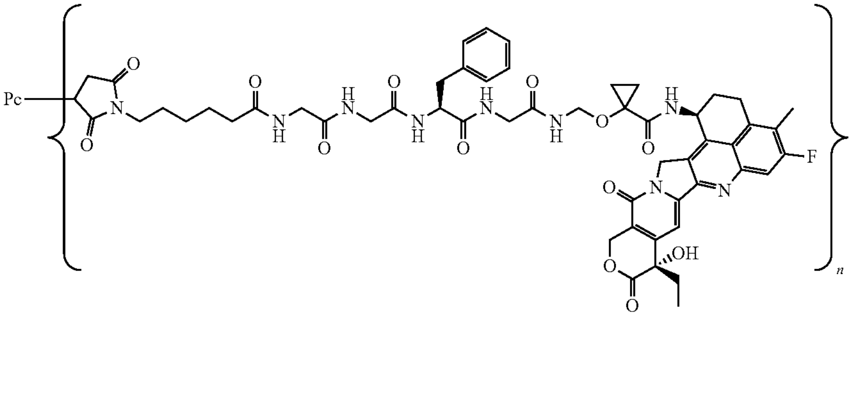 |

-continued
| Structure |
| --- |
| 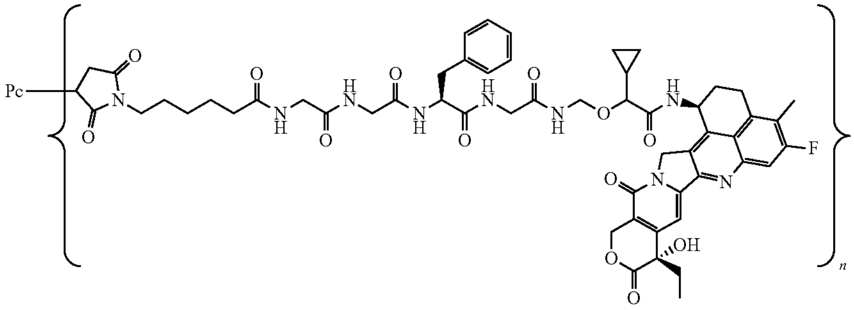 |
| 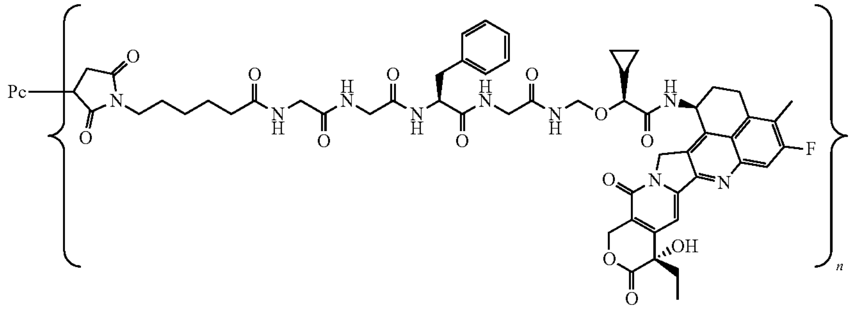 |
| 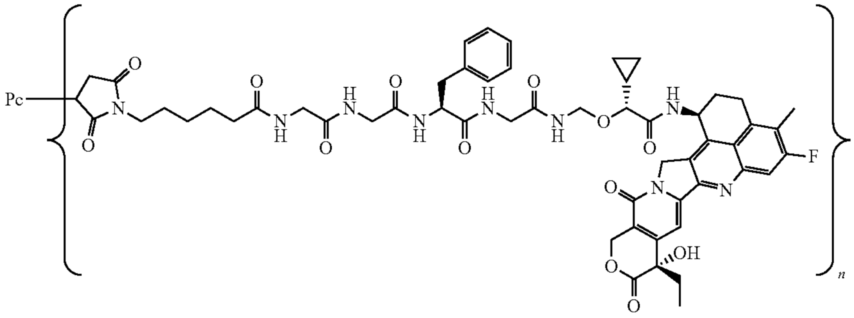 |
| 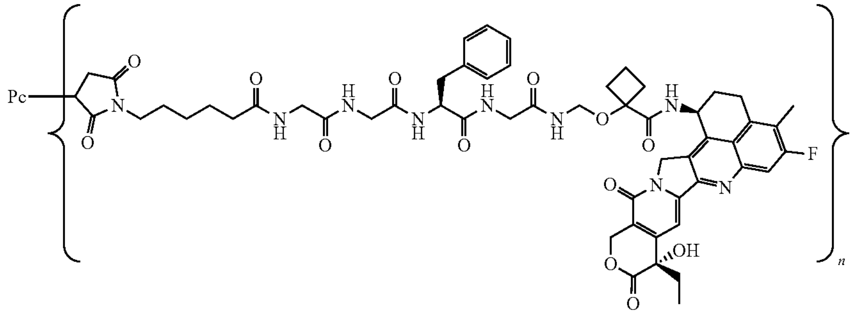 |
| 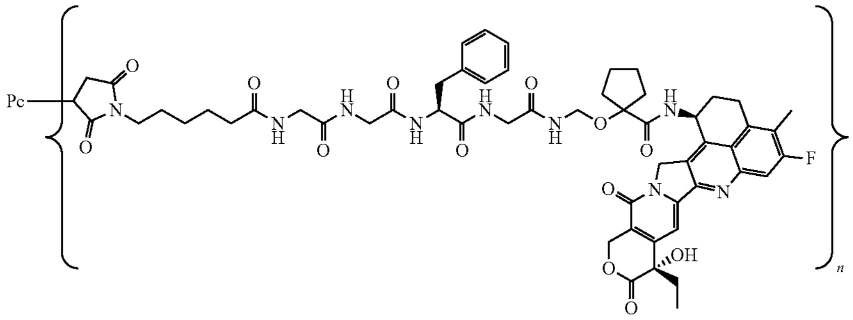 |

-continued
| Structure |
| --- |
| 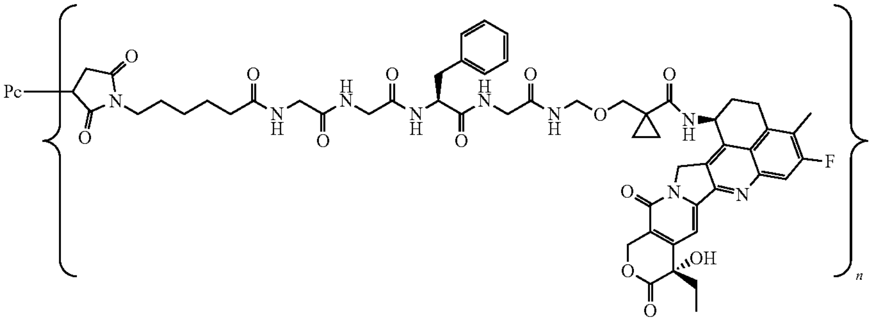 |
| 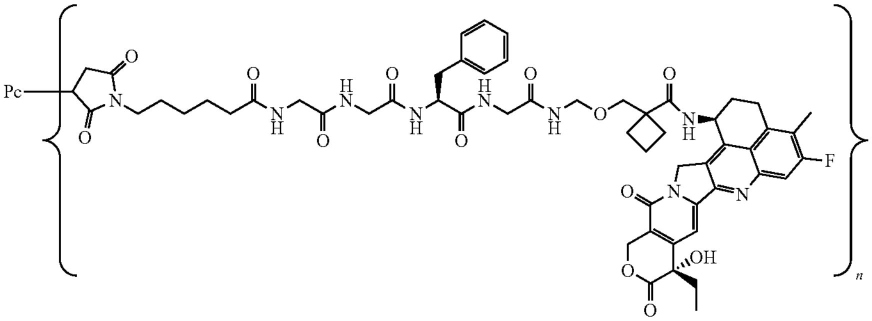 |
| 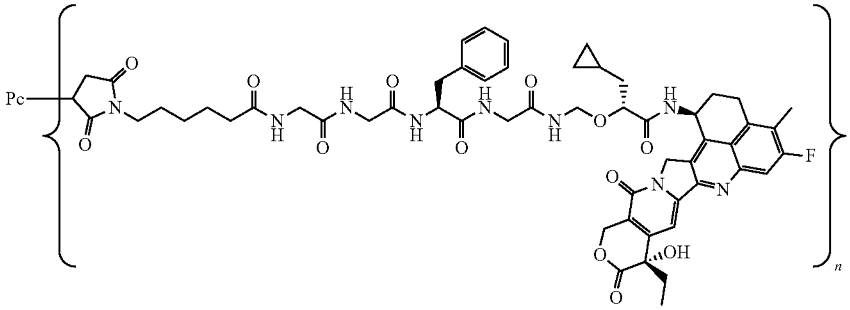 |
| 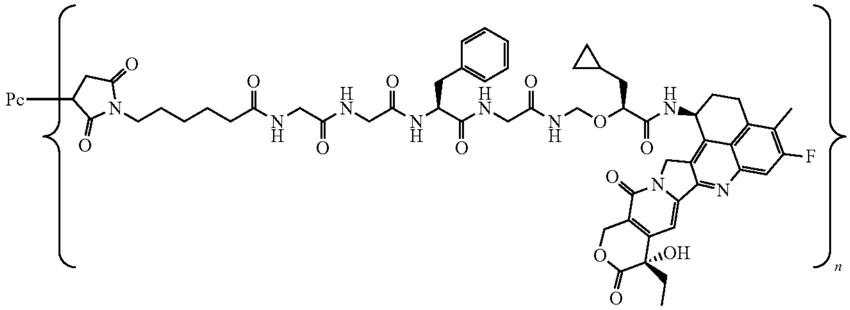 |
| 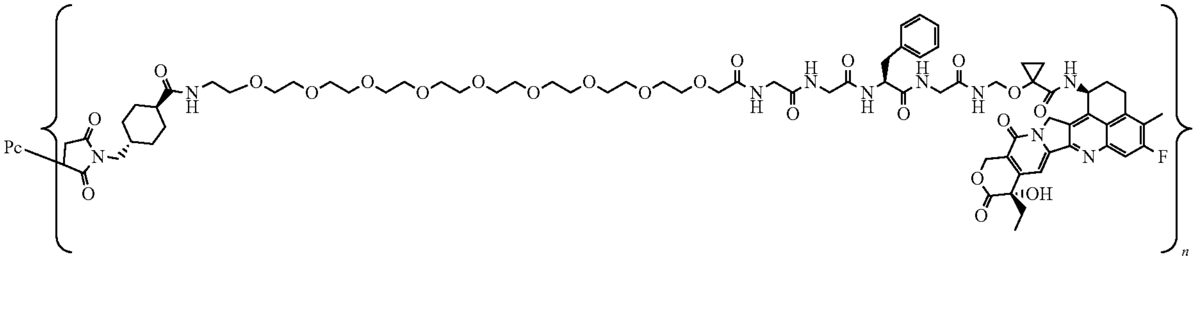 |

-continued

| Structure |
|---|
| 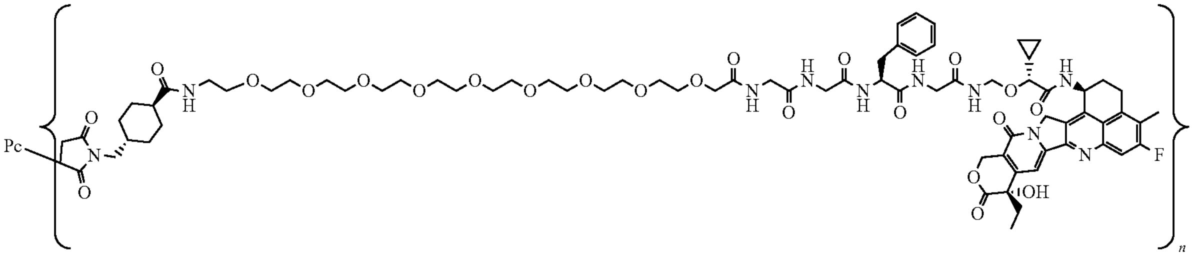 |
| 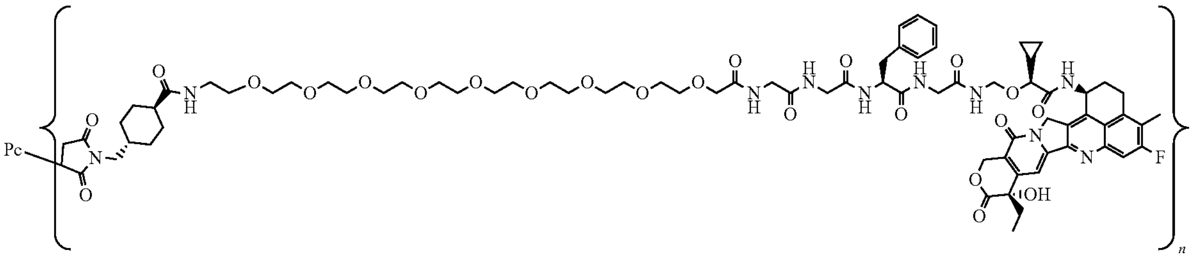 |

wherein Pc and n are as defined in formula (Pc-La-Y-Dr).

In some other embodiments of the present disclosure, in the ligand-drug conjugate or the pharmaceutically acceptable salt or solvate thereof, Pc is an antibody or an antigen-binding fragment thereof, the antibody is selected from the group consisting of chimeric antibody, humanized antibody and fully humanized antibody, and preferably a monoclonal antibody.

In some other embodiments of the present disclosure, in the ligand-drug conjugate or the pharmaceutically acceptable salt or solvate thereof, the antibody or antigen-binding fragment thereof is selected from the group consisting of anti-HER2 (ErbB2) antibody, anti-EGFR antibody, anti-B7-H3 antibody, anti-c-Met antibody, anti-HER3 (ErbB3) antibody, anti-HER4 (ErbB4) antibody, anti-CD20 antibody, anti-CD22 antibody, anti-CD30 antibody, anti-CD33 antibody, anti-CD44 antibody, anti-CD56 antibody, anti-CD70 antibody, anti-CD73 antibody, anti-CD105 antibody, anti-CEA antibody, anti-A33 antibody, anti-Cripto antibody, anti-EphA2 antibody, anti-G250 antibody, anti-MUC1 antibody, anti-Lewis Y antibody, anti-VEGFR antibody, anti-GPNMB antibody, anti-Integrin antibody, anti-PSMA antibody, anti-Tenascin-C antibody, anti-SLC44A4 antibody and anti-Mesothelin antibody, and antigen-binding fragments thereof.

In some other embodiments of the present disclosure, in the ligand-drug conjugate or the pharmaceutically acceptable salt or solvate thereof, the antibody or antigen-binding fragment thereof is selected from the group consisting of Trastuzumab, Pertuzumab, Nimotuzumab, Enoblituzumab, Emibetuzumab, Inotuzumab, Pinatuzumab, Brentuximab, Gemtuzumab, Bivatuzumab, Lorvotuzumab, cBR96 and Glematumamab, and antigen-binding fragments thereof.

The ligand-drug conjugates of formula (Pc-L-Y-Dr) of the present disclosure include, but are not limited to the following formulas:

| Exemplary ADC | Structure |
|---|---|
| ADC-3 | 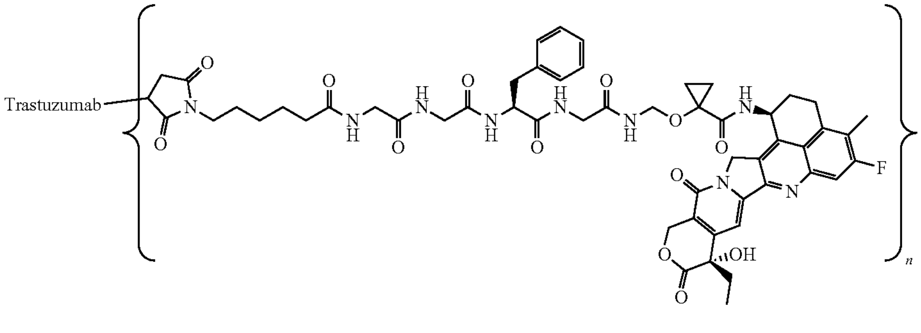 |

-continued
| Exemplary ADC | Structure |
| --- | --- |
| | 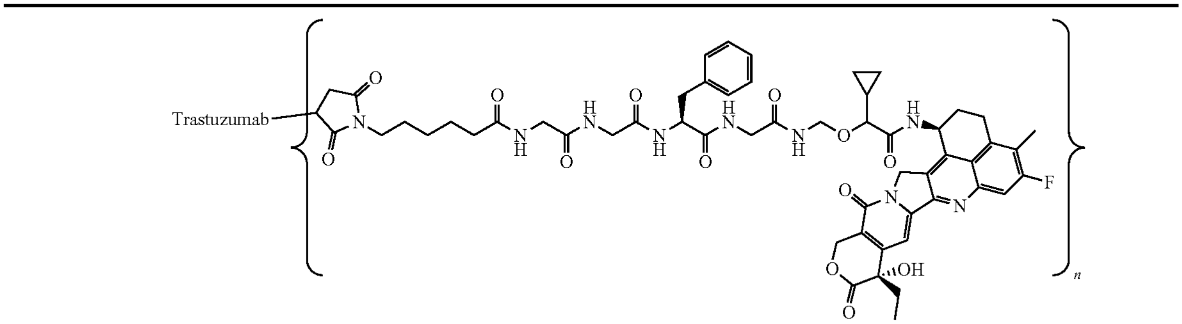 |
| ADC-6 | 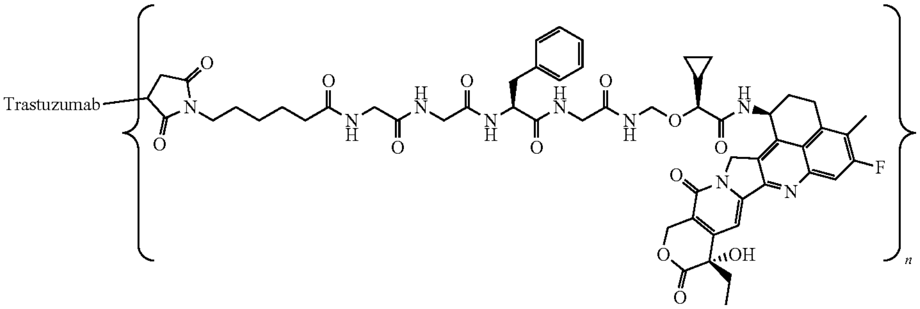 |
| ADC-4/ADC-5/ADC-17/ADC-19 | 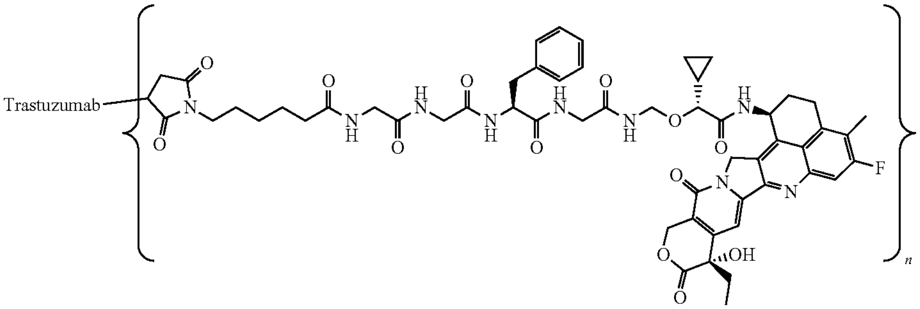 |
| ADC-7 | 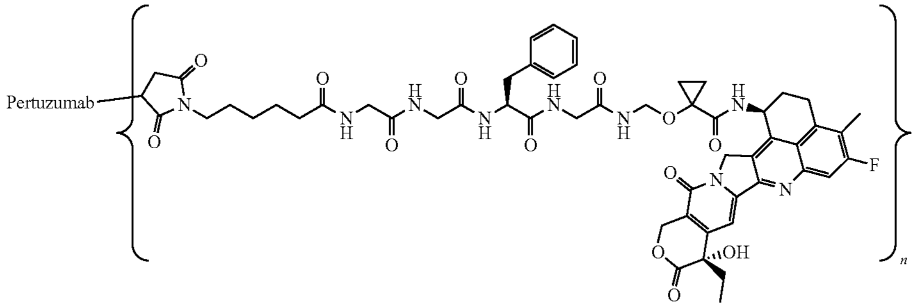 |
| | 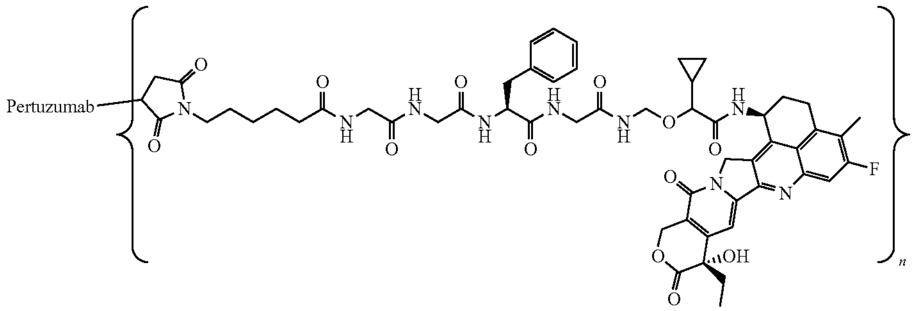 |

-continued
| Exemplary ADC | Structure |
| --- | --- |
| | 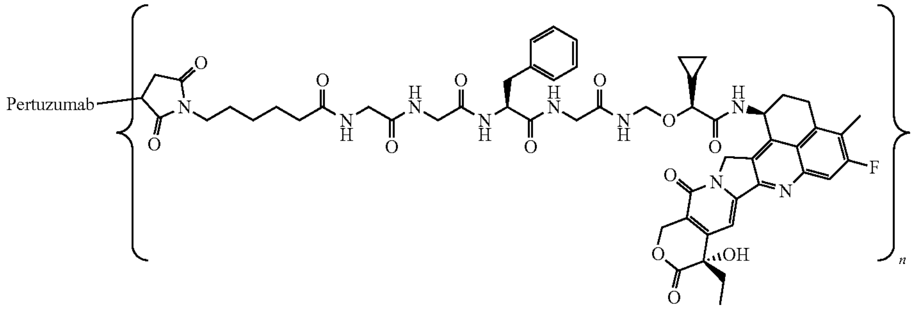 |
| | 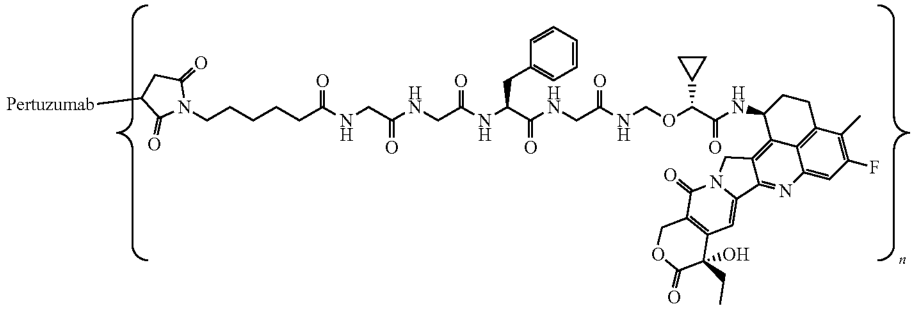 |
| ADC-10/ ADC-11 | 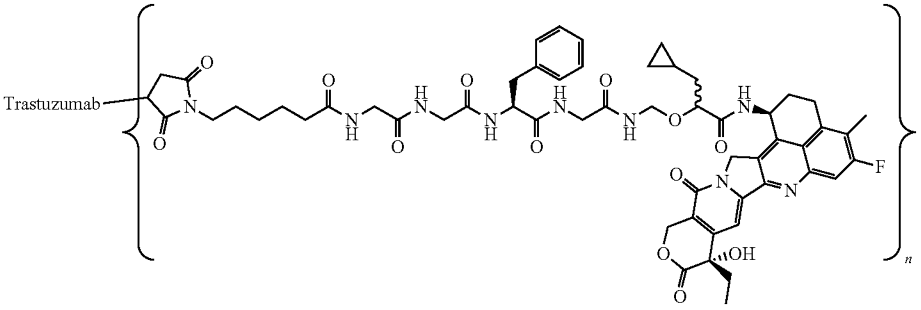 |
| | 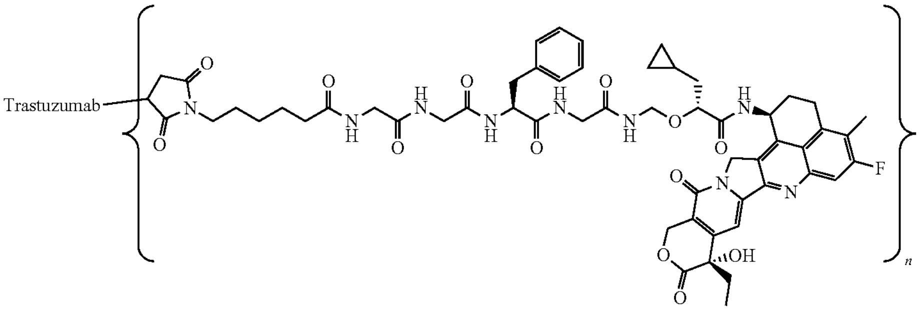 |

-continued
| Exemplary ADC | Structure |
|---|---|
| | 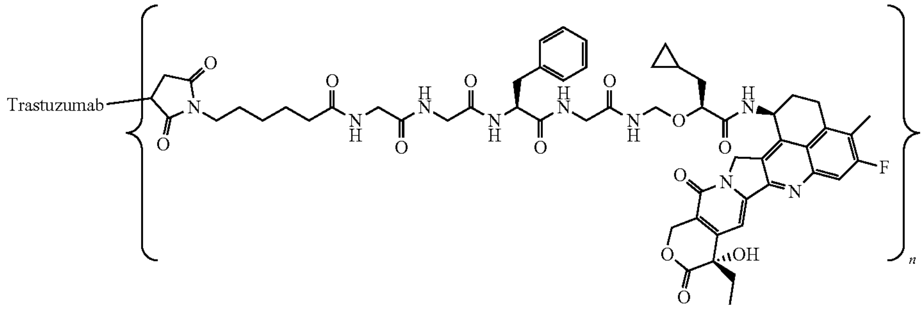 |
| ADC-12 | 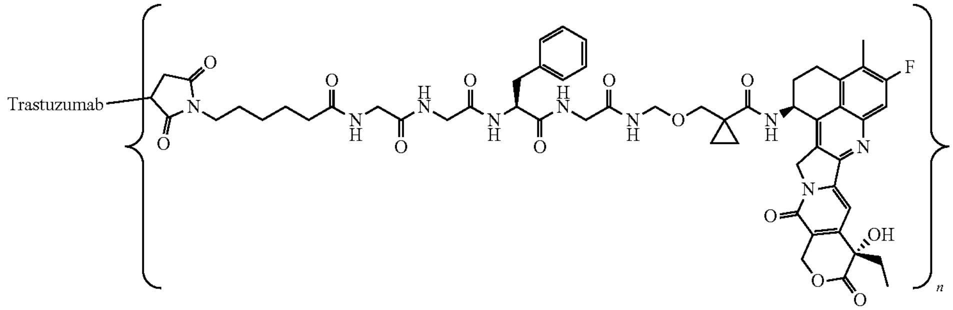 |
| ADC-13 | 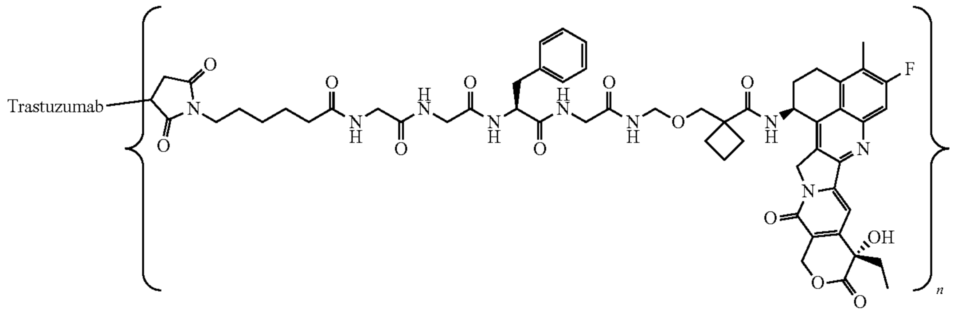 |
| ADC-14 | 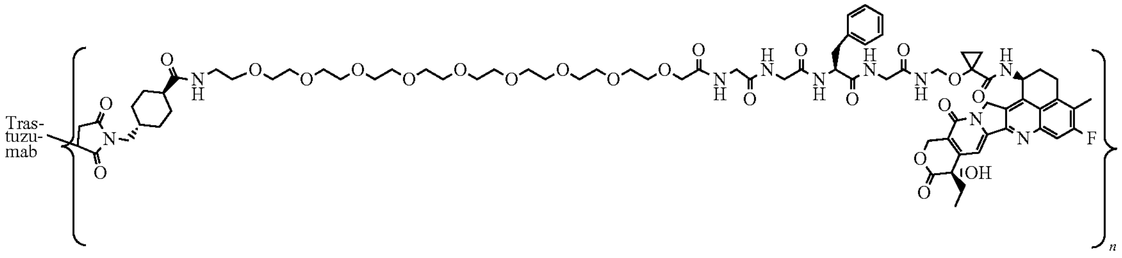 |
| ADC-15 | 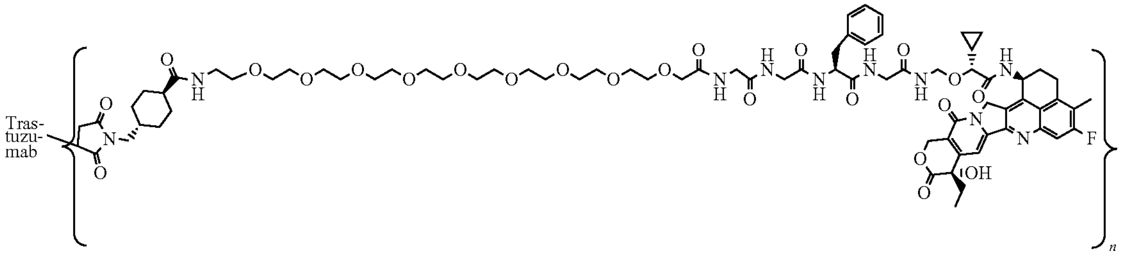 |

-continued

| Exemplary ADC | Structure |
| --- | --- |
| ADC-16 | 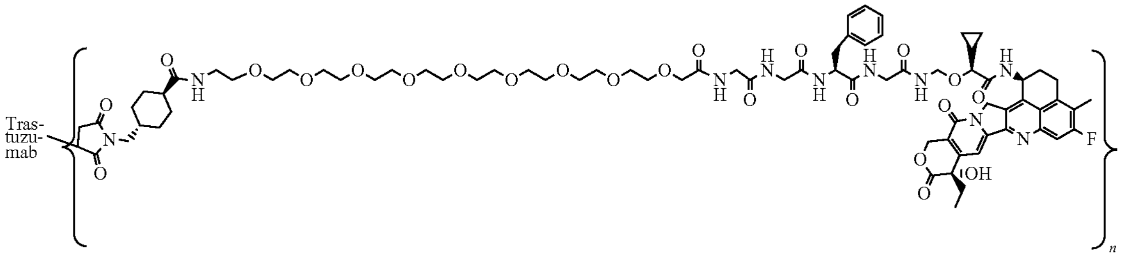 |
| ADC-25 ADC-27/ ADC-29 | 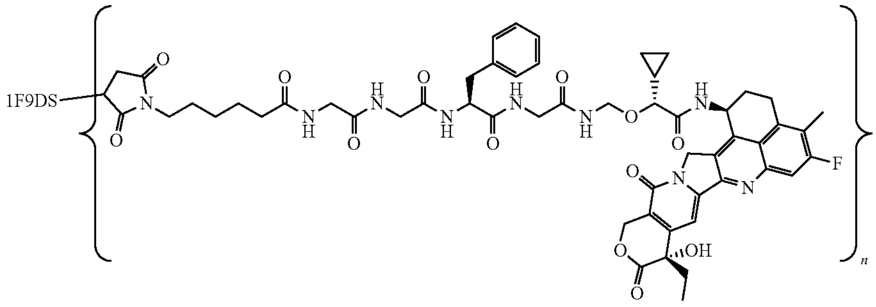 |
| ADC-31 | 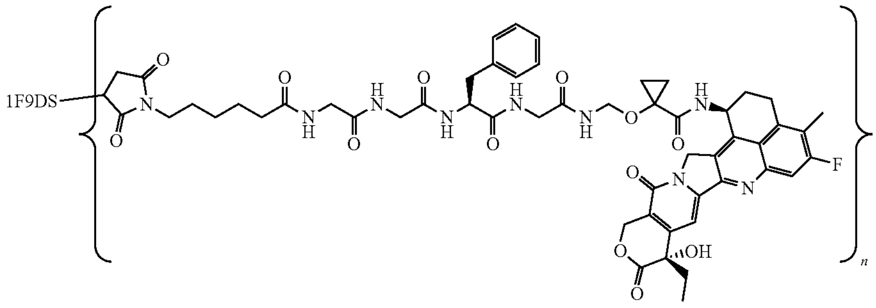 |

wherein, n is a non-zero integer or decimal from 0 to 10, preferably n is an integer or decimal from 1 to 10; more preferably n is 2 to 8, which can be an integer or a decimal; and most preferably n is 3 to 8, which can be an integer or a decimal.

Another aspect of the present disclosure provides a compound of formula (D) or a tautomer, mesomer, racemate, enantiomer, diastereomer thereof, or mixture thereof, or a pharmaceutically acceptable salt thereof, (D)

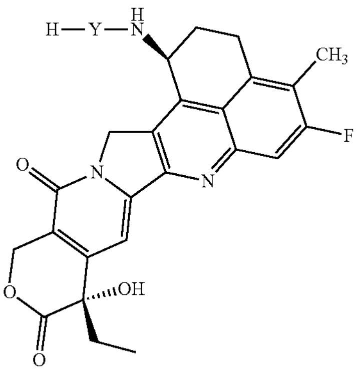

wherein:

Y is selected from the group consisting of $-O-(CR^aR^b)m-CR^1R^2-C(O)-$, $-O-CR^1R^2-(CR^aR^b)m-$, $-O-CR^1R^2-$, $-NH-(CR^aR^b)m-CR^1R^2-C(O)-$ and $-S-(CR^aR^b)m-CR^1R^2-C(O)-$;

$R^a$ and $R^b$ are identical or different and are each independently selected from the group consisting of hydrogen atom, deuterium atom, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$ together with the carbon atom to which they are attached form a cycloalkyl or heterocyclyl;

$R^1$ is selected from the group consisting of halogen, cycloalkylalkyl, deuterated alkyl, cycloalkyl, alkoxyalkyl, heterocyclyl, aryl and heteroaryl;

$R^2$ is selected from the group consisting of hydrogen atom, halogen, haloalkyl, deuterated alkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

or, $R^a$ and $R^2$ together with the carbon atom to which they are attached form a cycloalkyl or heterocyclyl;

m is an integer from 0 to 4.

In a preferred embodiment of another aspect of the present disclosure, the provided compound of formula (D)

or the tautomer, mesomer, racemate, enantiomer, diastereomer thereof, or mixture thereof, or the pharmaceutically acceptable salt thereof, is a compound of formula ($D_1$) or a tautomer, mesomer, racemate, enantiomer, diastereomer thereof, or mixture thereof, or a pharmaceutically acceptable salt thereof,

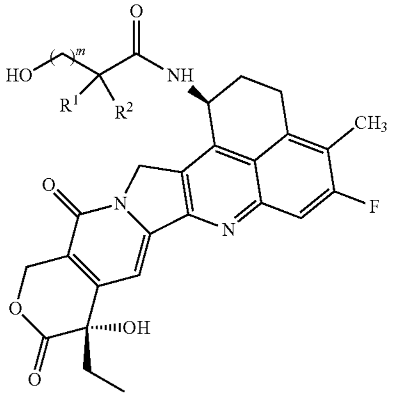

($D_1$)

wherein: $R^1$ is a $C_{3-6}$ cycloalkylalkyl or $C_{3-6}$ cycloalkyl;

$R^2$ is selected from the group consisting of hydrogen atom, haloalkyl and $C_{3-6}$ cycloalkyl;

or, $R^1$ and $R^2$ together with the carbon atom to which they are attached form a $C_{3-6}$ cycloalkyl;

m is 0 or 1.

The compounds of formula (D) of the present disclosure include, but are not limited to:

| No. | Structure |
|---|---|
| 1 | 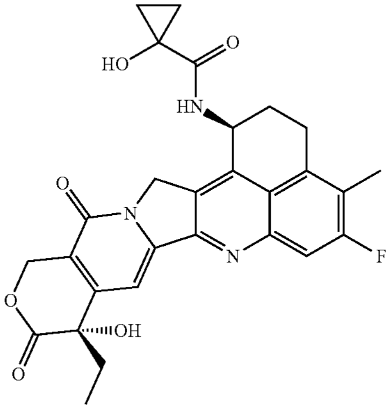 1 N-((1S,9S)-9-Ethyl-5-fluoro-9-hydroxy-4-methyl-10,13-dioxo-2,3,9,10,13,15-hexahydro-1H,12H-benzo[de]pyrano[3′,4′:6,7]-indolizino[1,2-b]quinolin-1-yl)-1-hydroxy-cyclopropane-1-carboxamide 1 |

-continued

| No. | Structure |
|---|---|
| 2 | 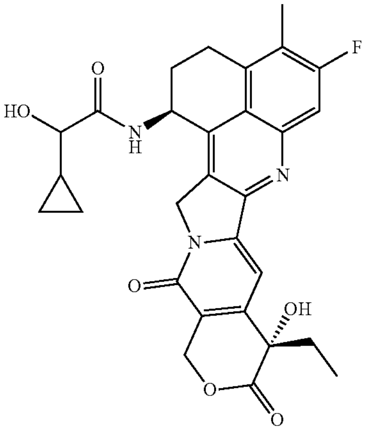 2 2-Cyclopropyl-N-((1S,9S)-9-ethyl-5-fluoro-9-hydroxy-4-methyl-10,13-dioxo-1,2,3,9,10,12,13,15-octahydro-benzo[de]pyrano[3′,4′:6,7]indolizino-[1,2-b]quinolin-1-yl)-2-hydroxy-acetamide 2 |
| 2-A | 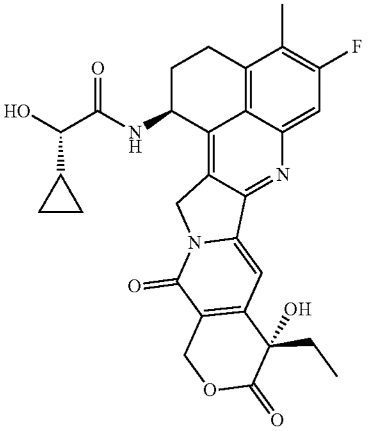 2-A (S)-2-Cyclopropyl-N-((1S,9S)-9-ethyl-5-fluoro-9-hydroxy-4-methyl-10,13-dioxo-1,2,3,9,10,12,13,15-octahydrobenzo-[de]pyrano[3′,4′:6,7]indolizino[1,2-b]-quinolin-1-yl)-2-hydroxyacetamide 2-A |

-continued

| No. | Structure |
|---|---|
| 2-B | 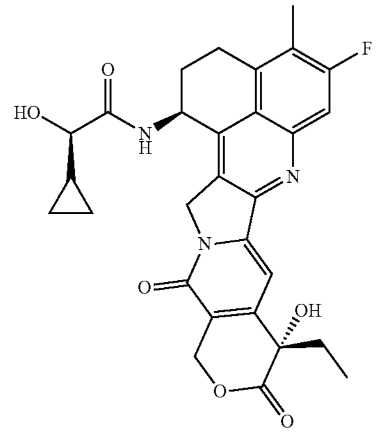 2-B (R)-2-Cyclopropyl-N-(1S,9S)-9-ethyl-5-fluoro-9-hydroxy-4-methyl-10,13-dioxo-1,2,3,9,10,12,13,15-octahydro-benzo[de]pyrano[3′,4′:6,7]indolizino-[1,2-b]quinolin-1-yl)-2-hydroxy-acetamide 2-B |
| 4 | 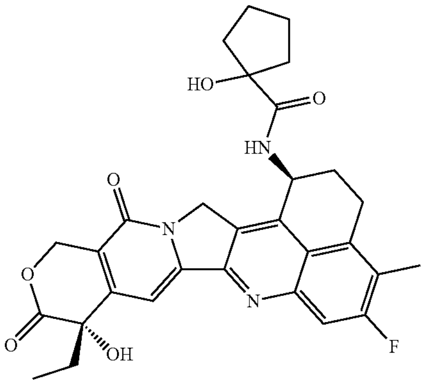 4 N-((1S,9S)-9-Ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]-quinolin-1-yl)-1-hydroxycyclopentane-1-carboxamide 4 |

-continued

| No. | Structure |
|---|---|
| 5 | 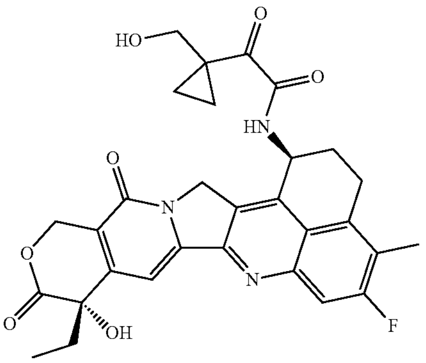 5 N-((1S,9S)-9-Ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]-quinolin-1-yl)-1-(hydroxymethyl)cyclopropane-1-carboxamide 5 |
| 6 | 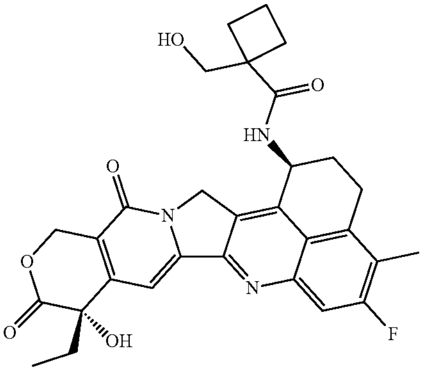 6 N-((1S,9S)-9-Ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]-quinolin-1-yl)-1-(hydroxymethyl)cyclobutane-1-carboxamide 6 |
| 7 | 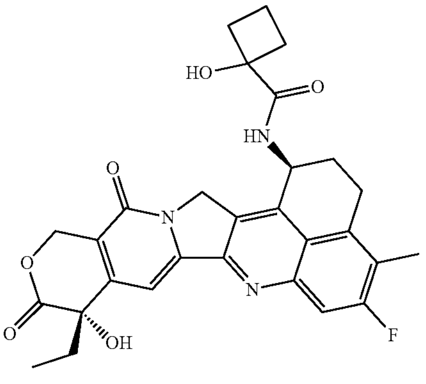 7 N-((1S,9S)-9-Ethyl-5-fluoro-9-hydroxy-4-methyl-10,13-dioxo-2,3,9,10,13,15-hexahydro-1H,12H-benzo[de]pyrano-[3′,4′:6,7]indolizino[1,2-b]quinolin-1-yl)-1-hydroxycyclobutane-1-carboxamide 7 |

-continued

| No. | Structure |
| --- | --- |
| 12-A | 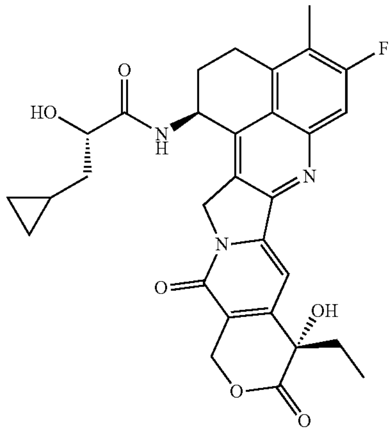 12-A (S)-3-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]-indolizino[1,2-b]quinolin-1-yl)-2-hydroxypropanamide 12-A |
| 12-B | 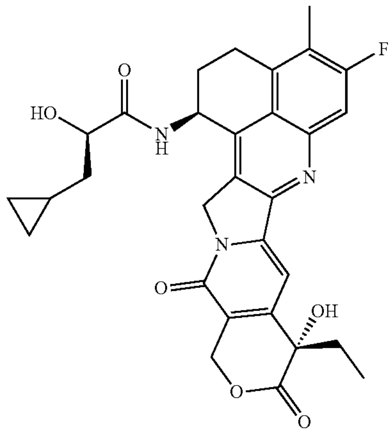 12-B (R)-3-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]-indolizino[1,2-b]quinolin-1-yl)-2-hydroxypropanamide 12-B |

or a tautomer, mesomer, racemate, enantiomer, diastereomer thereof, or mixture thereof, or a pharmaceutically acceptable salt thereof.

A preferred embodiment of another aspect of the present disclosure provides a compound of formula ($L_a$-Y-Dr) or a tautomer, mesomer, racemate, enantiomer, diastereomer thereof, or mixture thereof, or a pharmaceutically acceptable salt thereof:

($L_a$-Y-Dr)

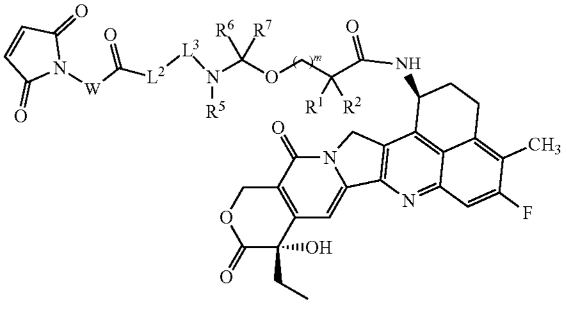

wherein

W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue composed of 2 to 7 amino acids, wherein the amino acids are optionally further substituted by one or more substituent(s) selected from the group consisting of halogen, hydroxy, cyano, amino, alkyl, chloroalkyl, deuterated alkyl, alkoxy and cycloalkyl, when substituted, the substituent group(s) can be substituted at any available connection point, the substituent group(s) is one or more group(s) independently selected from the group consisting of halogen, hydroxy, cyano, amino, alkyl, chloroalkyl, deuterated alkyl, alkoxy and cycloalkyl;

$R^1$ is selected from the group consisting of halogen, cycloalkylalkyl, deuterated alkyl, cycloalkyl, alkoxyalkyl, heterocyclyl, aryl and heteroaryl;

$R^2$ is selected from the group consisting of hydrogen atom, halogen, haloalkyl, deuterated alkyl, cycloalkyl, cycloalkylalkyl, alkoxyalkyl, heterocyclyl, aryl and heteroaryl; or, $R^1$ and $R^2$ together with the carbon atom to which they are attached form a cycloalkyl or heterocyclyl;

$R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

m is an integer from 0 to 4.

In a preferred embodiment of another aspect of the present disclosure, the provided compound of formula ($L_a$-Y-Dr) or the tautomer, mesomer, racemate, enantiomer, diastereomer thereof, or mixture thereof, or the pharmaceutically acceptable salt thereof, is a compound of formula ($L_b$-Y-Dr) or a tautomer, mesomer, racemate, enantiomer, diastereomer thereof, or mixture thereof, or a pharmaceutically acceptable salt thereof:

($L_b$-Y-Dr)

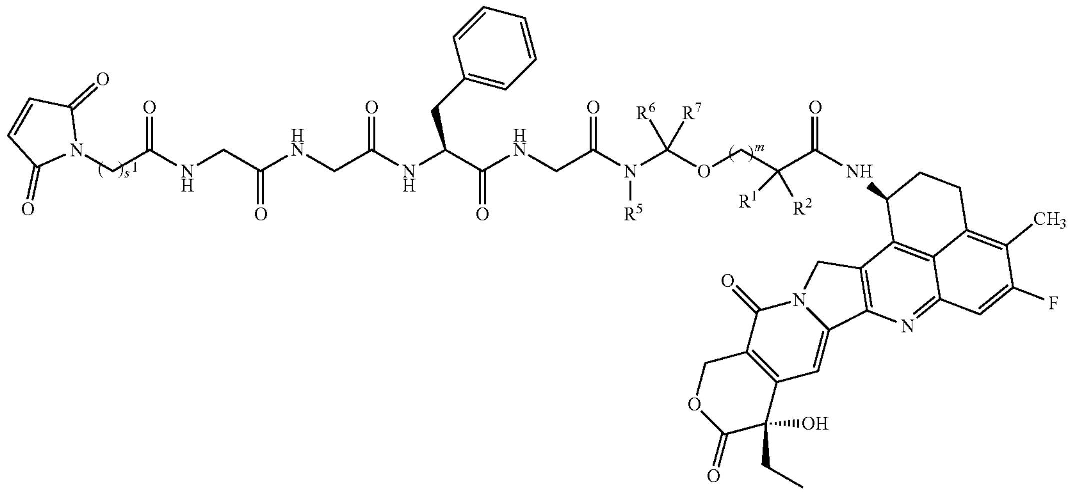

wherein $R^1$, $R^2$, $R^5$~$R^7$, $s^1$ and m are as defined in formula (La-Y-Dr).

The compounds of formula ($L_a$~Y-Dr) of the present disclosure include, but are not limited to:

| No. | Structure |
| --- | --- |
| 8 | 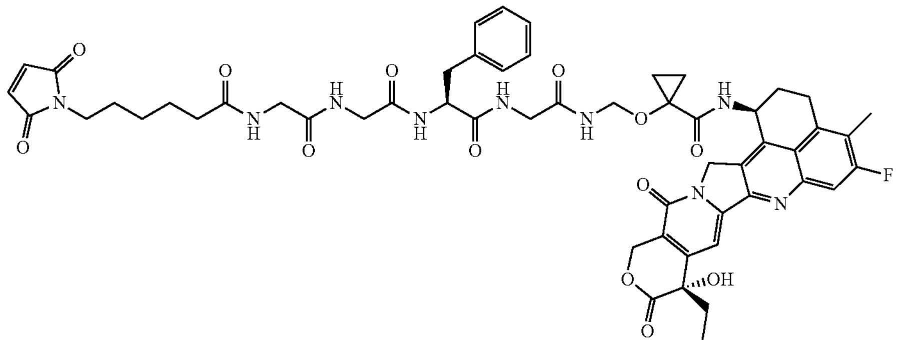<br>8<br>1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]-pyrano[3′,4′:6,7]indolizino[1,2-b]quinolin-1-yl)cyclopropane-1-carboxamide 8 |
| 9 | 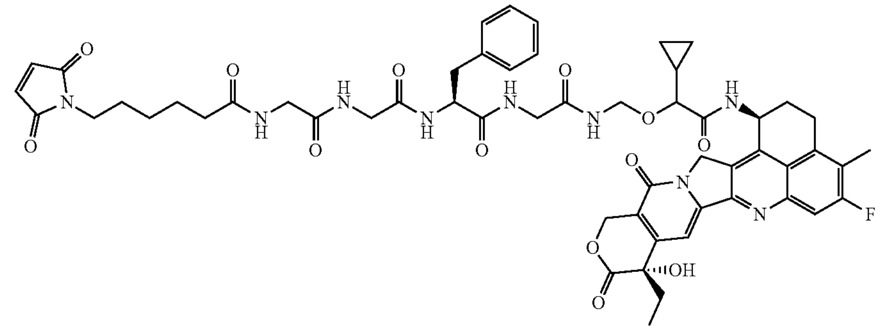<br>9<br>N-((10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9 |

-continued

| No. | Structure |
|---|---|
| 9-A | 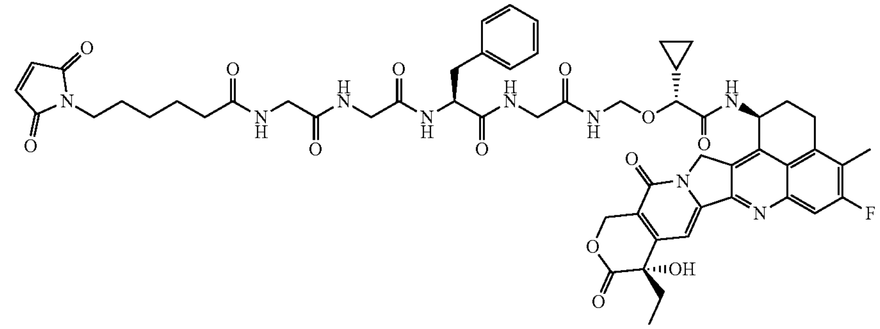<br>9-A<br>N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)-amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9-A |
| 9-B | 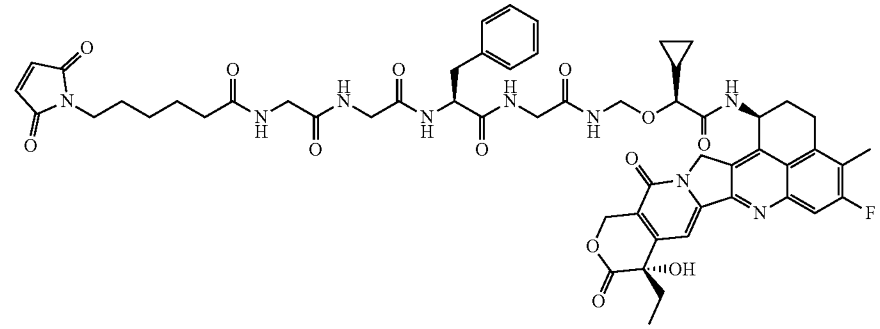<br>9-B<br>N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)-amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9-B |
| 11 | 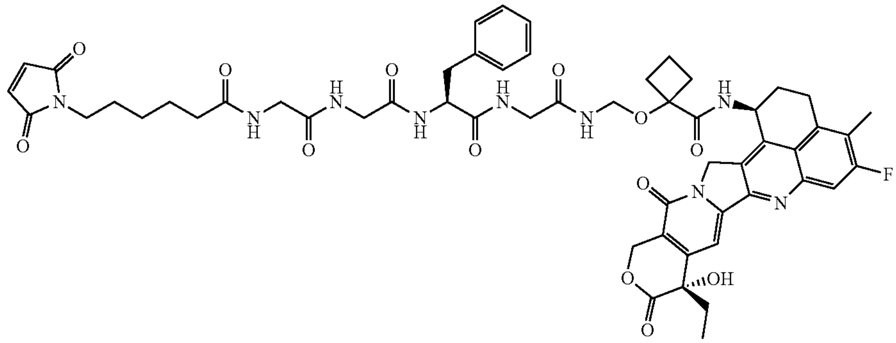<br>11<br>1-(((S)-7-Benzyl-20-(2,5-dioxo-2,5-dihydro-1H-pyrrol-1-yl)-3,6,9,12,15-pentaoxo-2,5,8,11,14-pentaazaicosyl)-oxy)-N-((1S,9S)-9-ethyl-5-fluoro-9-hydroxy-4-methyl-10,13-dioxo-2,3,9,10,13,15-hexahydro-1H,12H-benzo-[de]pyrano[3′,4′:6,7]indolizino[1,2-b]quinolin-1-yl)cyclobutane-1-carboxamide 11 |

-continued

| No. | Structure |
| --- | --- |
| 14-A | 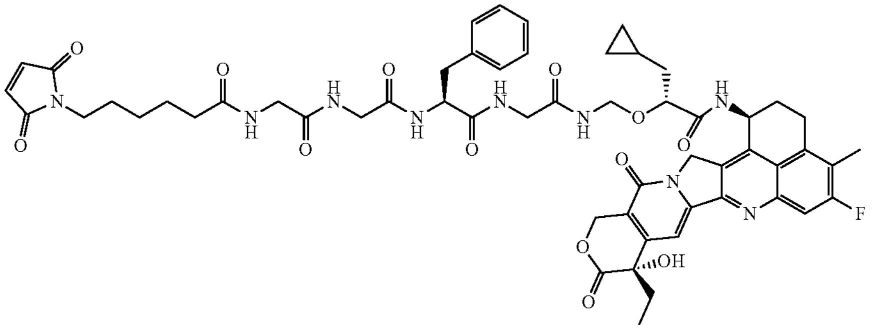 14-A N-((2R,10S)-10-Benzyl-2-(cyclopropylmethyl)-1-(((1S,9S)-9-ethyl-5-fluoro-9-hydroxy-4-methyl-10,13,-dioxo-2,3,9,10,13,15-hexahydro-1H,12H-benzo[de]pyrano[3′,4′:6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 14-A |
| 14-B | 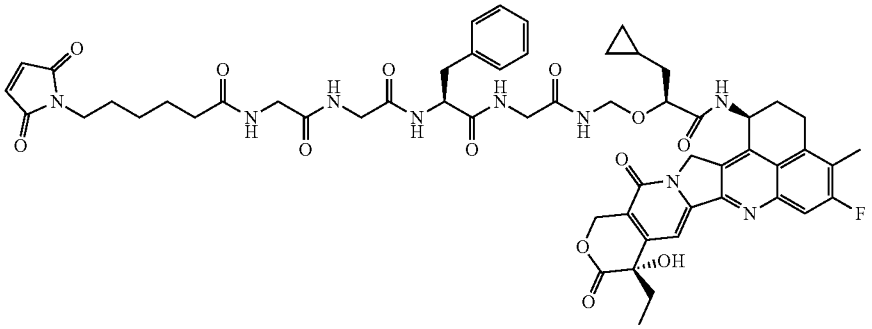 14-B N-((2S,10S)-10-Benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 14-B |
| 15 | 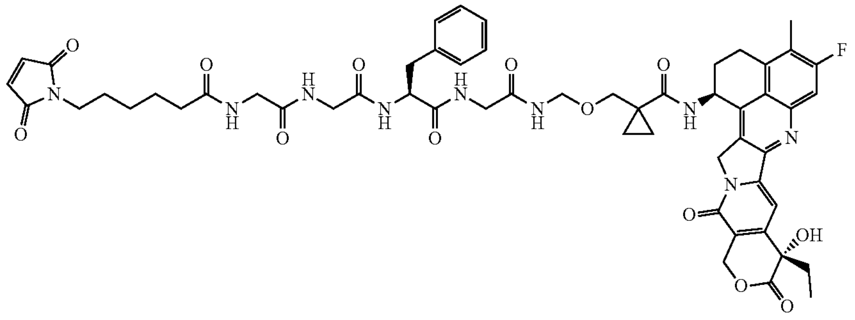 15 1-((S)-9-Benzyl-22-(2,5-dioxo-2,5-dihydro-1H-pyrrol-1-yl)-5,8,11,14,17-pentaoxo-2-oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3,4′:6,7]indolizino[1,2-b]quinolin-1-yl)cyclopropane-1-carboxamide 15 |

-continued

| No. | Structure |
|---|---|
| 16 | 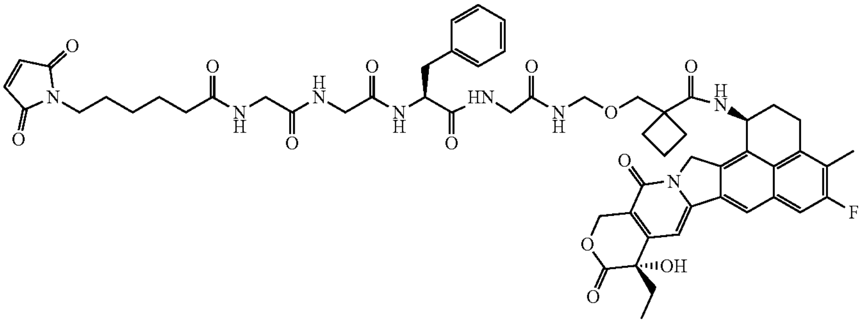 16 1-((S)-9-Benzyl-22-(2,5-dioxo-2,5-dihydro-1H-pyrrol-1-yl)-5,8,11,14,17-pentaoxo-2-oxa-4,7,10,13,16-penta-azadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)cyclobutane-1-carboxamide 16 |
| 17 | 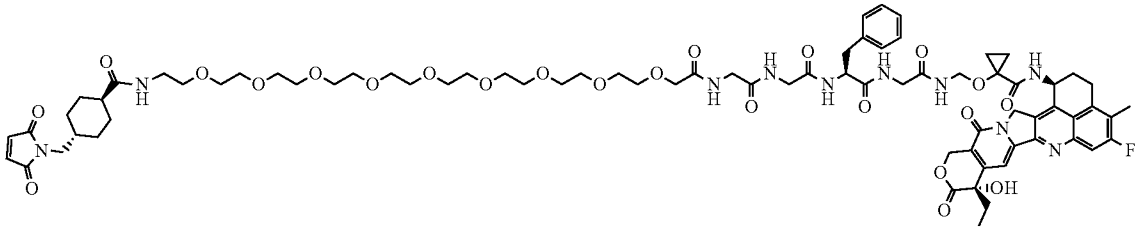 17 (1r,4r)-N-((S)-7-Benzyl-1-(1-(((1S,9S)-9-ethyl-5-fluoro-9-hydroxy-4-methyl-10,13-dioxo-2,3,9,10,13,15-hexahydro-1H,12H-benzo[de]-pyrano[3′,4′:6,7]indolizino[1,2-b]quinolin-1-yl)carbamoyl)cyclopropoxy)-3,6,9,12,15-pentaoxo-17,20,23,26,29,32,35,38,41-nonaoxa-2,5,8,11,14-pentaazatritetracontan-43-yl)-4-((2,5-dioxo-2,5-dihydro-1H-pyrrol-1-yl)methyl)cyclohexane-1-carboxamide 17 |
| 18 | 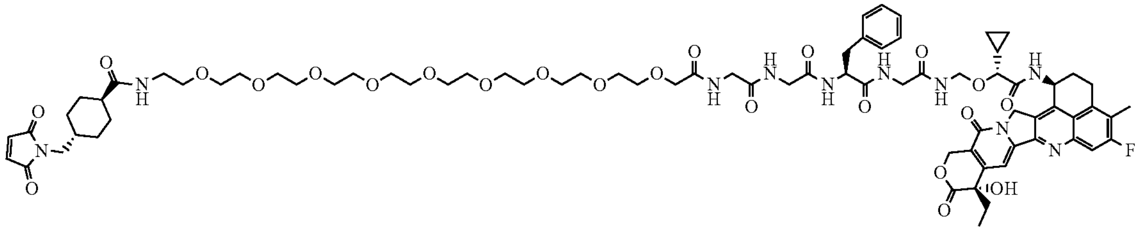 18 (1r,4r)-N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)amino)-1,6,9,12,15,18-hexaoxo-3,20,23,26,29,32,35,38,41,44-decaoxa-5,8,11,14,17-pentaazahexatetracontan-46-yl)-4-((2,5-dioxo-2,5-dihydro-1H-pyrrol-1-yl)methyl)cyclohexane-1-carboxamide 18 |
| 19 | 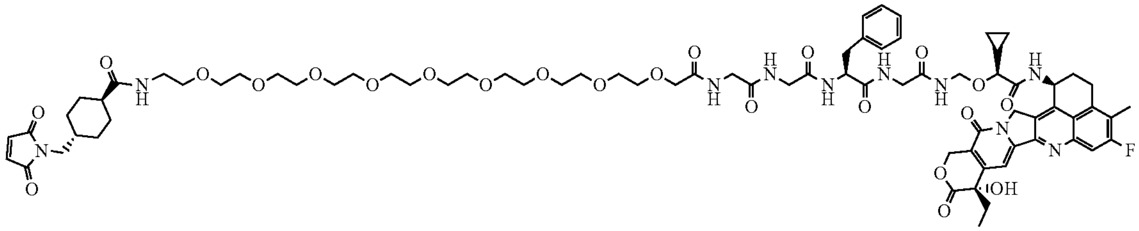 19 (1r,4r)-N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl)amino)-1,6,9,12,15,18-hexaoxo-3,20,23,26,29,32,35,38,41,44-decaoxa-5,8,11,14,17-pentaazahexatetracontan-46-yl)-4-((2,5-dioxo-2,5-dihydro-1H-pyrrol-1-yl)methyl)cyclohexane-1-carboxamide 19 |

or a tautomer, mesomer, racemate, enantiomer, diastereomer thereof, or mixture thereof, or a pharmaceutically acceptable salt thereof.

Another aspect of the present disclosure provides a method for preparing the compound of formula ($D_1$) or the tautomer, mesomer, racemate, enantiomer, diastereomer thereof, or mixture thereof, or the pharmaceutically acceptable salt thereof, comprising the following step of:

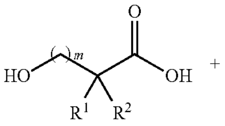

($Y_1$)

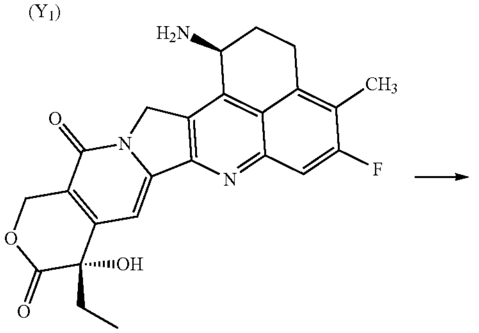

(Dr)

-continued

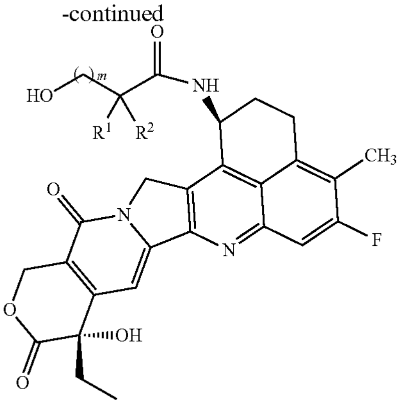

($D_1$)

condensing the compound of formula ($Y_1$) and the compound of formula (Dr) to obtain the compound of formula ($D_1$), wherein: $R^1$, $R^2$ and m are as defined in formula ($D_1$).

Another aspect of the present disclosure provides a method for preparing the compound of formula ($L_b$-Y-Dr) or the tautomer, mesomer, racemate, enantiomer, diastereomer thereof, or mixture thereof, or the pharmaceutically acceptable salt thereof, comprising the following step of:

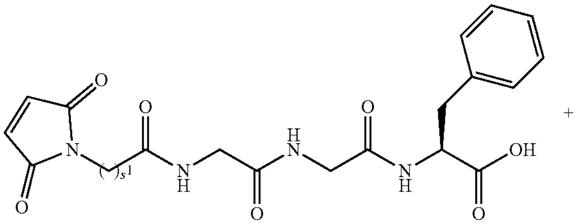

(IA)

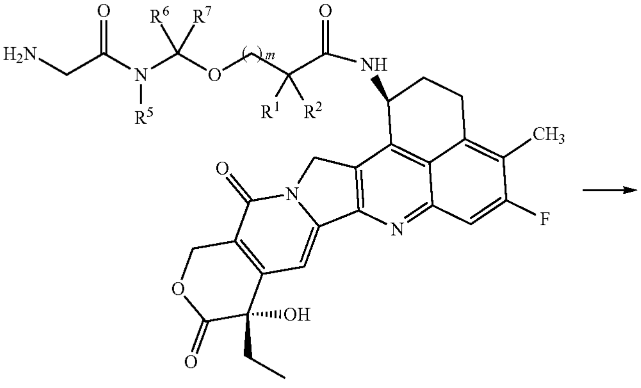

(IB)

-continued

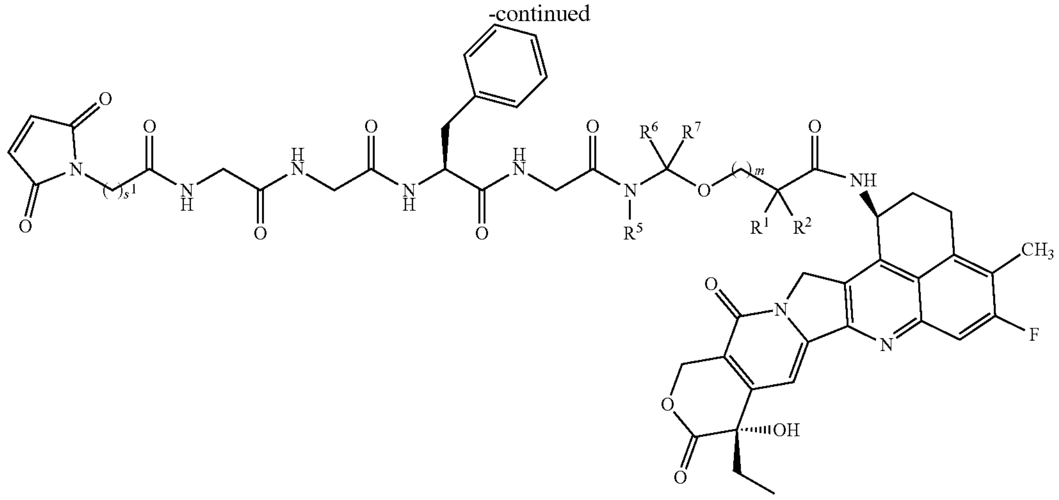

($L_b$-Y-Dr)

condensing the compound of formula (IA) and the compound of formula (TB) to obtain the compound of formula ($L_b$-Y-Dr), wherein: $R^1$, $R^2$, $R^5$~$R^7$, $s^1$ and m are as defined in formula ($L_b$-Y-Dr).

Another aspect of the present disclosure provides a method for preparing the compound of formula ($L_b$-Y-Dr) or the tautomer, mesomer, racemate, enantiomer, diastereomer thereof, or mixture thereof, or the pharmaceutically acceptable salt thereof, comprising the following step of:

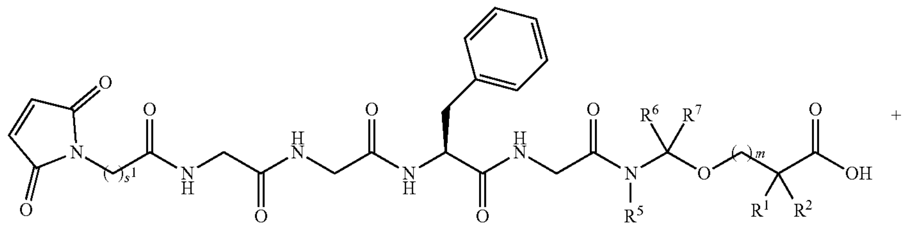

(IC)

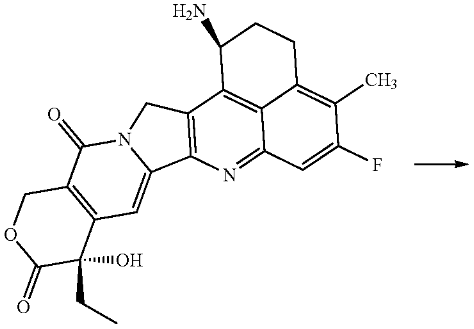

(Dr)

-continued

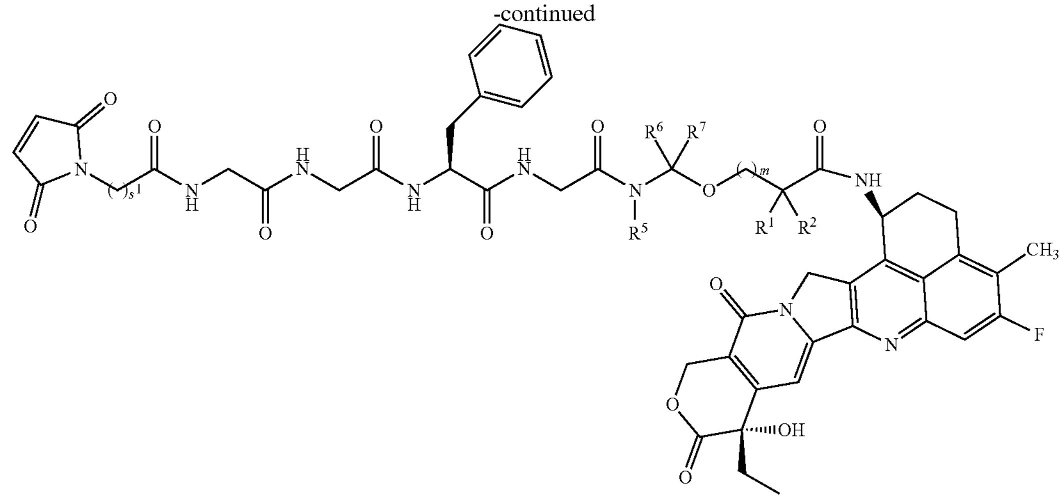

(Lb-Y-Dr)

condensing the compound of formula (IA) and the compound of formula (TB) to obtain the compound of formula ($L_b$-Y-Dr), wherein: $R^1$, $R^2$, $R^5$~$R^7$, $s^1$ and m are as defined in formula ($L_b$-Y-Dr).

Another aspect of the present disclosure provides a method for preparing the ligand-drug conjugate of formula (Pc-$L_a$-Y-Dr) or the pharmaceutically acceptable salt or solvate thereof, comprising the following step of:

Pc +

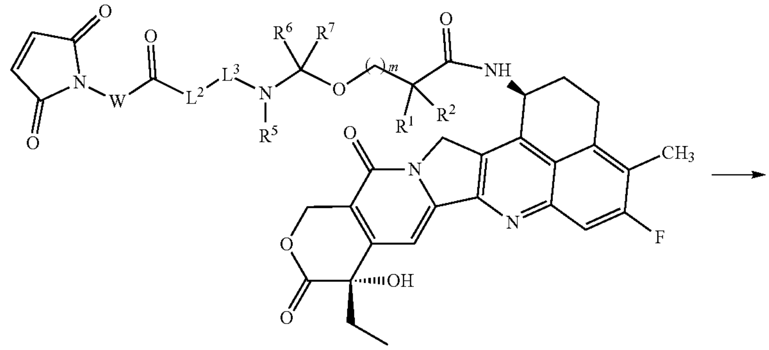

($L_a$-Y-Dr)

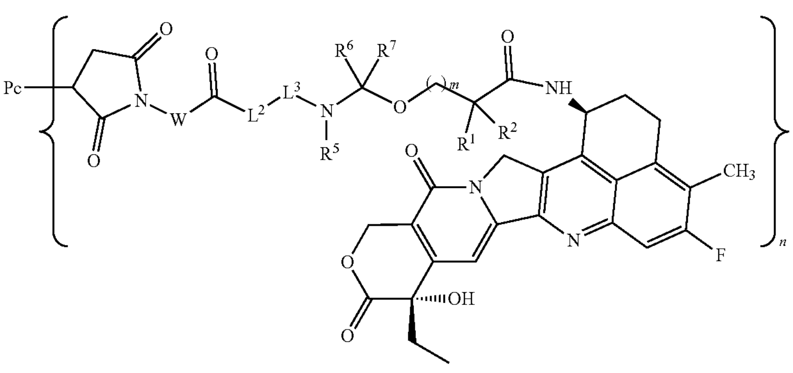

(Pc-$L_a$-Y-Dr)

Pc is coupled with the compound of formula ($L_a$-Y-Dr) after reduction to give the compound of formula (Pc-$L_a$-Y-Dr); the reducing agent is preferably TCEP;

wherein:

Pc is a ligand;

W, $L^2$, $L^3$, $R^1$, $R^2$, $R^5$~$R^7$, m and n are as defined in formula (Pc-$L_a$-Y-Dr).

Another aspect of the present disclosure further relates to a pharmaceutical composition comprising a therapeutically effective amount of the ligand-drug conjugate or compound or the pharmaceutically acceptable salt or solvate thereof according to the present disclosure, and one or more pharmaceutically acceptable carrier(s), diluent(s) or excipient(s).

Another aspect of the present disclosure further relates to a pharmaceutical composition comprising the compound of formula (D) or the tautomer, mesomer, racemate, enantiomer, diastereomer thereof, or mixture thereof, or the pharmaceutically acceptable salt thereof according to the present disclosure, and one or more pharmaceutically acceptable carrier(s), diluent(s) or excipient(s).

Another aspect of the present disclosure further relates to a ligand-drug conjugate or a pharmaceutically acceptable salt or solvate thereof comprising a ligand and a drug linked to the ligand, wherein the drug is selected from the group consisting of the compound of formula (D), the compound of formula ($L_a$-Y-Dr), or the tautomer, mesomer, racemate, enantiomer, diastereomer thereof, or mixture thereof, or the pharmaceutically acceptable salt thereof according to the present disclosure, the drug is preferably linked to the ligand via a linker, and the ligand is preferably a monoclonal antibody.

Another aspect of the present disclosure further relates to a method for preparing a ligand-drug conjugate or a pharmaceutically acceptable salt or solvate thereof, comprising a step of linking the compound of formula (D), the compound of formula ($L_a$-Y-Dr), or the tautomer, mesomer, racemate, enantiomer, diastereomer thereof, or mixture thereof, or the pharmaceutically acceptable salt thereof according to the present disclosure to the ligand, preferably via a linker, and the ligand is preferably a monoclonal antibody.

Another aspect of the present disclosure further relates to the ligand-drug conjugate or compound, or the pharmaceutically acceptable salt or solvate thereof according to the present disclosure, for use as a drug.

Another aspect of the present disclosure further relates to a use of the ligand-drug conjugate or compound, or the pharmaceutically acceptable salt or solvate thereof, or the pharmaceutical composition comprising the same according to the present disclosure in the preparation of a medicament for treating or preventing a tumor, and preferably the tumor is a cancer related to the expression of HER2, HER3 or EGFR.

Another aspect of the present disclosure further relates to a use of the ligand-drug conjugate or compound, or the pharmaceutically acceptable salt or solvate thereof, or the pharmaceutical composition comprising the same according to the present disclosure in the preparation of a medicament for treating or preventing a cancer, the cancer is preferably selected from the group consisting of breast cancer, ovarian cancer, cervical cancer, uterine cancer, prostate cancer, kidney cancer, urethral cancer, bladder cancer, liver cancer, stomach cancer, endometrial cancer, salivary gland cancer, esophageal cancer, melanoma, glioma, neuroblastoma, sarcoma, lung cancer (for example, small cell lung cancer and non-small cell lung cancer), colon cancer, rectal cancer, colorectal cancer, leukemia (for example, acute lymphocytic leukemia, acute myeloid leukemia, acute promyelocytic leukemia, chronic myeloid leukemia, chronic lymphocytic leukemia), bone cancer, skin cancer, thyroid cancer, pancreatic cancer, prostate cancer and lymphoma (for example, Hodgkin's lymphoma, non-Hodgkin's lymphoma, or recurrent anaplastic large cell lymphoma).

Another aspect of the present disclosure further relates to a method for treating and/or preventing a tumor, comprising administering to a patient in need thereof a therapeutically effective amount of the ligand-drug conjugate or compound, or the pharmaceutically acceptable salt or solvate thereof, or the pharmaceutical composition comprising the same according to the present disclosure, and preferably the tumor is a cancer related to the expression of HER2, HER3 or EGFR.

Another aspect of the present disclosure further relates to a method for treating or preventing a cancer, comprising administering to a patient in need thereof a therapeutically effective amount of the ligand-drug conjugate or compound, or the pharmaceutically acceptable salt or solvate thereof, or the pharmaceutical composition comprising the same according to the present disclosure, the cancer is preferably selected from the group consisting of breast cancer, ovarian cancer, cervical cancer, uterine cancer, prostate cancer, kidney cancer, urethral cancer, bladder cancer, liver cancer, stomach cancer, endometrial cancer, salivary gland cancer, esophageal cancer, melanoma, glioma, neuroblastoma, sarcoma, lung cancer (for example, small cell lung cancer and non-small cell lung cancer), colon cancer, rectal cancer, colorectal cancer, leukemia (for example, acute lymphocytic leukemia, acute myeloid leukemia, acute promyelocytic leukemia, chronic myeloid leukemia, chronic lymphocytic leukemia), bone cancer, skin cancer, thyroid cancer, pancreatic cancer and lymphoma (for example, Hodgkin's lymphoma, non-Hodgkin's lymphoma, or recurrent anaplastic large cell lymphoma).

The active compound can be formulated into a form suitable for administration by any appropriate route, and the active compound is preferably in the form of a unit dose, or in a form in which the patient can self-administer in a single dose. The form of the unit dose of the compound or composition of the present invention can be tablet, capsule, cachet, bottled portion, powder, granule, lozenge, suppository, regenerating powder or liquid preparation.

The dosage of the compound or composition used in the treatment method of the present invention will generally vary according to the severity of the disease, the weight of the patient, and the relative efficacy of the compound. However, as a general guide, a suitable unit dose can be 0.1 to 1000 mg.

In addition to the active compound, the pharmaceutical composition of the present invention can also comprise one or more auxiliaries including filler (diluent), binder, wetting agent, disintegrant, excipient and the like. Depending on the administration mode, the composition can comprise 0.1 to 99% by weight of the active compound.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir. An oral composition can be prepared according to any known method in the art for the preparation of pharmaceutical composition. Such composition can comprise binders, fillers, lubricants, disintegrants or pharmaceutically acceptable wetting agents and the like. Such composition can also comprise one or more components selected from the group consisting of sweeteners, flavoring agents, colorants and preservatives, in order to provide a pleasing and palatable pharmaceutical formulation.

An aqueous suspension comprises an active ingredient in admixture with excipients suitable for the manufacture of an aqueous suspension. The aqueous suspension can also comprise one or more preservative(s), one or more colorant(s), one or more flavoring agent(s), and one or more sweetener(s).

An oil suspension can be formulated by suspending the active ingredient in a vegetable oil. The oil suspension can comprise a thickener. The aforementioned sweeteners and flavoring agents can be added to provide a palatable formulation.

The pharmaceutical composition can also be a dispersible powder and granule for preparing an aqueous suspension, which provides the active ingredient by adding water to mix with one or more of dispersant(s), wetting agent(s), suspending agent(s) or preservative(s). Other excipients such as sweetening agents, flavoring agents and coloring agents can also be added. These compositions can be preserved by adding antioxidants such as ascorbic acid.

The pharmaceutical composition of the present disclosure can also be in the form of an oil-in-water emulsion.

The pharmaceutical composition can be in the form of a sterile injectable aqueous solution. Acceptable vehicles or solvents that can be used are water, Ringer's solution or isotonic sodium chloride solution. The sterile injectable formulation can be a sterile injectable oil-in-water micro-emulsion in which the active ingredient is dissolved in an oil phase. For example, the active ingredient is dissolved in a mixture of soybean oil and lecithin. The oil solution is then added to a mixture of water and glycerin, and processed to form a micro-emulsion. The injectable solution or micro-emulsion can be introduced into a patient's bloodstream by local bolus injection. Alternatively, the solution and micro-emulsion are preferably administrated in a manner that maintains a constant circulating concentration of the compound of the present disclosure. In order to maintain this constant concentration, a continuous intravenous delivery device can be used. An example of such a device is Deltec CADD-PLUS™ 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium.

The compound of the present disclosure can be administrated in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug. Such materials include cocoa butter, glycerin gelatin, hydrogenated vegetable oil, a mixture of polyethylene glycols of various molecular weights and fatty acid esters thereof It is well known to those skilled in the art that the dosage of a drug depends on a variety of factors including, but not limited to the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified according to traditional therapeutic regimens.

DESCRIPTION OF THE DRAWINGS

FIG. 7: Efficacy of ADC of the present disclosure on human glioma U87MG xenograft tumor in nude mice.

DETAILED DESCRIPTION OF THE INVENTION

Definitions

Figure 1A:
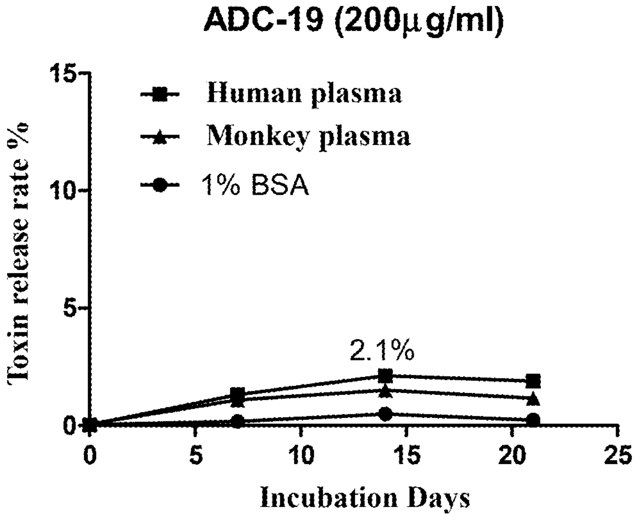
FIG. 1A: Plasma stability test results of ADC-19 of the present disclosure.

Unless otherwise defined, all technical and scientific terms used herein are consistent with the common understanding of those of ordinary skill in the art to which the present disclosure belongs. Although any methods and materials similar or equivalent to those described herein can be used in the practice or testing of the present disclosure, preferred methods and materials are described herein. When describing and pretecting the present disclosure, the following terms are used in accordance with the following definitions.

When a trade name is used in the present disclosure, the applicant is intended to include the preparations, the generic drug and the active ingredients of the product under the trade name.

Unless otherwise stated, the terms used in the specification and claims have the meanings described below.

"Ligand" refers to a macromolecule compound capable of recognizing and binding to an antigen or receptor associated with a target cell. The role of the ligand is to deliver the drug to the target cell population that binds to the ligand. Such ligands include, but are not limited to, protein hormones, lectins, growth factors, antibodies, or other molecules that can bind to cells. In an embodiment of the present disclosure, the ligand is represented by Pc. The ligand can form a bond with the linking unit via a heteroatom on the ligand. The ligand is preferably an antibody or an antigen-binding fragment thereof. The antibody is selected from the group consisting of chimeric antibody, humanized antibody, fully humanized antibody or murine antibody, and preferably a monoclonal antibody.

The term "drug" refers to a cytotoxic drug, which is represented by Dr, being a chemical molecule that can strongly disrupt the normal growth of tumor cells. In principle, all cytotoxic drugs can kill tumor cells at a sufficiently high concentration. However, it can cause the apoptosis of normal cell and serious side effects while killing tumor cells due to the lack of specificity. This term includes toxins, such as small molecule toxins or enzymatically active toxins of bacterial, fungal, plant or animal origin, radioisotopes (for example, radioisotopes of $At^{211}$, $I^{131}$, $I^{125}$, $Y^{90}$, $Re^{186}$, $Re^{188}$, $Sm^{153}$, $Bi^{212}$, $P^{32}$ and Lu), toxic drugs, chemotherapy drugs, antibiotics and nucleolytic enzymes, and preferably toxic drugs.

The term "linker unit", "linking fragment" or "linking unit" refers to a chemical structural fragment or bond, which is linked to a ligand at one end and linked to a drug at another end, or linked to other linkers and then linked to the drug. The preferred embodiments of the present disclosure are represented by L and $L^1$ to $L^4$, wherein the $L^1$ end is linked to the ligand, and the $L^4$ end is linked to the drug (Dr) through structural unit Y.

The linker, including extension unit, spacer unit, and amino acid unit, can be synthesized by methods known in the art, such as those described in US 2005-0238649A1. The linker can be a "cleavable linker" that facilitates the release of the drug in cell. For example, an acid labile linker (for example, hydrazone), a protease-sensitive (for example, peptidase-sensitive) linker, a light-labile linker, a dimethyl linker or a disulfide-containing linker can be used (Chari et al, Cancer Research 52: 127-131 (1992); U.S. Pat. No. 5,208,020).

The term "ligand-drug conjugate" means that a ligand is linked to a biologically active drug through a stable linking unit. In the present disclosure, the "ligand-drug conjugate" is preferably an antibody-drug conjugate (ADC), which means that a monoclonal antibody or antibody fragment is linked to a toxic drug with biological activity through a stable linking unit.

The three-letter codes and one-letter codes for amino acids used in the present disclosure are as described in J. biol. chem, 243, p 3558 (1968).

The term "antibody" refers to immunoglobulin, a four-peptide chain structure connected together by interchain disulfide bond between two identical heavy chains and two identical light chains. Different immunoglobulin heavy chain constant regions exhibit different amino acid compositions and sequences, hence present different antigenicity. Accordingly, immunoglobulins can be divided into five types, or called immunoglobulin isotypes, namely IgM, IgD, IgG, IgA and IgE, with corresponding heavy chain $\mu$, $\gamma$, $\alpha$ and $\varepsilon$, respectively. According to the amino acid composition of hinge region and the number and location of heavy chain disulfide bonds, the same type of Ig can further be divided into different sub-types, for example, IgG can be divided into IgG1, IgG2, IgG3 and IgG4. Light chain can be divided into $\kappa$ or $\lambda$ chain based on different constant region. Each five types of Ig can have a $\kappa$ or $\lambda$ chain. The antibodies described in the present disclosure are preferably specific antibodies against the cell surface antigens on the target cells, non-limiting examples are one or more of the following antibodies: anti-HER2 (ErbB2) antibody, anti-EGFR antibody, anti-B7-H3 antibody, anti-c-Met antibody, anti-HER3 (ErbB3) antibody, anti-HER4 (ErbB4) antibody, anti-CD20 antibody, anti-CD22 antibody, anti-CD30 antibody, anti-CD33 antibody, anti-CD44 antibody, anti-CD56 antibody, anti-CD70 antibody, anti-CD73 antibody, anti-CD105 antibody, anti-CEA antibody, anti-A33 antibody, anti-Cripto antibody, anti-EphA2 antibody, anti-G250 antibody, anti-MUC1 antibody, anti-Lewis Y antibody, anti-VEGFR antibody, anti-GPNMB antibody, anti-Integrin antibody, anti-PSMA antibody, anti-Tenascin-C antibody, anti-SLC44A4 antibody or anti-Mesothelin antibody, and preferably Trastuzumab (trade name Herceptin), Pertuzumab (also known as 2C4, trade name Perjeta), Nimotuzumab (trade name Taixinsheng), Enoblituzumab, Emibetuzumab, Inotuzumab, Pinatuzumab, Brentuximab, Gemtuzumab, Bivatuzumab, Lorvotuzumab, cBR96 and Glematumamab.

About 110 amino acid sequence adjacent to the N-terminus of the antibody heavy chains or light chains is highly variable, known as variable region (Fv region); the rest of amino acid sequence adjacent to the C-terminus is relatively stable, known as constant region. The variable region includes three hypervariable regions (HVR) and four relatively conservative framework regions (FR). The three hypervariable regions, which determine the specificity of the antibody, are also known as the complementarity determining regions (CDR). Each light chain variable region (LCVR) or each heavy chain variable region (HCVR) consists of three CDR regions and four FR regions, with sequential order from the amino terminus to carboxyl terminus in the following order: FR1, CDR1, FR2, CDR2, FR3, CDR3, FR4. The three CDR regions of the light chain refer to LCDR1, LCDR2, and LCDR3; and the three CDR regions of the heavy chain refer to HCDR1, HCDR2, and HCDR3.

Antibodies of the present disclosure include murine antibodies, chimeric antibodies, humanized antibodies and fully humanized antibodies, and preferably humanized antibodies and fully humanized antibodies.

The term "murine antibody" in the present disclosure refers to the antibody prepared from murine according to the knowledge and skills of the field. During the preparation, the test subject is injected with specific antigen, and then a hybridoma expressing the antibody which possesses the desired sequence or functional characteristics is isolated.

The term "chimeric antibody" is an antibody obtained by fusing a variable region of a murine antibody with a constant region of a human antibody, and the chimeric antibody can alleviate the murine antibody-induced immune response. To establish a chimeric antibody, a hybridoma secreting murine specific monoclonal antibody is established, and a variable region gene is cloned from the murine hybridoma cell; then a constant region gene of human antibody is cloned according to requirement; and the constant region gene of human is connected with the variable region gene of murine to form a chimeric gene, which is subsequently inserted into an expression vector; finally, the chimeric antibody molecule is expressed in an eukaryotic or prokaryotic system.

The term "humanized antibody", which is also known as CDR-grafted antibody, refers to an antibody generated by grafting murine CDR sequences into human antibody variable region framework, i.e., an antibody produced in different types of human germline antibody framework sequences. Humanized antibody can overcome heterologous responses induced by large number of murine protein components carried by chimeric antibody. Such framework sequences can be obtained from public DNA database covering germline antibody gene sequences or published references. For example, germline DNA sequences of human heavy and light chain variable region genes can be found in "VBase" human germline sequence database (available on the world wide web at: www.mrccpe.com.ac.uk/vbase), as well as in Kabat, E A, et al. 1991 Sequences of Proteins of Immunological Interest, 5th Ed. To avoid a decrease in activity caused by the decreased immunogenicity, the framework sequences in the variable region of human antibody can be subjected to minimal reverse mutations or back mutations to maintain the activity. The humanized antibody of the present disclosure also comprises humanized antibody on which CDR affinity maturation is performed by phage display. Documents that further describe methods of using murine antibodies involved in humanization include, for example, Queen et al., Proc., Natl. Acad. Sci. USA, 88, 2869, 1991 and Winter and colleagues' method [Jones et al., Nature, 321, 522(1986), Riechmann et al., Nature, 332, 323-327(1988), Verhoeyen et al., Science, 239, 1534(1988)].

The term "fully humanized antibody" is also known as "fully humanized monoclonal antibody", wherein the variable region and constant region of the antibody are both of human origin, eliminating immunogenicity and side effects. The development of monoclonal antibody has gone through four stages, namely: murine monoclonal antibody, chimeric monoclonal antibody, humanized monoclonal antibody and fully humanized monoclonal antibody. The antibody of the present disclosure is a fully humanized monoclonal antibody. The related technologies of fully humanized antibody preparation mainly include human hybridoma technology, EBV transformed B lymphocyte technology, phage display technology, transgenic mouse antibody preparation technology, single B cell antibody preparation technology and the like.

The term "antigen binding fragment" refers to one or more fragments of an antibody retaining the specific binding ability to the antigen. It has been shown that fragments of full-length antibody can be used to achieve the function of binding with an antigen. The examples of binding fragments in the term "antigen binding fragment" include (i) Fab fragment, a monovalent fragment composed of VL, VH, CL and CH1 domain; (ii) $F(ab')_2$ fragment, a bivalent fragment comprising two Fab fragments connected by a disulphide bond in the hinge region; (iii) Fd fragment, consisting of VH and $CH_1$ domains; (iv) Fv fragment, consisting of VH and VL domains of one-arm antibody; (v) single domain or dAb fragment (Ward et al. (1989) Nature 341:544-546) composed of VH domain; and (vi) an isolated complementary determining region (CDR) or (vii) a combination of two or more isolated CDRs optionally conneted by a synthetic linker. In addition, although the VL domain and VH domain of the Fv fragment are encoded by two separate genes, they can be connected by a synthetic linker by using recombinant methods, thereby generating a single protein chain of a monovalent molecular formed by pairing the VL and VH domain (referred to as single chain Fv (scFv); see, e.g., Bird et al. (1988) Science: 242:423-426, and Huston et al. (1988) Proc. Natl. Acad. Sci USA 85:5879-5883). This single chain antibody is also intended to be included in the term "antigen binding fragment" of the antibody. Such antibody fragments are obtained using conventional techniques known by those skilled in the art, and screened for functional fragments by using the same method as that for an intact antibody. Antigen binding sites can be produced by recombinant DNA technology or by enzymatic or chemical disruption of an intact immunoglobulin. Antibodies can be antibodies of different isotypes, e.g., IgG (e.g., IgG1, IgG2, IgG3 or IgG4 subtype), IgA1, IgA2, IgD, IgE or IgM antibody.

Fab is an antibody fragment obtained by treating an IgG antibody molecule with a papain (which cleaves the amino acid residue at position 224 of the H chain). The Fab fragment has a molecular weight of about 50,000 and has antigen binding activity, in which about a half of the N-terminal side of H chain and the entire L chain are bound together through a disulfide bond.

$F(ab')_2$ is an antibody fragment obtained by digesting the downstream part of the two disulfide bonds in the hinge region of IgG with pepsin, which has a molecular weight of about 100,000 and has antigen binding activity and comprises two Fab regions which are bound at the hinge position.

Fab' is an antibody fragment obtained by cleaving the disulfide bond at the hinge region of the above $F(ab')_2$, which has a molecular weight of about 50,000 and has antigen binding activity.

Moreover, the Fab' can be produced by inserting DNA encoding Fab' fragment of the antibody into a prokaryotic expression vector or eukaryotic expression vector which is then introduced into a prokaryote or eukaryote to express the Fab'.

The term "single chain antibody", "single chain Fv" or "scFv" refers to a molecule comprising an antibody heavy chain variable domain (or region; VH) and an antibody light chain variable domain (or region; VL) connected by a linker. Such scFv molecules can have the general structure of $NH_2$—VL-linker-VH—COOH or $NH_2$—VH-linker-VL-COOH. A suitable linker in the prior art consists of repeated GGGGS amino acid sequence or variant thereof, for example, using a variant with 1-4 repeats (Holliger et al. (1993), Proc. Natl. Acad. Sci. USA 90:6444-6448). Other linkers that can be used for the present disclosure are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

The term "CDR" refers to one of the six hypervariable regions within the variable domain of an antibody that primarily contributes to antigen binding. One of the most commonly used definitions for the six CDRs is provided by Kabat E. A. et al. (1991) *Sequences of proteins of immunological interest. NIH Publication* 91-3242. As used herein, the Kabat definition of CDR only applies to CDR1, CDR2 and CDR3 of the light chain variable domain (CDR L1, CDR L2, CDR L3 or L1, L2, L3), as well as CDR2 and CDR3 of heavy chain variable domain (CDR H2, CDR H3 or H2, H3).

The term "antibody framework" refers to a portion of the variable domain VL or VH, which serves as a scaffold for the antigen binding loop (CDR) of the variable domain. Essentially, it is a variable domain without CDR.

The term "epitope" or "antigenic determinant" refers to a site of an antigen to which an immunoglobulin or antibody specifically binds. Epitopes typically include at least 3, 4, 5, 6, 7, 8, 9, 10, 11, 12, 13, 14 or 15 contiguous or non-contiguous amino acids in a unique spatial conformation. See, for example, Epitope Mapping Protocols in Methods in Molecular Biology, Vol. 66, G. E. Morris, Ed. (1996).

The terms "specific binding", "selective binding", "selectively bind" and "specifically bind" refer to the binding of an antibody to an epitope on a predetermined antigen. Typically, the antibody binds with an affinity (KD) of less than about $10^{-7}$M, such as approximately less than about $10^{-8}$ M, $10^{-9}$M or $10^{-10}$ M or less.

The term "nucleic acid molecule" refers to a DNA molecule and a RNA molecule. The nucleic acid molecule may be single stranded or double stranded, but is preferably a double stranded DNA. A nucleic acid is "effectively linked" when it is placed into functional relationship with another nucleic acid sequence. For example, if a promoter or enhancer affects transcription of a coding sequence, the promoter or enhancer is effectively linked to the coding sequence.

The term "vector" refers to a nucleic acid molecule capable of transporting another nucleic acid to which it has been linked. In one embodiment, the vector is a "plasmid" which refers to a circular double stranded DNA loop into which additional DNA segment can be ligated. In another embodiment, the vector is a viral vector, wherein an additional DNA segment can be ligated into viral genome. The vectors disclosed herein are capable of self-replicating in a host cell into which they have been introduced (for example, a bacterial vector having a bacterial replication origin and a episomal mammalian vector) or can be integrated into the genome of a host cell upon introduction into host cell, thereby is replicated along with the host genome (e.g., a non-episomal mammalian vector).

Methods for producing and purifying antibodies and antigen binding fragments are well known in the art, such as Cold Spring Harbor Antibody Technical Guide, Chapters 5-8 and 15. The antigen binding fragment can also be prepared by conventional methods. The antibodies or antigen binding fragments of the invention are genetically engineered to add one or more human FR regions in non-human CDR regions. The human FR germline sequence(s) can be obtained by aligning IMGT human antibody variable germlines gene databases and MOE software from the ImMunoGeneTics (IMGT) website at http://imgt.cines.fr or from the Journal of Immunoglobulins 20011SBN012441351.

The term "host cell" refers to a cell into which an expression vector has been introduced. Host cells can include bacterial, microbial, plant or animal cells. Bacteria susceptible to be transformed include members of the Enterobacteriaceae, such as strains of *Escherichia coli* or *Salmonella*; Bacillaceae such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

The engineered antibody or antigen binding fragment of the present disclosure can be prepared and purified by conventional methods. For example, cDNA sequence(s) encoding a heavy chain and a light chain can be cloned and recombined into a GS expression vector. The recombinant immunoglobulin expression vector can be stably transfected in CHO cells. As a more recommended existing technology, mammalian expression systems can result in glycosylation of antibodies, particularly at the highly conserved N-terminal site of the Fc region. Positive clones are expanded in serum-free medium in a bioreactor to produce antibodies. The culture medium containing the secreted antibody can be purified by conventional technique. For example, purification is carried out using an A or G Sepharose FF column that contains an adjusted buffer. The non-specifically bound components are removed by eluting. The bound antibody is eluted by a pH gradient method, and the antibody fragments are detected by SDS-PAGE and collected. The antibody can be filtered and concentrated by a conventional method. Soluble aggregate and multimers can also be removed by conventional methods such as size exclusion or ion exchange. The resulting product needs to be frozen immediately, such as at −70° C., or lyophilization.

The term "peptide" refers to a compound fragment between amino acid and protein, consisting of two or more amino acid molecules connected to each other through peptide bonds. Peptides are structural and functional fragments of proteins. Hormones, enzymes and the like are essentially peptides.

The term "saccharide" refers to a biological macromolecule composed of three elements of C, H, and O, which can be divided into monosaccharides, disaccharides and polysaccharides.

The term "fluorescent probe" refers to a kind of fluorescent molecules with characteristic fluorescence in the ultraviolet-visible-near infrared region. The fluorescence property of fluorescent probe (excitation and emission wavelengths, intensity, lifetime and polarization, etc.) can sensitively vary according to the property of the environment, such as polarity, refractive index, viscosity, etc. Non-covalently interaction between fluorescent probe and nucleic acid (DNA or RNA), protein or other macromolecular structure enables the change of one or more fluorescent properties, which can be used to study the property and behavior of macromolecular substance.

The term "toxic drug" refers to a substance that inhibits or stops the function of cells and/or causes cell death or destruction. Toxic drugs include toxins and other compounds that can be used in tumor treatment.

The term "toxin" refers to any substance that can have a harmful effect on the growth or proliferation of cells. Toxins can be small molecule toxins and their derivatives from bacteria, fungi, plants or animals, including Camptothecin derivatives such as exatecan, maytansinoid and its derivatives (CN101573384) such as DM1, DM3, DM4, auristatin F (AF) and its derivatives such as MMAF, MMAE, 3024 (WO 2016/127790 A1, compound 7), diphtheria toxin, exotoxin, ricin A chain, abrin A chain, modeccin, α-sarcin, Aleutites fordii toxic protein, dianthin toxic protein, *Phytolaca americana* toxic protein (PAPI, PAPII and PAP-S), *Momordica charantia* inhibitor, curcin, crotin, *Sapaonaria officinalis* inhibitor, gelonin, mitogellin, restrictocin, phenomycin, enomycin and trichothecenes.

The term "chemotherapeutic drug" refers to a chemical compound that can be used to treat tumors. This definition also includes antihormonal agents that act to modulate, reduce, block, or inhibit the effects of hormones that promote cancer growth, which are often in the form of systemic or holistic therapy. They can be hormones. Examples of chemotherapeutic drugs include alkylating agents, such as thiotepa; cyclosphamide (CYTOXAN™); alkyl sulfonate such as busulfan, improsulfan and piposulfan; aziridine such as benaodopa, carboquone, meturedopa and uredopa; aziridine and methylamelamine including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, nitrobin hydrochloride; melphalan, novembichin, phenesterine, prednimustine, trofosfamide, uramustine; nitrosureas such as carmustine, chlorozotocin, fotemustine, lomustine, nimustine, ranimustine; antibiotic such as aclacinomycin, actinomycin, authramycin, azaserine, bleomycin, cactinomycin C, calicheamicin, carabicin, chromomycin, carzinophilin, chromomycin, actinomycin D, daunorubicin, detorubicin, 6-diazo-5-oxy-L-norleucine, doxorubicin, epirubicin, esorubicin, idarubicin, marcellomycin, mitomycin, mycophenolic acid, nogalamycin, olivomycin, peplomycin, potfiromycin, puromycin, quelamycin, rodorubicin, streptonigrin; streptozocin, tuberculocidin, ubenimex, zinostatin, zorubicin; antimetabolites such as methotrexate, 5-fluorouracil (5-FU); folic acid analogs such as denopterin, methotrexate, pteropterin, trimetrexate; pterin analogs such as fludarabine, 6-mercaptopterin, thiomethopterin, thioguanopterin; pyrimidine analogs such as ancitabine, azacitidine, 6-azuridine, carmofur, cytarabine, dideoxyuridine, doxitluridine, enocitabine, floxuridine, 5-FU; androgens such as calusterone, dromostanolong propionate, epitiostanol, mepitiostane, testolactone; anti-adrenalines such as aminoglutethimide, mitotane, trilostane; folic acid supplements such as frolinic acid; aceglatone; aldophosphamideglycoside; aminolevulinic acid; amsacrine; bestrabucil; biasntrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pintostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorrotriethylamine; urethan; vindesine; dacarbazine; mannomustine; mitobronitol; dibromodulcitol; pipobroman; gacytosine; arabinoside ("Ara-C"); cyclophosphamide; thiotepa; taxanes such as paclitaxel (TAXOL®, Bristol-Myers Squibb Oncology, Princeton, NJ) and docetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunorubicin; aminopterin; xeloda; ibandronate; CPT-11; topoisomerase inhibitor RFS2000; difluoromethylornithine (DMFO); retinoic acid esperamicins; capecitabine; and pharmaceutically acceptable salt, acid or derivative of any of the above substances. This definition also includes anti-hormonal agents that can modulate or inhibit the effects of hormones on tumors, such as anti-estrogens, including tamoxifen, raloxifene, aromatase inhibitor 4(5)-imidazole, 4-hydroxytamoxifen, trioxifene, keoxifene, LY117018, onapristone and Fareston; and anti-androgens such as flutamide, nilutamide, bicalutamide, leuprolide and goserelin; and pharmaceutically acceptable salt, acid or derivative of any of the above substances.

The term "alkyl" refers to a saturated aliphatic hydrocarbon group, which is a straight or branched chain group comprising 1 to 20 carbon atoms, preferably an alkyl having 1 to 12 carbon atoms, more preferably an alkyl having 1 to 10 carbon atoms, and most preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio and oxo.

The term "heteroalkyl" refers to an alkyl containing one or more heteroatom(s) selected from the group consisting of N, O and S, wherein the alkyl is as defined above.

The term "alkylene" refers to a saturated linear or branched aliphatic hydrocarbon group having two residues derived from the removal of two hydrogen atoms from the same carbon atom or two different carbon atoms of the parent alkane. The alkylene is a linear or branched group having 1 to 20 carbon atoms, preferably 1 to 12 carbon atoms, and more preferably 1 to 6 carbon atoms. Non-limiting examples of alkylene include, but are not limited to, methylene ($—CH_2—$), 1,1-ethylene ($—CH(CH_3)—$), 1,2-ethylene ($—CH_2CH_2)—$, 1,1-propylene ($—CH(CH_2CH_3)—$), 1,2-propylene ($—CH_2CH(CH_3)—$), 1,3-propylene ($—CH_2CH_2CH_2—$), 1,4-butylene ($—CH_2CH_2CH_2CH_2—$), 1,5-pentylene ($—CH_2CH_2CH_2CH_2CH_2—$), and the like. The alkylene can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio and oxo.

The term "alkoxy" refers to an —O-(alkyl) or an —O-(unsubstituted cycloalkyl) group, wherein the alkyl and cycloalkyl are as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 10 carbon atoms, and most preferably 3 to 8 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; and more preferably, 3 to 10 ring atoms. Non-limiting examples of monocyclic heterocyclyl include pyrrolidinyl, piperidinyl, piperazinyl, morpholinyl, thiomorpholinyl, homopiperazinyl and the like. Polycyclic heterocyclyl includes a heterocyclyl having a spiro ring, fused ring or bridged ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O and $S(O)_m$ (wherein m is an integer of 0 to 2), with the remaining ring atoms being carbon atoms, where the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

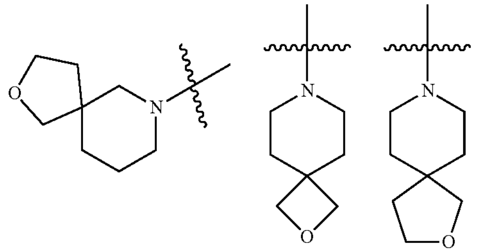

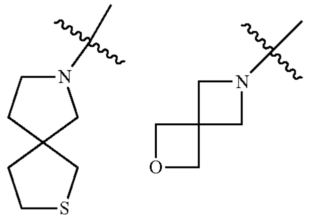

and

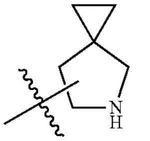

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and $S(O)_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and the fused heterocyclyl is preferably a bicyclic or tricyclic fused heterocyclyl, and more preferably a 5-membered/5-membered or 5-membered/6-membered bicyclic fused heterocyclyl. Non-limiting examples of fused heterocyclyl include:

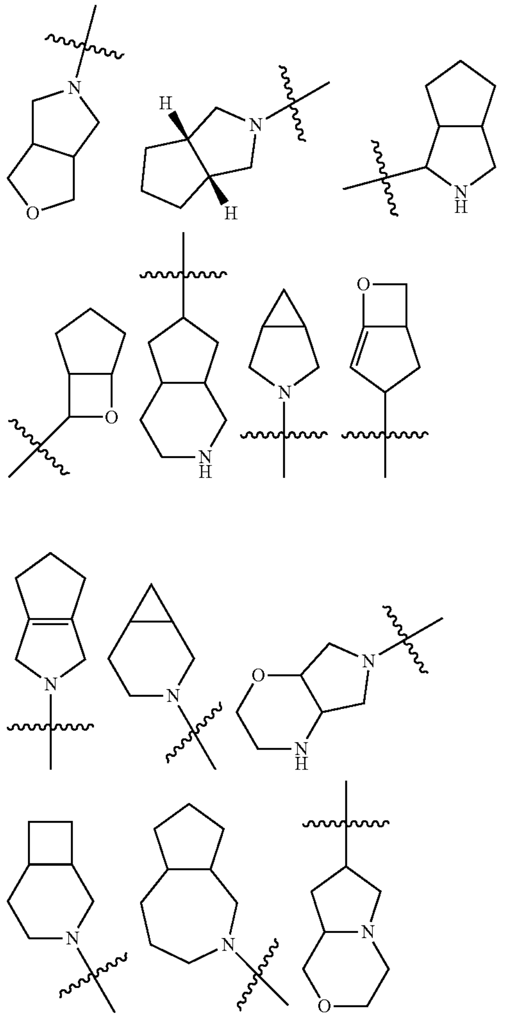

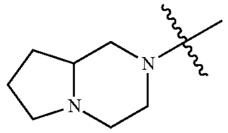

and

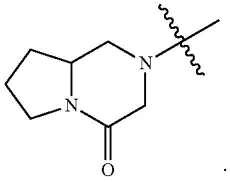

.

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and $S(O)_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

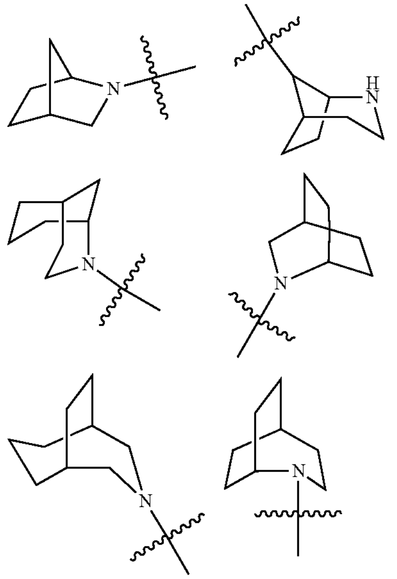

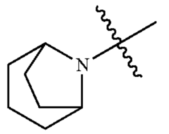

and

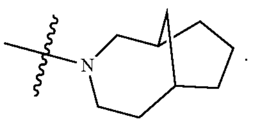

The heterocyclyl ring can be fused to the ring of aryl, heteroaryl or cycloalkyl, wherein the ring bound to the parent structure is heterocyclyl. Non-limiting examples thereof include:

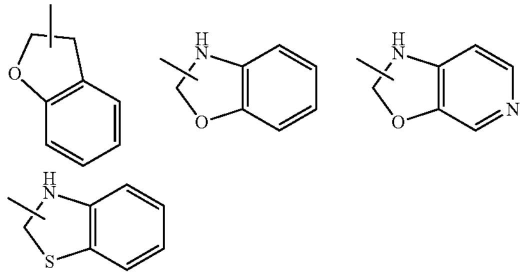

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio and oxo.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, for example, phenyl and naphthyl, and preferably phenyl. The aryl ring can be fused to the ring of heteroaryl, heterocyclyl or cycloalkyl, wherein the ring bound to the parent structure is aryl ring. Non-limiting examples thereof include:

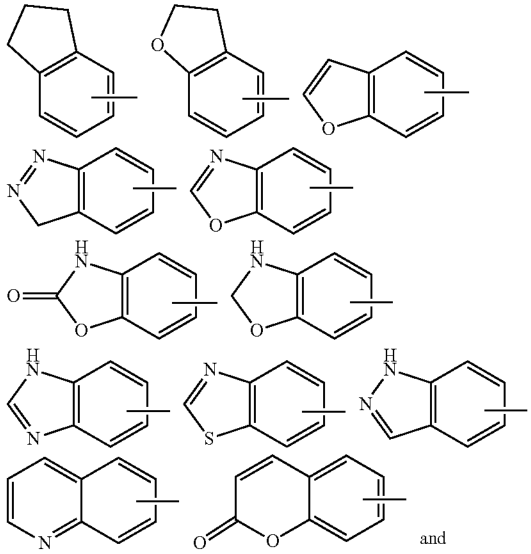

and

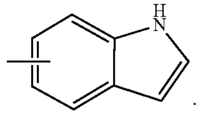

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "heteroaryl" refers to a 5 to 14 membered heteroaromatic system having 1 to 4 heteroatoms selected from the group consisting of O, S and N. The heteroaryl is preferably a 5 to 10 membered heteroaryl, more preferably a 5 or 6 membered heteroaryl, for example furyl, thienyl, pyridyl, pyrrolyl, N-alkylpyrrolyl, pyrimidinyl, pyrazinyl, imidazolyl, tetrazolyl and the like. The heteroaryl ring can be fused to the ring of aryl, heterocyclyl or cycloalkyl, wherein the ring bound to the parent structure is heteroaryl ring. Non-limiting examples thereof include:

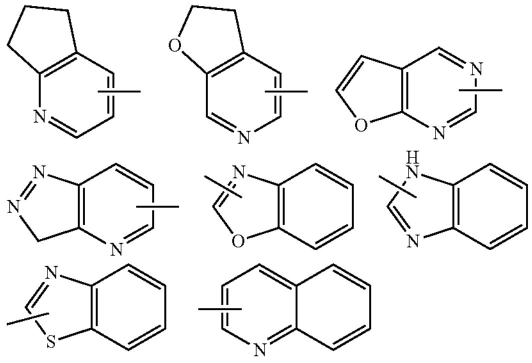

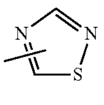

and

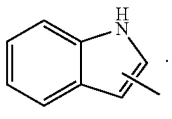

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "amino protecting group" refers to a group which prevents an amino group from reaction when other parts of the molecular are subject to a reaction, and can be easily removed. Non-limiting examples include 9-fluorenylmethyloxycarbonyl, tert-butoxycarbonyl, acetyl, benzyl, allyl, p-methoxybenzyl and the like. These groups can be optionally substituted by one to three substituent(s) selected from the group consisting of halogen, alkoxy and nitro. The amino protecting group is preferably 9-fluorenylmethyloxycarbonyl.

The term "cycloalkylalkyl" refers to an alkyl group substituted by one or more, preferably one, cycloalkyl(s), wherein the alkyl and cycloalkyl are as defined above.

The term "haloalkyl" refers to an alkyl group substituted by one or more halogen(s), wherein the alkyl is as defined above.

The term "deuterated alkyl" refers to an alkyl group substituted by one or more deuterium atom(s), wherein the alkyl is as defined above.

The term "hydroxy" refers to an —OH group.

The term "halogen" refers to fluorine, chlorine, bromine or iodine.

The term "amino" refers to a $—NH_2$ group.

The term "nitro" refers to a $—NO_2$ group.

The term "amide" refers to a —C(O)N(alkyl) or —C(O)N(cycloalkyl) group, wherein the alkyl and cycloalkyl are as defined above.

The term "alkoxycarbonyl" refers to a —C(O)O(alkyl) or —C(O)O(cycloalkyl) group, wherein the alkyl and cycloalkyl are as defined above.

The present disclosure also comprises the compounds of formula (I) in various deuterated forms. Each of the available hydrogen atoms attached to the carbon atom can be independently replaced by a deuterium atom. Those skilled in the art can synthesize a compound of formula (I) in a deuterated form with reference to the relevant literatures. The compound of formula (I) in deuterated form can be prepared by employing commercially available deuterated raw materials, or they can be synthesized by conventional techniques with deuterated reagents including, but not limited to, deuterated borane, trideuterated borane in tetrahydrofuran, deuterated lithium aluminum hydride, deuterated iodoethane, deuterated iodomethane and the like.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive effort. For example, the combination of amino or hydroxy having free hydrogen and carbon atoms having unsaturated bonds (such as olefinic) may be unstable.

The term "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

The term "pharmaceutically acceptable salt" or "pharmaceutical salt" refers to a salt of the ligand-drug conjugate of the present disclosure or a salt of the compound of the present disclosure, which is safe and effective in mammals and has the desired biological activity. The ligand-drug conjugate of the present disclosure contains at least one amino, so it can form a salt with an acid. Non-limiting examples of pharmaceutically acceptable salts include hydrochloride, hydrobromide, hydroiodide, sulfate, bisulfate, citrate, acetate, succinate, ascorbate, oxalate, nitrate, sorbate, hydrogen phosphate, dihydrogen phosphate, salicylate, hydrogen citrate, tartrate, maleate, fumarate, formate, benzoate, methanesulfonate, ethanesulfonate, benzenesulfonate, p-toluenesulfonate.

The term "solvate" refers to a pharmaceutically acceptable solvate formed by a ligand-drug conjugate of the present disclosure with one or more solvent molecule(s). Non-limiting examples of solvent molecules include water, ethanol, acetonitrile, isopropanol, DMSO, ethyl acetate.

The term "drug loading" refers to the average number of cytotoxic drugs loaded on each ligand in the compound of formula (I), and can also be expressed as the ratio of the number of drug to the number of antibody. The drug loading can range from 0 to 12, preferably from 1 to 10 cytotoxic drugs (D) per ligand (Pc). In an embodiment of the present invention, the drug loading is expressed as n, and exemplary values can be an average of 1, 2, 3, 4, 5, 6, 7, 8, 9, 10. The average number of drugs per ADC molecule after coupling reaction can be determined by conventional methods such as UV/visible spectroscopy, mass spectrometry, ELISA test and HPLC characterization.

In an embodiment of the present invention, the cytotoxic drug is conjugated to the N-terminal amino and/or the ε-amino of lysine residues of the ligand via a linking unit. Typically, the number of drug molecules conjugated to the antibody in a coupling reaction will be less than the theoretical maximum.

The following non-limiting methods can be used to control the loading of the ligand-cytotoxic drug conjugates:

(1) controlling the molar ratio of the linking reagent to the monoclonal antibody, (2) controlling the reaction time and temperature, (3) selecting different reaction reagents.

The preparation of conventional pharmaceutical compositions can be found in the Chinese Pharmacopoeia.

The term "carrier" used in the composition of the present disclosure refers to a system that can change the way a drug enters the human body and distribution, control the drug release rate, and deliver the drug to the targeted organ. Drug carrier release and targeting systems can reduce drug degradation and loss, reduce side effects and improve bioavailability.

For example, the polymer surfactants which can be used as carriers can be self-assembled to form various forms of aggregates due to their unique amphiphilic structure. Preferred examples include micelles, microemulsions, gels, liquid crystals, vesicles and the like. These aggregates have the ability to encapsulate drug molecules, while having good permeability to the membrane, and can be used as an excellent drug carrier.

The term "excipient" is an adjunct in a pharmaceutical formulation other than a main drug, which can also be referred to as an adjuvant, such as adhesives, fillers, disintegrants, lubricants in tablets; matrix parts in the semi-solid preparations ointment and cream; preservatives, antioxidants, flavoring agents, fragrances, co-solvents, emulsifiers, solubilizers, osmotic pressure regulators, colorants in liquid preparations and the like.

The term "diluent", also known as filler, is primarily intended to increase the weight and volume of the tablet. The addition of diluent ensures a certain volume, reduces the dose deviation of the main components, and improves the compression profile of the drug. When the tablet contains an oily component, an absorbent is added to absorb the oily substance, thereby keeping the "dry" state to facilitate tablet formation. For example, diluent includes starch, lactose, inorganic salts of calcium, microcrystalline cellulose and the like.

The pharmaceutical composition can be in the form of a sterile injectable aqueous solution. Acceptable vehicles or solvents that can be used are water, Ringer's solution or isotonic sodium chloride solution. The sterile injectable formulation can be a sterile injectable oil-in-water micro-emulsion in which the active ingredient is dissolved in the oil phase. For example, the active ingredient is dissolved in a mixture of soybean oil and lecithin. The oil solution is then added to a mixture of water and glycerin, and processed to form a micro-emulsion. The injectable solution or micro-emulsion can be introduced into a patient's bloodstream by local bolus injection. Alternatively, the solution and micro-emulsion are preferably administrated in a manner that maintains a constant circulating concentration of the compound of the present disclosure. In order to maintain this constant concentration, a continuous intravenous delivery device can be used. An example of such a device is Deltec CADD-PLUS™ 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent, for example, a solution prepared in 1,3-butanediol. Moreover, sterile fixed oils can easily be used as a solvent or suspending medium. For this purpose, any blending fixed oils including synthetic mono- or di-glyceride can be employed. Moreover, fatty acids, such as oleic acid, can also be employed in the preparation of an injection.

The present disclosure relates to a cleavable linker arm with a specific structure and an active substance with a specific structure, and an antibody-drug conjugate (ADC) composed of a linker arm, an active substance and an antibody. This ADC is a complex formed by linking a toxic substance to an antibody via a spacer. The antibody-drug conjugate (ADC) is degraded in the body to release active molecules, thereby showing an anti-tumor effect.

Synthesis Method of the Present Disclosure

In order to achieve the object of the present disclosure, the present disclosure applies the following technical solutions:

Scheme I:

A method for preparing the compound of formula (D1) or the pharmaceutically acceptable salt or solvate thereof of the present disclosure, comprises the following step of:

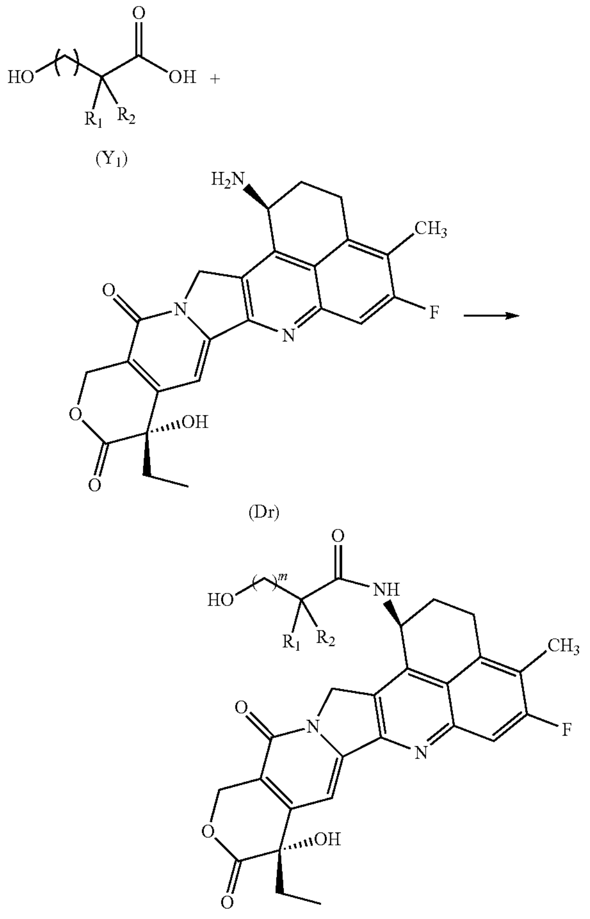

(Y1) (Dr) (D1)

reacting the compound of formula (Y1) and the compound of formula (Dr) in the presence of a condensing agent and optionally under an alkaline condition to obtain the compound of formula (D1), wherein: $R^1$, $R^2$ and m are as defined in formula (D1).

The reagent that provides an alkaline condition includes organic bases and inorganic bases. The organic bases include, but are not limited to, triethylamine, diethylamine, N-methylmorpholine, pyridine, hexahydropyridine, N,N-diisopropylethylamine, n-butyl lithium, lithium diisopropylamide, potassium acetate, sodium tert-butoxide and potassium tert-butoxide. The inorganic bases include, but are not limited to, sodium hydride, potassium phosphate, sodium carbonate, potassium carbonate, cesium carbonate, sodium hydroxide and lithium hydroxide.

The condensing agent can be selected from the group consisting of 4-(4,6-dimethoxy-1,3,5-triazin-2-yl)-4-methylmorpholinium chloride, 1-hydroxybenzotriazole, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethylurea tetrafluoroborate, 1-hydroxybenzotriazole, 1-hydroxy-7-azobenzotriazole, O-benzotriazole-N,N,N',N'- tetramethylurea hexafluorophosphate, 2-(7-azobenzotriazole)-N,N,N',N'-tetramethylurea hexafluorophosphate, benzotriazol-1-yloxytris(dimethyl-amino)phosphonium hexafluorophosphate and benzotriazol-1-yl-oxytripyrrolidinyl phosphorus hexafluorophosphate, and preferably 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride.

Scheme II:

A method for preparing the compound of formula ($L_b$-Y-Dr) or the pharmaceutically acceptable salt or solvate thereof of the present disclosure, comprises the following steps of:

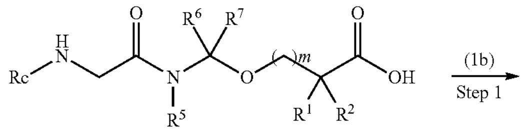

(IB-1)

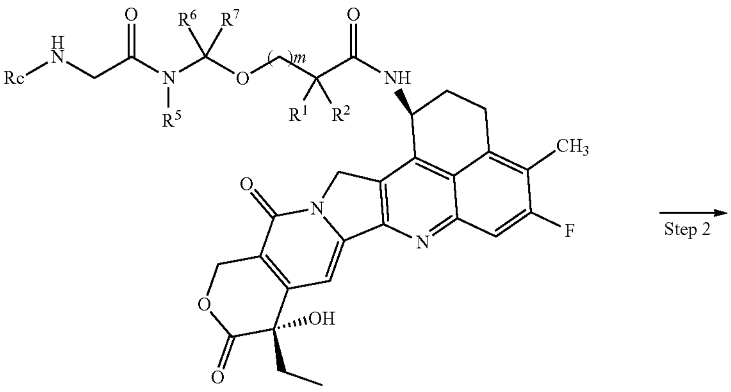

(IB-2)

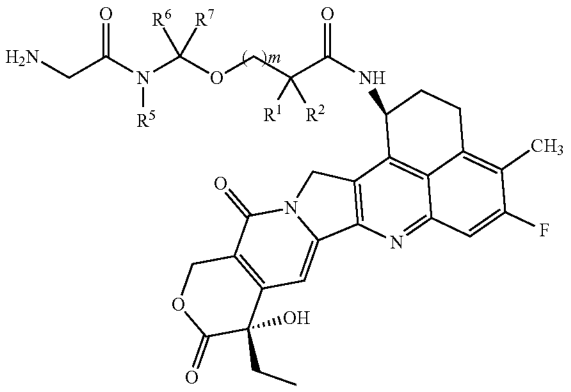

(IB)

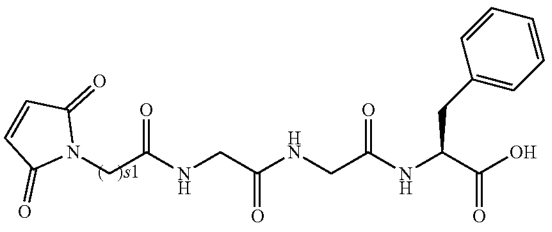

+

(IA)

-continued

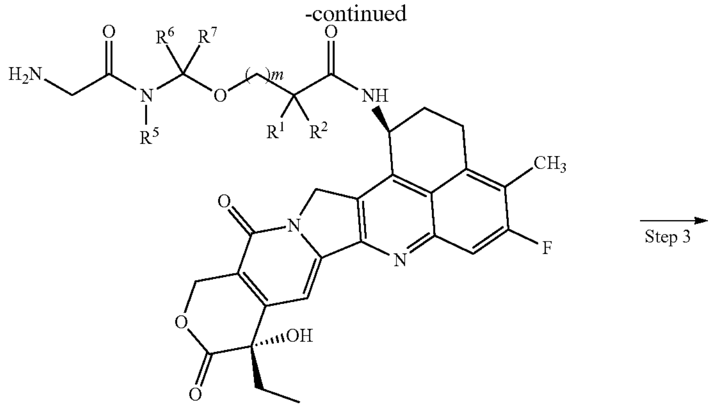

(IB)

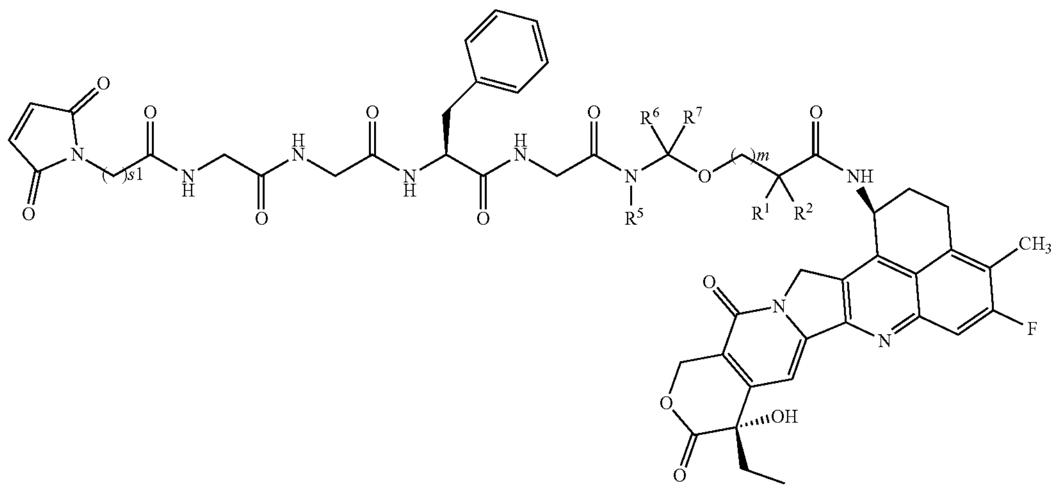

($L_b$-Y-Dr)

Step 1: the compound of formula (IB-1) and exatecan methanesulfonate (1b) are reacted in the presence of a condensing agent and optionally under an alkaline condition to obtain the compound of formula (IB-2);

Step 2: the compound of formula (IB-2) is deprotected to obtain the compound of formula (IB);

Step 3: the compound of formula (IA) and the compound of formula (IB) are reacted in the presence of a condensing agent and optionally under an alkaline condition to obtain the compound of formula ($L_b$-Y-Dr), wherein:

RC is an amino protecting group, and preferably 9-fluorenylmethyloxycarbonyl (Fmoc);

$R^1$, $R^2$, $R^5$~$R^7$, $s^1$ and m are as defined in formula ($L_b$-Y-Dr).

The reagent that provides an alkaline condition includes organic bases and inorganic bases. The organic bases include, but are not limited to, triethylamine, diethylamine, N-methylmorpholine, pyridine, hexahydropyridine, N,N-diisopropylethylamine, n-butyl lithium, lithium diisopropylamide, potassium acetate, sodium tert-butoxide and potassium tert-butoxide. The inorganic bases include, but are not limited to, sodium hydride, potassium phosphate, sodium carbonate, potassium carbonate, cesium carbonate, sodium hydroxide and lithium hydroxide.

The condensing agent is selected from the group consisting of 4-(4,6-dimethoxy-1,3,5-triazin-2-yl)-4-methylmorpholinium chloride, 1-hydroxybenzotriazole, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethylurea tetrafluoroborate, 1-hydroxybenzotriazole, 1-hydroxy-7-azobenzotriazole, O-benzotriazole-N,N,N',N'-tetramethylurea hexafluorophosphate, 2-(7-azobenzotriazole)-N,N,N',N'-tetramethylurea hexafluorophosphate, benzotriazol-1-yloxytris(dimethylamino)phosphonium hexafluorophosphate and benzotriazol-1-yl-oxytripyrrolidinyl phosphorus hexafluorophosphate, and preferably 4-(4,6-dimethoxy-1,3,5-triazin-2-yl)-4-methylmorpholinium chloride, 1-hydroxybenzotriazole and 1-(3-dimethylaminopropyl)-3-ethylcarbodiimide hydrochloride.

Scheme III:

A method for preparing the compound of formula (Pc-$L_a$-Y-Dr) of the present disclosure, comprises the following step of:

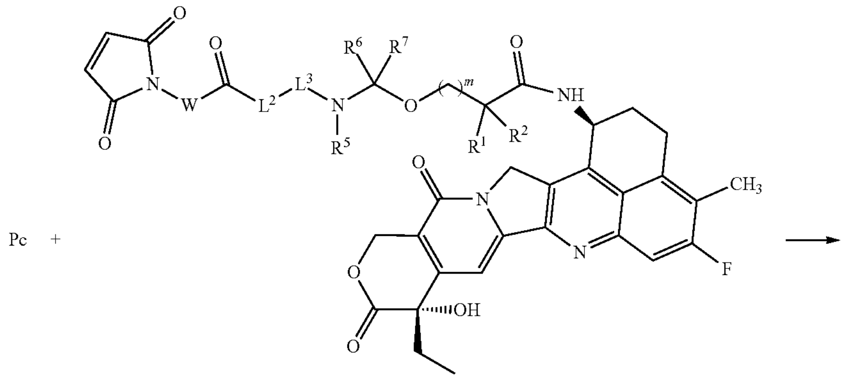

(La-Y-Dr)

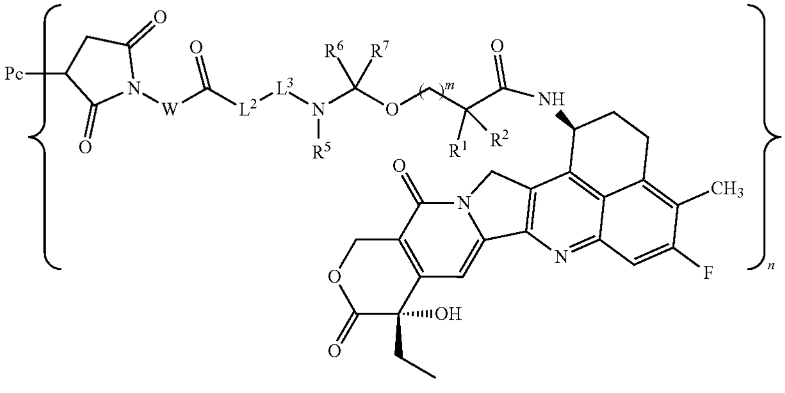

(Pc-La-Y-Dr)

Pc is reacted with the compound of formula ($L_a$-Y-Dr) after reduction to obtain the compound of formula (Pc-La-Y-Dr); the reducing agent is preferably TCEP, particularly, it is preferable to reduce the disulfide bond on the antibody;

wherein:

Pc is a ligand;

W, $L^2$, $L^3$, $R^1$, $R^2$, $R^5$~$R^7$, m and n are as defined in formula (Pc-$L_a$-Y-Dr).

The present disclosure will be further described with reference to the following examples, but the examples should not be considered as limiting the scope of the present disclosure.

The experimental methods in the examples of the present disclosure for which the specific conditions are not indicated were carried out according to conventional conditions or the conditions recommended by the material or product manufacturers. The reagents for which the specific sources are not indicated are conventional reagents purchased from market.

EXAMPLES

The structures of the compounds are identified by nuclear magnetic resonance (NMR) or mass spectrometry (MS). NMR is determined by a Bruker AVANCE-400 machine. The solvents for determination are deuterated-dimethyl sulfoxide (DMSO-$d_6$), deuterated-chloroform ($CDCl_3$) and deuterated-methanol ($CD_3OD$), and the internal standard is tetramethylsilane (TMS). Chemical shifts are given in $10^{-6}$ (ppm).

MS is determined by a FINNIGAN LCQAd (ESI) mass spectrometer (manufacturer: Thermo, type: Finnigan LCQ advantage MAX).

UPLC is determined by a Waters Acquity UPLC SQD liquid chromatograph/mass spectrometer.

High performance liquid chromatography (HPLC) is determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

UV-HPLC is determined on a Thermo nanodrop2000 UV spectrophotometer.

The proliferation inhibition rates and $IC_{50}$ values are determined by a PHERA starFS microplate reader (BMG Co., Germany).

Yantai Huanghai HSGF254 or Qingdao GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is generally used as a carrier for column chromatography.

The known starting materials of the present disclosure can be prepared by the known methods in the art, or can be purchased from ABCR GmbH & Co. KG, Acros Organnics, Aldrich Chemical Company, Accela ChemBio Inc., Dari chemical Company etc.

Unless otherwise stated, the reactions are carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reaction is performed on a Parr 3916EKX hydrogenation instrument and a Qinglan QL-500 hydrogen generator or HC2-SS hydrogenation instrument.

In hydrogenation reactions, the reaction system is generally vacuumed and filled with hydrogen, and the above operation is repeated three times.

CEM Discover-S 908860 type microwave reactor is used in microwave reactions.

Unless otherwise stated, the solution of the reaction refers to an aqueous solution.

Unless otherwise stated, the reaction temperature of the reaction is room temperature.

Room temperature from 20° C. to 30° C. is the most suitable reaction temperature.

Preparation of PBS buffer (pH=6.5) in the examples: 8.5 g of $KH_2PO_4$, 8.56 g of $K_2HPO_4.3H_2O$, 5.85 g of NaCl and 1.5 g of EDTA are set to 2 L in a flask, the mixture is subjected to ultrasonication to dissolve completely, and shaked well to give the buffer.

The eluent system in column chromatography and the developing solvent system in thin layer chromatography for purification of the compounds include: A: dichloromethane and isopropanol system, B: dichloromethane and methanol system, C: petroleum ether and ethyl acetate system. The ratio of the volume of the solvent is adjusted according to the polarity of the compounds, and a small quantity of acidic reagent or alkaline reagent such as triethylamine could also be added for adjustment.

Some of the compounds of the present disclosure are characterized by Q-TOF LC/MS. Regarding to Q-TOF LC/MS, Agilent 6530 Accurate-Mass Quadrupole-Time of Flight Mass Spectrometer and Agilent 1290-Infinity UHPLC (Agilent Poroshell 300SB-C8 5 μm, 2.1×75 mm column) are used.

Example 1

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclopropane-1-carboxamide 1

1

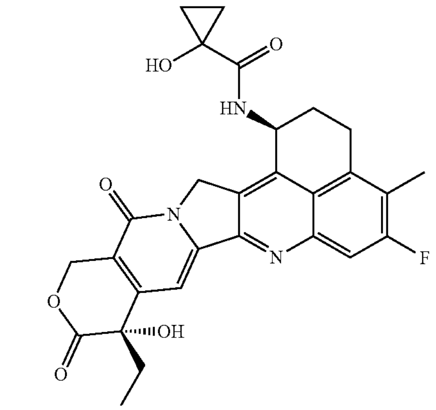

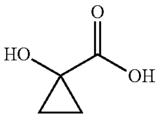

+

1a

-continued

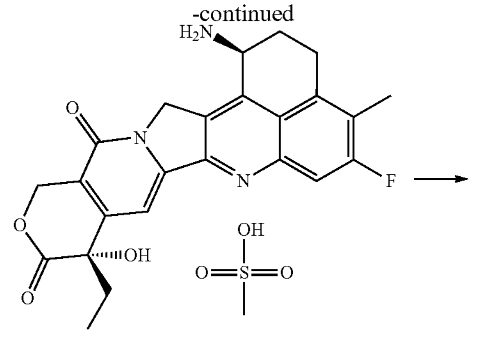

1b

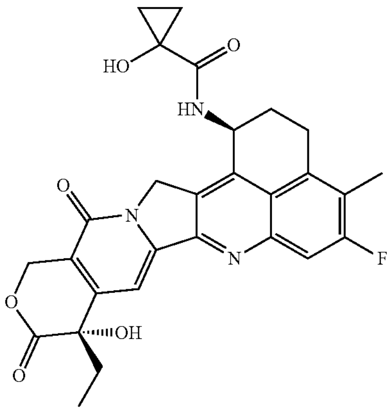

1

1 mL of N,N-dimethylformamide was added to exatecan methanesulfonate 1b (2.0 mg, 3.76 μmol, prepared according to the method disclosed in the patent application "EP0737686A1"), and the solution was cooled to 0-5° C. in an ice-water bath. One drop of triethylamine was added dropwise, and the reaction solution was stirred until clear. 1-Hydroxycyclopropylcarboxylic acid 1a (1.4 mg, 3.7 μmol, prepared according to the known method disclosed in "Tetrahedron Letters, 25(12), 1269-72; 1984") and 4-(4,6-dimethoxy-1,3,5-triazin-2-yl)-4-methylmorpholinium chloride (3.8 mg, 13.7 μmol) were added successively to the reaction solution. After completion of the addition, the reaction solution was stirred at 0-5° C. for 2 hours. 5 mL of water was added to the reaction solution to quench the reaction, and the reaction solution was extracted with ethyl acetate (8 mL×3). The organic phases were combined, washed with saturated sodium chloride solution (5 mL×2), dried over anhydrous sodium sulfate and filtered. The filtrate was concentrated under reduced pressure, and the resulting residues were purified by thin layer chromatography with developing solvent system B to obtain the title product 1 (1.6 mg, yield: 82.1%).

MS m/z (ESI): 520.2 [M+1]

$^1H$ NMR (400 MHz, $CDCl_3$): δ 7.90-7.84 (m, 1H), 7.80-7.68 (m, 1H), 5.80-5.70 (m, 1H), 5.62-5.54 (m, 2H), 5.44-5.32 (m, 2H), 5.28-5.10 (m, 2H), 3.40-3.15 (m, 3H), 2.44 (s, 3H), 2.23 (t, 1H), 2.06-1.75 (m, 2H), 1.68-1.56 (m, 1H), 1.22-1.18 (m, 2H), 1.04-0.98 (m, 2H), 0.89 (t, 3H).

Example 2
(S)-2-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide 2-A
(R)-2-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide 2-B
2-A
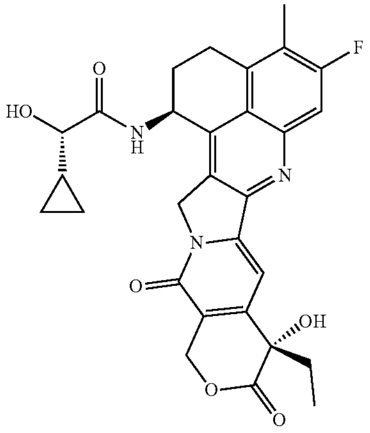
2-B
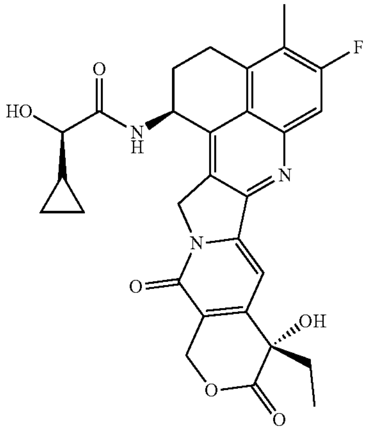
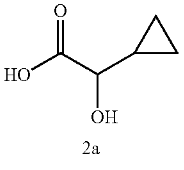
+
2a
-continued
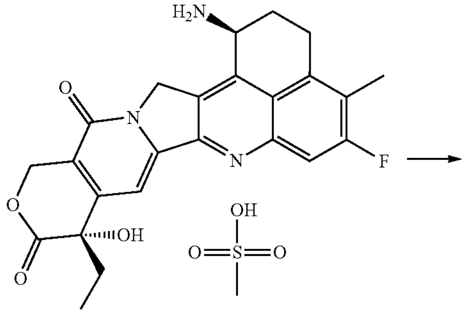
1b
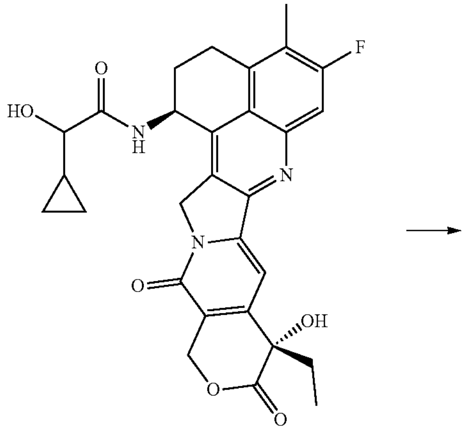
2
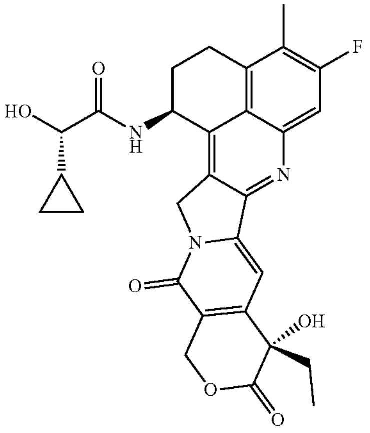
+
2-A -continued

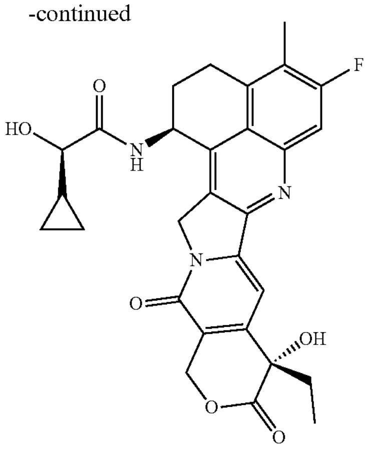

2-B 2 mL of ethanol and 0.4 mL of N,N-dimethylformamide were added to 1b (4 mg, 7.53 μmol). The solution was purged with argon three times, and cooled to 0-5° C. in an ice-water bath. 0.3 mL of N-methylmorpholine was added dropwise, and the reaction solution was stirred until clear. 2-Cyclopropyl-2-hydroxyacetic acid 2a (2.3 mg, 19.8 μmol, prepared according to the method disclosed in the patent application "WO2013106717"), 1-hydroxybenzotriazole (3 mg, 22.4 μmol) and 1-(3-dimethylaminopropyl)-3-ethylcarbodiimide hydrochloride (4.3 mg, 22.4 μmol) were added successively to the reaction solution. After completion of the addition, the reaction solution was stirred at 0-5° C. for one hour. The ice-water bath was removed, and the reaction solution was heated to 30° C. and stirred for 2 hours. The reaction solution was concentrated under reduced pressure, and the resulting crude compound 2 was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product (2-A: 1.5 mg, 2-B: 1.5 mg).

MS m/z (ESI): 534.0 [M+1].

Compound 2-B with single configuration (having shorter retention time)

UPLC analysis: retention time: 1.06 minutes, purity: 88% (column: ACQUITY UPLC BEHC18 1.7 μm 2.1*50 mm, mobile phase: A-water (5 mmol $NH_4OAc$), B-acetonitrile).

$^1H$ NMR (400 MHz, DMSO-$d_6$): δ 8.37 (d, 1H), 7.76 (d, 1H), 7.30 (s, 1H), 6.51 (s, 1H), 5.58-5.56 (m, 1H), 5.48 (d, 1H), 5.41 (s, 2H), 5.32-5.29 (m, 2H), 3.60 (t, 1H), 3.19-3.13 (m, 1H), 2.38 (s, 3H), 2.20-2.14 (m, 1H), 1.98 (q, 2H), 1.87-1.83 (m, 1H), 1.50-1.40 (m, 1H), 1.34-1.28 (m, 1H), 0.86 (t, 3H), 0.50-0.39 (m, 4H).

Compound 2-A with single configuration (having longer retention time)

UPLC analysis: retention time: 1.10 minutes, purity: 86% (column: ACQUITY UPLC BEHC18 1.7 μm 2.1*50 mm, mobile phase: A-water (5 mmol $NH_4OAc$), B-acetonitrile).

$^1H$ NMR (400 MHz, DMSO-$d_6$): δ 8.35 (d, 1H), 7.78 (d, 1H), 7.31 (s, 1H), 6.52 (s, 1H), 5.58-5.53 (m, 1H), 5.42 (s, 2H), 5.37 (d, 1H), 5.32 (t, 1H), 3.62 (t, 1H), 3.20-3.15 (m, 2H), 2.40 (s, 3H), 2.25-2.16 (m, 1H), 1.98 (q, 2H), 1.87-1.82 (m, 1H), 1.50-1.40 (m, 1H), 1.21-1.14 (m, 1H), 0.87 (t, 3H), 0.47-0.35 (m, 4H).

Example 3

(S)—N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3,3,3-trifluoro-2-hydroxypropanamide 3-A (R)—N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3,3,3-trifluoro-2-hydroxypropanamide 3-B

3-A

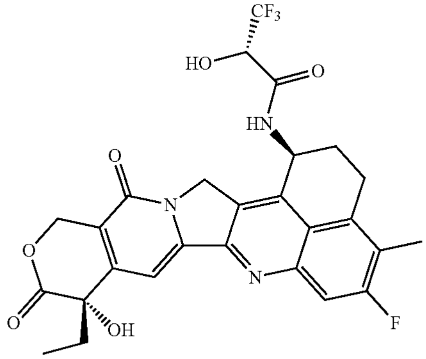

3-B

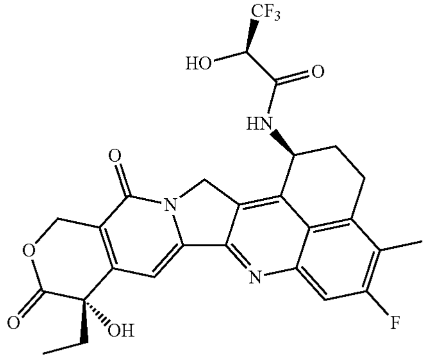

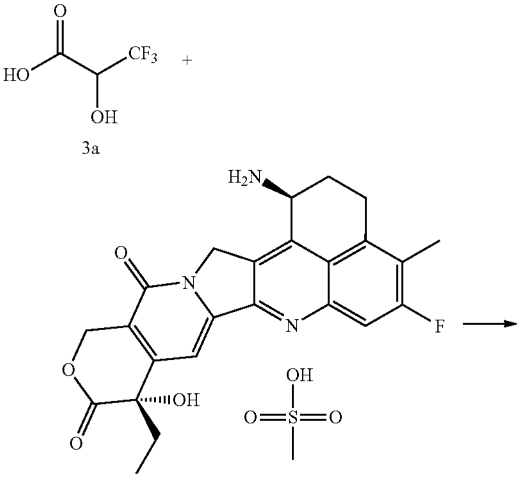

3a

1b

-continued

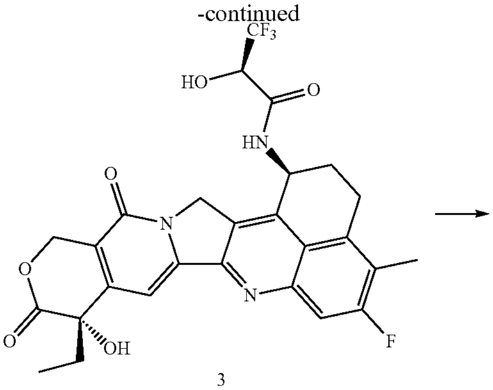

3

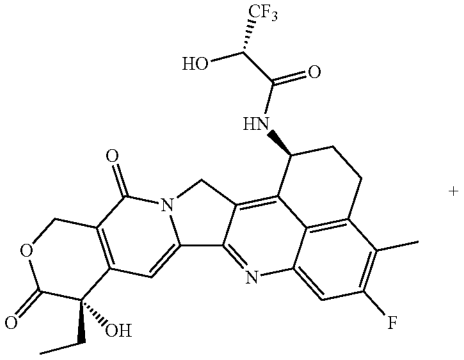

3-A

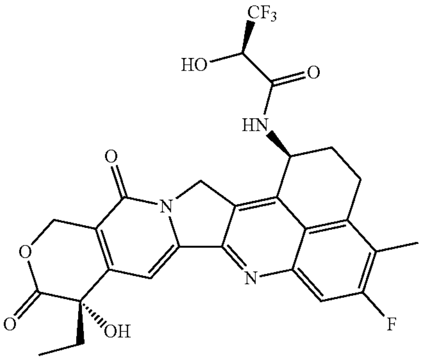

3-B 2 mL of ethanol and 0.4 mL of N,N-dimethylformamide were added to 1b (5.0 mg, 9.41 μmol), and the solution was cooled to 0-5° C. in an ice-water bath. 0.3 mL of N-methylmorpholine was added dropwise, and the reaction solution was stirred until clear. 3,3,3-Trifluoro-2-hydroxypropionic acid 3a (4.1 mg, 28.4 μmol, supplier: Alfa), 1-hydroxybenzotriazole (3.8 mg, 28.1 μmol) and 1-(3-dimethylaminopropyl)-3-ethylcarbodiimide hydrochloride (5.4 mg, 28.2 μmol) were added successively to the reaction solution. After completion of the addition, the reaction solution was stirred at 0-5° C. for 10 minutes. The ice-water bath was removed, and the reaction solution was heated to 30° C. and stirred for 8 hours. The reaction solution was concentrated under reduced pressure, and the resulting crude compound 3 was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product (1.5 mg, 1.5 mg).

MS m/z (ESI): 561.9 [M+1].

Compound with single configuration (having shorter retention time)

UPLC analysis: retention time: 1.11 minutes, purity: 88% (column: ACQUITY UPLC BEHC18 1.7 μm 2.1*50 mm, mobile phase: A-water (5 mmol $NH_4OAc$), B-acetonitrile).

$^1H$ NMR (400 MHz, DMSO-$d_6$): δ 8.94 (d, 1H), 7.80 (d, 1H), 7.32 (s, 1H), 7.20 (d, 1H), 6.53 (s, 1H), 5.61-5.55 (m, 1H), 5.45-5.23 (m, 3H), 5.15-5.06 (m, 1H), 4.66-4.57 (m, 1H), 3.18-3.12 (m, 1H), 2.40 (s, 3H), 2.26-2.20 (m, 1H), 2.16-2.08 (m, 1H), 2.02-1.94 (m, 1H), 1.89-1.82 (m, 1H), 1.50-1.40 (m, 1H), 0.87 (t, 3H).

Compound with single configuration (having longer retention time)

UPLC analysis: retention time: 1.19 minutes, purity: 90% (column: ACQUITY UPLC BEHC18 1.7 μm 2.1*50 mm, mobile phase: A-water (5 mmol $NH_4OAc$), B-acetonitrile).

$^1H$ NMR (400 MHz, DMSO-$d_6$): δ 8.97 (d, 1H), 7.80 (d, 1H), 7.31 (s, 1H), 7.16 (d, 1H), 6.53 (s, 1H), 5.63-5.55 (m, 1H), 5.45-5.20 (m, 3H), 5.16-5.07 (m, 1H), 4.66-4.57 (m, 1H), 3.18-3.12 (m, 1H), 2.40 (s, 3H), 2.22-2.14 (m, 1H), 2.04-1.95 (m, 2H), 1.89-1.82 (m, 1H), 1.50-1.40 (m, 1H), 0.87 (t, 3H).

Example 4

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclopentane-1-carboxamide 4

4

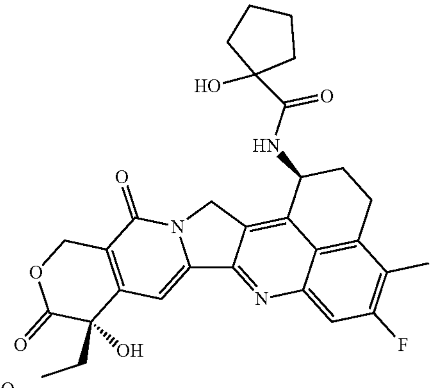

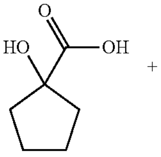

4a

-continued

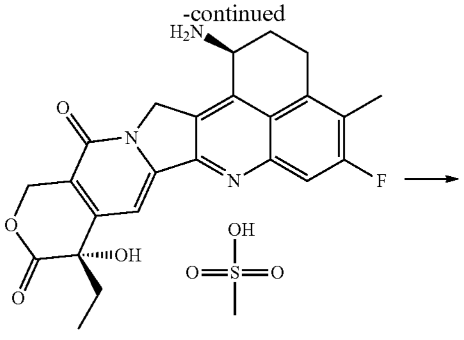

1b

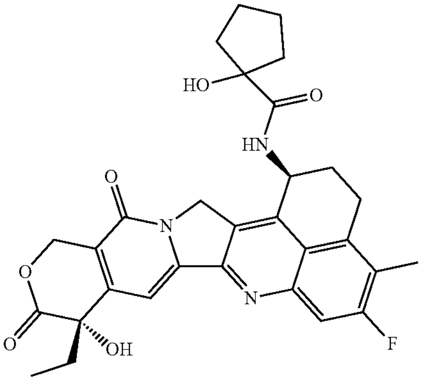

4

1 mL of N,N-dimethylformamide was added to 1b (3.0 mg, 5.64 μmol), and the solution was cooled to 0-5° C. in an ice-water bath. One drop of triethylamine was added dropwise, and the reaction solution was stirred until clear. 1-Hydroxy-cyclopentanecarboxylic acid 4a (2.2 mg, 16.9 μmol, prepared according to the method disclosed in the patent application "WO2013106717") and 4-(4,6-dimethoxy-1,3,5-triazin-2-yl)-4-methylmorpholinium chloride (4.7 mg, 16.9 μmol) were added successively to the reaction solution. After completion of the addition, the reaction solution was stirred at 0-5° C. for 1 hour. 5 mL of water was added to the reaction solution to quench the reaction, and the reaction solution was extracted with ethyl acetate (10 mL×3). The organic phases were combined, washed with saturated sodium chloride solution (5 mL×2), dried over anhydrous sodium sulfate and filtered. The filtrate was concentrated under reduced pressure, and the resulting residues were purified by thin layer chromatography with developing solvent system B to obtain the title product 4 (2.5 mg, yield: 80.9%).

MS m/z (ESI): 548.0 [M+1].

$^1$H NMR (400 MHz, $CDCl_3$): δ 7.73-7.62 (m, 2H), 5.75-5.62 (m, 1H), 5.46-5.32 (m, 2H), 5.26-5.10 (m, 1H), 3.30-3.10 (m, 1H), 2.43 (s, 3H), 2.28-2.20 (m, 2H), 2.08-1.84 (m, 8H), 1.69-1.58 (m, 2H), 1.04-1.00 (m, 2H), 0.89 (t, 3H).

Example 5

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-(hydroxymethyl)cyclopropane-1-carboxamide 5

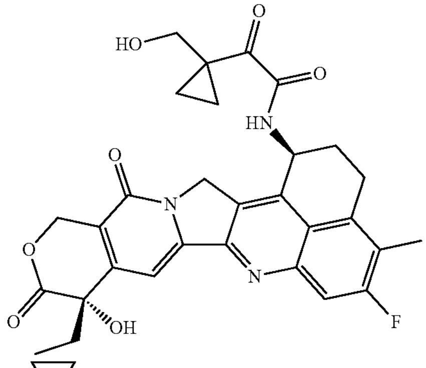

5

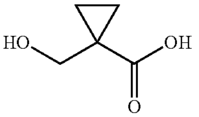

+

5a

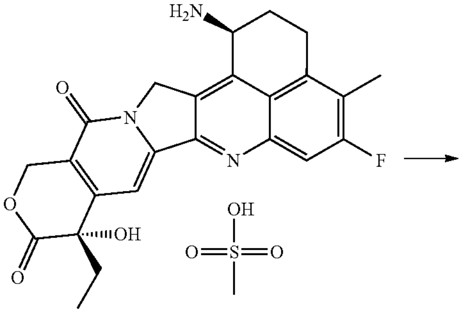

1b

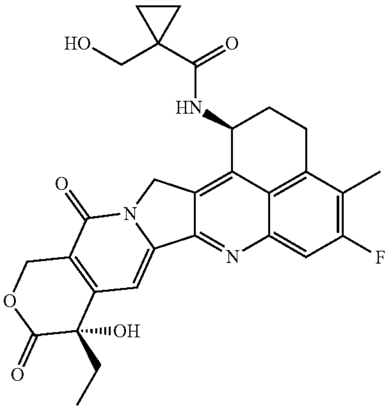

5

1 mL of N,N-dimethylformamide was added to 1b (2.0 mg, 3.76 μmol), and the solution was cooled to 0-5° C. in an ice-water bath. One drop of triethylamine was added dropwise, and the reaction solution was stirred until clear. 1-(Hydroxymethyl)-cyclopentanecarboxylic acid 5a (0.87 mg, 7.5 μmol, prepared according to the method disclosed in the patent application "WO201396771") and 4-(4,6-dimethoxy-1,3,5-triazin-2-yl)-4-methylmorpholinium chloride (2 mg, 7.24 μmol) were added successively to the reaction solution. After completion of the addition, the reaction solution was stirred at 0-5° C. for 2 hours. 5 mL of water was added to the reaction solution to quench the reaction, and the reaction solution was extracted with ethyl acetate (8 mL×3). The organic phases were combined, washed with saturated sodium chloride solution (5 mL×2), dried over anhydrous sodium sulfate and filtered. The filtrate was concentrated under reduced pressure, and the resulting residues were purified by thin layer chromatography with developing solvent system B to obtain the title product 5 (1.0 mg, yield: 50%).

MS m/z (ESI): 533.9 [M+1].

$^1$H NMR (400 MHz, $CDCl_3$): δ 8.07 (s, 1H), 7.23-7.18 (m, 2H), 6.71-6.64 (m, 1H), 6.55-6.51 (m, 1H), 5.36-5.27 (m, 2H), 4.67-4.61 (m, 2H), 3.53-3.48 (m, 1H), 3.30-3.22 (m, 2H), 3.18-3.13 (m, 1H), 2.71-2.61 (m, 2H), 2.35-2.28 (m, 1H), 2.04-1.91 (m, 4H), 1.53-1.40 (m, 3H), 0.91-0.75 (m, 4H).

Example 6

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-(hydroxymethyl)cyclobutane-1-carboxamide 6

6

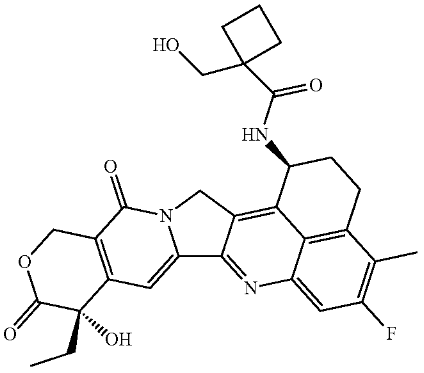

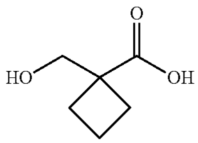

+

6a

-continued

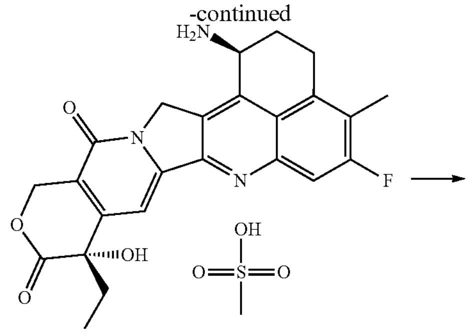

1b

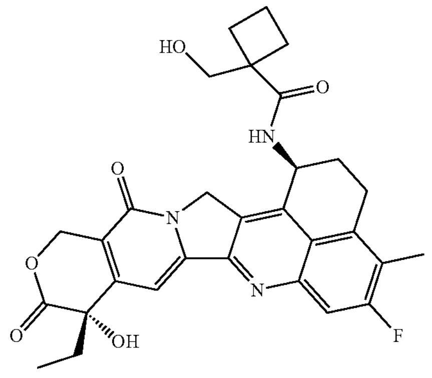

6

1 mL of N,N-dimethylformamide was added to 1b (3.0 mg, 5.64 μmol), and the solution was cooled to 0-5° C. in an ice-water bath. One drop of triethylamine was added dropwise, and the reaction solution was stirred until clear. 1-(Hydroxymethyl)cyclobutane-1-carboxylic acid 6a (2.2 mg, 16.9 prepared according to the known method disclosed in "*Journal of the American Chemical Society,* 2014, vol. 136, #22, p. 8138-8142") and 4-(4,6-dimethoxy-1,3,5-triazin-2-yl)-4-methylmorpholinium chloride (4.7 mg, 16.9 μmol) were added successively to the reaction solution. After completion of the addition, the reaction solution was stirred at 0-5° C. for 1 hour. 5 mL of water was added to the reaction solution to quench the reaction, and the reaction solution was extracted with ethyl acetate (10 mL×3). The organic phases were combined, washed with saturated sodium chloride solution (5 mL×2), dried over anhydrous sodium sulfate and filtered. The filtrate was concentrated under reduced pressure, and the resulting residues were purified by thin layer chromatography with developing solvent system B to obtain the title product 6 (2.1 mg, yield: 67.9%).

MS m/z (ESI): 548.0 [M+1].

$^1$H NMR (400 MHz, DMSO-$d_6$): δ 7.85-7.62 (m, 1H), 6.88 (br, 1H), 5.87-5.48 (m, 2H), 5.47-5.33 (m, 1H), 5.31-5.06 (m, 1H), 4.25-3.91 (m, 2H), 3.25 (br, 1H), 2.60-2.32 (m, 3H), 2.23 (t, 1H), 2.15-1.95 (m, 3H), 1.70-1.56 (m, 2H), 1.41-1.17 (m, 9H), 1.03 (s, 1H), 0.95-0.80 (m, 2H).

Example 7

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclobutane-1-carboxamide 7

7

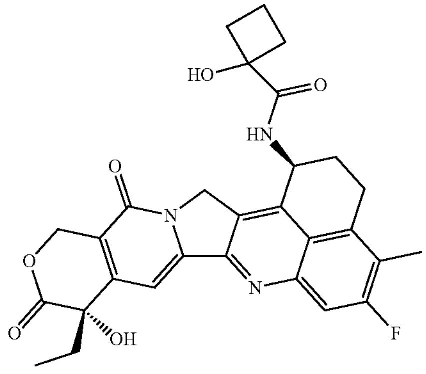

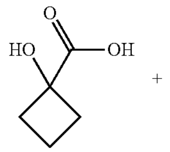

7a

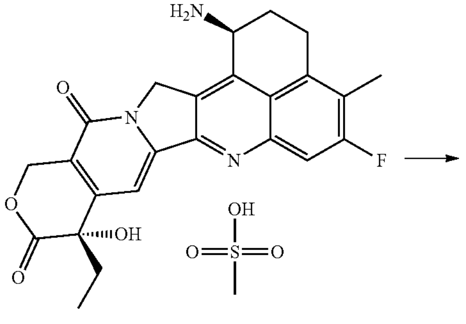

1b

-continued

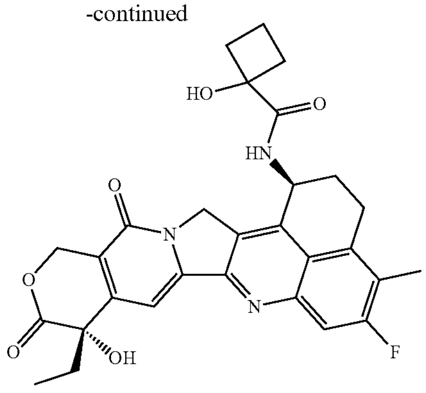

7

2 mL of ethanol and 0.4 mL of N,N-dimethylformamide were added to 1b (3.0 mg, 5.64 μmol), and the solution was cooled to 0-5° C. in an ice-water bath. 0.3 mL of N-methylmorpholine was added dropwise, and the reaction solution was stirred until clear. 1-Hydroxycyclobutanecarboxylic acid 7a (2.0 mg, 17.22 μm', supplier: PharmaBlock Sciences), 1-hydroxybenzotriazole (2.3 mg, 17.0 μmol) and 1-(3-dimethylaminopropyl)-3-ethylcarbodiimide hydrochloride (3.2 mg, 16.7 μmol) were added successively to the reaction solution. After completion of the addition, the reaction solution was stirred at 0-5° C. for 10 minutes. The ice-water bath was removed, and the reaction solution was stirred at room temperature for 2 hours. The reaction solution was concentrated under reduced pressure, and the resulting residue was purified by thin layer chromatography with developing solvent system B to obtain the title product 7 (2.5 mg, yield: 83.1%).

MS m/z (ESI): 534.0 [M+1].

$^1$H NMR (400 MHz, DMSO-$d_6$): δ 8.28 (d, 1H), 7.75 (d, 1H), 7.29 (s, 1H), 6.51 (s, 1H), 6.12 (s, 1H), 5.59-5.51 (m, 1H), 5.41 (s, 2H), 5.20-5.01 (m, 2H), 3.27-3.17 (m, 1H), 3.15-3.05 (m, 1H), 2.71-2.63 (m, 1H), 2.37 (s, 3H), 2.12-2.05 (m, 1H), 2.03-1.94 (m, 2H), 1.92-1.78 (m, 4H), 1.50-1.42 (m, 1H), 0.90-0.83 (m, 4H).

Example 8

1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 8

8

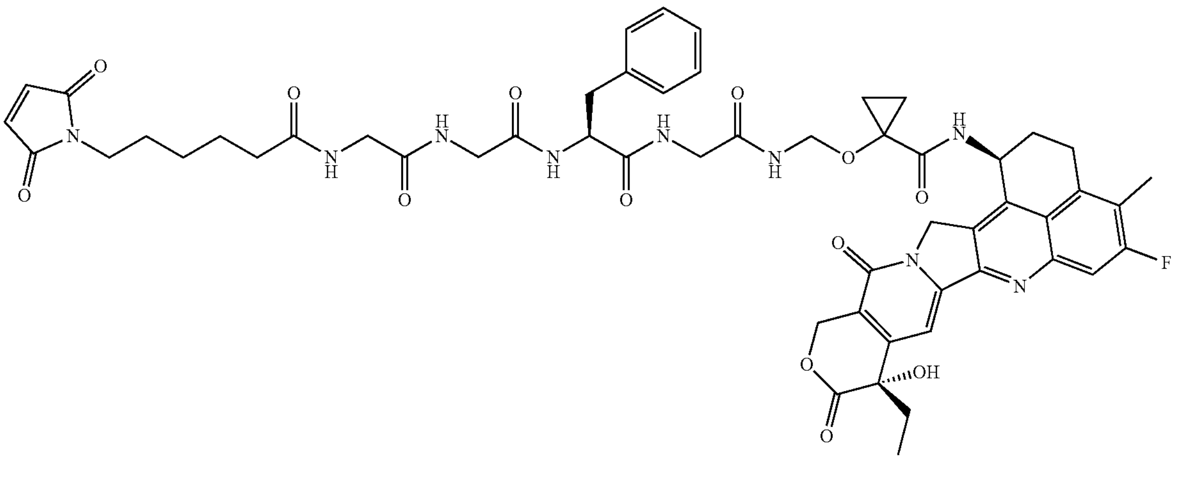

-continued
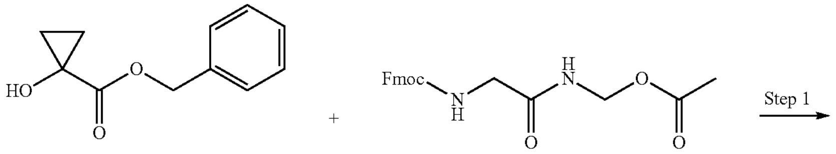
8a 8b
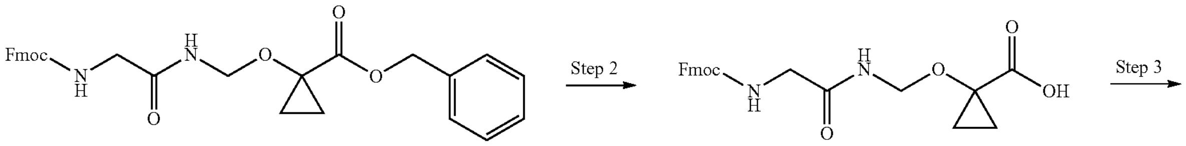
8c 8d
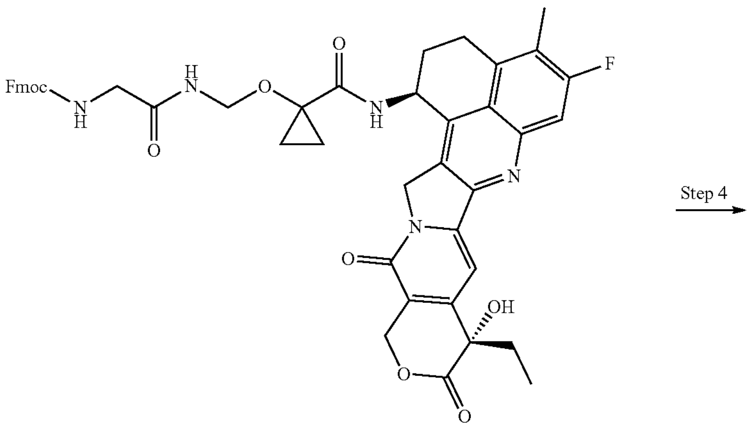
8e
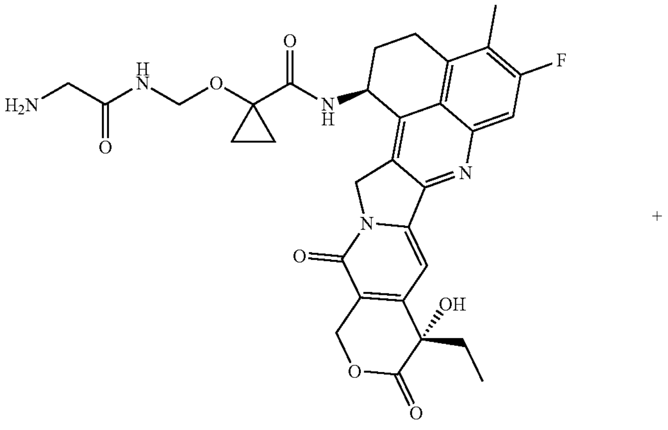
8f
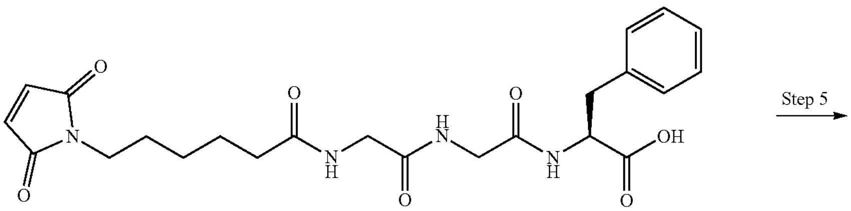
8g -continued

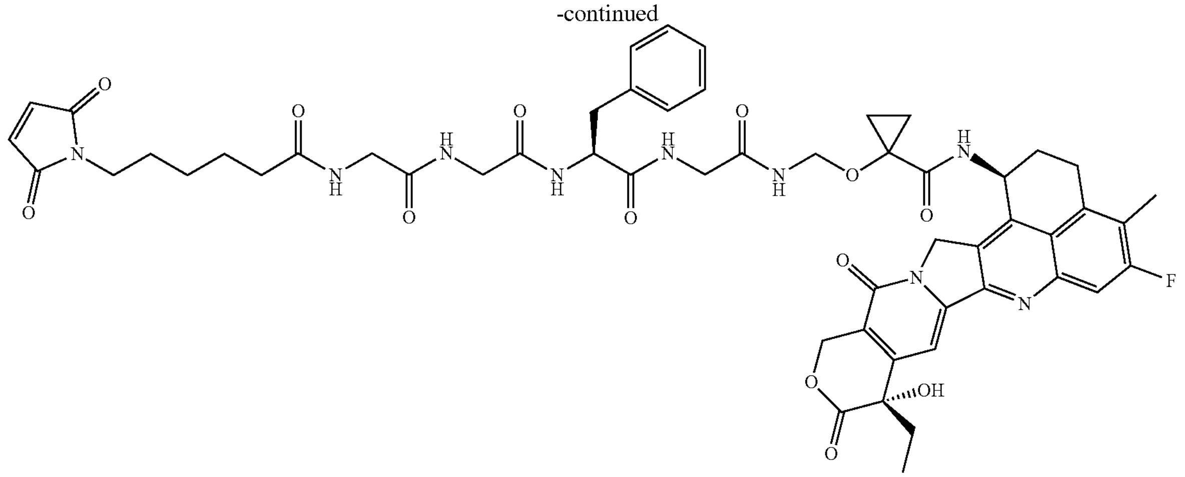

8

Step 1

Benzyl 1-((2-((((9H-Fluoren-9-yl)methoxy)carbonyl)amino)acetamido)methoxy)cyclopropane-1-carboxylate 8c Benzyl 1-hydroxycyclopropane-1-carboxylate 8a (104 mg, 0.54 mmol, prepared according to the method disclosed in the patent application "US2005/20645") and (2-((((9H-fluoren-9-yl)methoxy)carbonyl)amino)acetamido)methyl acetate 8b (100 mg, 0.27 mmol, prepared according to the method disclosed in the patent application "CN105829346A") were added to a reaction flask, followed by the addition of 5 mL of tetrahydrofuran. The reaction solution was purged with argon three times and cooled to 0-5° C. in an ice-water bath, followed by the addition of potassium tert-butoxide (61 mg, 0.54 mmol). The ice-water bath was removed, and the reaction solution was warmed up to room temperature and stirred for 10 minutes. 20 mL ice water was added to the reaction solution, which was then extracted with ethyl acetate (5 mL×2) and chloroform (5 mL×5). The organic phases were combined and concentrated. The resulting residues were dissolved in 3 mL of 1,4-dioxane. 0.6 mL of water, sodium bicarbonate (27 mg, 0.32 mmol) and 9-fluorene methyl chloroformate (70 mg, 0.27 mmol) were added, and the reaction solution was stirred at room temperature for 1 hour. 20 mL of water was added, and the reaction solution was extracted with ethyl acetate (8 mL×3). The organic phase was washed with saturated sodium chloride solution (20 mL), dried over anhydrous sodium sulfate and filtered. The filtrate was concentrated under reduced pressure, and the resulting residues were purified by silica gel column chromatography with developing solvent system B to obtain the title product 8c (100 mg, yield: 73.6%).

MS m/z (ESI): 501.0 [M+1]

Step 2

1-((2-((((9H-Fluoren-9-yl)methoxy)carbonyl)amino)acetamido)methoxy)cyclopropane-1-carboxylic acid 8d 8c (50 mg, 0.10 mmol) was dissolved in 3 mL of a mixed solvent of tetrahydrofuran and ethyl acetate (V:V=2:1), followed by the addition of palladium on carbon (25 mg, content: 10%). The reaction solution was purged with hydrogen three times and stirred at room temperature for 1 hour. The reaction solution was filtered through celite, and the filter cake was rinsed with tetrahydrofuran. The filtrate was concentrated to obtain the title product 8d (41 mg, yield: 100%).

MS m/z (ESI): 411.0 [M+1].

Step 3

(9H-Fluoren-9-yl)methyl (2-(((1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclopropoxy)methyl)amino)-2-oxoethyl)carbamate 8e 1b (7 mg, 0.013 mmol) was added to a reaction flask, followed by the addition of 1 mL of N,N-dimethylformamide. The solution was purged with argon three times, and cooled to 0-5° C. in an ice-water bath. One drop of triethylamine, 8d (7 mg, 0.017 mmol) in 0.5 mL of N,N-dimethylformamide, and 4-(4,6-dimethoxy-1,3,5-triazin-2-yl)-4-methylmorpholinium chloride (7 mg, 0.026 mmol) were added, and the reaction solution was stirred in an ice bath for 35 minutes. 10 mL of water was added, and the reaction solution was extracted with ethyl acetate (5 mL×3). The organic phase was washed with saturated sodium chloride solution (10 mL), dried over anhydrous sodium sulfate and filtered. The filtrate was concentrated under reduced pressure, and the resulting residues were purified by thin layer chromatography with developing solvent system B to obtain the title product 8e (8.5 mg, yield: 78.0%).

MS m/z (ESI): 828.0 [M+1].

Step 4

1-((2-Aminoacetamido)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 8f 8e (4 mg, 4.84 μmol) was dissolved in 0.2 mL of dichloromethane, followed by the addition of 0.1 mL of diethylamine. The reaction solution was stirred at room temperature for 2 hours. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 8f (2.9 mg), which was used directly in the next step without purification.

MS m/z (ESI): 606.0 [M+1].

Step 5

1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 8

The crude compound 8f (2.9 mg, 4.84 μmol) was dissolved in 0.5 mL of N,N-dimethylformamide. The solution was purged with argon three times, and cooled to 0-5° C. in an ice-water bath. (S)-2(-2-(-2-(6-(2,5-Dioxo-1H-pyrrol-1-yl)hexanamido)acetamido)acetamido)-3-phenylpropionic acid 8g (2.7 mg, 5.80 μmol, prepared according to the method disclosed in the patent application "EP2907824") in 0.3 mL of N,N-dimethylformamide, and 4-(4,6-dimethoxy-1,3,5-triazin-2-yl)-4-methylmorpholinium chloride (2.7 mg, 9.67 μmol) were added, and the reaction solution was stirred in an ice bath for 30 minutes. The ice bath was removed, and the reaction solution was warmed up to room temperature and stirred for 15 minutes. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product 8 (2 mg, yield: 39.0%).

MS m/z (ESI): 1060.0 [M+1].

$^1H$ NMR (400 MHz, DMSO-$d_6$): δ 9.01 (d, 1H), 8.77 (t, 1H), 8.21 (t, 1H), 8.08-7.92 (m, 2H), 7.73 (d, 1H), 7.28 (s, 1H), 7.24-7.07 (m, 4H), 6.98 (s, 1H), 6.50 (s, 1H), 5.61 (q, 1H), 5.40 (s, 2H), 5.32 (t, 1H), 5.12 (q, 2H), 4.62 (t, 1H), 4.52 (t, 1H), 4.40-4.32 (m, 1H), 3.73-3.47 (m, 8H), 3.16-3.04 (m, 2H), 2.89 (dd, 1H), 2.69-2.55 (m, 2H), 2.37-2.23 (m, 4H), 2.12-1.93 (m, 4H), 1.90-1.74 (m, 2H), 1.52-1.38 (m, 4H), 1.33-1.11 (m, 5H), 0.91-0.81 (m, 4H).

Example 9

N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9-A N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9-B

9-A

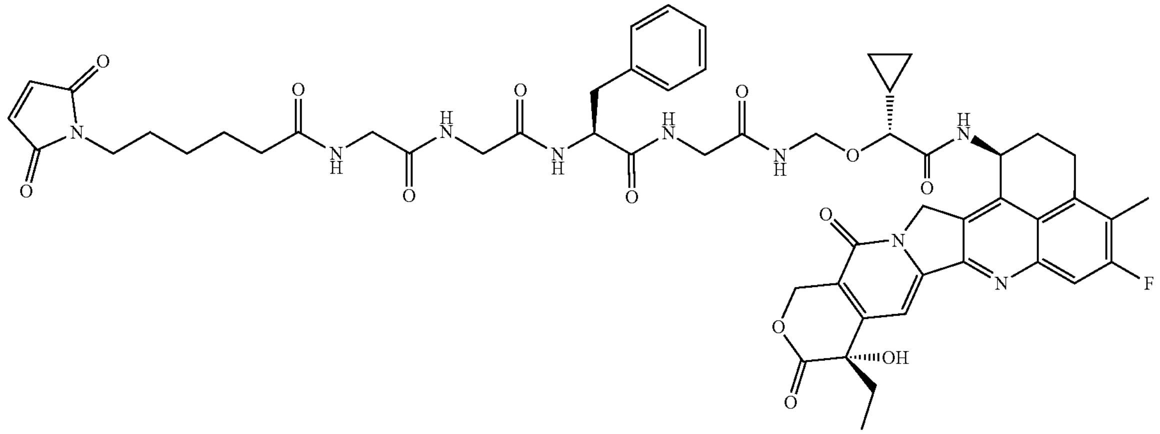

-continued
9-B
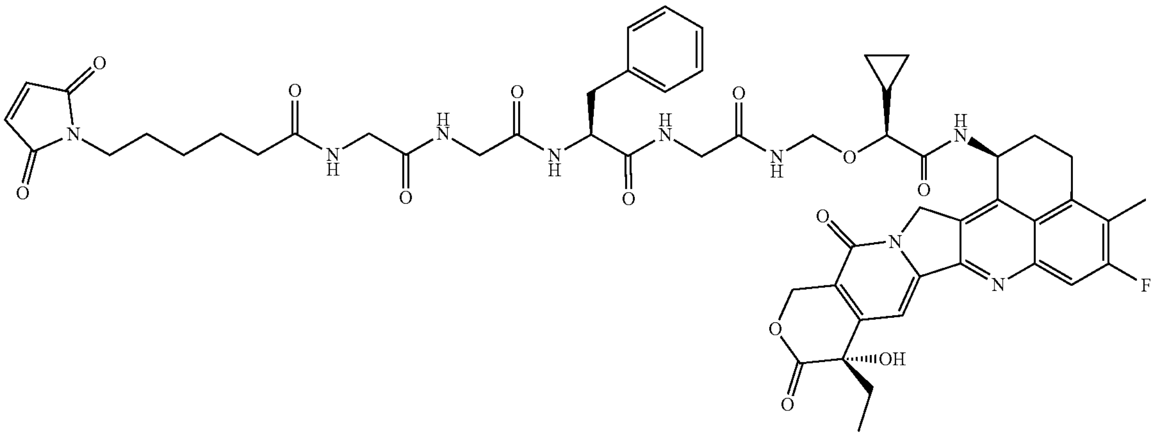
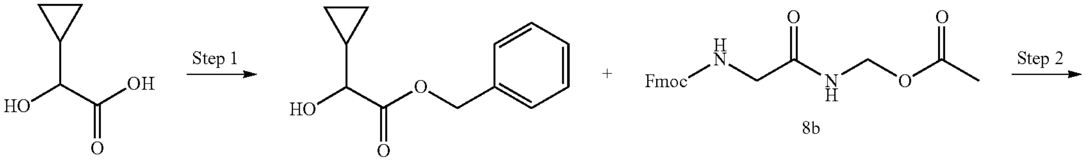
2a 9a 8b
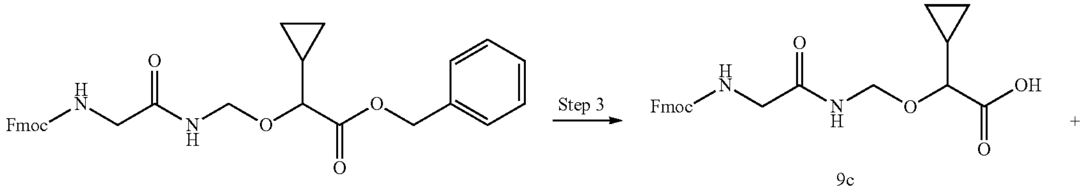
9b 9c
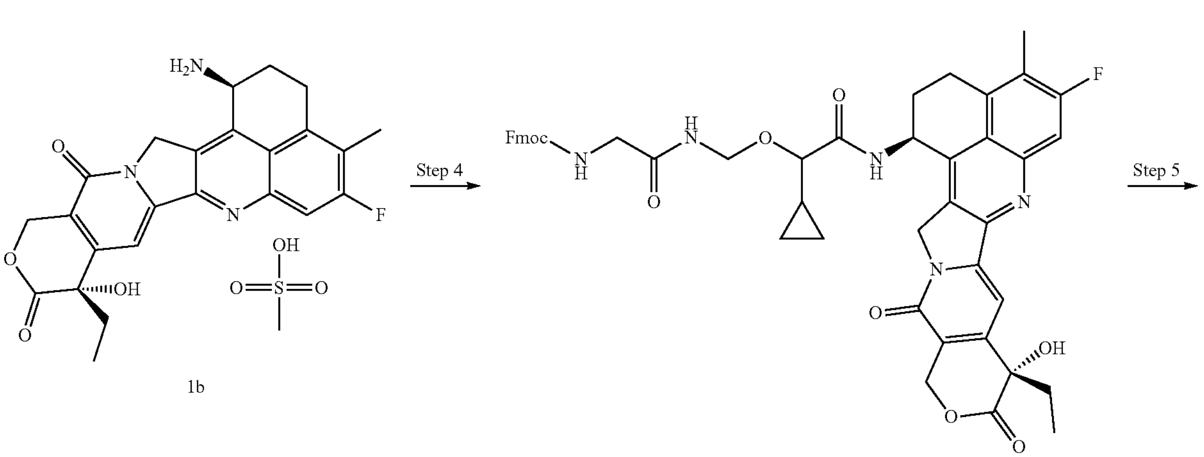
1b 9d -continued
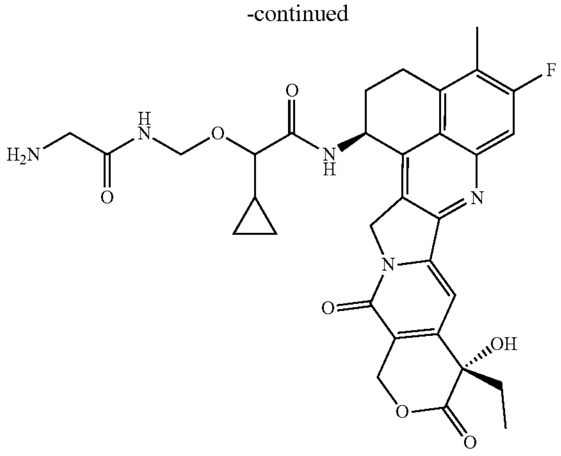
9e
+
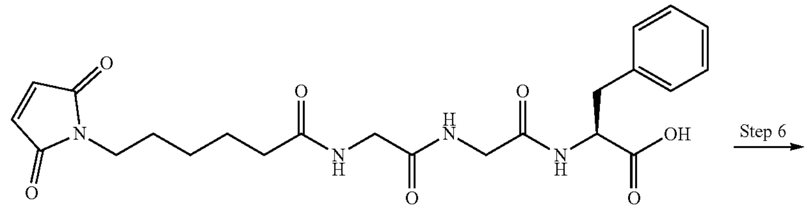
8g
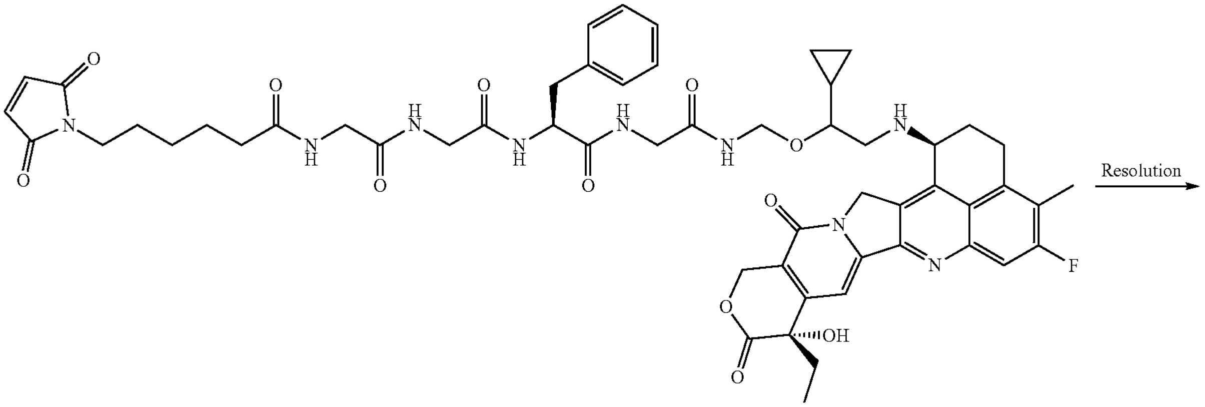
9
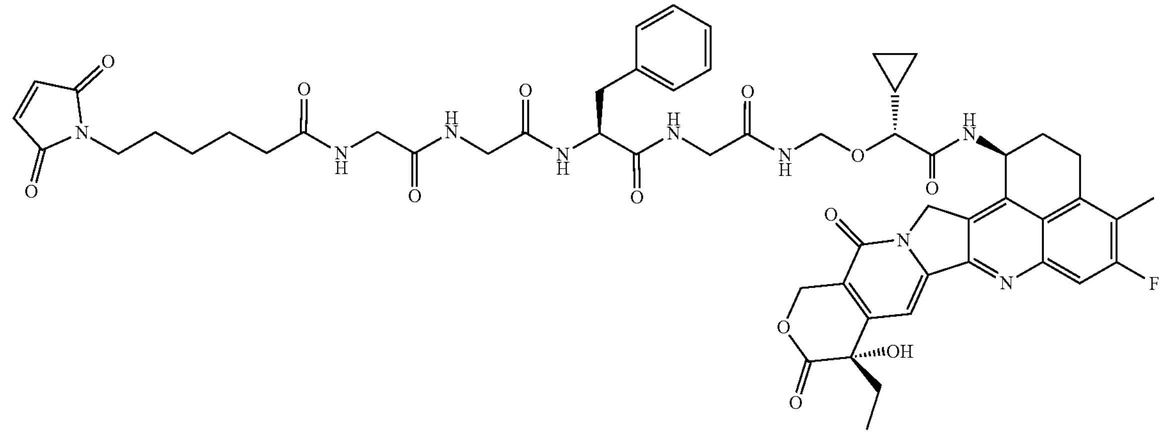
9-A
+

-continued

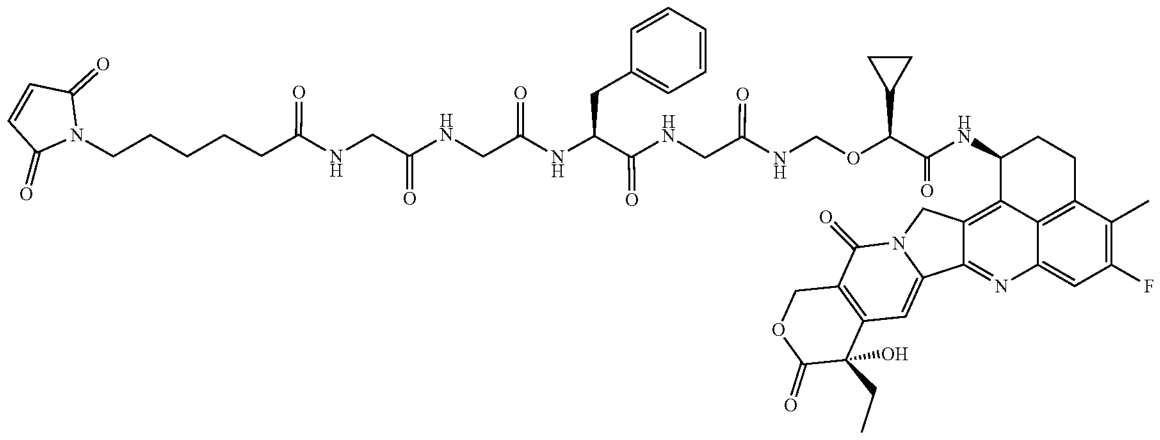

9-B

Step 1

Benzyl 2-cyclopropyl-2-hydroxyacetate 9a 2a (1.3 g, 11.2 mmol, prepared according to the method disclosed in the patent application "WO2013/106717") was dissolved in 50 mL of acetonitrile, and then added with potassium carbonate (6.18 g, 44.8 mmol), benzyl bromide (1.33 mL, 11.2 mmol) and tetrabutylammonium iodide (413 mg, 1.1 mmol) successively. The reaction solution was stirred at room temperature for 48 hours, and filtered through celite. The filter cake was rinsed with ethyl acetate (10 ml), and the filtrates were combined and concentrated under reduced pressure. The resulting residues were purified by silica gel column chromatography with developing solvent system C to obtain the title product 9a (2 g, yield: 86.9%).

Step 2

Benzyl 10-cyclopropyl-1-(9H-fluoren-9-yl)-3,6-dioxo-2,9-dioxa-4,7-diazaundecan-11-oate 9b 9a (120.9 mg, 0.586 mmol) and 8b (180 mg, 0.489 mmol) were added to a reaction flask, followed by the addition of 4 mL of tetrahydrofuran. The reaction solution was purged with argon three times and cooled to 0-5° C. in an ice-water bath. Potassium tert-butoxide (109 mg, 0.98 mmol) was added and the ice-water bath was removed. The reaction solution was warmed up to room temperature and stirred for 40 minutes. 10 mL ice water was added to the reaction solution, which was then extracted with ethyl acetate (20 mL×2) and chloroform (10 mL×5). The organic phases were combined and concentrated. The resulting residues were dissolved in 4 mL of dioxane. 2 mL of water, sodium bicarbonate (49.2 mg, 0.586 mmol) and 9-fluorene methyl chloroformate (126 mg, 0.49 mmol) were added, and the reaction solution was stirred at room temperature for 2 hours. 20 mL of water was added, and the reaction solution was extracted with ethyl acetate (10 mL×3). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 9b (48 mg, yield: 19%).

MS m/z (ESI): 515.0 [M+1].

Step 3

10-Cyclopropyl-1-(9H-fluoren-9-yl)-3,6-dioxo-2,9-dioxa-4,7-diazaundecan-11-oic acid 9c 9b (20 mg, 0.038 mmol) was dissolved in 4.5 mL of a mixed solvent of tetrahydrofuran and ethyl acetate (V:V=2:1), followed by the addition of palladium on carbon (12 mg, content: 10%, dry). The reaction solution was purged with hydrogen three times and stirred at room temperature for 1 hour. The reaction solution was filtered through celite, and the filter cake was rinsed with ethyl acetate. The filtrate was concentrated to obtain the crude title product 9c (13 mg), which was used directly in the next step without purification.

MS m/z (ESI): 424.9 [M+1].

Step 4

(9H-Fluoren-9-yl)methyl (2-(((1-cyclopropyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl)carbamate 9d 1b (10 mg, 18.8 μmol) was added to a reaction flask, followed by the addition of 1 mL of N,N-dimethylformamide. The solution was purged with argon three times, and cooled to 0-5° C. in an ice-water bath. One drop of triethylamine, crude compound 9c (13 mg, 30.6 μmol) and 4-(4,6-dimethoxy-1,3,5-triazin-2-yl)-4-methylmorpholinium chloride (16.9 mg, 61.2 μmol) were added, and the reaction solution was stirred in an ice bath for 40 minutes. 10 mL of water was added, and the reaction solution was extracted with ethyl acetate (10 mL×3). The organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 9d (19 mg, yield: 73.6%).

MS m/z (ESI): 842.1[M+1].

Step 5

2-((2-Aminoacetamido)methoxy)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)acetamide 9e 9d (19 mg, 22.6 μmol) was dissolved in 2 mL of dichloromethane, followed by the addition of 1 mL of diethylamine. The reaction solution was stirred at room temperature for 2 hours. The reaction solution was concentrated under reduced pressure. 1 mL of toluene was added and the solution was concentrated under reduced pressure, which was repeated twice. 3 mL of n-hexane was added to the residues to pulp, and the supernatant was poured out after standing to retain the solid. The solid residues were concentrated under reduced pressure by an oil pump until dryness to obtain the crude title product 9e (17 mg), which was used directly in the next step without purification.

MS m/z (ESI): 638.0[M+18].

Step 6

N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9-A N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 9-B The crude compound 9e (13.9 mg, 22.4 μmol) was dissolved in 0.6 mL of N,N-dimethylformamide. The solution was purged with argon three times, and cooled to 0-5° C. in an ice-water bath. 8g (21.2 mg, 44.8 μmol) in 0.3 mL of N,N-dimethylformamide, and 4-(4,6-dimethoxy-1,3,5-triazin-2-yl)-4-methylmorpholinium chloride (18.5 mg, 67.3 μmol) were added, and the reaction solution was stirred in an ice bath for 10 minutes. The ice bath was removed, and the reaction solution was warmed up to room temperature and stirred for 1 hour to obtain compound 9. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product (9-A: 2.4 mg, 9-B: 1.7 mg).

MS m/z (ESI): 1074.4 [M+1].

Compound 9-A with single configuration (having shorter retention time):

UPLC analysis: retention time: 1.14 minutes, purity: 85% (column: ACQUITY UPLC BEHC18 1.7 μm 2.1*50 mm, mobile phase: A-water (5 mmol $NH_4OAc$), B-acetonitrile).

$^1$H NMR (400 MHz, DMSO-$d_6$): δ 8.60 (t, 1H), 8.51-8.49 (d, 1H), 8.32-8.24 (m, 1H), 8.13-8.02 (m, 2H), 8.02-7.96 (m, 1H), 7.82-7.75 (m, 1H), 7.31 (s, 1H), 7.26-7.15 (m, 4H), 6.99 (s, 1H), 6.55-6.48 (m, 1H), 5.65-5.54 (m, 1H), 5.41 (s, 2H), 5.35-5.15 (m, 3H), 4.74-4.62 (m, 1H), 4.54-4.40 (m, 2H), 3.76-3.64 (m, 4H), 3.62-3.48 (m, 2H), 3.20-3.07 (m, 2H), 3.04-2.94 (m, 1H), 2.80-2.62 (m, 1H), 2.45-2.30 (m, 3H), 2.25-2.15 (m, 2H), 2.15-2.04 (m, 2H), 1.93-1.78 (m, 2H), 1.52-1.39 (m, 3H), 1.34-1.12 (m, 5H), 0.87 (t, 3H), 0.64-0.38 (m, 4H).

Compound 9-B with single configuration (having longer retention time):

UPLC analysis: retention time: 1.16 minutes, purity: 89% (column: ACQUITY UPLC BEHC18 1.7 μm 2.1*50 mm, mobile phase: A-water (5 mmol $NH_4OAc$), B-acetonitrile).

$^1$H NMR (400 MHz, DMSO-$d_6$): δ 8.68-8.60 (m, 1H), 8.58-8.50 (m, 1H), 8.32-8.24 (m, 1H), 8.13-8.02 (m, 2H), 8.02-7.94 (m, 1H), 7.82-7.75 (m, 1H), 7.31 (s, 1H), 7.26-7.13 (m, 3H), 6.99 (s, 1H), 6.55-6.48 (m, 1H), 5.60-5.50 (m, 1H), 5.41 (s, 2H), 5.35-5.15 (m, 2H), 4.78-4.68 (m, 1H), 4.60-4.40 (m, 2H), 3.76-3.58 (m, 4H), 3.58-3.48 (m, 1H), 3.20-3.10 (m, 2H), 3.08-2.97 (m, 2H), 2.80-2.72 (m, 2H), 2.45-2.30 (m, 3H), 2.25-2.13 (m, 2H), 2.13-2.04 (m, 2H), 2.03-1.94 (m, 2H), 1.91-1.78 (m, 2H), 1.52-1.39 (m, 3H), 1.34-1.12 (m, 4H), 0.91-0.79 (m, 3H), 0.53-0.34 (m, 4H).

Example 10

N-((2S,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 10-A N-((2R,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 10-B

10-A

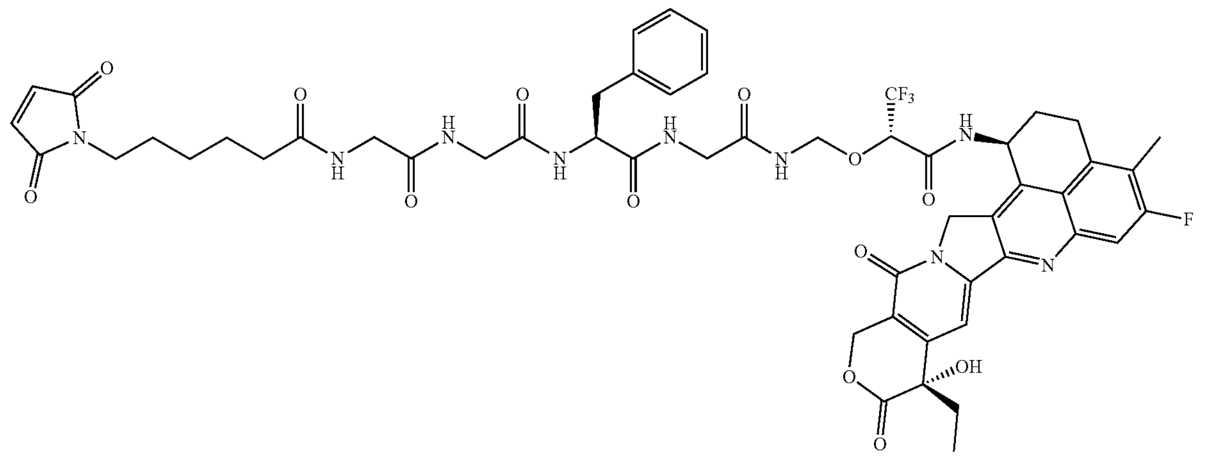

10-B

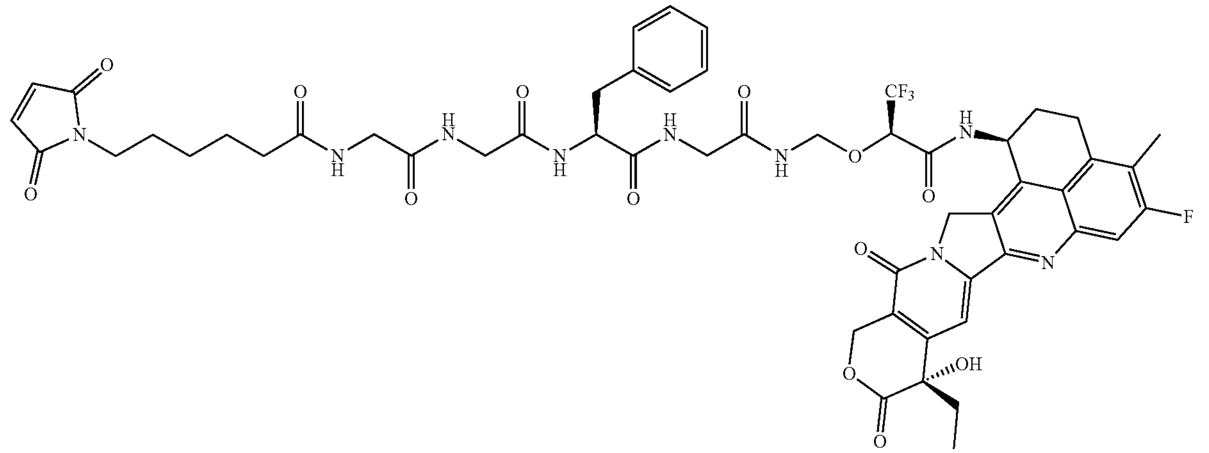

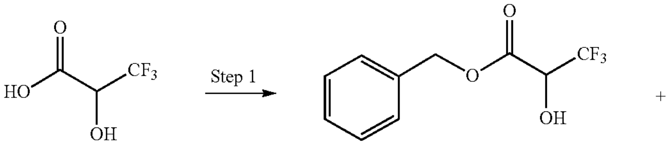

3a

10a

-continued
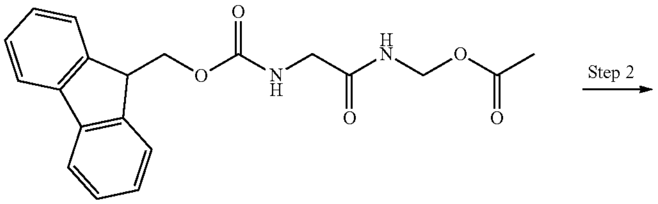
8b
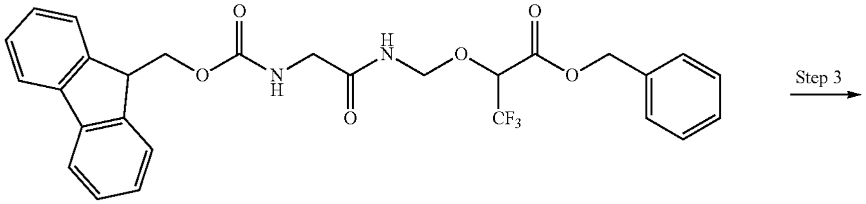
10b
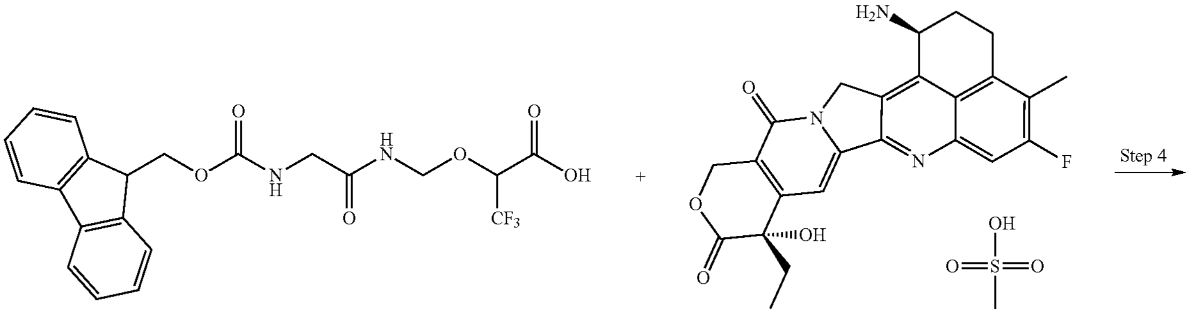
10c 1b
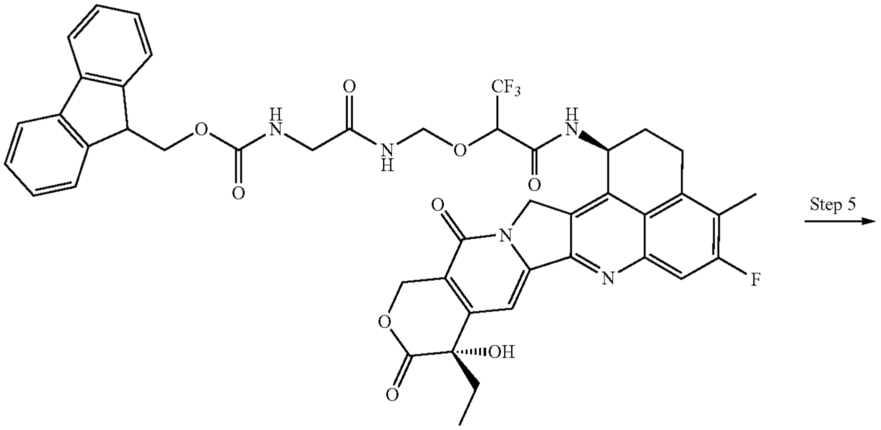
10d
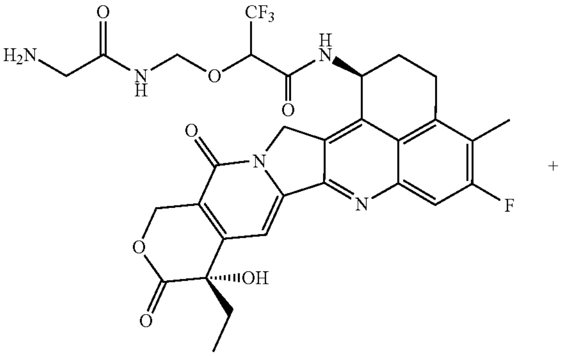
10e -continued
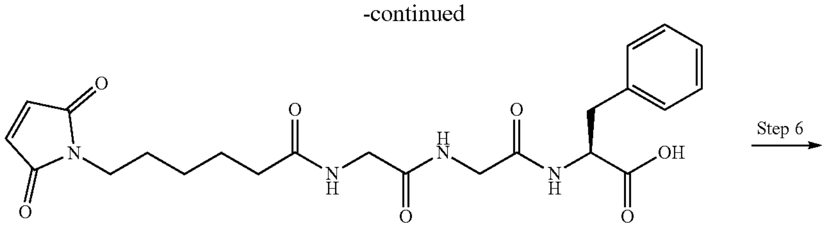
8g
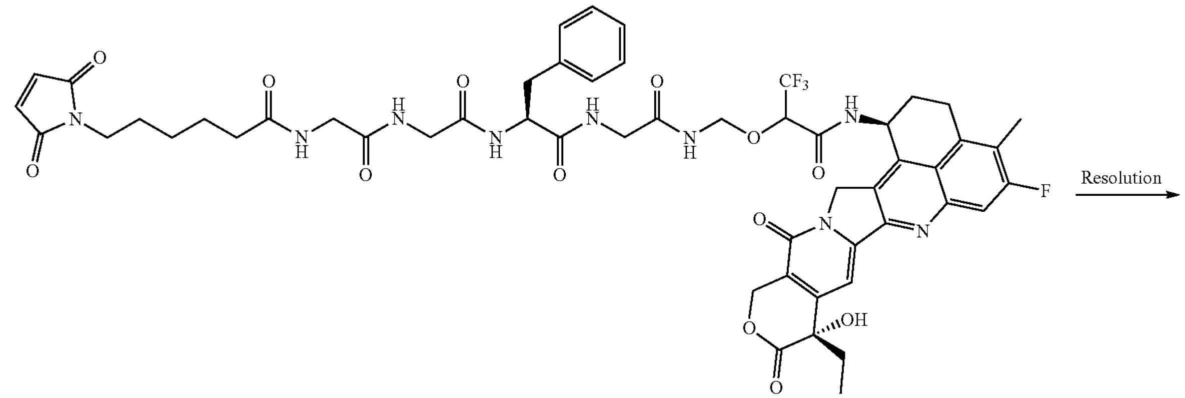
10
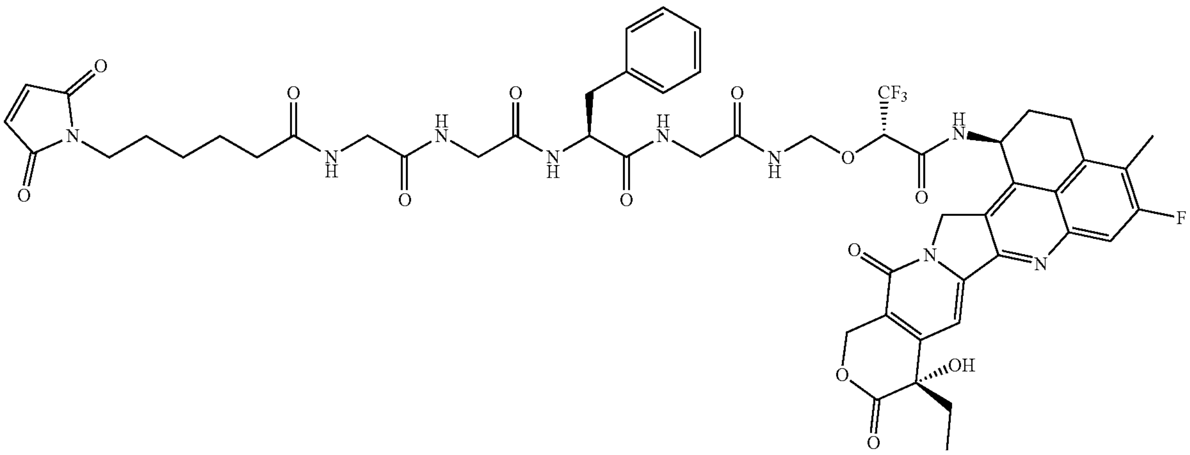
10-A
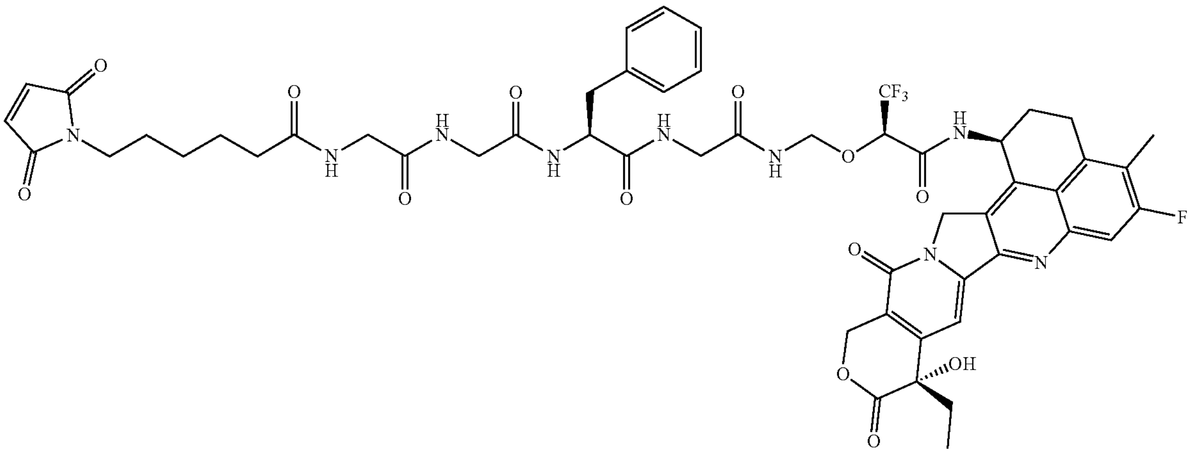
10-B Step 1

Benzyl 3,3,3-trifluoro-2-hydroxypropanoate 10a 3a (1.80 g, 12.5 mmol) was dissolved in 100 mL of acetonitrile, and then added with potassium carbonate (5.17 g, 37.5 mmol), benzyl bromide (4.48 mL, 37.5 mmol) and tetrabutylammonium iodide (231 mg, 0.63 mmol) successively. The reaction solution was heated to 60° C. and stirred for 5 hours. The reaction solution was cooled to room temperature and filtered. The filtrate was concentrated under reduced pressure, and the resulting residues were purified by silica gel column chromatography with developing solvent system C to obtain the title product 10a (980 mg, yield: 33.5%).

$^1H$ NMR (400 MHz, $CDCl_3$): δ 7.43-7.36 (m, 5H), 5.34 (s, 2H), 4.53 (s, 1H), 3.44 (s, 1H).

Step 2

Benzyl 1-(9H-fluoren-9-yl)-3,6-dioxo-10-(trifluoromethyl)-2,9-dioxa-4,7-diazaundecan-11-oate 10b 8b (63 mg, 0.17 mmol) and 10a (80 mg, 0.34 mmol) were added to a reaction flask, followed by the addition of 3 mL of tetrahydrofuran. The reaction solution was purged with argon three times and cooled to 0-5° C. in an ice-water bath. Potassium tert-butoxide (38 mg, 0.34 mmol) was added and the ice-water bath was removed. The reaction solution was warmed up to room temperature and stirred for 20 minutes. 10 mL ice water was added to the reaction solution, which was then extracted with ethyl acetate (20 mL×2) and chloroform (10 mL×5). The organic phases were combined and concentrated, and the resulting residues were dissolved in 2 mL of dioxane. 0.4 mL of water, sodium bicarbonate (19 mg, 0.23 mmol) and 9-fluorene methyl chloroformate (49 mg, 0.19 mmol) were added, and the reaction solution was stirred at room temperature for 1 hour. 20 mL of water was added, and the reaction solution was extracted with ethyl acetate (10 mL×3). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 10b (51 mg, yield: 55.3%).

MS m/z (ESI): 559.9 [M+18].

Step 3

1-(9H-Fluoren-9-yl)-3,6-dioxo-10-(trifluoromethyl)-2,9-dioxa-4,7-diazaundecan-11-oic acid 10c 10b (15 mg, 0.28 mmol) was dissolved in 3 mL of a mixed solvent of tetrahydrofuran and ethyl acetate (V:V=2:1), followed by the addition of palladium on carbon (15 mg, content: 10%). The reaction solution was purged with hydrogen three times and stirred at room temperature for 1 hour. The reaction solution was filtered through celite, and the filter cake was rinsed with tetrahydrofuran. The filtrate was concentrated to obtain the crude title product 10c (13 mg).

MS m/z (ESI): 452.9 [M+1].

Step 4

(9H-Fluoren-9-yl)methyl (2-((((3-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,1,1-trifluoro-3-oxopropan-2-yl)oxy)methyl)amino)-2-oxoethyl)carbamate 10d 1b (10 mg, 18.8 μmol) was added to a reaction flask, followed by the addition of 1 mL of N,N-dimethylformamide. The solution was purged with argon three times, and cooled to 0-5° C. in an ice-water bath. One drop of triethylamine, 10c (13 mg, 28.7 μmol) in 0.5 mL of N,N-dimethylformamide, and 4-(4,6-dimethoxy-1,3,5-triazin-2-yl)-4-methylmorpholinium chloride (11 mg, 39.7 μmol) were added, and the reaction solution was stirred in an ice bath for 30 minutes. 10 mL of water was added, and the reaction solution was extracted with ethyl acetate (10 mL×3). The organic phase were combined, washed with saturated sodium chloride solution (10 mL×2), dried over anhydrous sodium sulfate and filtered. The filtrate was concentrated under reduced pressure, and the resulting residues were purified by thin layer chromatography with developing solvent system B to obtain the title product 10d (16 mg, yield: 97.8%).

MS m/z (ESI): 870.0[M+1].

Step 5

2-((2-Aminoacetamido)methoxy)-N-((1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)-3,3,3-trifluoropropanamide 10e 10d (16 mg, 18.4 μmol) was dissolved in 0.6 mL of dichloromethane, followed by the addition of 0.3 mL of diethylamine. The reaction solution was stirred at room temperature for 2 hours. The reaction solution was concentrated under reduced pressure. 2 mL of toluene was added and the solution was concentrated under reduced pressure, which was repeated twice. 3 mL of n-hexane was added to the residue to pulp, and the supernatant was poured out after standing for a while to retain the solid, which was repeated three times. The solid residues were concentrated under reduced pressure by an oil pump until dryness to obtain the crude title product 10e (12 mg), which was used directly in the next step without purification.

MS m/z (ESI): 647.9 [M+1].

Step 6

N-((2S,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 10-A N-((2R,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 10-B The crude compound 10e (12 mg, 18.5 μmol) was dissolved in 1.0 mL of N,N-dimethylformamide. The solution was purged with argon three times, and cooled to 0-5° C. in an ice-water bath. 8g (14 mg, 29.6 μmol) in 0.3 mL of N,N-dimethylformamide, and 4-(4,6-dimethoxy-1,3,5-triazin-2-yl)-4-methylmorpholinium chloride (15 mg, 54.2 μmol) were added, and the reaction solution was stirred in an ice bath for 30 minutes. The ice bath was removed, and the reaction solution was warmed up to room temperature and stirred for 1 hour to obtain compound 10. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title products (2.7 mg, 2.6 mg).

MS m/z (ESI): 1102.0 [M+1].

Compound with single configuration (having shorter retention time):

UPLC analysis: retention time: 1.18 minutes, purity: 91% (column: ACQUITY UPLC BEHC18 1.7 μm 2.1*50 mm, mobile phase: A-water (5 mmol $NH_4OAc$), B-acetonitrile).

$^1H$ NMR (400 MHz, DMSO-$d_6$): δ 8.97 (d, 1H), 8.85-8.76 (m, 1H), 8.37-8.27 (m, 1H), 8.12-8.02 (m, 1H), 8.02-7.95 (m, 1H), 7.80 (d, 1H), 7.31 (s, 1H), 7.26-7.10 (m, 4H), 6.99 (s, 1H), 6.66 (br, 1H), 6.52 (s, 1H), 5.65-5.54 (m, 1H), 5.41 (s, 1H), 5.37-5.25 (m, 3H), 5.23-5.13 (m, 1H), 4.81-4.68 (m, 2H), 4.51-4.41 (m, 1H), 3.78-3.45 (m, 6H), 3.21-3.13 (m, 1H), 3.02-2.93 (m, 1H), 2.77-2.63 (m, 2H), 2.45-2.29 (m, 3H), 2.24-2.05 (m, 3H), 2.04-1.93 (m, 5H), 1.90-1.75 (m, 2H), 1.52-1.38 (m, 4H), 0.90-0.78 (m, 5H).

Compound with single configuration (having longer retention time):

UPLC analysis: retention time: 1.23 minutes, purity: 90% (column: ACQUITY UPLC BEHC18 1.7 μm 2.1*50 mm, mobile phase: A-water (5 mmol $NH_4OAc$), B-acetonitrile).

$^1H$ NMR (400 MHz, DMSO-$d_6$): δ 9.05 (d, 1H), 8.97-8.88 (m, 1H), 8.35-8.27 (m, 1H), 8.11-8.03 (m, 1H), 8.02-7.95 (m, 1H), 7.80 (d, 1H), 7.34 (s, 1H), 7.29-7.13 (m, 4H), 6.99 (s, 1H), 6.66 (br, 1H), 6.54 (s, 1H), 5.64-5.55 (m, 1H), 5.43 (s, 1H), 5.36-5.20 (m, 3H), 4.92-4.85 (m, 1H), 4.82-4.72 (m, 2H), 4.52-4.42 (m, 1H), 3.77-3.48 (m, 6H), 3.21-3.14 (m, 1H), 3.03-2.95 (m, 1H), 2.79-2.65 (m, 2H), 2.47-2.28 (m, 3H), 2.25-2.05 (m, 3H), 2.05-1.94 (m, 5H), 1.91-1.76 (m, 2H), 1.52-1.37 (m, 4H), 0.92-0.77 (m, 5H).

Example 11

1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 11

11

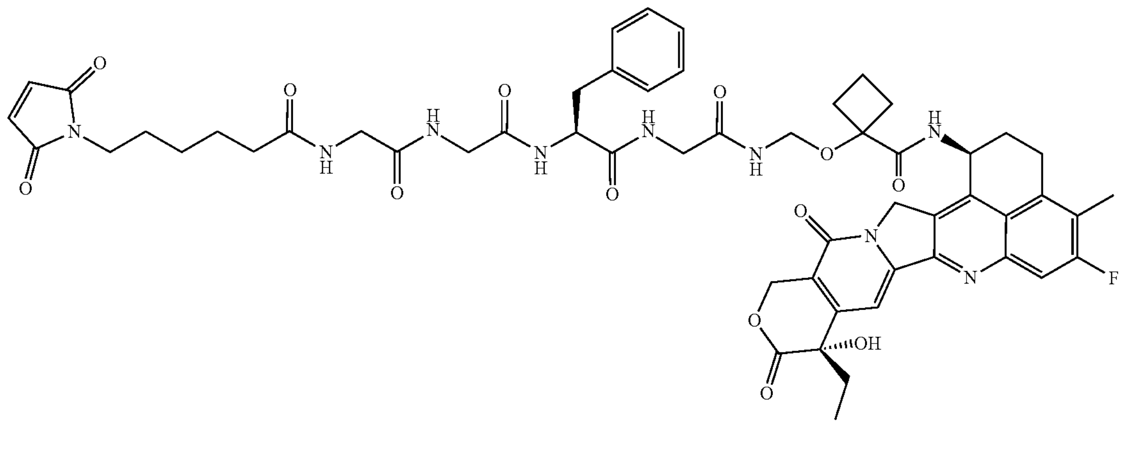

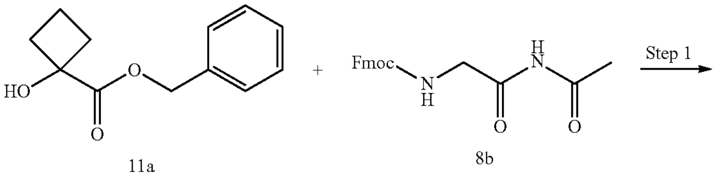

11a

8b

-continued
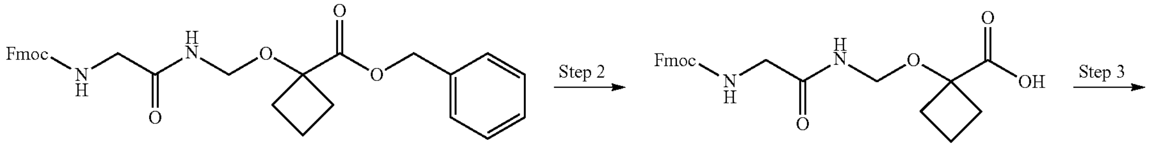
11b 11c
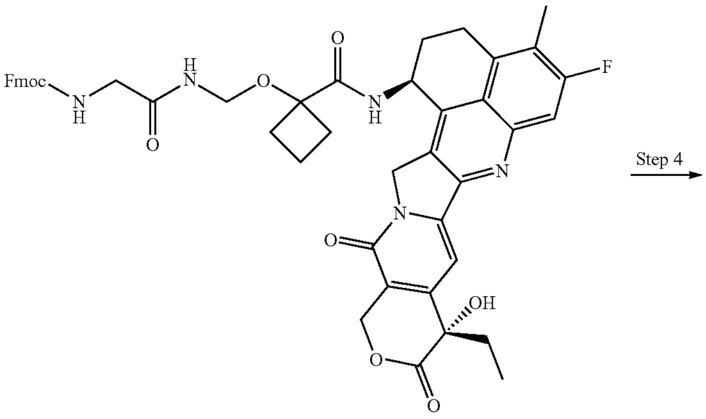
11d
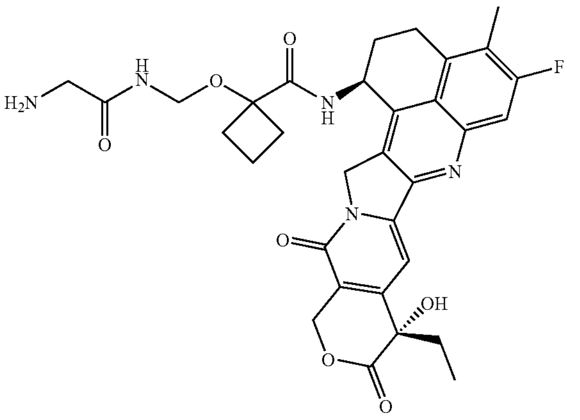
+
11e
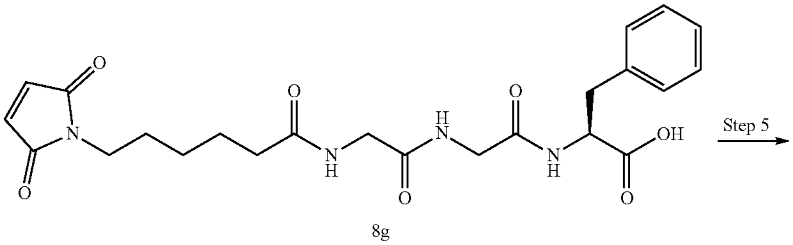
8g

-continued

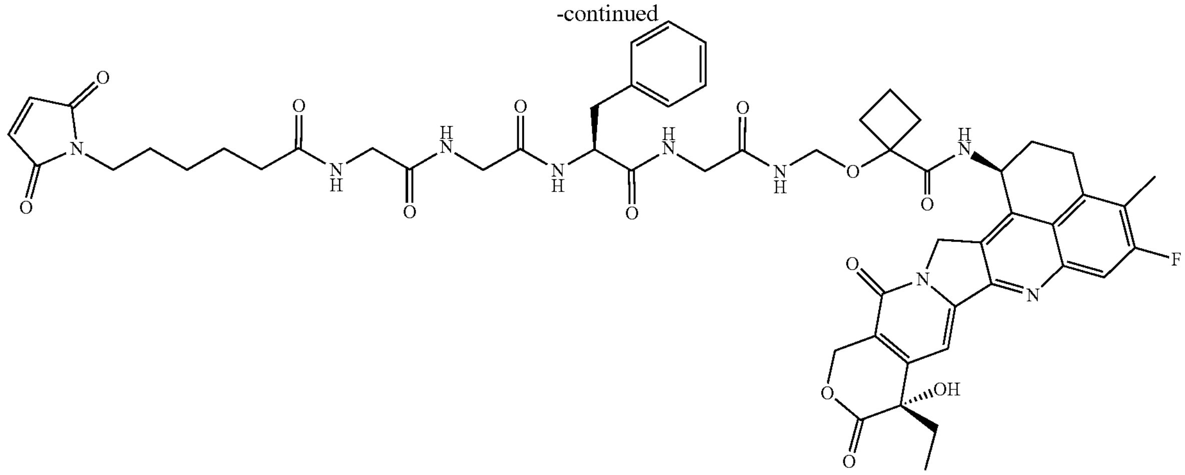

11

Step 1

Benzyl 1-((2-((((9H-fluoren-9-yl)methoxy)carbonyl)amino)acetamido)methoxy)cyclobutane-1-carboxylate 11b Benzyl 1-hydroxycyclobutane-carboxylate 11a (167 mg, 0.81 mmol, prepared according to the known method disclosed in "*Journal of Medicinal Chemistry,* 2013, vol. 56, #13, p. 5541-5552") and 8b (150 mg, 0.41 mmol) were added to a reaction flask, followed by the addition of 5 mL of tetrahydrofuran. The reaction solution was purged with argon three times and cooled to 0-5° C. in an ice-water bath, followed by the addition of potassium tert-butoxide (92 mg, 0.82 mmol). The ice-water bath was removed, and the reaction solution was warmed up to room temperature and stirred for 10 minutes. 20 mL ice water was added to the reaction solution, which was then extracted with ethyl acetate (5 mL×2) and chloroform (5 mL×5). The organic phases were combined and concentrated, and the resulting residues were dissolved in 3 mL of dioxane. 0.6 mL of water, sodium bicarbonate (41 mg, 0.48 mmol) and 9-fluorene methyl chloroformate (105 mg, 0.41 mmol) were added, and the reaction solution was stirred at room temperature for 1 hour. 20 mL of water was added, and the reaction solution was extracted with ethyl acetate (8 mL×3). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 11b (37 mg, yield: 17.6%).

MS m/z (ESI): 514.6 [M+1].

Step 2

1-((2-((((9H-Fluoren-9-yl)methoxy)carbonyl)amino)acetamido)methoxy)cyclobutane-1-carboxylic acid 11c 11b (37 mg, 71.9 μmol) was dissolved in 3 mL of a mixed solvent of tetrahydrofuran and ethyl acetate (V:V=2:1), followed by the addition of palladium on carbon (15 mg, content: 10%). The reaction solution was purged with hydrogen three times and stirred at room temperature for 2 hours. The reaction solution was filtered through celite, and the filter cake was rinsed with tetrahydrofuran. The filtrate was concentrated to obtain the title product 11c (35 mg, yield: 82%), which was used directly in the next step.

Step 3

(9H-Fluoren-9-yl)methyl (2-(((1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclobutoxy)methyl)amino)-2-oxoethyl)carbamate 11d 1b (10 mg, 0.018 mmol) was added to a reaction flask, followed by the addition of 1 mL of N,N-dimethylformamide. The solution was purged with argon three times, and cooled to 0-5° C. in an ice-water bath. One drop of triethylamine, 11c (13 mg, 0.031 mmol) in 0.5 mL of N,N-dimethylformamide, and 4-(4,6-dimethoxy-1,3,5-triazin-2-yl)-4-methylmorpholinium chloride (25 mg, 0.091 mmol) were added, and the reaction solution was stirred in an ice bath for 40 minutes. 8 mL of water was added, and the reaction solution was extracted with ethyl acetate (5 mL×3). The organic phase was washed with saturated sodium chloride solution (8 mL), dried over anhydrous sodium sulfate and filtered. The filtrate was concentrated under reduced pressure, and the resulting residues were purified by thin layer chromatography with developing solvent system A to obtain the title product 11d (19 mg, yield: 73.9%).

MS m/z (ESI): 842.3 [M+1].

Step 4

1-((2-Aminoacetamido)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 11e 11d (19 mg, 22.6 μmol) was dissolved in 2 mL of dichloromethane, followed by the addition of 1 mL of diethylamine. The reaction solution was stirred at room temperature for 1.5 hours. The reaction solution was concentrated under reduced pressure. 1 mL of toluene was added and the solution was concentrated under reduced pressure, which was repeated twice. 4 mL of n-hexane was added to pulp, and the upper layer of hexane was poured, which was repeated three times. The solution was concentrated under reduced pressure to obtain the crude title product 11e (15 mg), which was used directly in the next step without purification.

Step 5

1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 11

The crude compound 11e (2 mg, 3.22 μmol) was dissolved in 0.5 mL of N,N-dimethylformamide. The solution was purged with argon three times, and cooled to 0-5° C. in an ice-water bath. 8g (1.5 mg, 3.17 μmol) in 0.3 mL of N,N-dimethylformamide, and 4-(4,6-dimethoxy-1,3,5-triazin-2-yl)-4-methylmorpholinium chloride (2.7 mg, 9.67 μmol) were added, and the reaction solution was stirred at room temperature for 30 minutes. The reaction solution was concentrated to dryness through rotary evaporation by an oil pump to remove DMF. The residues were dissolved in DCM, and purified by thin layer chromatography twice (developing solvent polarity: DCM/MeOH=10/1) to obtain the title product 11 (1 mg, yield: 28.8%).

MS m/z (ESI): 1073.6 [M+1].

$^1$H NMR (400 MHz, $CDCl_3$): δ 8.70-8.60 (m, 1H), 8.28-8.19 (m, 1H), 8.13-7.91 (m, 3H), 7.79-7.71 (d, 1H), 7.29 (s, 1H), 7.25-7.09 (m, 4H), 6.98 (s, 1H), 6.71-6.62 (m, 1H), 6.55-6.47 (m, 1H), 5.64-5.54 (m, 2H), 5.40 (s, 1H), 5.35-5.27 (t, 2H), 5.17-5.10 (m, 2H), 4.60-4.51 (m, 1H), 4.51-4.35 (m, 2H), 3.93-3.78 (m, 3H), 3.71-3.59 (m, 3H), 3.01-2.88 (m, 3H), 2.70-2.64 (m, 2H), 2.44-2.30 (m, 3H), 2.28-2.14 (m, 3H), 2.11-1.92 (m, 6H), 1.90-1.76 (m, 3H), 1.51-1.39 (m, 4H), 0.92-0.75 (m, 6H).

Example 12

(S)-3-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxypropanamide 12-A (R)-3-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxypropanamide 12-B

12-A

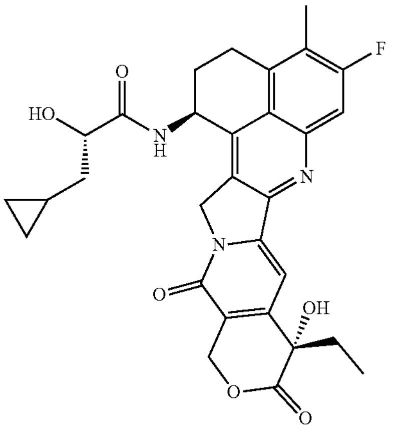

12-B

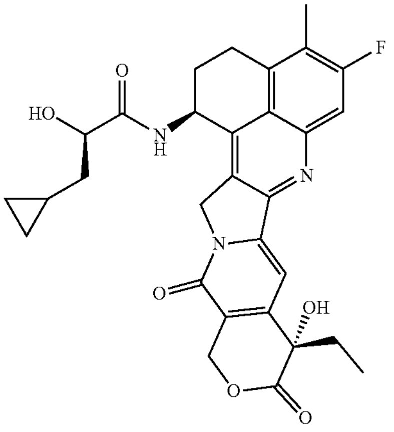

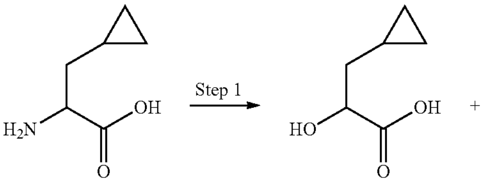

12a

12b

-continued

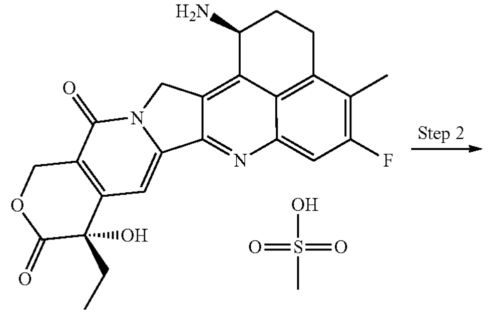

1b

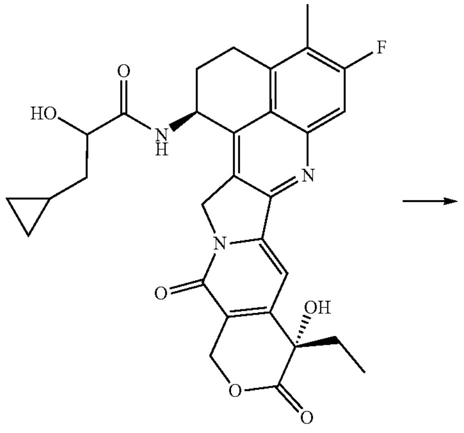

12

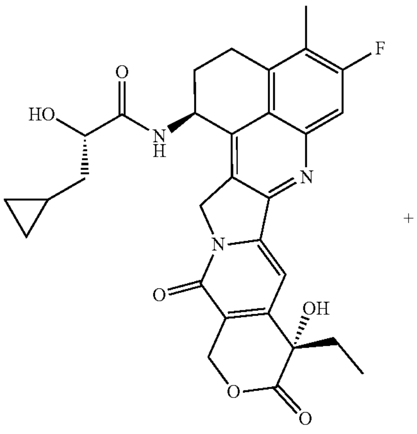

12-A

+

-continued

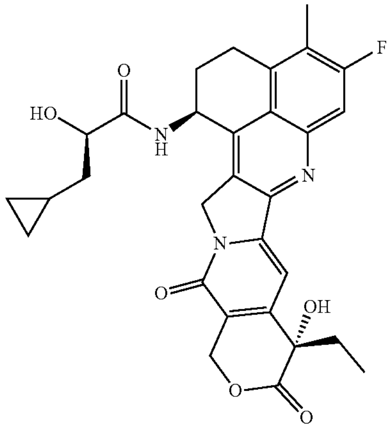

12-B

Step 1

3-Cyclopropyl-2-hydroxypropanoic acid 12b 12a (0.5 g, 3.87 mmol, supplier: Adamas) was dissolved in 35 mL of a mixed solvent of water and acetic acid (V:V=4:1), and the solution was cooled to 0-5° C. in an ice-water bath. 2M aqueous solution of sodium nitrite (0.53 g, 7.74 mmol) was added dropwise, and the reaction solution was warmed up to room temperature and stirred for 3 hours. Solid sodium chloride was added to the reaction solution to saturate the aqueous phase. The solution was extracted with ethyl acetate (8 mL×8), dried over anhydrous sodium sulfate, and filtered. The filtrate was concentrated to obtain the title product 12b (0.45 g, yield: 89.3%).

Step 2

(S)-3-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxypropanamide 12-A (R)-3-Cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxypropanamide 12-B 1.5 mL of ethanol and 1.5 mL of N,N-dimethylformamide were added to 1b (45 mg, 0.085 mmol). The solution was purged with argon three times. 0.1 mL of N-methylmorpholine was added dropwise, and the reaction solution was stirred until clear. 12b (90 mg, 0.691 mmol), 1-hydroxybenzotriazole (34 mg, 0.251 mmol) and 1-(3-dimethylaminopropyl)-3-ethylcarbodiimide hydrochloride (49 mg, 0.256 mmol) were added successively to the reaction solution. After completion of the addition, the reaction solution was stirred at room temperature for 3 hours. The reaction solution was concentrated under reduced pressure, and the resulting crude compound 12 was purified by high performance liquid chromatography (separation conditions: column: Sharpsil-T C18 5 μm 21.2*250 mm; mobile phase: A-water (10 mmol $NH_4OAc$), B-acetonitrile, gradient elution, flow rate: 18 mL/min) to obtain the title product (7 mg, 15 mg).

MS m/z (ESI): 547.9 [M+1].

Compound with single configuration (having shorter retention time):

UPLC analysis: retention time: 1.345 minutes, purity: 72% (column: ZORBAX Ecliphase Plus C18 1.8 μm 2.1*50 mm, mobile phase: A-water (5 mmol $NH_4OAc$), B-acetonitrile).

$^1H$ NMR (400 MHz, DMSO-$d_6$): δ 8.42 (d, 1H), 7.78 (d, 1H), 7.30 (s, 1H), 6.51 (s, 1H), 5.60-5.50 (m, 2H), 5.42 (s, 1H), 5.19 (q, 2H), 4.02-4.00 (m, 1H), 3.21-3.11 (m, 2H), 2.39 (s, 3H), 2.21-2.07 (m, 2H), 2.05-1.95 (m, 1H), 1.92-1.68 (m, 4H), 1.53-1.41 (m, 1H), 0.87 (t, 3H), 0.48-0.34 (m, 2H), 0.14-0.01 (m, 2H).

Compound with single configuration (having longer retention time):

UPLC analysis: retention time: 1.399 minutes, purity: 88% (column: ZORBAX Ecliphase Plus C18 1.8 μm 2.1*50 mm, mobile phase: A-water (5 mmol $NH_4OAc$), B-acetonitrile).

$^1H$ NMR (400 MHz, DMSO-$d_6$): δ 8.36 (d, 1H), 7.77 (d, 1H), 7.31 (s, 1H), 6.51 (s, 1H), 5.58-5.51 (m, 1H), 5.48 (d, 1H), 5.42 (s, 1H), 5.20 (q, 2H), 4.09-4.02 (m, 1H), 3.22-3.11 (m, 2H), 2.39 (s, 3H), 2.27-2.06 (m, 2H), 2.05-1.95 (m, 1H), 1.93-1.81 (m, 2H), 1.65-1.43 (m, 2H), 1.32-1.21 (m, 1H), 0.87 (t, 3H), 0.48-0.33 (m, 2H), 0.14-0.01 (m, 2H).

Example 13 (Reference Example)

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide

13

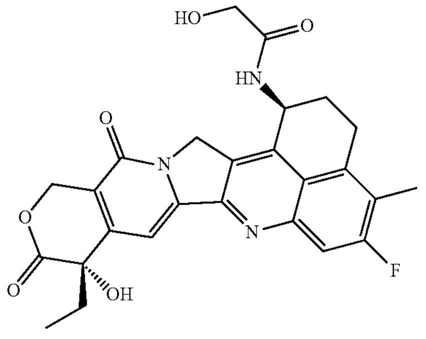

The title compound 13 was prepared according to the method disclosed in Example 76 on page 147 of the description of the patent application EP2907824A1.

Example 14

N-((2R,10S)-10-Benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 14-A N-((2S,10S)-10-Benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 14-B

14-A

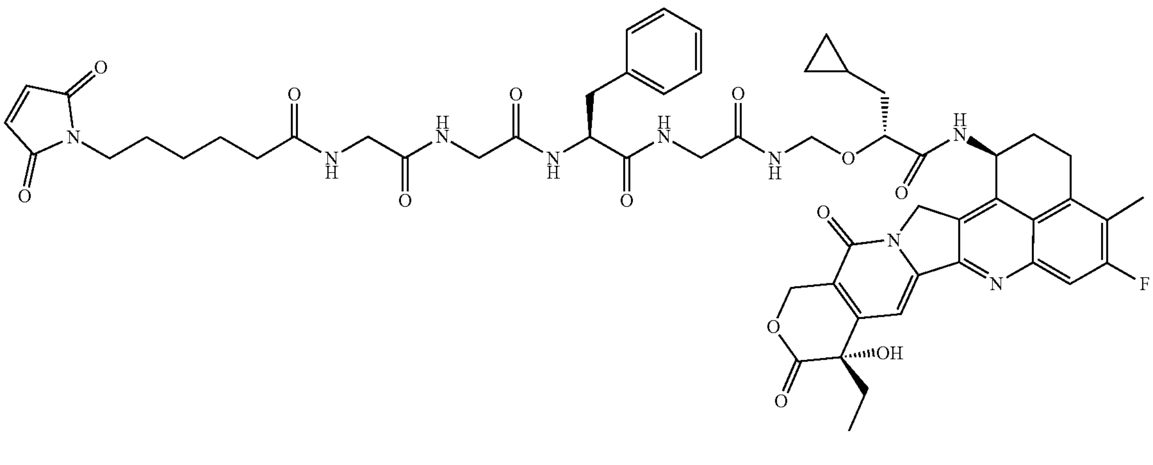

-continued
14-B
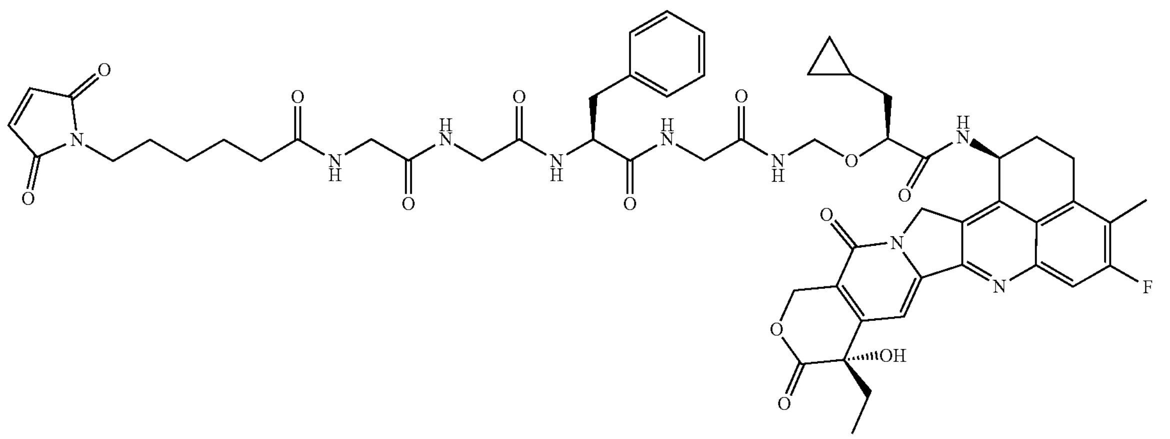
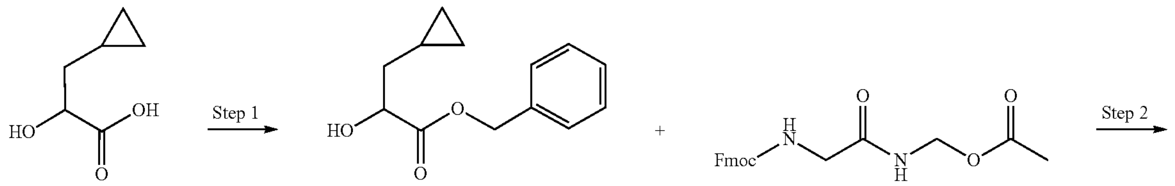
12b 14a 8b
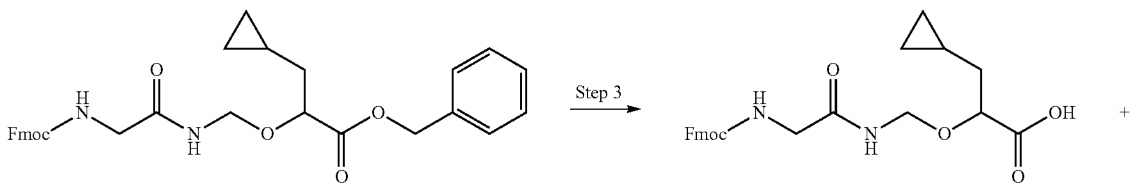
14b 14c
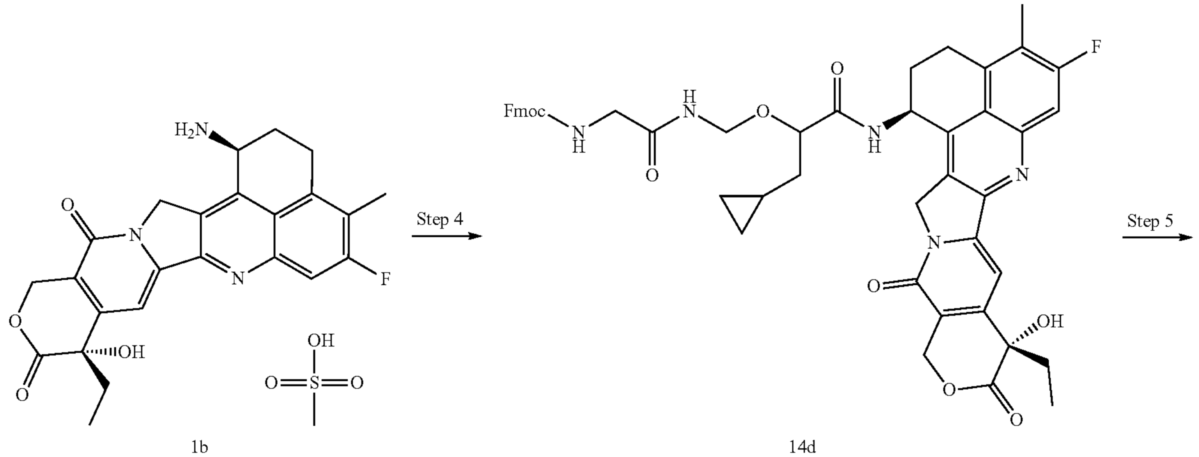
1b 14d -continued
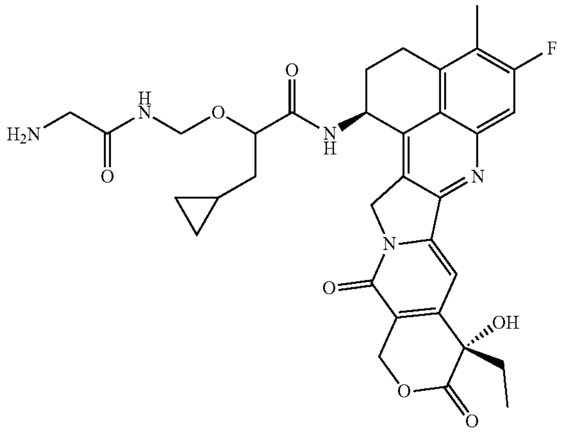
14e
+
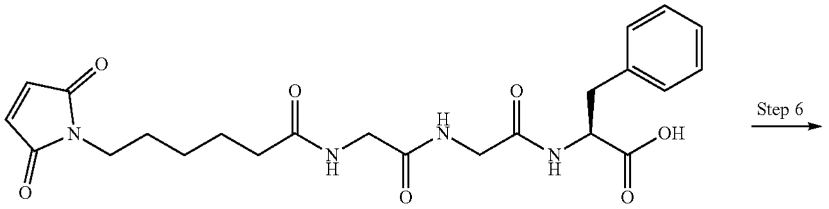
8g
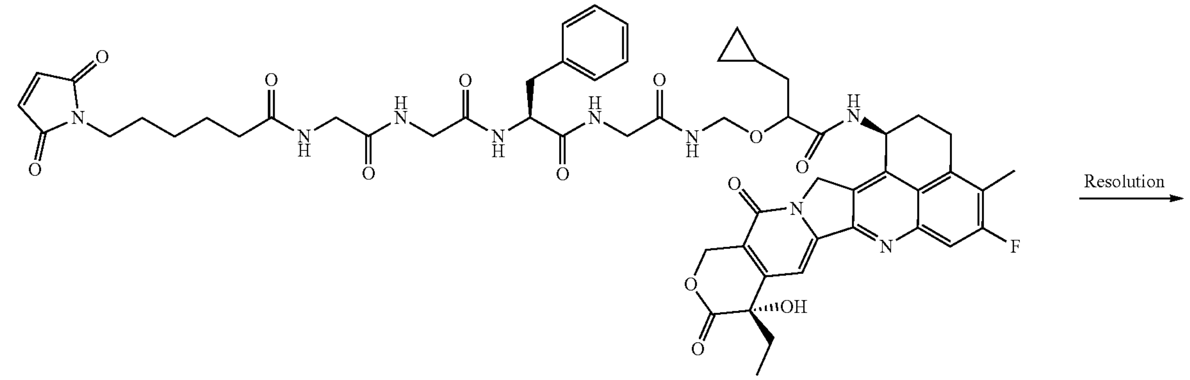
14
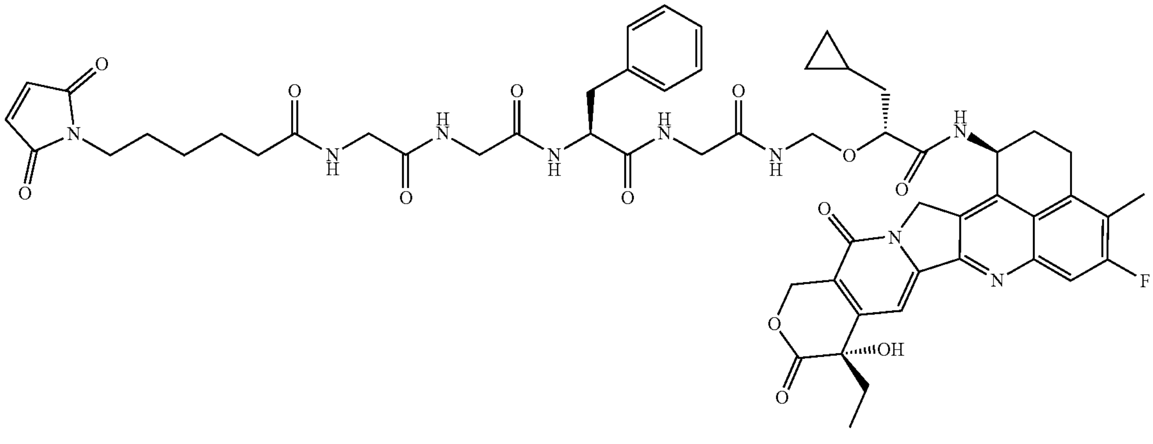
+
14-A -continued

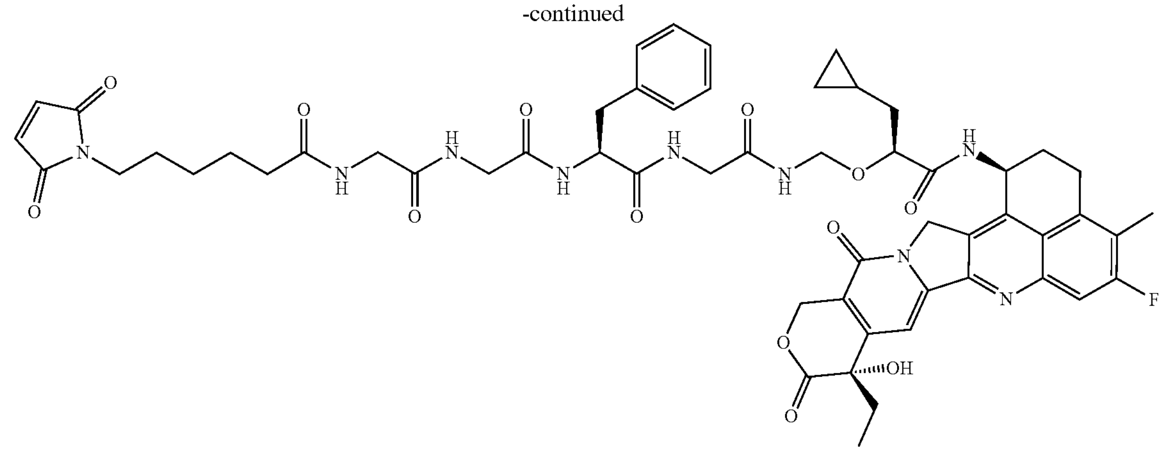

14-B

Step 1

Benzyl 3-cyclopropyl-2-hydroxypropanoate 14a 12b (200 mg, 1.54 mmol) was dissolved in 20 mL of acetonitrile, and then added with potassium carbonate (1.06 g, 7.68 mmol), benzyl bromide (0.16 mL, 1.34 mmol) and tetrabutylammonium iodide (28 mg, 0.07 mmol) successively. The reaction solution was stirred at room temperature for 48 hours, and filtered through celite. The filter cake was rinsed with ethyl acetate (10 ml), and the filtrates were combined and concentrated under reduced pressure. The resulting residues were purified by silica gel column chromatography with developing solvent system C to obtain the title product 14a (140 mg, yield: 41.3%).

Step 2

Benzyl 10-(cyclopropylmethyl)-1-(9H-fluoren-9-yl)-3,6-dioxo-2,9-dioxa-4,7-diazaundecan-11-oate 14b 14a (94 mg, 0.427 mmol) and 8b (130 mg, 0.353 mmol) were added to a reaction flask, followed by the addition of 10 mL of tetrahydrofuran. The reaction solution was purged with argon three times and cooled to 0-5° C. in an ice-water bath, followed by the addition of potassium tert-butoxide (79 mg, 0.704 mmol). The ice-water bath was removed, and the reaction solution was warmed up to room temperature and stirred for 10 minutes. 20 mL ice water was added to the reaction solution, which was then extracted with ethyl acetate (10 mL×4). The organic phase was washed with saturated sodium chloride solution (20 mL), dried over anhydrous sodium sulfate, and filtered. The filtrate was concentrated under reduced pressure. The resulting residues were purified by silica gel column chromatography with developing solvent system C to obtain the title product 14b (50 mg, yield: 26.8%).

MS m/z (ESI): 529.2 [M+1].

Step 3

10-(Cyclopropylmethyl)-1-(9H-fluoren-9-yl)-3,6-dioxo-2,9-dioxa-4,7-diazaundecan-11-oic acid 14c 14b (27 mg, 0.051 mmol) was dissolved in 3 mL of ethyl acetate, followed by the addition of palladium on carbon (7 mg, content: 10%, dry). The reaction solution was purged with hydrogen three times and stirred at room temperature for 1 hour. The reaction solution was filtered through celite, and the filter cake was rinsed with ethyl acetate. The filtrate was concentrated to obtain the crude title product 14c (23 mg), which was used directly in the next step without purification.

MS m/z (ESI): 439.1 [M+1].

Step 4

(9H-Fluoren-9-yl)methyl (2-((((3-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1-oxopropan-2-yl)oxy)methyl)amino)-2-oxoethyl)carbamate 14d 1b (22 mg, 42.38 μmol) was added to a reaction flask, followed by the addition of 3 mL of N,N-dimethylformamide. The solution was purged with argon three times, and cooled to 0-5° C. in an ice-water bath. Triethylamine (4.3 mg, 42.49 μmol) was added dropwise, and then added with crude compound 14c (23 mg, 51.1 μmol) and 4-(4,6-dimethoxy-1,3,5-triazin-2-yl)-4-methylmorpholinium chloride (17.6 mg, 63.6 μmol). The reaction solution was stirred in an ice bath for 40 minutes. 15 mL of water was added, and the reaction solution was extracted with ethyl acetate (8 mL×3). The organic phases were combined. The organic phase was washed with saturated sodium chloride solution (15 mL), dried over anhydrous sodium sulfate and filtered. The filtrate was concentrated under reduced pressure. The resulting residues were purified by thin layer chromatography with developing solvent system B to obtain the title product 14d (29 mg, yield: 79.9%).

MS m/z (ESI): 856.1[M+1].

Step 5

2-((2-Aminoacetamido)methoxy)-3-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)propanamide 14e 14d (29 mg, 33.9 μmol) was dissolved in 0.8 mL of dichloromethane, followed by the addition of 0.4 mL of diethylamine. The reaction solution was stirred at room temperature for 1.5 hours. The reaction solution was concentrated under reduced pressure. 1 mL of toluene was added and the solution was concentrated under reduced pressure, which was repeated twice. 3 mL of n-hexane was added to the residues to pulp, and the supernatant was poured out after standing for a while, which was repeated three times. The residues were concentrated under reduced pressure by an oil pump until dryness to obtain the crude title product 14e (22 mg), which was used directly in the next step without purification.

MS m/z (ESI): 634.1[M+1].

Step 6

N-((2R,10S)-10-Benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 14-A N-((2S,10S)-10-Benzyl-2-(cyclopropylmethyl)-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 14-B The crude compound 14e (22 mg, 33.9 μmol) was dissolved in 2.5 mL of N,N-dimethylformamide. The solution was purged with argon three times, and cooled to 0-5° C. in an ice-water bath. 8g (24 mg, 50.8 μmol) and 4-(4,6-dimethoxy-1,3,5-triazin-2-yl)-4-methylmorpholinium chloride (14 mg, 50.6 μmol) were added successively. The ice-water bath was removed, and the reaction solution was warmed up to room temperature and stirred for 1 hour to obtain compound 14. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min) to obtain the title products (2 mg, 2 mg).

MS m/z (ESI): 1088.4 [M+1].

Compound with single configuration (having shorter retention time):

UPLC analysis: retention time: 1.18 minutes, purity: 88% (column: ACQUITY UPLC BEHC18 1.7 μm 2.1*50 mm, mobile phase: A-water (5 mmol $NH_4OAc$), B-acetonitrile).

Compound with single configuration (having longer retention time):

UPLC analysis: retention time: 1.23 minutes, purity: 96% (column: ACQUITY UPLC BEHC18 1.7 μm 2.1*50 mm, mobile phase: A-water (5 mmol $NH_4OAc$), B-acetonitrile).

Example 15

1-((S)-9-Benzyl-22-(2,5-dioxo-2,5-dihydro-1H-pyrrol-1-yl)-5,8,11,14,17-pentaoxo-2-oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3,4':6,7]indolizino[1,2-b]quinolin-1-yl)cyclopropane-1-carboxamide 15

15

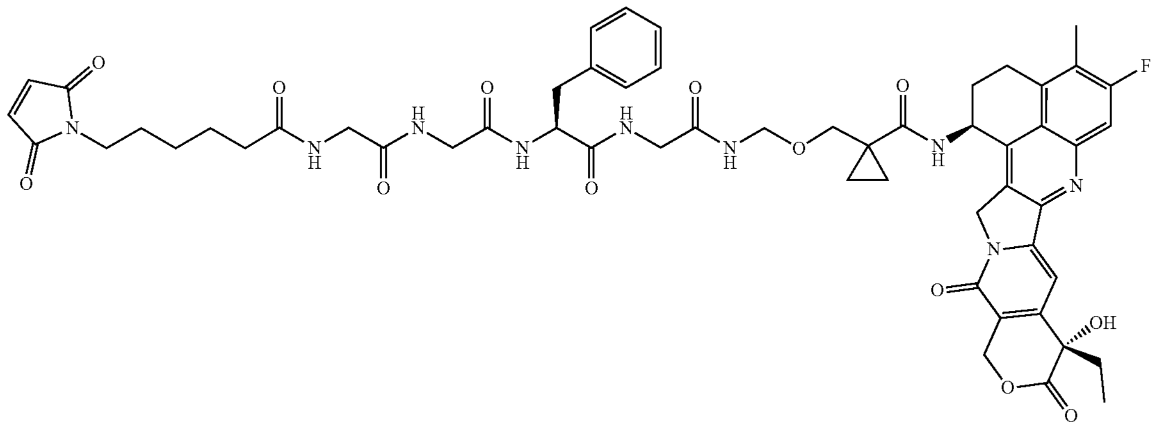

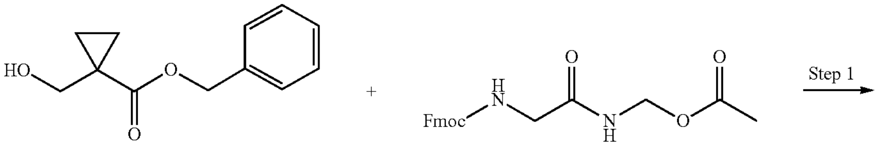

15a 8b

-continued
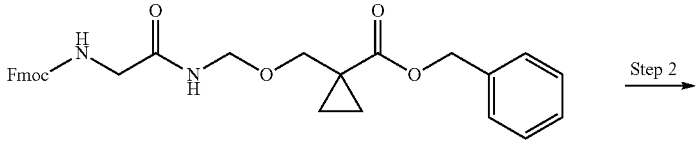
15b
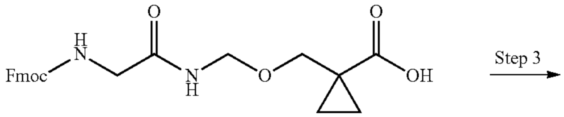
15c
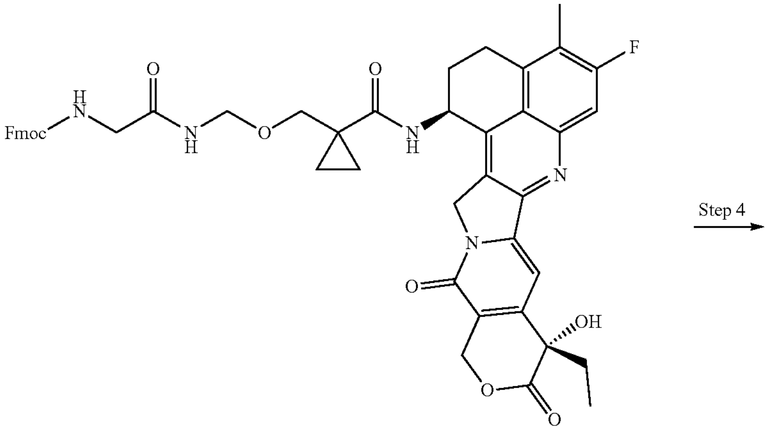
15d
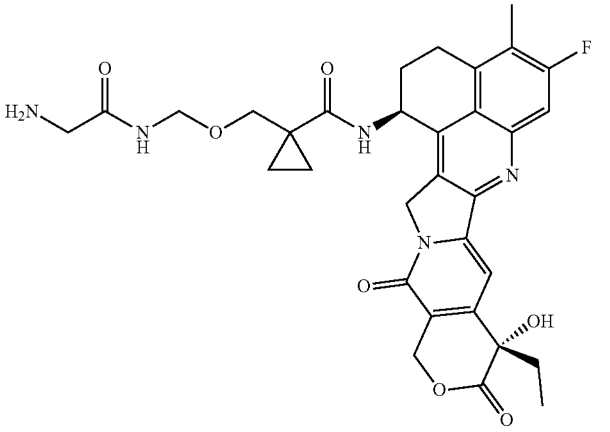
15e
+
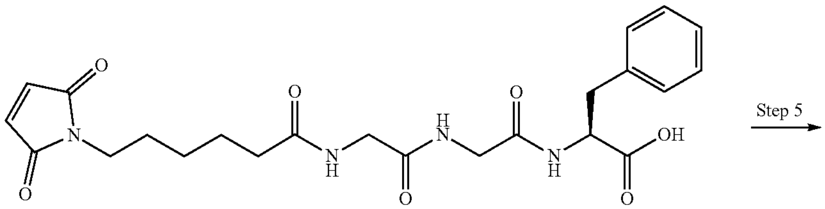
8g -continued

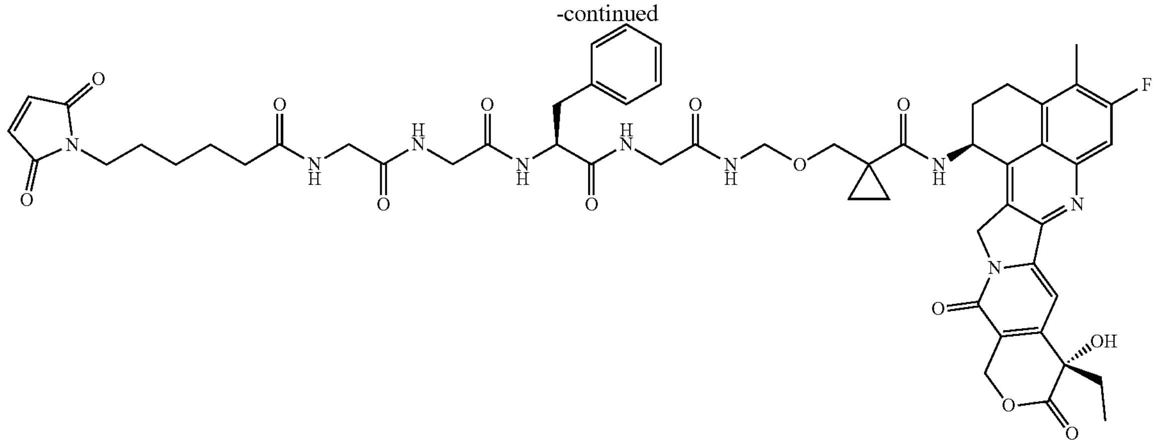

Step 1

Benzyl 1-(10-(9H-fluoren-9-yl)-5,8-dioxo-2,9-dioxa-4,7-diazadecyl)cyclopropane-1-carboxylate 15b 8b (500 mg, 1.35 mmol) was added to a reaction flask, followed by the addition of 6 mL of tetrahydrofuran. Benzyl 1-hydroxymethylcyclopropane-1-carboxylate 15a (233 mg, 1.13 mmol; prepared according to the method disclosed in Example 22-2 on page 262 of the description of the patent application "EP2862856A1") was added to the reaction flask. The reaction solution was purged with argon three times and cooled to 0-5° C. in an ice-water bath, followed by the addition of sodium hydride (54 mg, 1.35 mmol). The ice-water bath was removed, and the reaction solution was warmed up to room temperature and stirred for 40 minutes. The reaction solution was cooled to 0° C., to which 20 mL ice water was added. The solution was extracted with ethyl acetate (5 mL×2) and chloroform (5 mL×5). The organic phases were combined, washed with saturated sodium chloride solution (20 mL), dried over anhydrous sodium sulfate and filtered. The filtrate was concentrated under reduced pressure, and the resulting residues were purified by silica gel column chromatography with developing solvent system B to obtain the title product 15b (15 mg, yield: 2.5%).

MS m/z (ESI): 515.2 [M+1].

Step 2

1-(10-(9H-Fluoren-9-yl)-5,8-dioxo-2,9-dioxa-4,7-diazadecyl)cyclopropane-1-carboxylic acid 15c 15b (15 mg, 0.029 mmol) was dissolved in 2 mL of ethyl acetate, followed by the addition of palladium on carbon (3 mg, content: 10%, dry). The reaction solution was purged with hydrogen three times and stirred at room temperature for 4.5 hours. The reaction solution was filtered through celite, and the filter cake was rinsed with ethyl acetate. The filtrate was concentrated to obtain the title product 15c (11 mg, yield: 89%).

MS m/z (ESI): 425.2 [M+1].

Step 3

(9H-Fluoren-9-yl)methyl (2-((((1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclopropyl)methoxy)methyl)amino)-2-oxoethyl)carbamate 15d 1b (10 mg, 0.021 mmol) was added to a reaction flask, followed by the addition of 1 mL of N,N-dimethylformamide. The solution was purged with argon three times, and cooled to 0-5° C. in an ice-water bath. One drop of triethylamine, 15c (11 mg, 0.026 mmol) and 4-(4,6-dimethoxy-1,3,5-triazin-2-yl)-4-methylmorpholinium chloride (10.7 mg, 0.039 mmol) were added. After completion of the addition, the reaction solution was stirred at room temperature for 60 minutes. 10 mL of water was added, and the reaction solution was extracted with ethyl acetate (5 mL×3). The organic phase was washed with saturated sodium chloride solution (10 mL), dried over anhydrous sodium sulfate and filtered. The filtrate was concentrated under reduced pressure, and the resulting residues were purified by thin layer chromatography with developing solvent system B to obtain the title product 15d (19 mg, yield: 87.0%).

MS m/z (ESI): 842.2 [M+1].

Step 4

1-(((2-Aminoacetamido)methoxy)methyl)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 15e 15d (19 mg, 22.56 μmol) was dissolved in 2 mL of dichloromethane, followed by the addition of 1 mL of diethylamine. The reaction solution was stirred at room temperature for 1.5 hours. The reaction solution was concentrated under reduced pressure at 0° C. 1 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 15e (13.9 mg), which was used directly in the next step without purification.

MS m/z (ESI): 620.1 [M+1].

Step 5

1-((S)-9-Benzyl-22-(2,5-dioxo-2,5-dihydro-1H-pyrrol-1-yl)-5,8,11,14,17-pentaoxo-2-oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3,4':6,7]indolizino[1,2-b]quinolin-1-yl)cyclopropane-1-carboxamide 15

The crude compound 15e (13.9 mg, 22.4 μmol) was dissolved in 1 mL of N,N-dimethylformamide. The solution was purged with argon three times, and cooled to 0-5° C. in an ice-water bath. 8g (15.8 mg, 33.4 μmol) and 4-(4,6-dimethoxy-1,3,5-triazin-2-yl)-4-methylmorpholinium chloride (9.3 mg, 33.6 μmol) were added. The reaction solution was warmed up to room temperature and stirred for 60 minutes. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product 15 (2.5 mg, yield: 10.3%).

MS m/z (ESI): 1074.2 [M+1].

$^1$H NMR (400 MHz, DMSO-$d_6$): δ 8.51-8.37 (m, 1H), 8.22 (t, 1H), 8.14-8.02 (m, 2H), 8.011-7.94 (m, 1H), 7.82-7.73 (m, 1H), 7.29 (s, 1H), 7.26-7.10 (m, 3H), 6.98 (s, 1H), 6.53-6.47 (m, 1H), 5.62-5.50 (m, 1H), 5.45-5.36 (m, 1H), 5.35-5.23 (m, 2H), 5.13-5.02 (m, 2H), 4.61-4.50 (m, 2H), 4.42-4.28 (m, 2H), 3.76-3.61 (m, 3H), 3.60-3.45 (m, 3H), 3.27-3.23 (m, 1H), 3.20-2.81 (m, 7H), 2.75-2.61 (m, 3H), 241-2.28 (m, 3H), 2.23-2.13 (m, 2H), 2.11-2.01 (m, 1H), 2.03-1.94 (m, 1H), 1.90 (s, 1H), 1.87-1.74 (m, 2H), 1.53-1.36 (m, 3H), 1.29-1.08 (m, 4H), 0.90-0.68 (m, 4H).

Example 16

1-((S)-9-Benzyl-22-(2,5-dioxo-2,5-dihydro-1H-pyrrol-1-yl)-5,8,11,14,17-pentaoxo-2-oxa-4,7,10,13,16-pentaazadocosyl)-N-(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 16

16

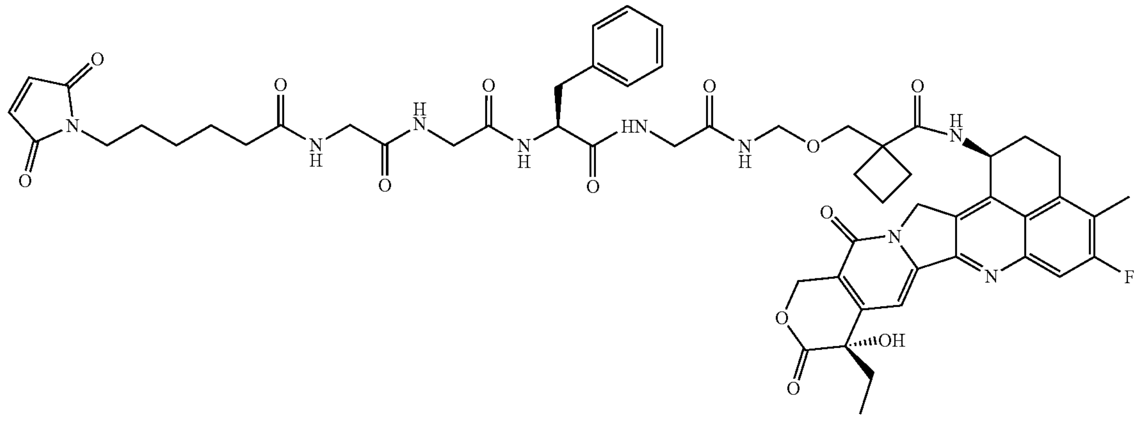

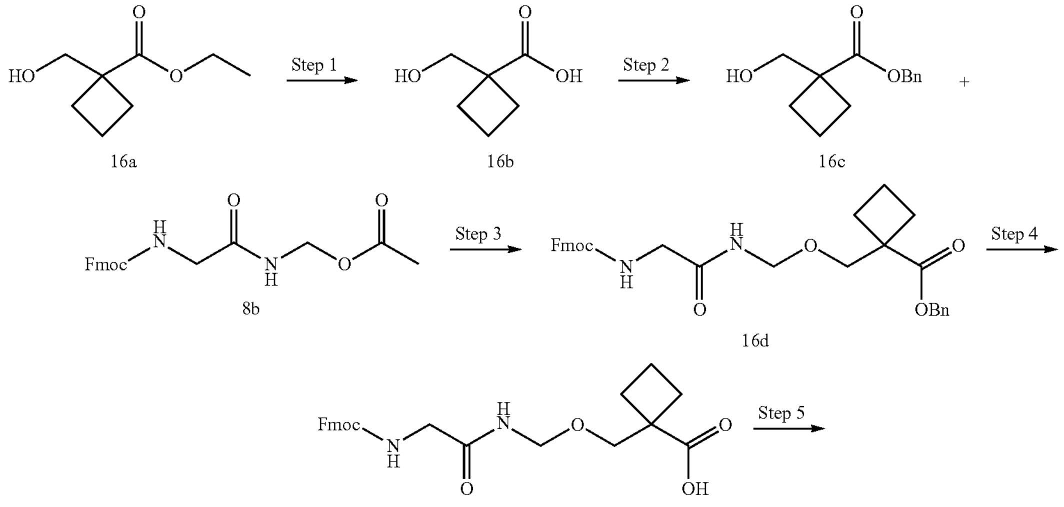

16a 16b 16c 8b 16d 16e

-continued

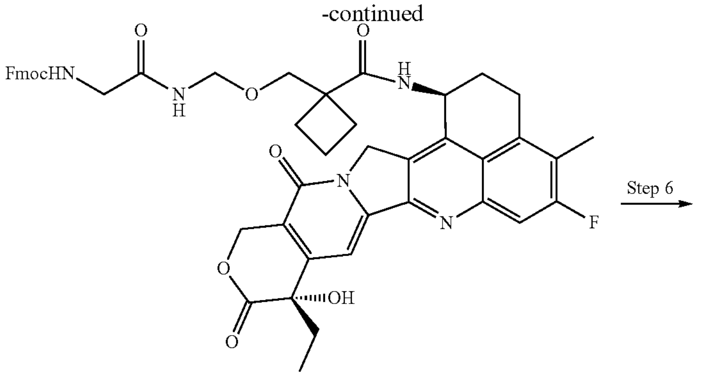

16f

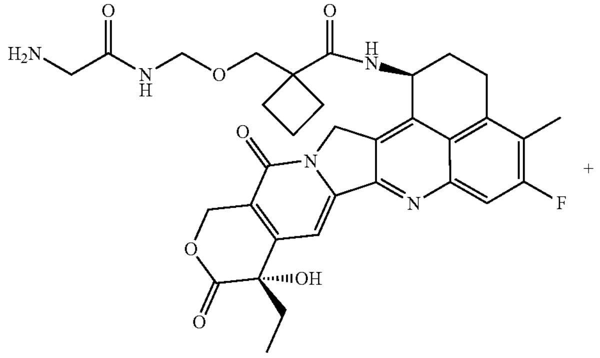

16g

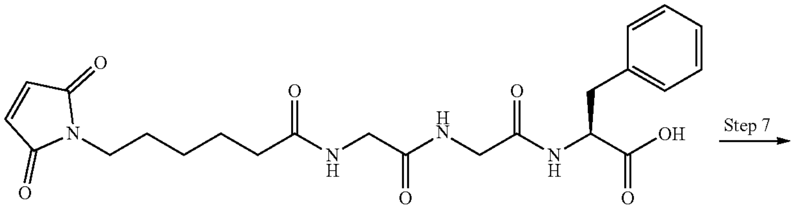

8g

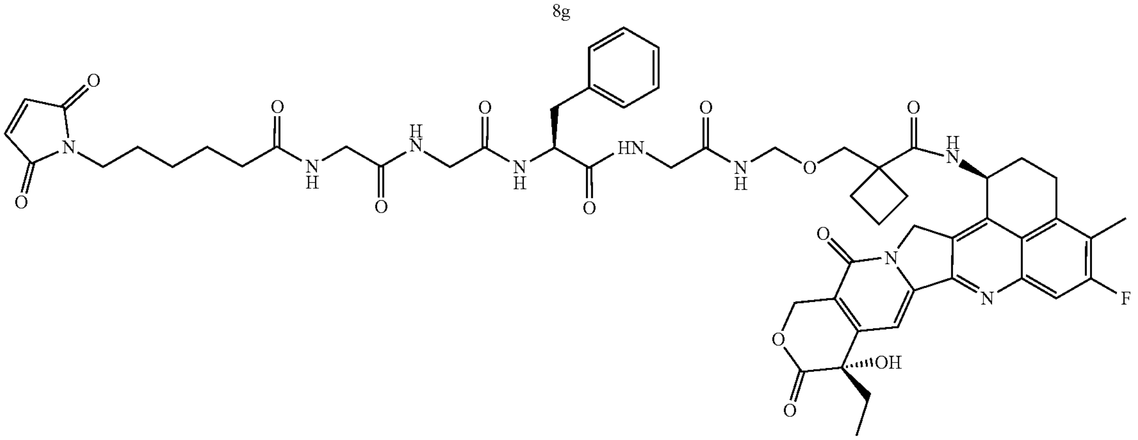

16

Step 1

1-(Hydroxymethyl)cyclobutane-1-carboxylic acid 16b

Ethyl 1-(hydroxymethyl)cyclobutanecarboxylate 16a (250 mg, 1.58 mmol, supplier: Alfa) was dissolved in methanol (2 mL) and water (1 mL), followed by the addition of sodium hydroxide (126 mg, 3.15 mmol). The reaction solution was warmed up to 40° C. and stirred for 3 hours. The reaction solution was cooled to room temperature, and concentrated under reduced pressure to remove the organic solvent. The solution was extracted with ether (10 mL), and the aqueous phase was collected. The aqueous phase was adjusted to pH 3-4 with 6N aqueous hydrochloric acid, and concentrated under reduced pressure to obtain a solid. 3 mL of toluene was added and the solution was concentrated under reduced pressure to dryness, which was repeated three times. The residues were dried by an oil pump to obtain the crude title product 16b (206 mg), which was used directly in the next step without purification.

MS m/z (ESI, NEG): 129.2 [M−1].

Step 2

Benzyl 1-(hydroxymethyl)cyclobutane-1-carboxylate 16c

The crude compound 16b (206 mg, 1.58 mmol) was dissolved in acetonitrile (15 mL), followed by the addition of anhydrous potassium carbonate (1.09 g, 7.90 mmol), tetrabutylammonium iodide (29 mg, 78.51 μmol) and benzyl bromide (216 mg, 1.26 mmol). The reaction solution was stirred at room temperature overnight. The reaction solution was filtered, and the filtrate was concentrated under reduced pressure. The resulting residues were purified by silica gel column chromatography with developing solvent system C to obtain the title product 16c (112 mg, yield: 32.1%).

MS m/z (ESI): 221.1 [M+1].

Step 3

Benzyl 1-(10-(9H-fluoren-9-yl)-5,8-dioxo-2,9-dioxa-4,7-diazadecyl)cyclobutane-1-carboxylate 16d 16c (77 mg, 0.35 mmol) and 8b (100 mg, 0.27 mmol) were added to a reaction flask, followed by the addition of 3 mL of tetrahydrofuran. The reaction solution was purged with argon three times and cooled to 0-5° C. in an ice-water bath, followed by the addition of potassium tert-butoxide (61 mg, 0.54 mmol). The reaction solution was stirred in the ice-water bath for 10 minutes. 20 mL ice water was added to the reaction solution, which was then extracted with ethyl acetate (5 mL) and chloroform (5 mL×5). The organic phases were combined and concentrated. The resulting residues were dissolved in 3 mL of 1,4-dioxane. 0.5 mL of water, sodium bicarbonate (27 mg, 0.32 mmol) and 9-fluorene methyl chloroformate (70 mg, 0.27 mmol) were added, and the reaction solution was stirred at room temperature for 1 hour. 20 mL of water was added, and the reaction solution was extracted with ethyl acetate (10 mL×3). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 16d (24 mg, yield: 16.7%).

MS m/z (ESI): 551.3 [M+23].

Step 4

1-(10-(9H-Fluoren-9-yl)-5,8-dioxo-2,9-dioxa-4,7-diazadecyl)cyclobutane-1-carboxylic acid 16e 16d (12 mg, 22.7 μmol) was dissolved in 1.5 mL of a mixed solvent of tetrahydrofuran and ethyl acetate (V:V=2:1), followed by the addition of palladium on carbon (5 mg, content: 10%). The reaction solution was purged with hydrogen three times and stirred at room temperature for 2 hours. The reaction solution was filtered through celite, and the filter cake was rinsed with ethyl acetate. The filtrate was concentrated under reduced pressure to obtain the crude title product 16e (10 mg), which was used directly in the next step without purification.

Step 5

(9H-Fluoren-9-yl)methyl (2-((((1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclobutyl)methoxy)methyl)amino)-2-oxoethyl)carbamate 16f 1b (7.5 mg, 0.014 mmol) was added to a reaction flask, followed by the addition of 1 mL of N,N-dimethylformamide. The solution was purged with argon three times, and cooled to 0-5° C. in an ice-water bath. One drop of triethylamine, the crude compound 16e (10 mg) in 0.5 mL of N,N-dimethylformamide, and 4-(4,6-dimethoxy-1,3,5-triazin-2-yl)-4-methylmorpholinium chloride (6 mg, 0.026 mmol) were added, and the reaction solution was stirred in an ice bath for 30 minutes. 10 mL of water was added, and the reaction solution was extracted with ethyl acetate (10 mL×3). The organic phase was washed with saturated sodium chloride solution (10 mL), dried over anhydrous sodium sulfate and filtered. The filtrate was concentrated under reduced pressure, and the resulting residues were purified by thin layer chromatography with developing solvent system B to obtain the title product 16f (10.6 mg, yield: 87.8%).

MS m/z (ESI): 856.2 [M+1].

Step 6

1-(((2-Aminoacetamido)methoxy)methyl)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 16g 16f (10.6 mg, 12.4 μmol) was dissolved in 0.6 mL of dichloromethane, followed by the addition of 0.3 mL of diethylamine. The reaction solution was stirred at room temperature for 2 hours. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 16g (8 mg), which was used directly in the next step without purification.

MS m/z (ESI): 634.1 [M+1].

Step 7

1-((S)-9-Benzyl-22-(2,5-dioxo-2,5-dihydro-1H-pyrrol-1-yl)-5,8,11,14,17-pentaoxo-2-oxa-4,7,10,13,16-pentaazadocosyl)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclobutane-1-carboxamide 16

The crude compound 16g (8 mg) was dissolved in 1 mL of N,N-dimethylformamide. 8g (8.8 mg, 18.6 μmol) and 4-(4,6-dimethoxy-1,3,5-triazin-2-yl)-4-methylmorpholinium chloride (5.2 mg, 18.8 μmol) were added. The reaction solution was stirred at room temperature for 30 minutes. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min) to obtain the title product 16 (1.0 mg, yield: 7.2%).

MS m/z (ESI): 1088.0 [M+1].

Example 17

(1r,4r)-N—((S)-7-Benzyl-1-(1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclopropoxy)-3,6,9,12,15-pentaoxo-17,20,23,26,29,32,35,38,41-nonaoxa-2,5,8,11,14-pentaazatritetracontan-43-yl)-4-((2,5-dioxo-2,5-dihydro-1H-pyrrol-1-yl)methyl)cyclohexane-1-carboxamide 17

17

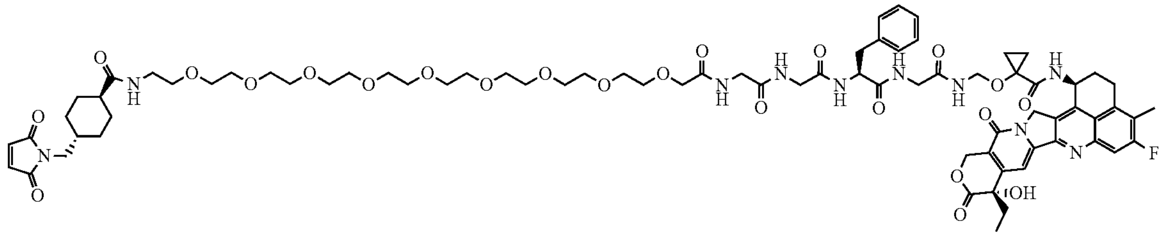

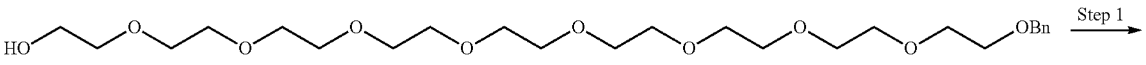

17a

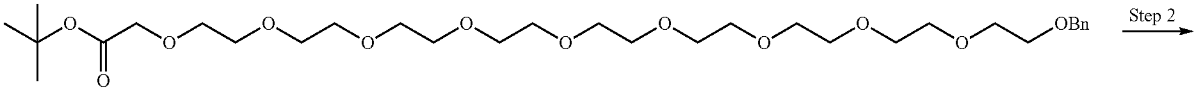

17b

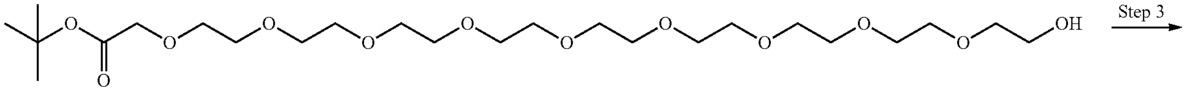

17c

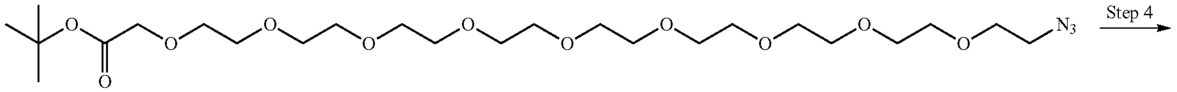

17d

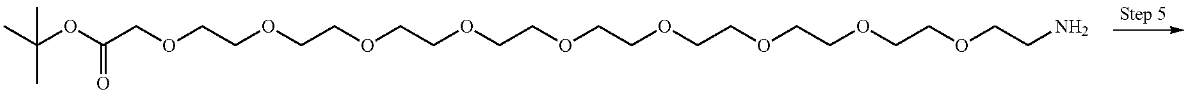

17e

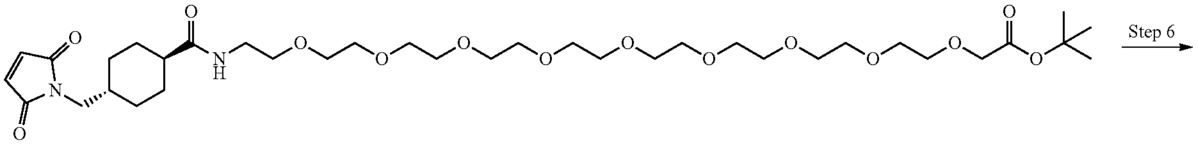

17f

-continued
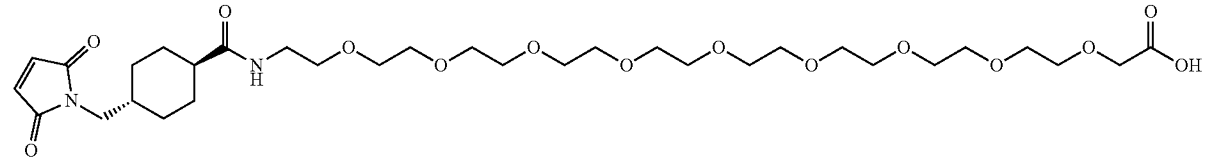
17g
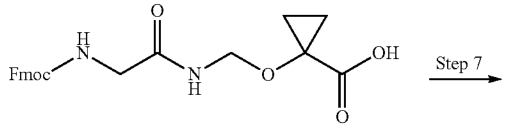
8d
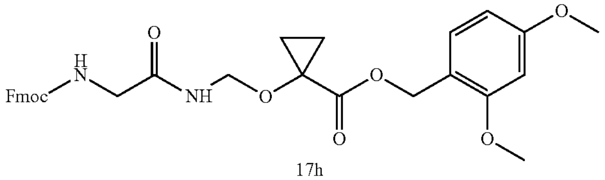
+
17h
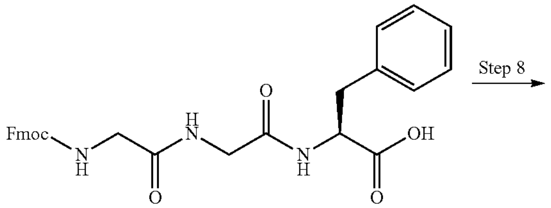
17i
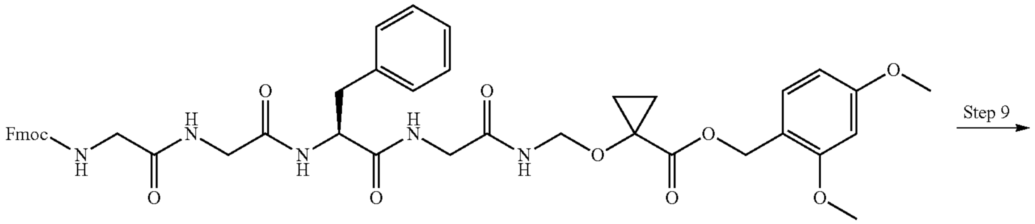
17j
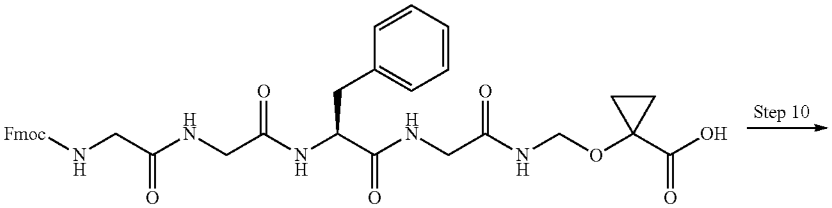
17k
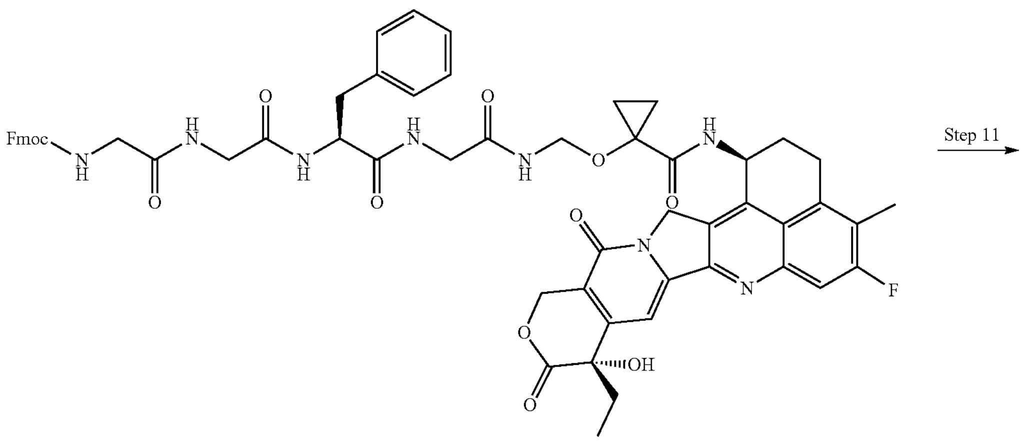
17l -continued

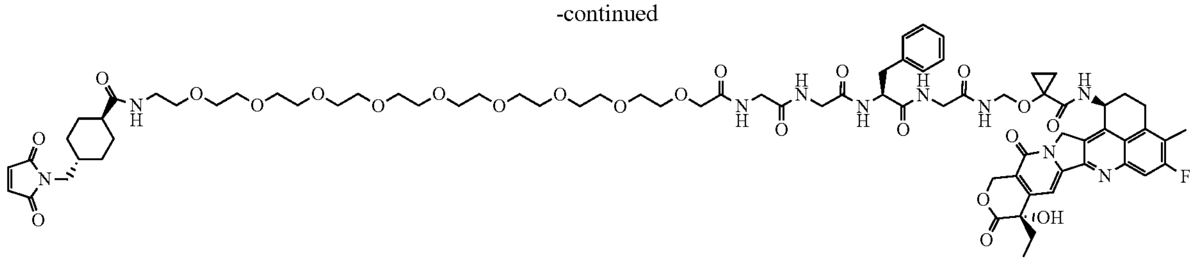

17

Step 1

Tert-butyl 1-phenyl-2,5,8,11,14,17,20,23,26,29-decaoxahentriacontan-31-oate 17b

1-Phenyl-2,5,8,11,14,17,20,23,26-nonaoxaoctacosan-28-ol 17a (0.34 g, 0.67 mmol, supplier: Bide Pharmatech Ltd.) was dissolved in 10 mL of dichloromethane, and then added with silver oxide (0.24 g, 1.01 mmol), tert-butyl bromoacetate (0.16 g, 0.81 mmol) and potassium iodide (0.07 g, 0.40 mmol) successively. The reaction solution was stirred at room temperature for 3 hours. The reaction solution was filtered, and the filtrate was concentrated under reduced pressure. The resulting residues were purified by silica gel column chromatography with developing solvent system B to obtain the title product 17b (0.42 g, yield: 100%).

MS m/z (ESI): 636.3 [M+18].

Step 2

Tert-butyl 29-hydroxy-3,6,9,12,15,18,21,24,27-nonaoxanonacosan-1-oate 17c 17b (417 mg, 0.67 mmol) was dissolved in 15 mL of tetrahydrofuran, followed by the addition of palladium on carbon (110 mg, content: 10%, dry). The reaction solution was purged with hydrogen three times, warmed up to 60° C. and stirred for 3 hours. The reaction solution was filtered through celite, and the filter cake was rinsed with tetrahydrofuran. The filtrate was concentrated to obtain the crude title product 17c (357 mg), which was used directly in the next step without purification.

MS m/z (ESI): 546.2 [M+18].

Step 3

Tert-butyl 29-azido-3,6,9,12,15,18,21,24,27-nonaoxanonacosan-1-oate 17d 17c (357 mg, 0.675 mmol) was dissolved in 10 mL of toluene, followed by the addition of diphenyl azide phosphate (279 mg, 1.014 mmol) and 1,8-diazabicycloundec-7-ene (206 mg, 1.353 mmol). The reaction solution was purged with argon three times, and stirred at room temperature for 2 hours, followed by stirring at 105° C. for 19 hours. The reaction solution was cooled to room temperature and concentrated. 20 mL of water was added, and the solution was extracted with ethyl acetate (10 mL×4). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system B to obtain the crude title product 17d (412 mg).

MS m/z (ESI): 571.3 [M+18].

Step 4

Tert-butyl 29-amino-3,6,9,12,15,18,21,24,27-nonaoxanonacosan-1-oate 17e 17d (230 mg, 0.415 mmol) was dissolved in 8 mL of tetrahydrofuran, followed by the addition of palladium on carbon (58 mg, content: 10%, dry). The reaction solution was purged with hydrogen three times, and stirred at room temperature for 2 hours. The reaction solution was filtered through celite, and the filter cake was rinsed with tetrahydrofuran. The filtrate was concentrated to obtain the crude title product 17e (220 mg), which was used directly in the next step without purification.

MS m/z (ESI): 528.2 [M+1].

Step 5

Tert-butyl 1-((1r,4r)-4-((2,5-dioxo-2,5-dihydro-1H-pyrrol-1-yl)methyl)cyclohexyl)-1-oxo-5,8,11,14,17,20,23,26,29-nonaoxa-2-azahentriacontan-31-oate 17f (1r,4r)-4-((2,5-Dioxo-2,5-dihydro-1H-pyrrol-1-yl)methyl)cyclohexane-1-carboxylic acid (98.5 mg, 0.415 mmol) was dissolved in 10 mL of dichloromethane, followed by the addition of 2-(7-oxabenzotriazole)-N,N,N',N'-tetramethylurea hexafluorophosphate (190 mg, 0.500 mmol) and N,N-diisopropylethylamine (162 mg, 1.253 mmol). The reaction solution was purged with argon three times, and then added with the crude compound 17e (220 mg, 0.417 mmol). The reaction solution was stirred at room temperature for 1 hour. 15 mL of water was added, and the reaction solution was extracted with dichloromethane (8 mL×3). The organic phases were combined. The organic phase was washed with saturated sodium chloride solution (15 mL), dried over anhydrous sodium sulfate and filtered. The filtrate was concentrated under reduced pressure. The resulting residues were purified by silica gel column chromatography with developing solvent system B to obtain the title product 17f (122 mg, yield: 39.2%).

MS m/z (ESI): 747.2[M+1].

Step 6

1-((1r,4r)-4-((2,5-Dioxo-2,5-dihydro-1H-pyrrol-1-yl)methyl)cyclohexyl)-1-oxo-5,8,11,14,17,20,23,26,29-nonaoxa-2-azahentriacontan-31-oic acid 17g 17f (122 mg, 0.163 mmol) was dissolved in 0.8 mL of dichloromethane, followed by the addition of 0.4 mL of trifluoroacetic acid. The reaction solution was stirred at room temperature for 1 hour. 15 mL of dichloromethane was added to dilute the reaction solution, and then concentrated under reduced pressure. 10 mL of n-hexane was added and the solution was concentrated under reduced pressure, which was repeated twice. 10 mL of toluene was added and the solution was concentrated under reduced pressure. 10 mL of a mixed solvent of n-hexane:ether=5:1 was added to pulp, which was repeated three times until the pH was close to 7. The solution was concentrated by an oil pump until dryness to obtain the title product 17g (98 mg, yield: 86.8%).

MS m/z (ESI): 691.2[M+1].

Step 7

2,4-Dimethoxybenzyl 1-((2-((((9H-fluoren-9-yl)methoxy)carbonyl)amino)acetamido)methoxy)cyclopropane-1-carboxylate 17h 8d (164 mg, 0.40 mmol) was dissolved in dichloromethane (5 mL), and then added with 2,4-dimethoxybenzyl alcohol (81 mg, 0.48 mmol), 1-ethyl-(3-dimethylaminopropyl)carbodiimide hydrochloride (115 mg, 0.60 mmol) and 4-dimethylaminopyridine (5 mg, 0.041 mmol). After completion of the addition, the reaction solution was stirred at room temperature for 1 hour. 20 mL of water was added, and the solution was partitioned after shaking. The aqueous phase was extracted with dichloromethane (8 mL×3), and the organic phases were combined. The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 17h (124 mg, yield: 55.4%).

MS m/z (ESI): 583.1[M+23].

Step 8

2,4-Dimethoxybenzyl (S)-1-((11-benzyl-1-(9H-fluoren-9-yl)-3,6,9,12,15-pentaoxo-2-oxa-4,7,10,13,16-pentaazaheptadecan-17-yl)oxy)cyclopropane-1-carboxylate 17j 17h (39 mg, 69.6 μmol) was dissolved in 0.6 mL of dichloromethane, followed by the addition of 0.3 mL of diethylamine. The reaction solution was stirred at room temperature for 1 hour. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure. The resulting crude product was dissolved in 2 mL of N,N-dimethylformamide, followed by the addition of (((9H-fluoren-9-yl)methoxy)carbonyl)glycylglycyl-L-phenylalanine 17i (35 mg, 69.8 μmol, prepared according to the method disclosed in Example 7-12 on page 13 of the description of the patent application “CN108853514A”) and 4-(4,6-dimethoxy-1,3,5-triazin-2-yl)-4-methylmorpholinium chloride (23 mg, 83.1 μmol). The reaction solution was stirred at room temperature for 1 hour. 10 mL of water was added, and the solution was extracted with ethyl acetate (10 mL×3). The organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 17j (48 mg, yield: 83.9%).

MS m/z (ESI): 822.0[M+1].

Step 9

(S)-1-((11-Benzyl-1-(9H-fluoren-9-yl)-3,6,9,12,15-pentaoxo-2-oxa-4,7,10,13,16-pentaazaheptadecan-17-yl)oxy)cyclopropane-1-carboxylic acid 17k 17j (48 mg, 58.4 μmol) was dissolved in 1.4 mL of 3% (v/v) dichloroacetic acid in dichloromethane, and the solution was cooled to 0-5° C. in an ice-water bath. Triethylsilane (21 mg, 180.6 μmol) was added, and the reaction solution was stirred in an ice bath for 3 hours. The reaction solution was concentrated under reduced pressure in the ice bath to remove half of the organic solvent. 5 mL of ether was added, and the solution was naturally warmed up to room temperature and pulped. A white solid was precipitated and filtered. The filter cake was collected and dried by an oil pump to obtain the title product 17k (33 mg, yield: 84.1%).

Step 10

(9H-Fluoren-9-yl)methyl ((S)-7-benzyl-1-(1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclopropoxy)-3,6,9,12-tetraoxo-2,5,8,11-tetraazatridecan-13-yl)carbamate 17l 1b (20 mg, 42.4 μmol) was added to a reaction flask, followed by the addition of 1 mL of 10% (v/v) methanol in dichloromethane. The solution was purged with argon three times, and cooled to 0-5° C. in an ice-water bath. One drop of triethylamine was added, and the reaction solution was stirred until 1b dissolved. 17k (33 mg, 49.1 μmol) was dissolved in 1 mL of 10% (v/v) methanol in dichloromethane. The resulting solution was added dropwise to the above reaction solution, followed by the addition of 4-(4,6-dimethoxy-1,3,5-triazin-2-yl)-4-methylmorpholinium chloride (17.6 mg, 63.6 μmol). The reaction solution was warmed up to room temperature and stirred for 1 hour. 10 mL of dichloromethane and 5 mL of water were added, and the solution was stirred for 5 minutes and left to partition. The organic phase was collected. The aqueous phase was extracted with dichloromethane (10 mL×3), and the organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 17l (37 mg, yield: 80.2%).

MS m/z (ESI): 1090.1[M+1].

Step 11

(1r,4r)-N—((S)-7-Benzyl-1-(1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)cyclopropoxy)-3,6,9,12,15-pentaoxo-17,20,23,26,29,32,35,38,41-nonaoxa-2,5,8,11,14-pentaazatritetracontan-43-yl)-4-((2,5-dioxo-2,5-dihydro-1H-pyrrol-1-yl)methyl)cyclohexane-1-carboxamide 17

17l (15.5 mg, 14.23 μmol) was dissolved in 0.6 mL of dichloromethane, followed by the addition of 0.3 mL of diethylamine. The reaction solution was stirred at room temperature for 1.5 hours. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure and dried by an oil pump. The resulting crude product was dissolved in 1 mL of N,N-dimethylformamide. 17g (11 mg, 15.92 μmol) and 4-(4,6-dimethoxy-1,3,5-triazin-2-yl)-4-methylmorpholinium chloride (6.0 mg, 21.68 μmol) were added. The reaction solution was purged with argon three times, and stirred at room temperature for 30 minutes. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product 17 (16 mg, yield: 27.4%).

MS m/z (ESI): 1556.4 [M+18].

$^1H$ NMR (400 MHz, DMSO-$d_6$): δ 8.98 (d, 1H), 8.76 (s, 1H), 8.20 (br, 1H), 8.12-7.95 (m, 3H), 7.93-7.76 (m, 2H), 7.75-7.66 (m, 2H), 7.24 (s, 1H), 7.20-7.05 (m, 6H), 6.97 (s, 1H), 6.64 (br, 1H), 6.55 (d, 1H), 6.47 (s, 1H), 5.61-5.52 (m, 2H), 5.37 (s, 1H), 5.33-5.23 (m, 2H), 5.18 (s, 1H), 5.13 (s, 1H), 5.05 (s, 1H), 5.00 (s, 1H), 4.65-4.55 (m, 2H), 4.53-4.45 (m, 1H), 4.38-4.28 (m, 2H), 3.84 (s, 2H), 3.67 (d, 3H), 3.60-3.40 (m, 33H), 3.18 (d, 1H), 3.15-3.08 (m, 3H), 2.28 (s, 3H), 2.00-1.92 (m, 3H), 1.85 (s, 2H), 1.82-1.73 (m, 2H), 1.68-1.52 (m, 4H), 1.29-1.15 (m, 3H), 0.86-0.76 (m, 5H).

Example 18

(1r,4r)-N-((2R,10S)-10-Benzyl-2-cyclopropyl-1-(((1S, 9S)-9-ethyl-5-fluoro-9-hydroxy-4-methyl-10,13-dioxo-2,3, 9,10,13,15-hexahydro-1H,12H-benzo[de]pyrano[3',4':6,7] indolizino[1,2-b]quinolin-1-yl)amino)-1,6,9,12,15,18-hexaoxo-3,20,23,26,29,32,35,38,41,44-decaoxa-5,8,11,14, 17-pentaazahexatetracontan-46-yl)-4-((2,5-dioxo-2,5-dihydro-1H-pyrrol-1-yl)methyl)cyclohexane-1-carboxamide 18

18

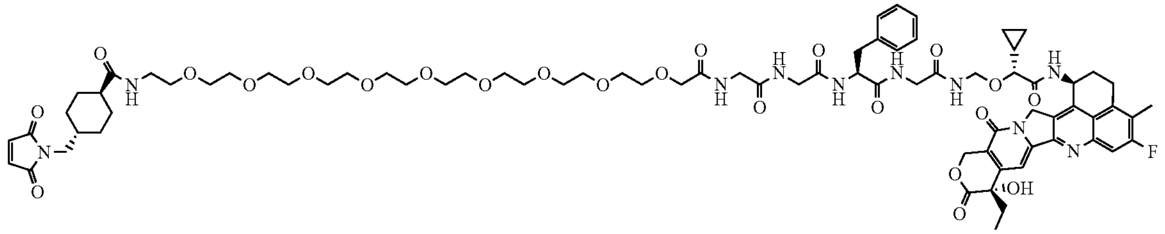

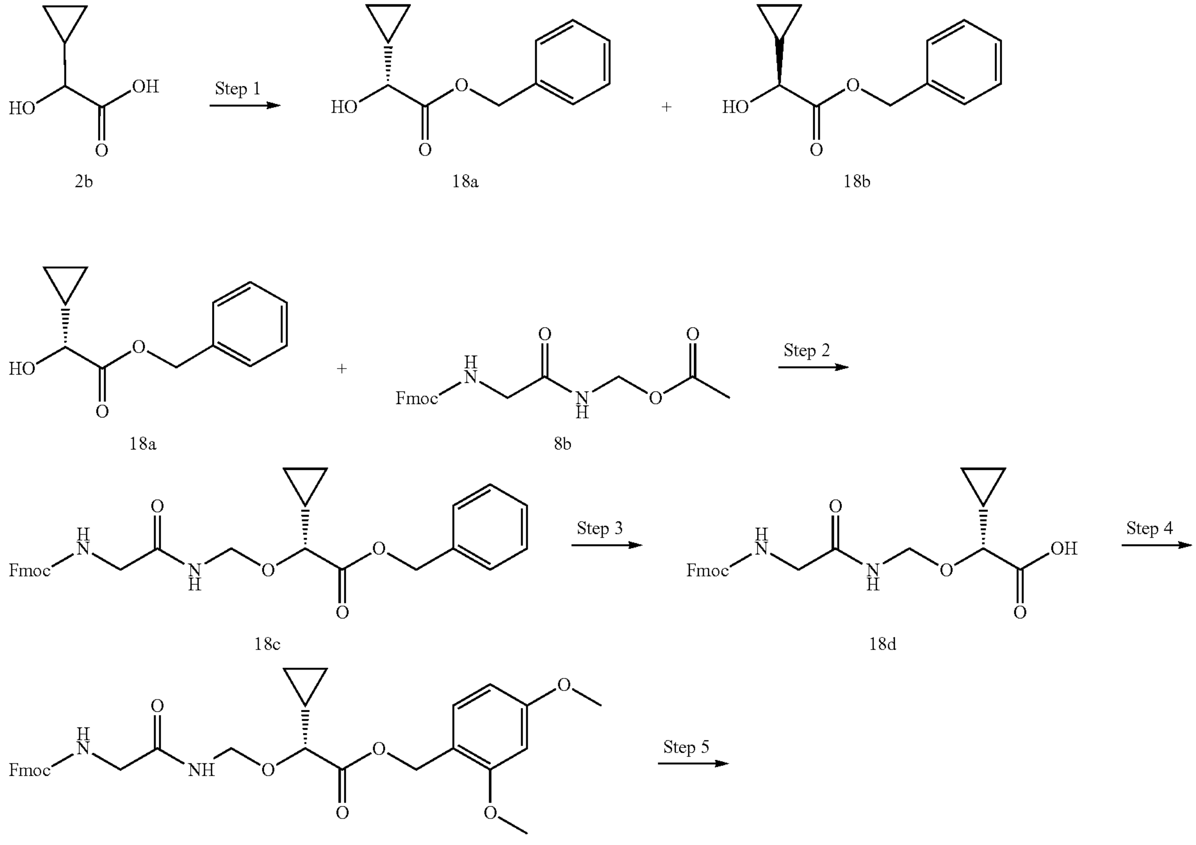

2b 18a 18b 18a 8b 18c 18d

18e

-continued
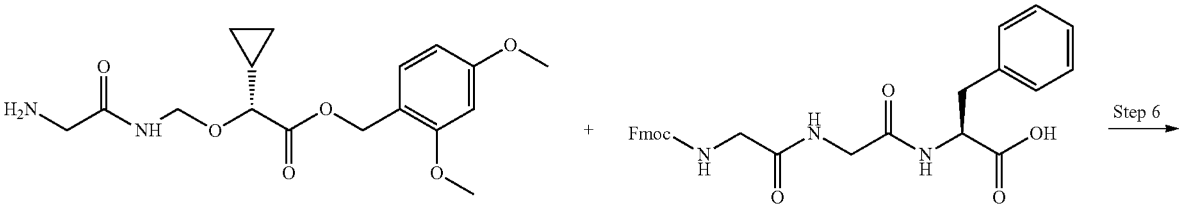
18f 17i
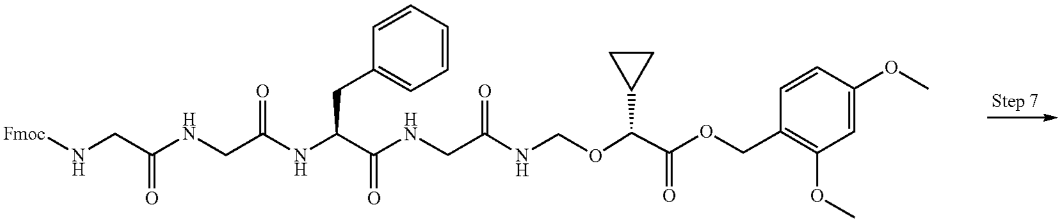
18g
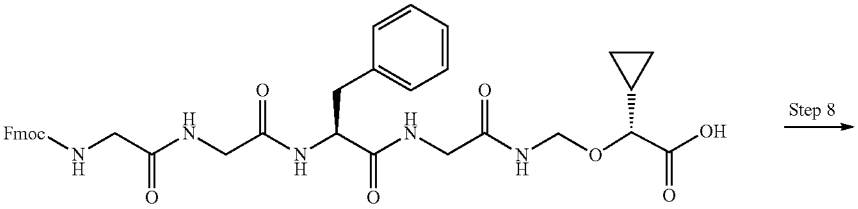
18h
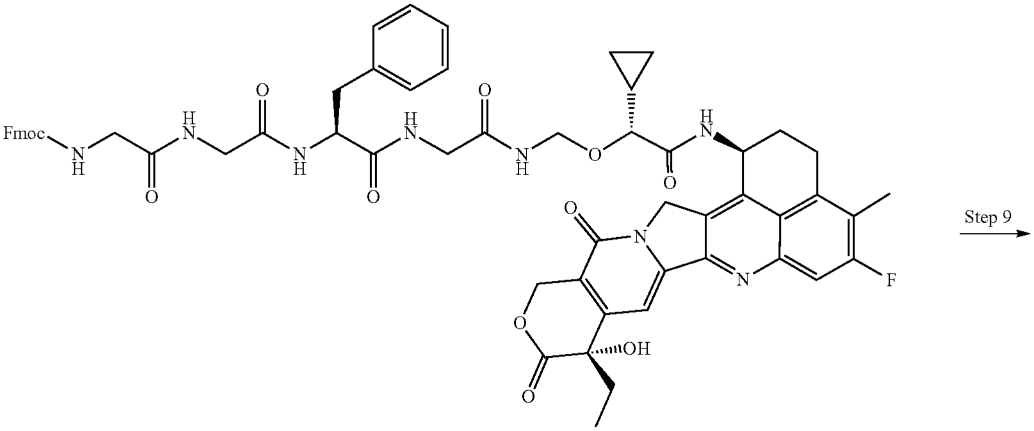
18i
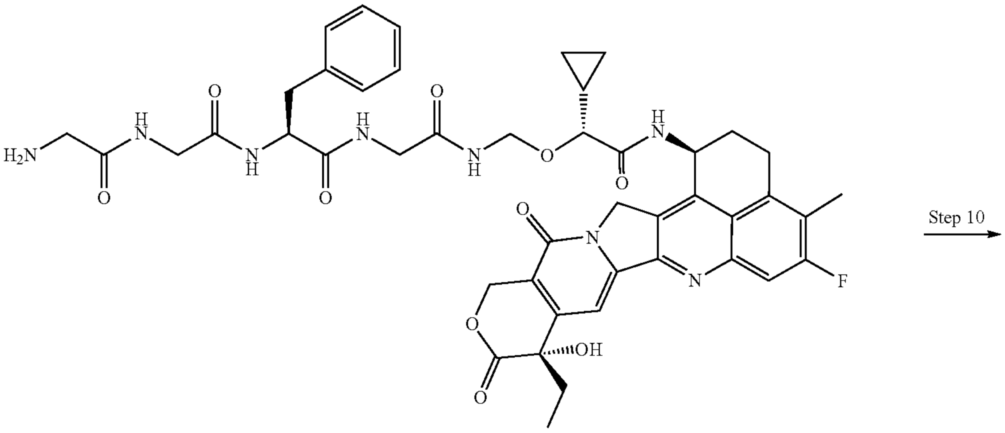
18j -continued

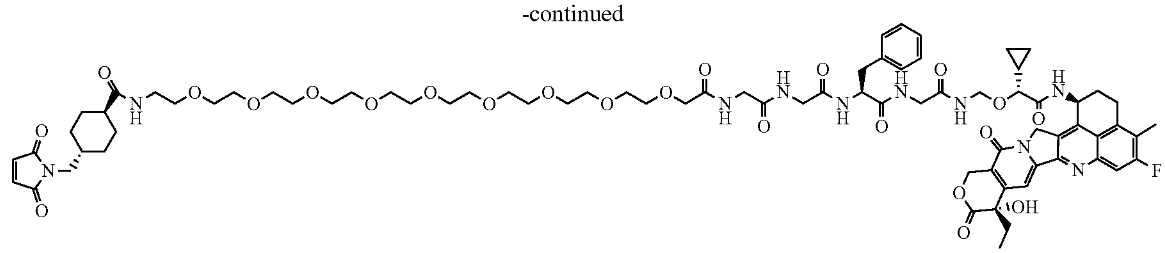

18

Step 1

Benzyl (R)-2-cyclopropyl-2-hydroxyacetate 18a

Benzyl (S)-2-cyclopropyl-2-hydroxyacetate 18b 2a (7.4 g, 63.7 mmol) was dissolved in 200 mL of acetonitrile, and then added with potassium carbonate (35 g, 253.6 mmol), benzyl bromide (9.3 g, 54.4 mmol) and tetrabutylammonium iodide (500 mg, 1.36 mmol) successively. The reaction solution was stirred at room temperature for 16 hours, and filtered through celite. The filter cake was rinsed with ethyl acetate (10 ml), and the filtrates were combined and concentrated under reduced pressure. 4.1 g of the resulting residues were purified by silica gel column chromatography with developing solvent system C. Chiral resolution was further carried out to obtain the title products 18a (1.1 g) and 18b (1.2 g).

Step 2

Benzyl (R)-10-cyclopropyl-1-(9H-fluoren-9-yl)-3,6-dioxo-2,9-dioxa-4,7-diazaundecan-11-oate 18c 8b (3.1 g, 8.41 mmol) was dissolved in tetrahydrofuran (55 mL), followed by the addition of 18a (2.0 g, 9.70 mmol). The reaction solution was cooled to 0-5° C. in an ice-water bath, followed by the addition of potassium tert-butoxide (1.89 g, 16.84 mmol). The reaction solution was stirred in the ice-water bath for 10 minutes. Ethyl acetate (30 mL) and water (20 mL) were added, and the solution was left to partition. The aqueous phase was extracted with chloroform (30 mL×5), and the organic phases were combined. The organic phase was concentrated under reduced pressure, and the resulting residues were dissolved in 1,4-dioxane (32 mL) and water (8 mL). Sodium carbonate (1.78 g, 16.79 mmol) and 9-fluorene methyl chloroformate (2.18 g, 8.42 mmol) were added, and the reaction solution was stirred at room temperature for 2 hours. Water (30 mL) was added to the reaction solution, which was extracted with ethyl acetate (50 mL×3). The organic phases were combined. The organic phase was washed with saturated sodium chloride solution (30 mL×2), dried over anhydrous sodium sulfate and filtered. The filtrate was concentrated under reduced pressure. The resulting residues were purified by column chromatography with developing solvent system C to obtain the title product 18c (1.3 g, yield: 30.0%).

MS m/z (ESI): 515.2[M+1].

Step 3

(R)—10-Cyclopropyl-1-(9H-fluoren-9-yl)oxo-2,9-dioxa-4,7-diazaundecan-11-oic acid 18d 18c (1.29 g, 2.51 mmol) was dissolved in ethyl acetate (15 mL), followed by the addition of palladium on carbon (260 mg, content: 10%, dry). The reaction solution was purged with hydrogen three times and stirred at room temperature for 5 hours. The reaction solution was filtered through celite, and the filter cake was rinsed with ethyl acetate (20 mL) and methanol (20 mL). The filtrate was concentrated to obtain the crude title product 18d (980 mg), which was used directly in the next step without purification.

MS m/z (ESI): 425.1 [M+1].

Step 4

2,4-Dimethoxybenzyl (R)-10-cyclopropyl-1-(9H-fluoren-9-yl)-3,6-dioxo-2,9-dioxa-4,7-diazaundecan-11-oate 18e The crude compound 18d (980 mg, 2.31 mmol) was dissolved in dichloromethane (15 mL), and then added with 2,4-dimethoxybenzyl alcohol (777 mg, 4.62 mmol), 1-ethyl-(3-dimethylaminopropyl)carbodiimide hydrochloride (664 mg, 3.46 mmol) and 4-dimethylaminopyridine (28 mg, 0.23 mmol). The reaction solution was stirred at room temperature for 1 hour. The reaction solution was concentrated under reduced pressure to remove the organic solvent. 20 mL of water was added, and the solution was extracted with ethyl acetate (50 mL×3). The organic phases were combined. The organic phase was washed with saturated sodium chloride solution (30 mL×2), dried over anhydrous sodium sulfate and filtered. The filtrate was concentrated under reduced pressure. The resulting residues were purified by column chromatography with developing solvent system C to obtain the title product 18e (810 mg, yield: 61.1%).

MS m/z (ESI): 575.0[M+1].

Step 5

2,4-Dimethoxybenzyl (R)-2-((2-aminoacetamido)methoxy)-2-cyclopropylacetate 18f 18e (33 mg, 57.4 μmol) was dissolved in 0.6 mL of dichloromethane, followed by the addition of 0.3 mL of diethylamine. The reaction solution was stirred at room temperature for 1 hour. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 18f (21 mg), which was used directly in the next step without purification.

Step 6

2,4-Dimethoxybenzyl (11S,19R)-11-benzyl-19-cyclopropyl-1-(9H-fluoren-9-yl)-3,6,9,12,15-pentaoxo-2,18-dioxa-4,7,10,13,16-pentaazaicosan-20-oate 18g The crude compound 18f (21 mg, 57.4 μmol) was dissolved in 3 mL of N,N-dimethylformamide. 17i (29 mg, 57.8 μmol) and 4-(4,6-dimethoxy-1,3,5-triazin-2-yl)-4-methylmorpholinium chloride (19 mg, 68.7 μmol) were added. The reaction solution was stirred at room temperature for 1 hour. 10 mL of water was added, and the reaction solution was extracted with ethyl acetate (10 mL×3). The organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 18g (37 mg, yield: 77.1%).

MS m/z (ESI): 853.0[M+18].

Step 7

(11S,19R)-11-Benzyl-19-cyclopropyl-1-(9H-fluoren-9-yl)-3,6,9,12,15-pentaoxo-2,18-dioxa-4,7,10,13,16-pentaazaicosan-20-oic acid 18h 18g (37 mg, 44.3 μmol) was dissolved in 1.4 mL of 3% (v/v) dichloroacetic acid in dichloromethane, and the solution was cooled to 0-5° C. in an ice-water bath. Triethylsilane (15.4 mg, 132.4 μmol) was added, and the reaction solution was stirred in an ice bath for 3 hours. The reaction solution was concentrated under reduced pressure in the ice bath to remove half of the organic solvent. 5 mL of ether was added, and the solution was naturally warmed up to room temperature and pulped. A white solid was precipitated and filtered. The filter cake was collected and dried by an oil pump to obtain the title product 18h (24 mg, yield: 79.1%).

MS m/z (ESI): 708.2[M+23].

Step 8

(9H-Fluoren-9-yl)methyl ((2R,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)carbamate 18i 1b (30 mg, 63.6 μmol) was added to a reaction flask, followed by the addition of 1 mL of 10% (v/v) methanol in dichloromethane. The solution was purged with argon three times, and cooled to 0-5° C. in an ice-water bath. One drop of triethylamine was added, and the reaction solution was stirred until 1b dissolved. 18h (65 mg, 94.8 μmol) was dissolved in 1 mL of 10% (v/v) methanol in dichloromethane, and the resulting solution was added dropwise to the above reaction solution, followed by the addition of 4-(4,6-dimethoxy-1,3,5-triazin-2-yl)-4-methylmorpholinium chloride (27 mg, 97.6 μmol). The reaction solution was warmed up to room temperature and stirred for 1 hour. 10 mL of dichloromethane and 5 mL of water were added, and the solution was stirred for 5 minutes and left to partition. The organic phase was collected. The aqueous phase was extracted with dichloromethane (10 mL×3), and the organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 18i (25 mg, yield: 35.6%).

MS m/z (ESI): 1104.4[M+1].

Step 9

(S)-2-(2-(2-Aminoacetamido)acetamido)-N-(2-((((R)-1-cyclopropyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl)-3-phenylpropanamide 18j 18i (12 mg, 10.9 μmol) was dissolved in 0.6 mL of dichloromethane, followed by the addition of 0.3 mL of diethylamine. The reaction solution was stirred at room temperature for 1.5 hours. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 18j (10 mg), which was used directly in the next step without purification.

MS m/z (ESI): 881.0 [M+1].

Step 10

(1r,4r)-N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15,18-hexaoxo-3,20,23,26,29,32,35,38,41,44-decaoxa-5,8,11,14,17-pentaazahexatetracontan-46-yl)-4-((2,5-dioxo-2,5-dihydro-1H-pyrrol-1-yl)methyl)cyclohexane-1-carboxamide 18

The crude compound 18j (10 mg) was dissolved in 1 mL of N,N-dimethylformamide. 17g (8.5 mg, 12.3 μmol) and 4-(4,6-dimethoxy-1,3,5-triazin-2-yl)-4-methylmorpholinium chloride (4.6 mg, 16.6 μmol) were added. The reaction solution was stirred at room temperature for 30 minutes. The reaction solution was filtered, and purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product 18 (9.5 mg, yield: 56.2%).

MS m/z (ESI): 1570.2 [M+18].

$^1H$ NMR (400 MHz, DMSO-$d_6$): δ 8.77 (d, 1H), 8.59-8.55 (m, 1H), 8.42 (d, 1H), 8.37-8.28 (m, 1H), 8.25-8.06 (m, 2H), 7.96-7.86 (m, 1H), 7.86-7.70 (m, 2H), 7.32-7.28 (m, 1H), 7.25-7.14 (m, 3H), 6.67 (m, 1H), 5.96 (s, 1H), 5.80-5.72 (m, 1H), 5.62-5.52 (m, 2H), 5.43-5.30 (m, 3H), 5.28-5.17 (m, 2H), 5.12-5.08 (m, 1H), 4.72-4.35 (m, 8H), 3.95-3.70 (m, 13H), 3.35-3.22 (m, 14H), 2.42-2.32 (m, 3H), 2.05-1.98 (m, 4H), 1.88-1.82 (m, 12H), 1.47-1.39 (m, 3H), 1.32-1.18 (m, 11H), 0.90-0.80 (m, 4H), 0.52-0.37 (m, 3H), 0.32-0.18 (m, 2H).

Example 19
(1r,4r)-N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15,18-hexaoxo-3,20,23,26,29,32,35,38,41,44-decaoxa-5,8,11,14,17-pentaazahexatetracontan-46-yl)-4-((2,5-dioxo-2,5-dihydro-1H-pyrrol-1-yl)methyl)cyclohexane-1-carboxamide 19
19
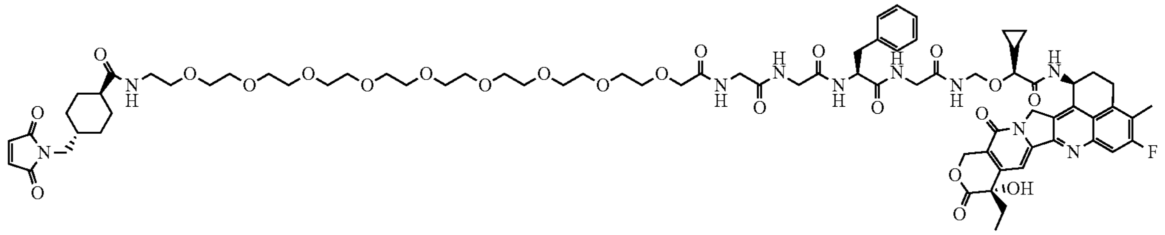
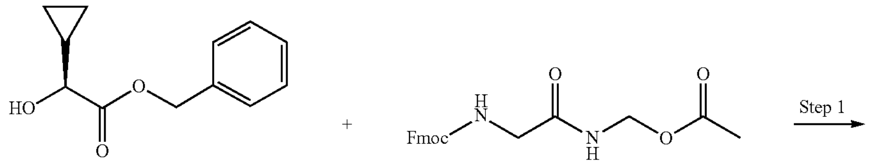
18b
8b
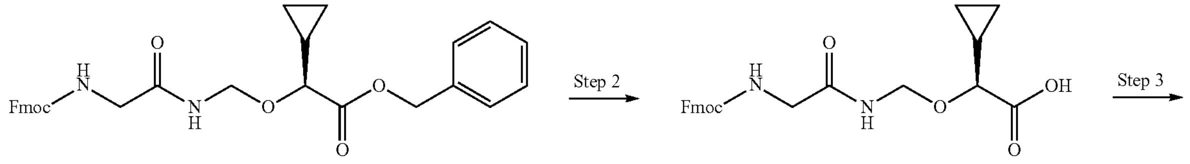
19a
19b
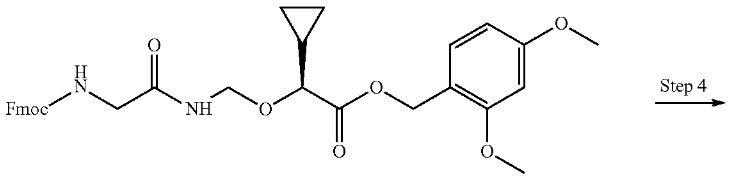
19c
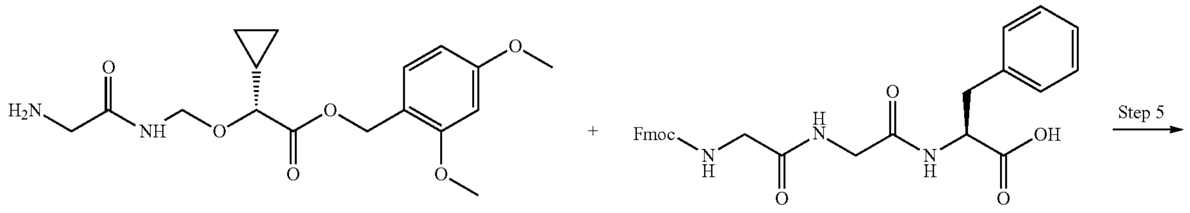
19d
17i
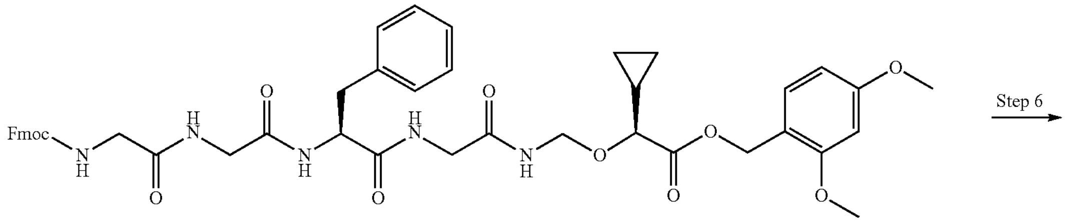
19e -continued
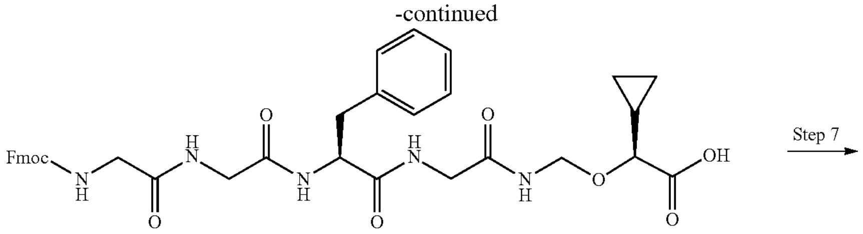
19f
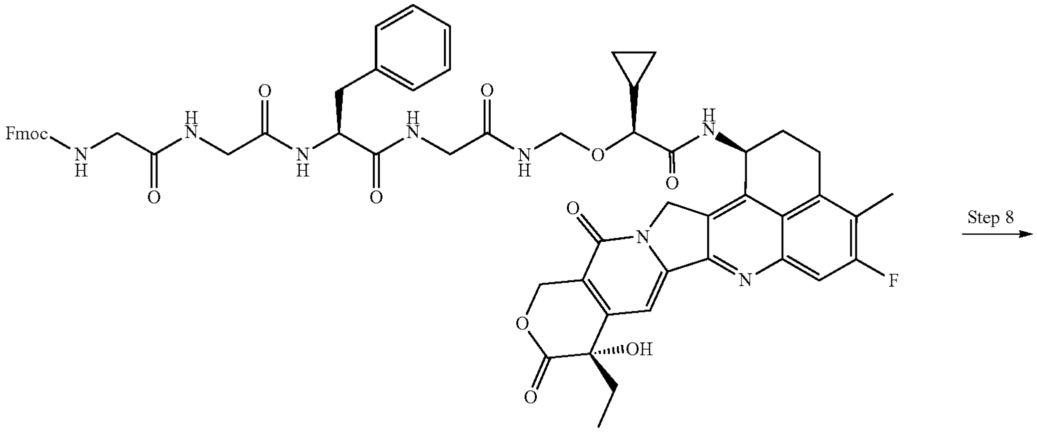
19g
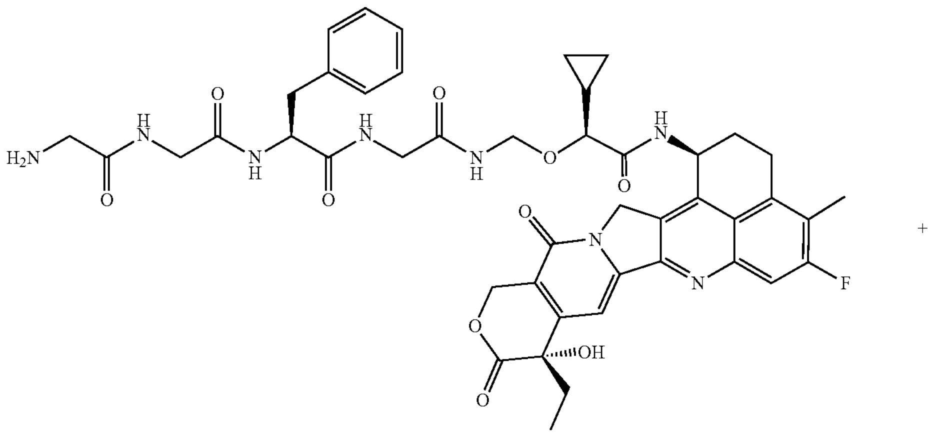
19h
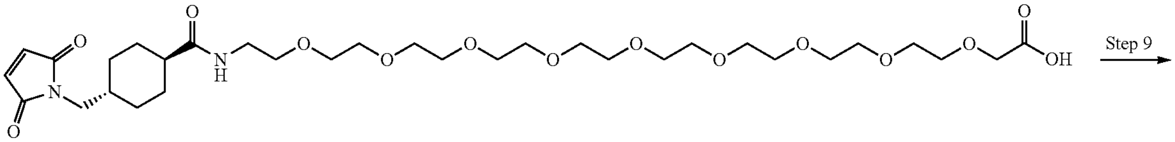
17g
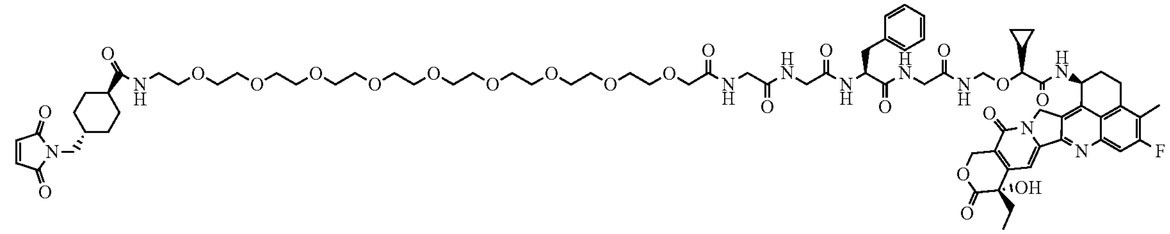
19

Step 1

Benzyl (S)-10-cyclopropyl-1-(9H-fluoren-9-yl)-3,6-dioxo-2,9-dioxa-4,7-diazaundecan-11-oate 19a 18b (252 mg, 1.22 mmol) was added to a reaction flask, followed by the addition of 4 mL of dichloromethane. The reaction solution was purged with argon three times and cooled to 0-5° C. in an ice-water bath, followed by the addition of lithium tert-butoxide (98 mg, 1.22 mmol). The reaction solution was stirred in the ice-water bath for 15 minutes and became clear. 8b (300 mg, 814.3 μmol) was added, and the reaction solution was stirred in the ice-water bath for 2.5 hours. Water (10 mL) was added, and the solution was partitioned. The aqueous phase was extracted with dichloromethane (8 mL×2). The organic phases were combined, washed with water (10 mL×1) and saturated brine (10 mL×2), dried over anhydrous sodium sulfate and filtered. The filtrate was concentrated to obtain the crude product. The resulting residues were purified by silica gel column chromatography with developing solvent system C to obtain the title product 19a (282 mg, yield: 67.2%).

Step 2

(S)-10-Cyclopropyl-1-(9H-fluoren-9-yl)-3,6-dioxo-2,9-dioxa-4,7-diazaundecan-11-oic acid 19b 19a (280 mg, 0.554 mmol) was dissolved in 8 mL of ethyl acetate, followed by the addition of palladium on carbon (84 mg, content: 10%, dry). The reaction solution was purged with hydrogen three times and stirred at room temperature for 3 hours. The reaction solution was filtered through celite, and the filter cake was rinsed with ethyl acetate. The filtrate was concentrated to obtain the crude title product 19b (230 mg), which was used directly in the next step without purification.

Step 3

2,4-Dimethoxybenzyl (S)-10-cyclopropyl-1-(9H-fluoren-9-yl)-3,6-dioxo-2,9-dioxa-4,7-diazaundecan-11-oate 19c The crude compound 19b (230 mg, 541.8 μmol) was dissolved in 7 mL of dichloromethane, and then added with 2,4-dimethoxybenzyl alcohol (136.7 mg, 812.7 μmol), 1-ethyl-(3-dimethylaminopropyl)carbodiimide hydrochloride (155 mg, 808.5 μmol) and 4-dimethylaminopyridine (6.6 mg, 53.5 μmol) successively. The reaction solution was stirred at room temperature for 16 hours. The reaction solution was diluted with 10 mL of dichloromethane, washed with water (10 mL×1) and saturated brine (10 mL×2), dried over anhydrous sodium sulfate and filtered. The filtrate was concentrated to obtain the crude product. The resulting residues were purified by thin layer chromatography with developing solvent system B to obtain the title product 19c (159 mg, yield: 51.0%).

Step 4

2,4-Dimethoxybenzyl (S)-2-((2-aminoacetamido)methoxy)-2-cyclopropylacetate 19d 19c (60 mg, 104.4 μmol) was dissolved in 1 mL of dichloromethane, followed by the addition of 0.5 mL of diethylamine. The reaction solution was stirred at room temperature for 1 hour. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 19d (21 mg), which was used directly in the next step without purification.

Step 5

2,4-Dimethoxybenzyl (11S,19S)-11-benzyl-19-cyclopropyl-1-(9H-fluoren-9-yl)-3,6,9,12,15-pentaoxo-2,18-dioxa-4,7,10,13,16-pentaazaicosan-20-oate 19e The crude compound 19d (36 mg, 102.2 μmol) was dissolved in 4 mL of N,N-dimethylformamide. 17i (52 mg, 103.6 μmol) and 4-(4,6-dimethoxy-1,3,5-triazin-2-yl)-4-methylmorpholinium chloride (34.6 mg, 125.0 μmol) were added. The reaction solution was stirred at room temperature for 1 hour. 10 mL of water was added, and the reaction solution was extracted with ethyl acetate (10 mL×3). The organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 19e (70 mg, yield: 80.2%).

Step 6

(11S,19S)-11-Benzyl-19-cyclopropyl-1-(9H-fluoren-9-yl)-3,6,9,12,15-pentaoxo-2,18-dioxa-4,7,10,13,16-pentaazaicosan-20-oic acid 19f 19e (70 mg, 83.7 μmol) was dissolved in 2.5 mL of 3% (v/v) dichloroacetic acid in dichloromethane, and the solution was cooled to 0-5° C. in an ice-water bath. Triethylsilane (29 mg, 249.4 μmol) was added, and reaction solution was stirred in an ice bath for 3 hours. The reaction solution was concentrated under reduced pressure in the ice bath to remove half of the organic solvent. 5 mL of ether was added, and the solution was naturally warmed up to room temperature and pulped. A white solid was precipitated and filtered. The filter cake was collected and dried by an oil pump to obtain the title product 19f (57 mg, yield: 99.2%).

Step 7

(9H-Fluoren-9-yl)methyl ((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)carbamate 19g 1b (30 mg, 63.6 μmol) was added to a reaction flask, followed by the addition of 1 mL of 10% (v/v) methanol in dichloromethane. The solution was purged with argon three times, and cooled to 0-5° C. in an ice-water bath. One drop of triethylamine was added, and the reaction solution was stirred until 1b dissolved. 19f (57 mg, 83.1 μmol) was dissolved in 1 mL of 10% (v/v) methanol in dichloromethane, and the resulting solution was added dropwise to the above reaction solution, followed by the addition of 4-(4,6- dimethoxy-1,3,5-triazin-2-yl)-4-methylmorpholinium chloride (26 mg, 93.9 μmol). The reaction solution was warmed up to room temperature and stirred for 1 hour. 10 mL of dichloromethane and 5 mL of water were added, and the solution was stirred for 5 minutes and left to partition. The organic phase was collected. The aqueous phase was extracted with dichloromethane (10 mL×3), and the organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 19g (56 mg, yield: 79.8%).

MS m/z (ESI): 1103.1[M+1]

Step 8

(S)-2-(2-(2-Aminoacetamido)acetamido)-N-(2-((((S)-1-cyclopropyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl)-3-phenylpropanamide 19h 19g (4.6 mg, 4.16 μmol) was dissolved in 1.5 mL of dichloromethane, followed by the addition of 0.75 mL of diethylamine. The reaction solution was stirred at room temperature for 1.6 hours. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The solution was concentrated under reduced pressure to obtain the crude title product 19h (4.0 mg), which was used directly in the next step without purification.

Step 9

(1r,4r)-N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15,18-hexaoxo-3,20,23,26,29,32,35,38,41,44-decaoxa-5,8,11,14,17-pentaazahexatetracontan-46-yl)-4-((2,5-dioxo-2,5-dihydro-1H-pyrrol-1-yl)methyl)cyclohexane-1-carboxamide 19

The crude compound 19h (4.0 mg) was dissolved in 1 mL of N,N-dimethylformamide. 17g (2.9 mg, 4.2 μmol) and 4-(4,6-dimethoxy-1,3,5-triazin-2-yl)-4-methylmorpholinium chloride (1.5 mg, 5.4 μmol) were added. The reaction solution was stirred at room temperature for 40 minutes. The reaction solution was filtered, and purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product 19 (2.1 mg, yield: 32.4%).

$^1H$ NMR (400 MHz, DMSO-$d_6$): δ 8.71-8.62 (m, 1H), 8.59-8.51 (m, 1H), 8.34-8.26 (m, 1H), 8.14-8.02 (m, 2H), 7.95-7.86 (m, 1H), 7.83-7.69 (m, 2H), 7.35-7.31 (m, 1H), 7.29-7.11 (m, 3H), 7.01 (s, 1H), 6.72-6.50 (m, 3H), 5.59-5.50 (m, 2H), 5.42 (s, 2H), 5.38-5.18 (m, 3H), 4.79-4.69 (m, 2H), 4.61-4.42 (m, 3H), 3.91 (s, 2H), 3.79-3.65 (m, 4H), 3.63-3.44 (m, 13H), 3.41-3.30 (m, 2H), 3.26-3.09 (m, 5H), 3.08-2.84 (m, 4H), 2.81-2.64 (m, 3H), 2.42-2.28 (m, 3H), 2.24-2.12 (m, 2H), 2.05-1.93 (m, 4H), 1.89-1.77 (m, 2H), 1.72-1.56 (m, 3H), 1.53-1.38 (m, 3H), 1.34-1.10 (m, 11H), 0.94-0.78 (m, 5H), 0.52-0.35 (m, 3H).

Example 20 (Reference Example)

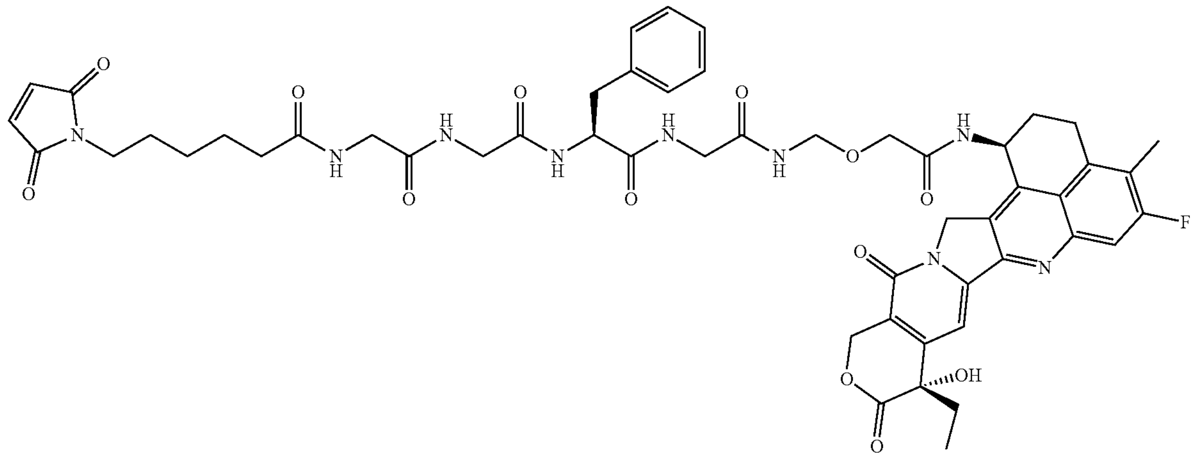

20

The title compound 20 was prepared based on the method disclosed in Example 58 on page 163 of the description of the patent application CN104755494A.

The following antibodies were prepared according to conventional methods, for example, vector construction, eukaryotic cell transfection such as HEK293 cell (Life Technologies Cat. No. 11625019) transfection, purification and expression.

The following is the sequence of Trastuzumab:

```
Light chain
                                        SEQ ID NO. 1
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy chain
                                        SEQ ID NO. 2
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYVVGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

QKSLSLSPGK
```

The following is the sequence of Pertuzumab:

```
Light chain
                                        SEQ ID NO. 3
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

-continued

```
Heavy chain
                                        SEQ ID NO. 4
EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK
```

The following is the sequence of B7H3 antibody 1F9DS:

```
Light chain
                                        SEQ ID NO. 5
DTVVTQEPSFSVSPGGTVTLTCGLSSGSVSTSHYPSWYQQTPGQAPRML

IYNTNTRSSGVPDRFSGSILGNKAALTITGAQADDESDYYCAIHVDRDI

WVFGGGTKLTVLGQPKANPTVTLFPPSSEELQANKATLVCLISDFYPGA

VTVAWKADGSPVKAGVETTKPSKQSNNKYAASSYLSLTPEQWKSHRSYS

CQVTHEGSTVEKTVAPTEC

Heavy chain
                                        SEQ ID NO. 6
QVQLVQSGGGVVQPGTSLRLSCAASGFIFSSSAMHWVRQAPGKGLEWVA

VISYDGSNKYYVDSVKGRFTISRDNSKNTLYLQMNSLRAEDTAVYYCAR

SARLYASFDYWGQGALVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK
```

Example 21 ADC-1

FADC-1

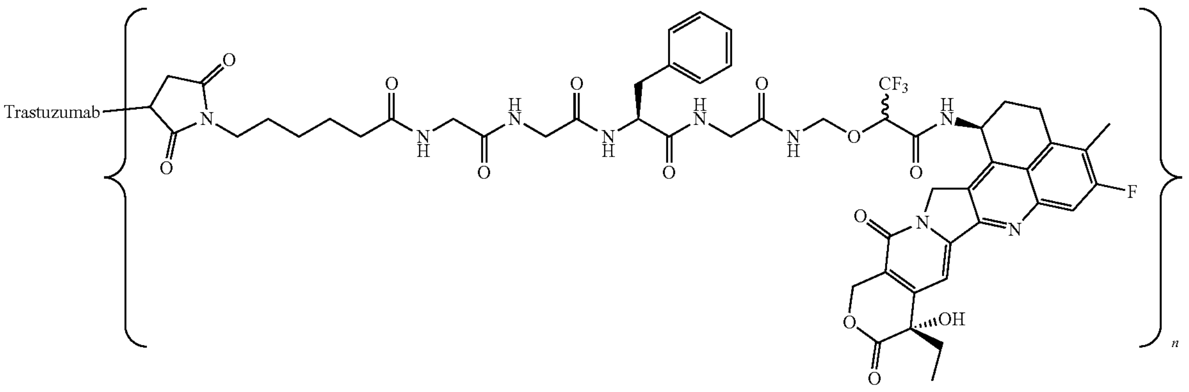

A formulated aqueous solution of tris(2-carboxyethyl) phosphine (10 mM, 0.082 mL, 0.82 μmol) was added to a PBS-buffered aqueous solution of antibody Trastuzumab (0.05 M PBS-buffered aqueous solution with pH=6.5; 2.5 ml, 9.96 mg/ml, 0.168 μmol) at 37° C. The reaction solution was placed in a water bath shaker, and shaked at 37° C. for 3 hours before stopping the reaction. The reaction solution was cooled to 25° C. in a water bath, and diluted to 5.0 mg/ml. 2.0 ml of the solution was taken for the next reaction.

Compound 10, the compound having shorter retention time (2.1 mg, 2.02 μmop was dissolved in 0.10 mL of DMSO, and then added to 2.0 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-1 of formula FADC-1 (5.0 mg/mL, 1.1 mL), which was stored at 4° C.

The average value calculated by UV-HPLC: n=5.09.

Example 22 ADC-2

FADC-1

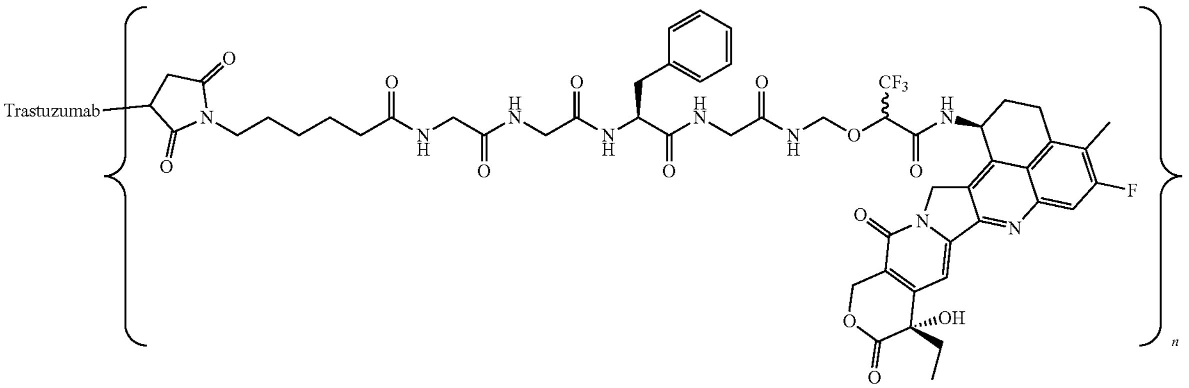

A formulated aqueous solution of tris(2-carboxyethyl) phosphine (10 mM, 0.082 mL, 0.82 μmol) was added to a PBS-buffered aqueous solution of antibody Trastuzumab (0.05 M PBS-buffered aqueous solution with pH=6.5; 2.5 ml, 9.96 mg/ml, 0.168 μmol) at 37° C. The reaction solution was placed in a water bath shaker, and shaked at 37° C. for 3 hours before stopping the reaction. The reaction solution was cooled to 25° C. in a water bath, and diluted to 5.0 mg/ml. 2.0 ml of the solution was taken for the next reaction.

Compound 10, the compound having longer retention time (2.1 mg, 2.02 μmop was dissolved in 0.10 mL of DMSO, and then added to 2.0 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-2 of formula FADC-1 (4.95 mg/mL, 1.1 mL), which was stored at 4° C.

The average value calculated by UV-HPLC: n=7.39.

Example 23 ADC-3

FADC-3

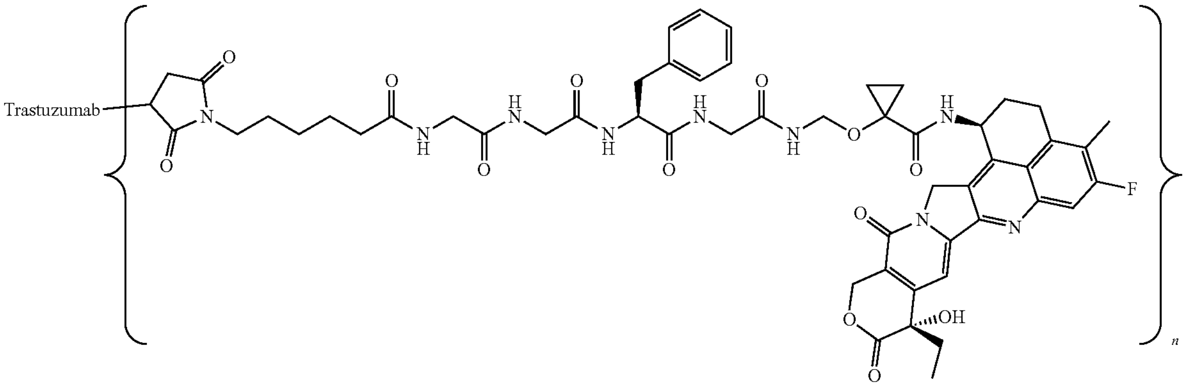

A formulated aqueous solution of tris(2-carboxyethyl) phosphine (10 mM, 0.082 mL, 0.82 μmol) was added to a PBS-buffered aqueous solution of antibody Trastuzumab (0.05 M PBS-buffered aqueous solution with pH=6.5; 2.5 ml, 9.96 mg/ml, 0.168 μmol) at 37° C. The reaction solution was placed in a water bath shaker, and shaked at 37° C. for 3 hours before stopping the reaction. The reaction solution was cooled to 25° C. in a water bath, and diluted to 5.0 mg/ml. 2.0 ml of the solution was taken for the next reaction.

Compound 8 (2.1 mg, 2.02 μmol) was dissolved in 0.10 mL of DMSO, and then added to 2.0 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-3 of formula FADC-3 (5.24 mg/mL, 1.1 mL), which was stored at 4° C.

The average value calculated by UV-HPLC: n=7.36.

Example 24 ADC-4

FADC-4A

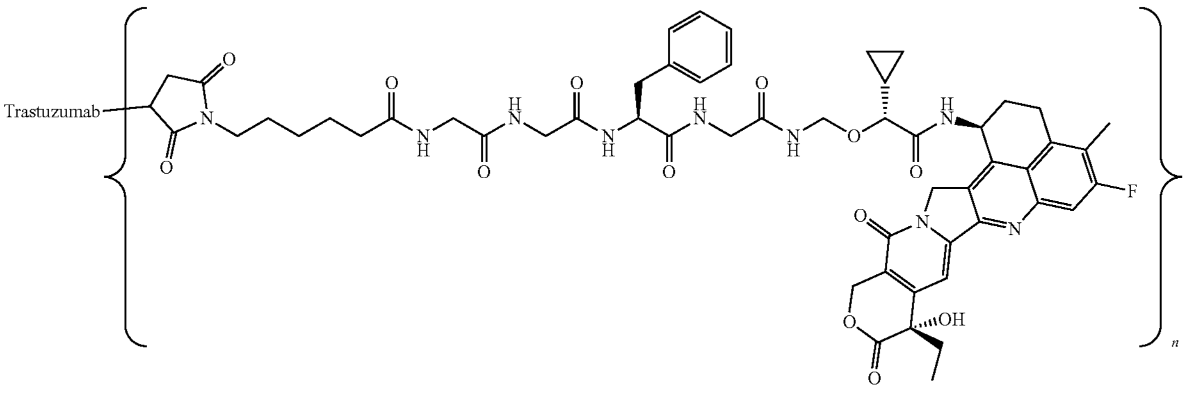

A formulated aqueous solution of tris(2-carboxyethyl) phosphine (10 mM, 0.173 mL, 1.73 μmol) was added to a PBS-buffered aqueous solution of antibody Trastuzumab (0.05 M PBS-buffered aqueous solution with pH=6.5; 3.74 ml, 13.38 mg/ml, 0.338 μmol) at 37° C. The reaction solution was placed in a water bath shaker, and shaked at 37° C. for 3 hours before stopping the reaction. The reaction solution was cooled to 25° C. in a water bath, and diluted to 6.7 mg/ml. 1.3 ml of the solution was taken for the next reaction.

Compound 9-having shorter retention time, the compound 9-A (1.0 mg, 0.93 μmol) was dissolved in 0.10 mL of DMSO, and then added to 1.3 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-4 of formula FADC-4A (1.72 mg/mL, 2.36 mL), which was stored at 4° C.

The average value calculated by UV-HPLC: n=7.39.

Example 25 ADC-5

FADC-4A

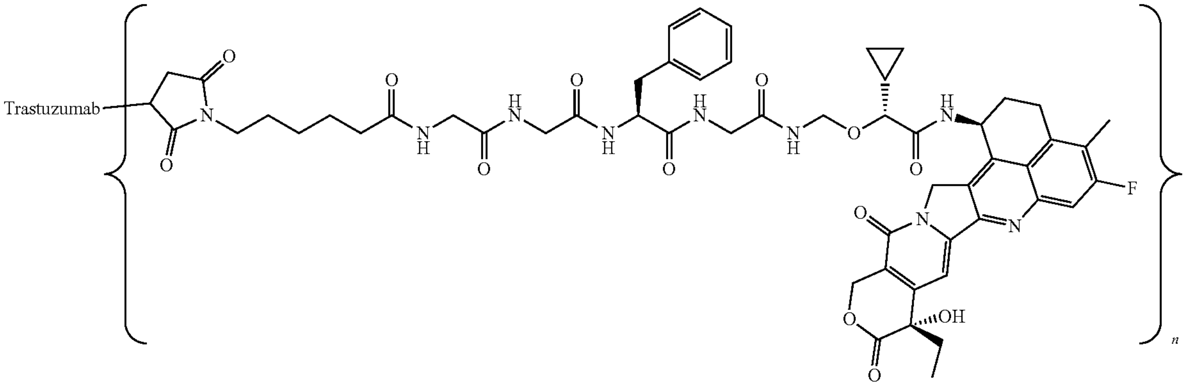

A formulated aqueous solution of tris(2-carboxyethyl) phosphine (10 mM, 0.067 mL, 0.67 μmol) was added to a PBS-buffered aqueous solution of antibody Trastuzumab (0.05 M PBS-buffered aqueous solution with pH=6.5; 3.0 ml, 6.70 mg/ml, 0.136 μmol) at 37° C. The reaction solution was placed in a water bath shaker, and shaked at 37° C. for 3 hours before stopping the reaction. The reaction solution was cooled to 25° C. in a water bath, and 0.614 ml of the solution was taken for the next reaction.

Compound 9-having shorter retention time, the compound 9-A (0.5 mg, 0.42 μmol) was dissolved in 0.031 mL of DMSO, and then added to 0.614 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-5 of formula FADC-4A (3.08 mg/mL, 0.82 mL), which was stored at 4° C.

The average value calculated by UV-HPLC: n=3.16.

Example 26 ADC-6

FADC-4B

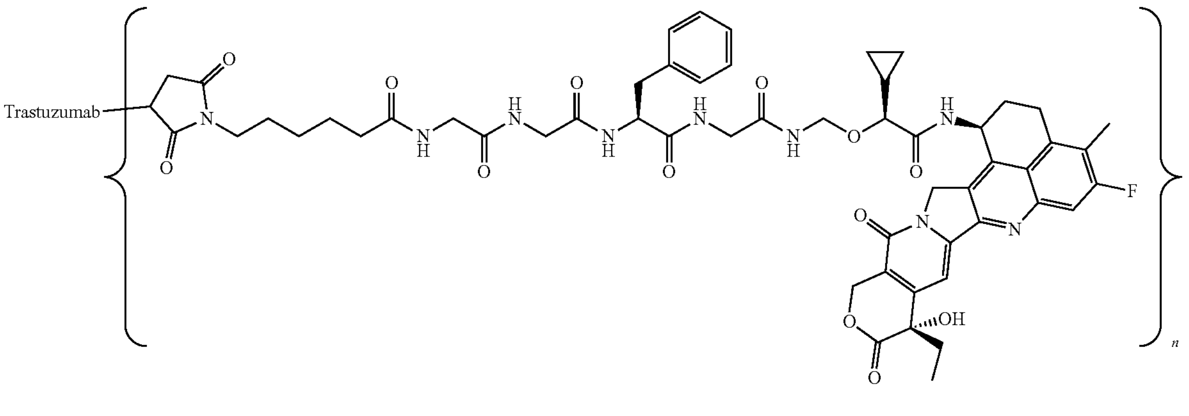

A formulated aqueous solution of tris(2-carboxyethyl) phosphine (10 mM, 0.173 mL, 1.73 μmol) was added to a PBS-buffered aqueous solution of antibody Trastuzumab (0.05 M PBS-buffered aqueous solution with pH=6.5; 3.74 ml, 13.38 mg/ml, 0.338 μmol) at 37° C. The reaction solution was placed in a water bath shaker, and shaked at 37° C. for 3 hours before stopping the reaction. The reaction solution was cooled to 25° C. in a water bath, and diluted to 6.7 mg/ml. 0.75 ml of the solution was taken for the next reaction.

Compound 9-having longer retention time, the compound 9-B (0.68 mg, 0.63 μmol) was dissolved in 0.10 mL of DMSO, and then added to 0.75 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-6 of formula FADC-4B (1.78 mg/mL, 1.78 mL), which was stored at 4° C.

The average value calculated by UV-HPLC: n=3.94.

Example 27 ADC-7

FADC-7

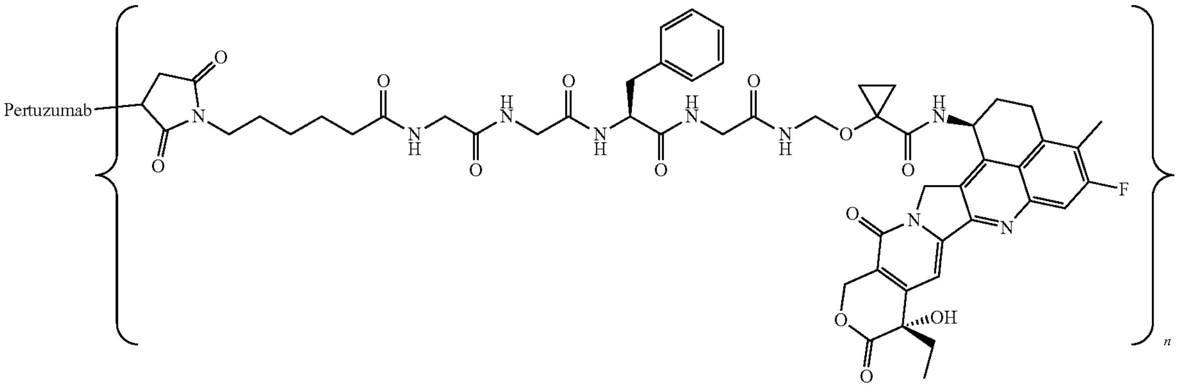

A formulated aqueous solution of tris(2-carboxyethyl) phosphine (10 mM, 0.173 mL, 1.73 μmol) was added to a PBS-buffered aqueous solution of antibody Pertuzumab (0.05 M PBS-buffered aqueous solution with pH=6.5; 5.0 ml, 10 mg/ml, 0.338 μmol) at 37° C. The reaction solution was placed in a water bath shaker, and shaked at 37° C. for 3 hours before stopping the reaction. The reaction solution was cooled to 25° C. in a water bath, and diluted to 5.0 mg/ml. 1.0 ml of the solution was taken for the next reaction.

Compound 8 (0.65 mg, 0.6 μmol) was dissolved in 0.1 mL of DMSO, and then added to 1.0 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-7 of formula FADC-7 (1.42 mg/mL, 2.15 mL), which was stored at 4° C.

The average value calculated by UV-HPLC: n=6.91.

Example 28 ADC-8

FADC-8

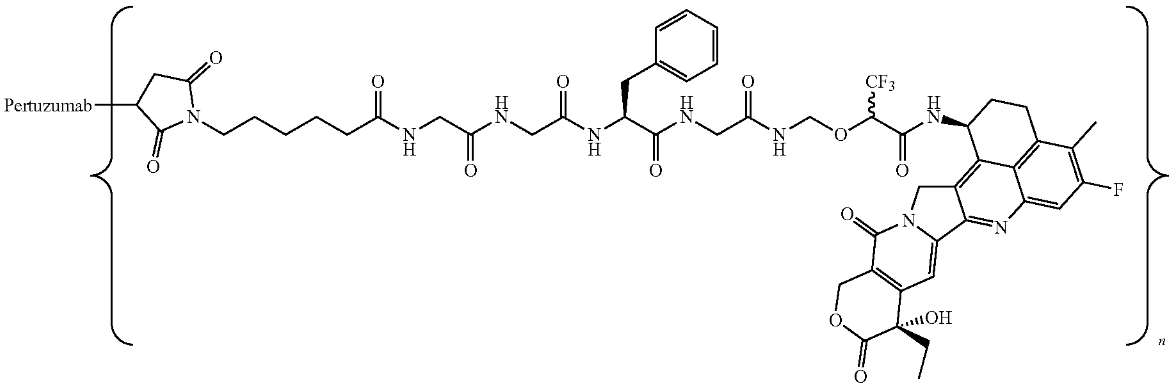

A formulated aqueous solution of tris(2-carboxyethyl) phosphine (10 mM, 0.173 mL, 1.73 μmol) was added to a PBS-buffered aqueous solution of antibody Pertuzumab (0.05 M PBS-buffered aqueous solution with pH=6.5; 5.0 ml, 10 mg/ml, 0.338 μmol) at 37° C. The reaction solution was placed in a water bath shaker, and shaked at 37° C. for 3 hours before stopping the reaction. The reaction solution was cooled to 25° C. in a water bath, and diluted to 5.0 mg/ml. 1.6 ml of the solution was taken for the next reaction.

Compound 10, the compound having shorter retention time (1.04 mg, 1.0 μmol) was dissolved in 0.1 mL of DMSO, and then added to 1.6 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-8 of formula FADC-8 (2.14 mg/mL, 2.31 mL), which was stored at 4° C.

The average value calculated by UV-HPLC: n=6.58.

Example 29 ADC-9

FADC-9A

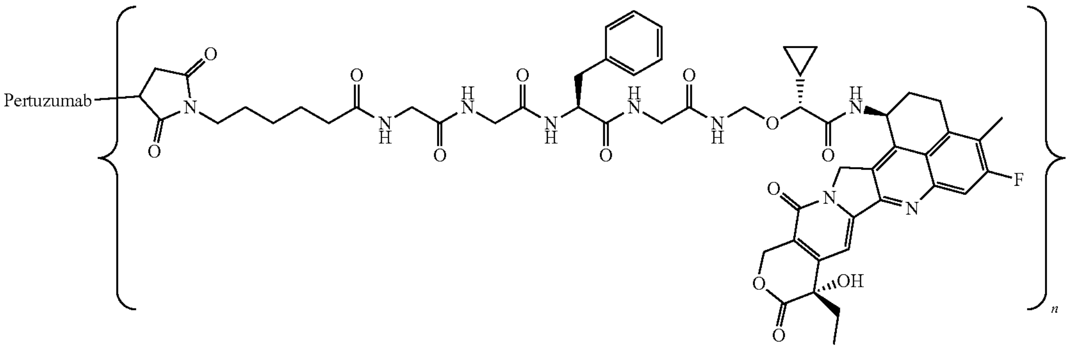

A formulated aqueous solution of tris(2-carboxyethyl) phosphine (10 mM, 0.173 mL, 1.73 μmol) was added to a PBS-buffered aqueous solution of antibody Pertuzumab (0.05 M PBS-buffered aqueous solution with pH=6.5; 5.0 ml, 10 mg/ml, 0.338 μmol) at 37° C. The reaction solution was placed in a water bath shaker, and shaked at 37° C. for 3 hours before stopping the reaction. The reaction solution was cooled to 25° C. in a water bath, and diluted to 5.0 mg/ml. 0.8 ml of the solution was taken for the next reaction.

Compound 9-having shorter retention time, the compound 9-A (0.55 mg, 0.5 μmol) was dissolved in 0.1 mL of DMSO, and then added to the above 0.8 ml of solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-9 of formula FADC-9A (2.27 mg/mL, 1.11 mL), which was stored at 4° C.

The average value calculated by UV-HPLC: n=3.16.

Example 30 ADC-10

FADC-10

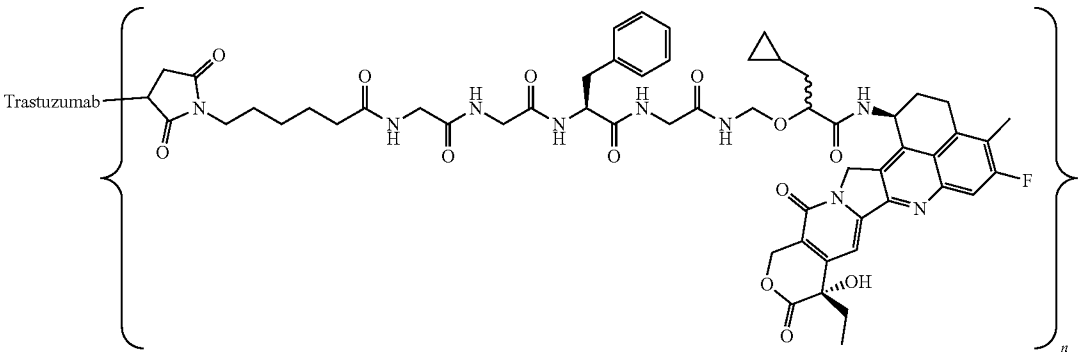

A formulated aqueous solution of tris(2-carboxyethyl) phosphine (TCEP) (10 mM, 19.76 μL, 197.6 μmol) was added to a PBS-buffered aqueous solution of antibody Trastuzumab (0.05 M PBS-buffered aqueous solution with pH=6.5; 10.0 mg/ml, 0.574 mL, 38.78 nmol) at 37° C. The reaction solution was placed in a water bath shaker, and shaked at 37° C. for 3 hours before stopping the reaction. The reaction solution was cooled to 25° C. in a water bath.

Compound 14, the compound having shorter retention time (0.64 mg, 588 nmol) was dissolved in 40 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-10 of formula FADC-10 (5.48 mg/mL, 1.03 mL), which was stored at 4° C.

The average value calculated by UV-Vis: n=6.25.

Example 31 ADC-11

FADC-10

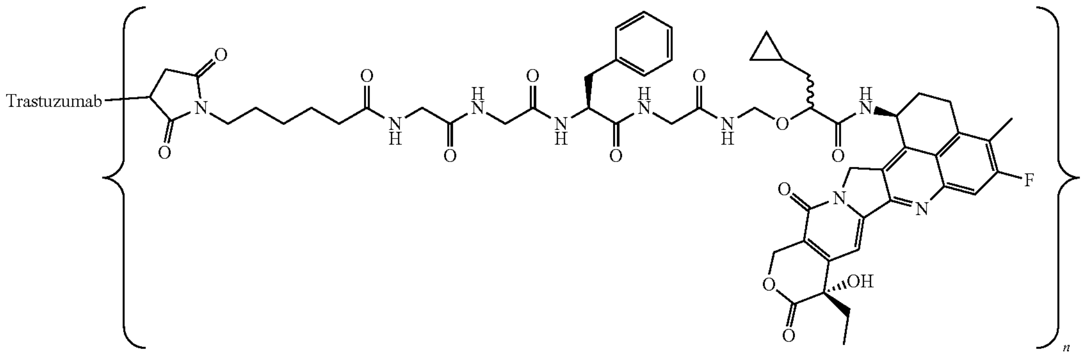

A formulated aqueous solution of tris(2-carboxyethyl) phosphine (TCEP) (10 mM, 22.24 μL, 222.4 nmol) was added to a PBS-buffered aqueous solution of antibody Trastuzumab (0.05 M PBS-buffered aqueous solution with pH=6.5; 10.0 mg/ml, 0.646 mL, 43.64 nmol) at 37° C. The reaction solution was placed in a water bath shaker, and shaked at 37° C. for 3 hours before stopping the reaction. The reaction solution was cooled to 25° C. in a water bath.

Compound 14, the compound having longer retention time (0.72 mg, 662 nmol) was dissolved in 40 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-11 of formula FADC-10 (2.13 mg/mL, 1.87 mL), which was stored at 4° C.

The average value calculated by UV-Vis: n=7.03.

Example 32 ADC-12

FADC-12

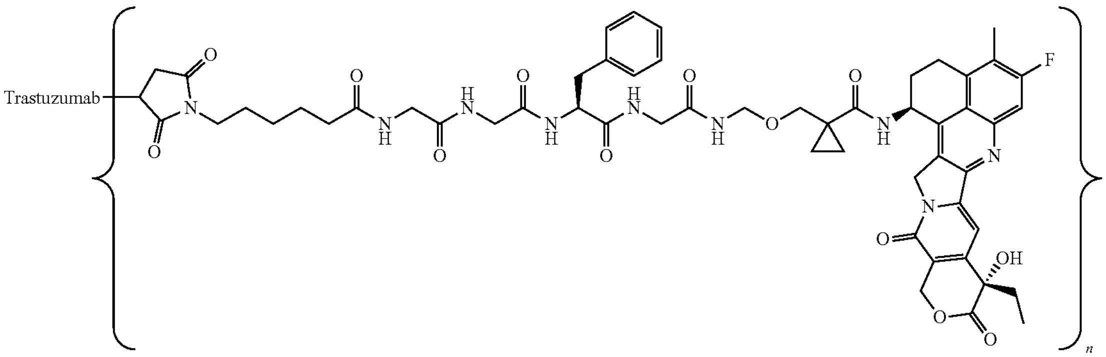

A formulated aqueous solution of tris(2-carboxyethyl) phosphine (TCEP) (10 mM, 25.0 μL, 250.0 nmol) was added to a PBS-buffered aqueous solution of antibody Trastuzumab (0.05 M PBS-buffered aqueous solution with pH=6.5; 10.0 mg/ml, 0.726 mL, 49.05 nmol) at 37° C. The reaction solution was placed in a water bath shaker, and shaked at 37° C. for 3 hours before stopping the reaction. The reaction solution was cooled to 25° C. in a water bath.

Compound 15 (0.81 mg, 754 nmol) was dissolved in 40 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-12 of formula FADC-12 (3.34 mg/mL, 1.45 mL), which was stored at 4° C.

The average value calculated by UV-Vis: n=6.93.

Example 33 ADC-13

FADC-13

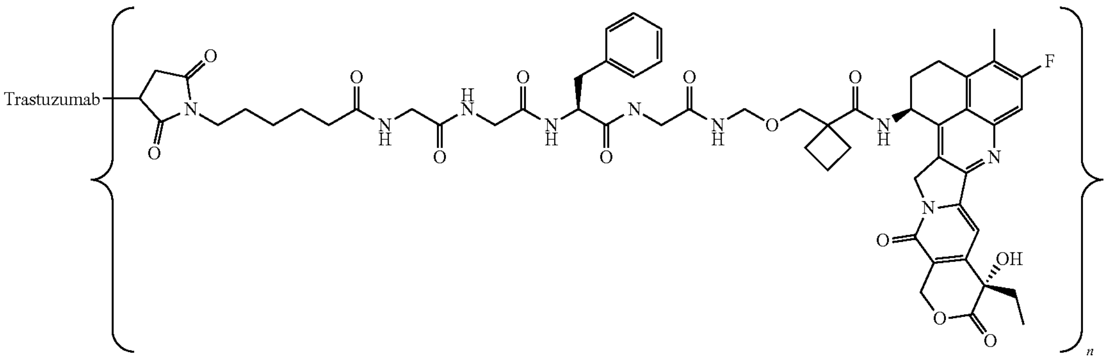

A formulated aqueous solution of tris(2-carboxyethyl) phosphine (TCEP) (10 mM, 9.88 μL, 98.8 nmol) was added to a PBS-buffered aqueous solution of antibody Trastuzumab (0.05 M PBS-buffered aqueous solution with pH=6.5; 10.0 mg/ml, 0.287 mL, 19.39 nmol) at 37° C. The reaction solution was placed in a water bath shaker, and shaked at 37° C. for 3 hours before stopping the reaction. The reaction solution was cooled to 25° C. in a water bath.

Compound 16 (0.32 mg, 294 nmol) was dissolved in 20 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-13 of formula FADC-13 (2.37 mg/mL, 0.88 mL), which was stored at 4° C.

The average value calculated by UV-Vis: n=6.53.

Example 34 ADC-14

FADC-14

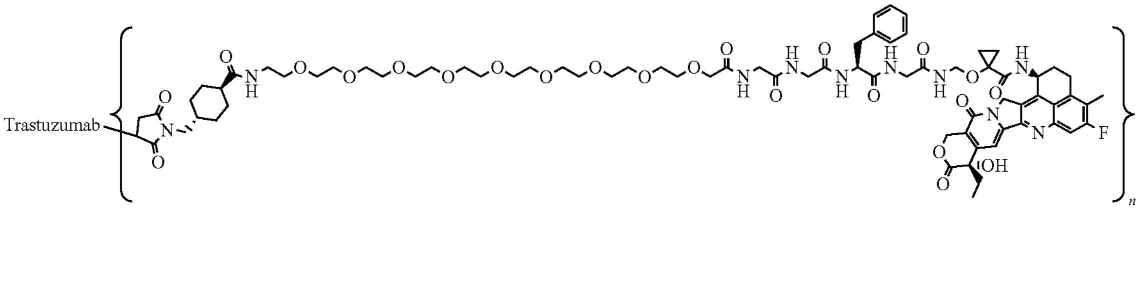

A formulated aqueous solution of tris(2-carboxyethyl) phosphine (TCEP) (10 mM, 20.38 μL, 203.8 nmol) was added to a PBS-buffered aqueous solution of antibody Trastuzumab (0.05 M PBS-buffered aqueous solution with pH=6.5; 10.0 mg/ml, 0.592 mL, 40.0 nmol) at 37° C. The reaction solution was placed in a water bath shaker, and shaked at 37° C. for 3 hours before stopping the reaction. The reaction solution was cooled to 25° C. in a water bath.

Compound 17 (0.92 mg, 598 nmol) was dissolved in 40 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-14 of formula FADC-14 (0.30 mg/mL, 12.0 mL), which was stored at 4° C.

The average value calculated by UV-Vis: n=7.61.

Example 35 ADC-15

FADC-15

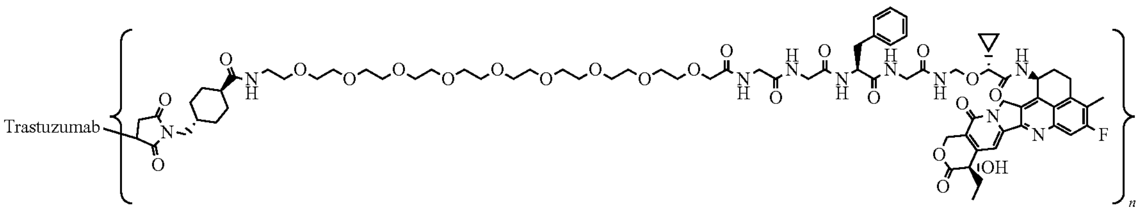

A formulated aqueous solution of tris(2-carboxyethyl) phosphine (TCEP) (10 mM, 20.38 μL, 203.8 nmol) was added to a PBS-buffered aqueous solution of antibody Trastuzumab (0.05 M PBS-buffered aqueous solution with pH=6.5; 10.0 mg/ml, 0.592 mL, 40.0 nmol) at 37° C. The reaction solution was placed in a water bath shaker, and shaked at 37° C. for 3 hours before stopping the reaction. The reaction solution was cooled to 25° C. in a water bath.

Compound 18 (0.93 mg, 599 nmol) was dissolved in 40 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-15 of formula FADC-15 (0.32 mg/mL, 11.8 mL), which was stored at 4° C.

The average value calculated by UV-Vis: n=7.89.

Example 36 ADC-16

FADC-16

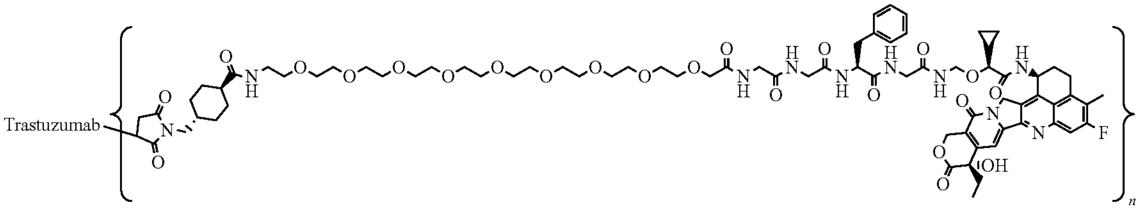

A formulated aqueous solution of tris(2-carboxyethyl) phosphine (TCEP) (10 mM, 18.25 μL, 182.5 nmol) was added to a PBS-buffered aqueous solution of antibody Trastuzumab (0.05 M PBS-buffered aqueous solution with pH=6.5; 10.0 mg/ml, 0.53 mL, 35.8 nmol) at 37° C. The reaction solution was placed in a water bath shaker, and shaked at 37° C. for 3 hours before stopping the reaction. The reaction solution was cooled to 25° C. in a water bath.

Compound 19 (0.83 mg, 534 nmol) was dissolved in 35 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-16 of formula FADC-16 (0.32 mg/mL, 12.0 mL), which was stored at 4° C.

The average value calculated by UV-Vis: n=7.43.

Example 37 ADC-17

FADC-4A

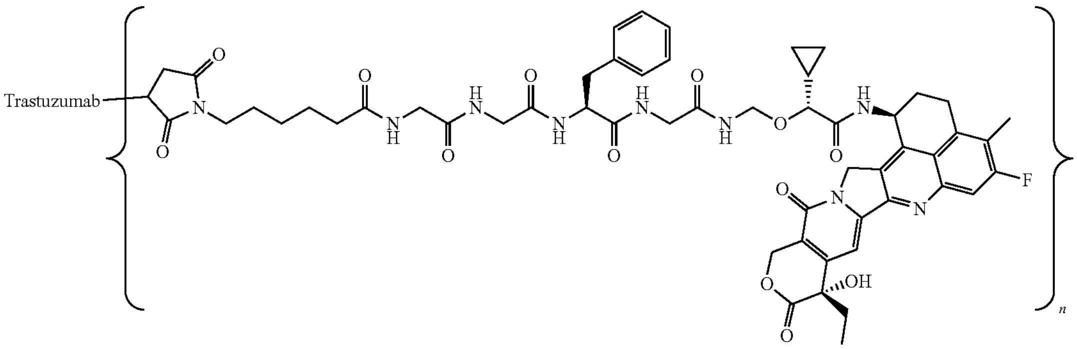

A formulated aqueous solution of tris(2-carboxyethyl) phosphine (TCEP) (10 mM, 43.2 μL, 432 nmol) was added to a PBS-buffered aqueous solution of antibody Trastuzumab (0.05 M PBS-buffered aqueous solution with pH=6.5; 10.0 mg/ml, 2.0 mL, 135.12 nmol) at 37° C. The reaction solution was placed in a water bath shaker, and shaked at 37° C. for 3 hours before stopping the reaction. The reaction solution was cooled to 25° C. in a water bath.

Compound 9-having shorter retention time, the compound 9-A (2.22 mg, 2067 nmol) was dissolved in 175 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-17 of formula FADC-4A (1.32 mg/mL, 12.0 mL), which was stored at 4° C.

The average value calculated by UV-Vis: n=5.42.

Example 38 ADC-18 (reference example)

FADC-18

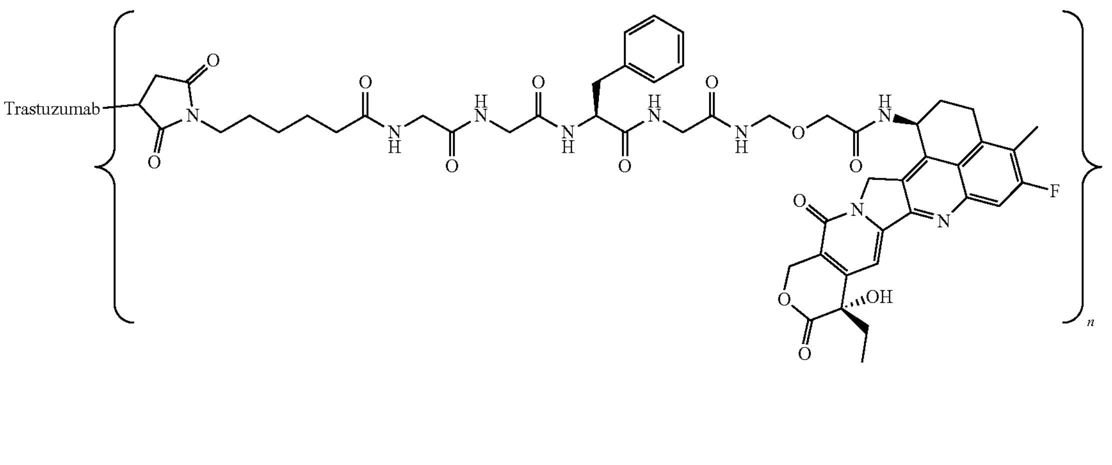

A formulated aqueous solution of tris(2-carboxyethyl) phosphine (TCEP) (10 mM, 51.7 μL, 517 nmol) was added to a PBS-buffered aqueous solution of antibody Trastuzumab (0.05 M PBS-buffered aqueous solution with pH=6.5; 10.0 mg/ml, 1.5 mL, 101.3 nmol) at 37° C. The reaction solution was placed in a water bath shaker, and shaked at 37° C. for 3 hours before stopping the reaction. The reaction solution was cooled to 25° C. in a water bath.

Compound 20 (2.0 mg, 1934 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-18 of formula FADC-18 (0.79 mg/mL, 13.0 mL), which was stored at 4° C.

The average value calculated by UV-Vis: n=7.23.

Example 39 ADC-19

FADC-4A

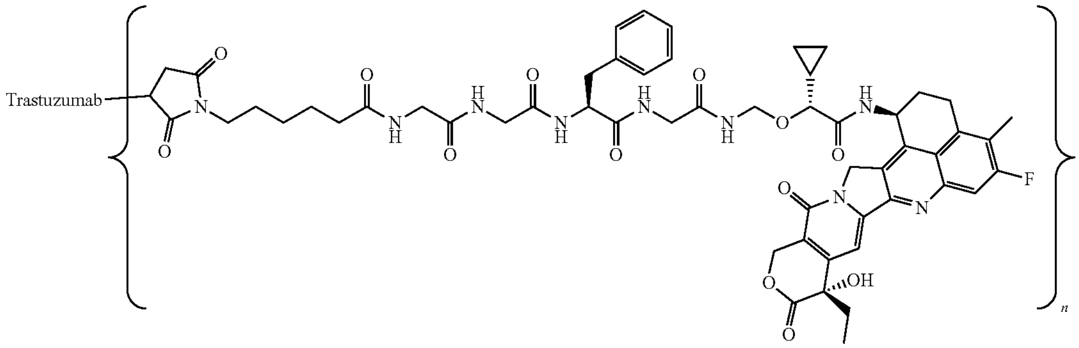

A formulated aqueous solution of tris(2-carboxyethyl) phosphine (TCEP) (10 mM, 46.9 μL, 469 nmol) was added to a PBS-buffered aqueous solution of antibody Trastuzumab (0.05 M PBS-buffered aqueous solution with pH=6.5; 10.0 mg/ml, 1.36 mL, 91.9 nmol) at 37° C. The reaction solution was placed in a water bath shaker, and shaked at 37° C. for 3 hours before stopping the reaction. The reaction solution was cooled to 25° C. in a water bath.

Compound 9-having shorter retention time, the compound 9-A (2.0 mg, 1862 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-19 of formula FADC-4A (0.73 mg/mL, 13.0 mL), which was stored at 4° C.

The average value calculated by UV-Vis: n=6.26.

Example 40 ADC-20

FADC-1

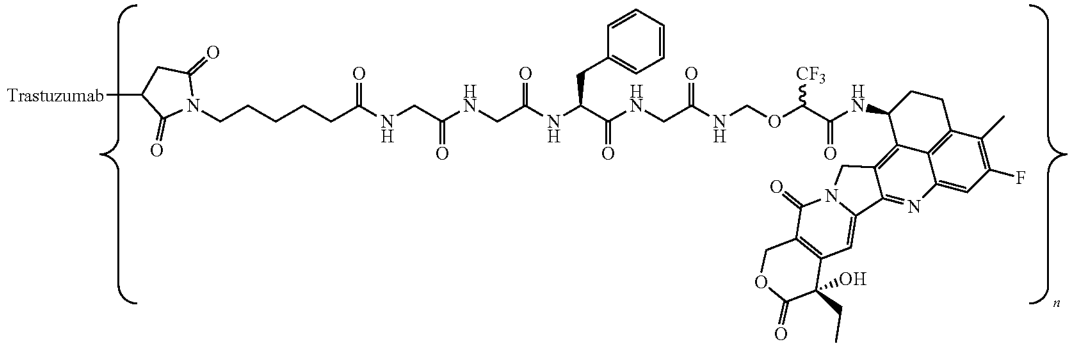

A formulated aqueous solution of tris(2-carboxyethyl) phosphine (TCEP) (10 mM, 51.7 μL, 517 nmol) was added to a PBS-buffered aqueous solution of antibody Trastuzumab (0.05 M PBS-buffered aqueous solution with pH=6.5; 10.0 mg/ml, 1.5 mL, 101.3 nmol) at 37° C. The reaction solution was placed in a water bath shaker, and shaked at 37° C. for 3 hours before stopping the reaction. The reaction solution was cooled to 25° C. in a water bath.

Compound 10, the compound having longer retention time (2.0 mg, 1815 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-20 of formula FADC-1 (0.73 mg/mL, 13.0 mL), which was stored at 4° C.

The average value calculated by UV-Vis: n=7.43.

Example 41 ADC-21 (reference example)

FADC-18

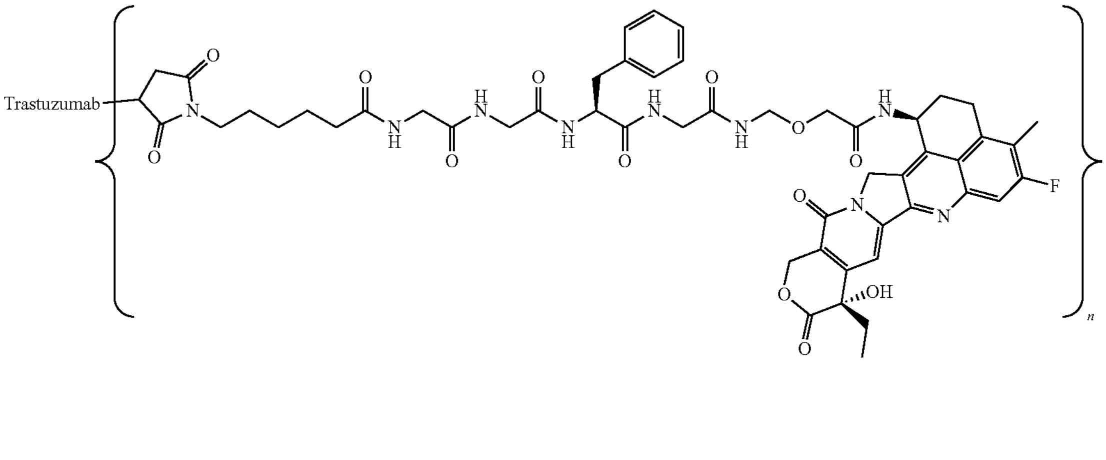

A formulated aqueous solution of tris(2-carboxyethyl) phosphine (TCEP) (10 mM, 63.9 μL, 639 nmol) was added to a PBS-buffered aqueous solution of antibody Trastuzumab (0.05 M PBS-buffered aqueous solution with pH=6.5; 10.0 mg/ml, 1.86 mL, 125.4 nmol) at 37° C. The reaction solution was placed in a water bath shaker, and shaked at 37° C. for 3 hours before stopping the reaction. The reaction solution was cooled to 25° C. in a water bath.

Compound 20 (2.07 mg, 2001 nmol) was dissolved in 150 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-21 of formula FADC-18 (2.91 mg/mL, 4.44 mL), which was stored at 4° C.

The average value calculated by UV-Vis: n=7.23.

Example 42 ADC-22

FADC-4A

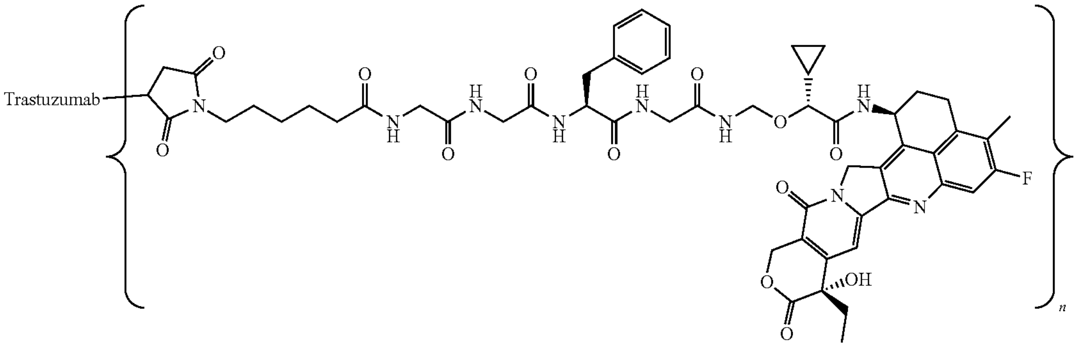

A formulated aqueous solution of tris(2-carboxyethyl) phosphine (TCEP) (10 mM, 64.9 μL, 649 nmol) was added to a PBS-buffered aqueous solution of antibody Trastuzumab (0.05 M PBS-buffered aqueous solution with pH=6.5; 10.0 mg/ml, 1.88 mL, 127.2 nmol) at 37° C. The reaction solution was placed in a water bath shaker, and shaked at 37° C. for 3 hours before stopping the reaction. The reaction solution was cooled to 25° C. in a water bath.

Compound 9—having shorter retention time, the compound 9-A (2.1 mg, 1955 nmol) was dissolved in 150 μL of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-22 of formula FADC-4A (3.56 mg/mL, 3.98 mL), which was stored at 4° C.

The average value calculated by UV-Vis: n=6.79.

Example 43 ADC-23 (Reference Example)

FADC-18

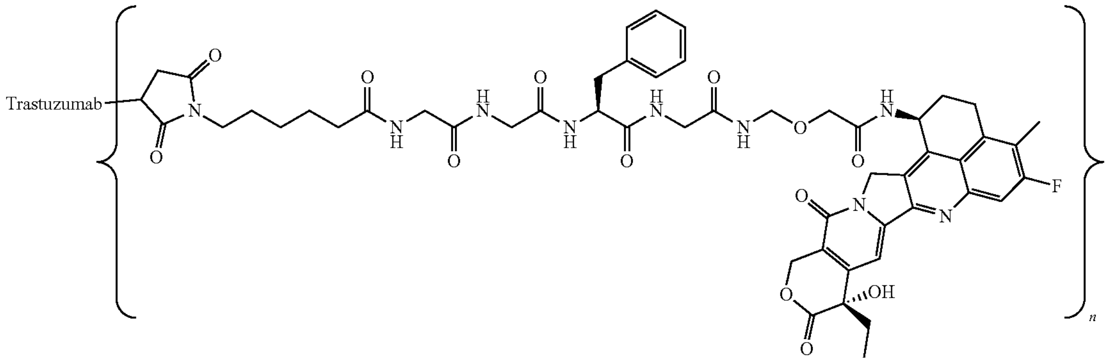

A formulated aqueous solution of tris(2-carboxyethyl) phosphine (TCEP) (10 mM, 11.89 mL, 118.9 μmol) was added to a PBS-buffered aqueous solution of antibody Trastuzumab (0.05 M PBS-buffered aqueous solution with pH=6.5; 10.0 mg/ml, 345 mL, 23.31 μmol) at 37° C. The reaction solution was placed in a water bath shaker, and shaked at 37° C. for 3.5 hours before stopping the reaction. The reaction solution was cooled to 25° C. in a water bath.

Compound 20 (362 mg, 350 μmol) was dissolved in 7.12 ml of MeCN and 3.56 mL of DMSO, and then added to the above reaction solution. The reaction solution was placed in a water bath shaker, and shaked at 25° C. for 3 hours before stopping the reaction. The reaction solution was desalted and purified by an ultrafiltration pack with PBS-buffered aqueous solution containing 2% (v/v) MeCN and 1% (v/v) DMSO (0.05 M PBS-buffered aqueous solution with pH=6.5) and succinic acid-buffered aqueous solution (0.01 M succinic acid-buffered aqueous solution with pH=5.3). Sucrose was added to 60 mg/mL, and Tween 20 was added to 0.2 mg/mL. The solution was bottled and lyophilized to obtain the lyophilized powder sample of the exemplary product ADC-23 of formula FADC-18, which was stored at 4° C.

The average value calculated by UV-Vis: n=7.05.

Example 44 ADC-24

FADC-4A

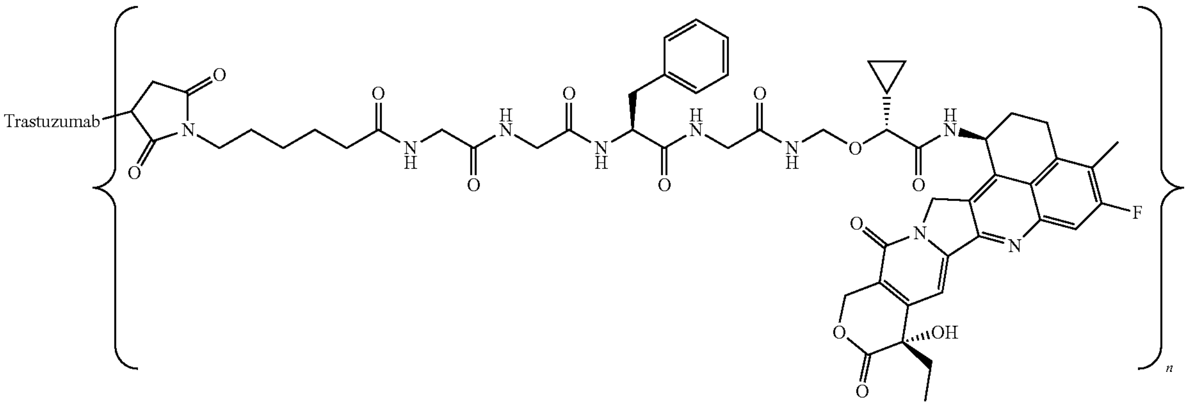

A formulated aqueous solution of tris(2-carboxyethyl) phosphine (TCEP) (10 mM, 11.44 mL, 114.4 μmol) was added to a PBS-buffered aqueous solution of antibody Trastuzumab (0.05 M PBS-buffered aqueous solution with pH=6.5; 10.0 mg/ml, 332 mL, 22.43 Nmol) at 37° C. The reaction solution was placed in a water bath shaker, and shaked at 37° C. for 3.5 hours before stopping the reaction. The reaction solution was cooled to 25° C. in a water bath.

Compound 9-having shorter retention time, the compound 9-A (241 mg, 224 Nmol) was dissolved in 13.76 ml of MeCN and 6.88 mL of DMSO, and then added to the above reaction solution. The reaction solution was placed in a water bath shaker, and shaked at 25° C. for 3 hours before stopping the reaction. The reaction solution was desalted and purified by an ultrafiltration pack with PBS-buffered aqueous solution containing 4% (v/v) MeCN and 2% (v/v) DMSO (0.05 M PBS-buffered aqueous solution with pH=6.5) and succinic acid-buffered aqueous solution (0.01 M succinic acid-buffered aqueous solution with pH=5.3). Sucrose was added to 60 mg/mL, and Tween 20 was added to 0.2 mg/mL. The solution was bottled and lyophilized to obtain the lyophilized powder sample of the exemplary product ADC-24 of formula FADC-4A, which was stored at 4° C.

The average value calculated by UV-Vis: n=7.07.

Example 45 ADC-25

FADC-25

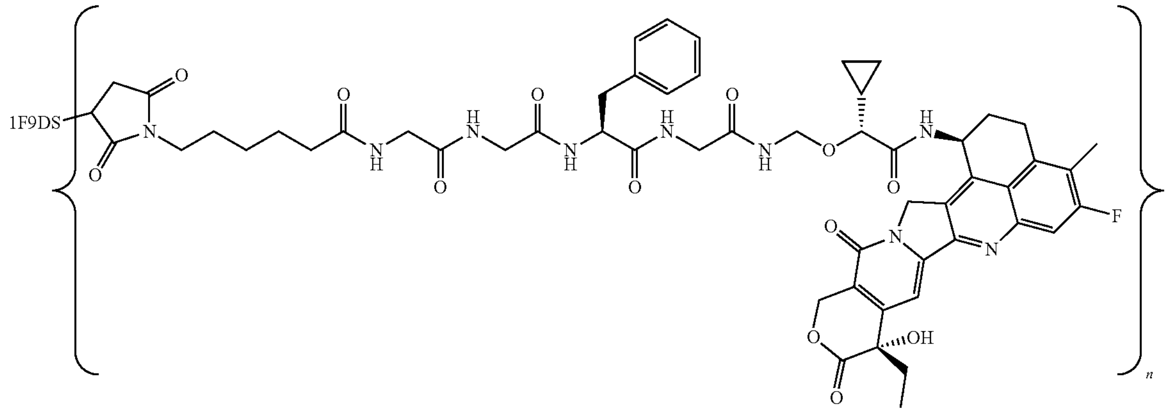

A formulated aqueous solution of tris(2-carboxyethyl) phosphine (TCEP) (10 mM, 73.7 μL, 740 nmol) was added to a PBS-buffered aqueous solution of antibody B7H3 antibody 1F9DS (0.05 M PBS-buffered aqueous solution with pH=6.5; 10.0 mg/ml, 2.14 mL, 144.60 nmol) at 37° C. The reaction solution was placed in a water bath shaker, and shaked at 37° C. for 3 hours before stopping the reaction. The reaction solution was cooled to 25° C. in a water bath.

Compound 9-having shorter retention time, the compound 9-A (3.0 mg, 2793 nmol) was dissolved in 150 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-25 of formula FADC-25 (1.28 mg/mL, 13.0 mL), which was stored at 4° C.

The average value calculated by UV-Vis: n=6.87.

Example 46 ADC-26 (Reference Example)

FADC-26

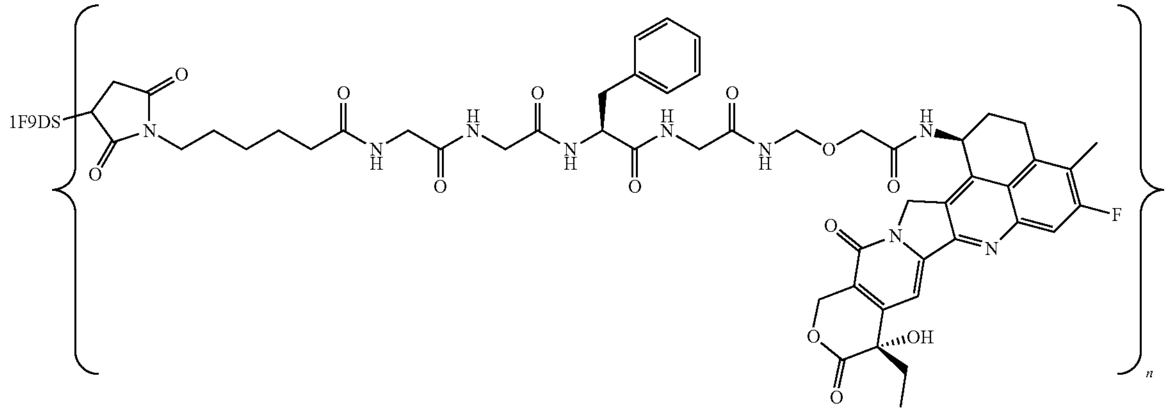

A formulated aqueous solution of tris(2-carboxyethyl) phosphine (TCEP) (10 mM, 30.1 μL, 300 nmol) was added to a PBS-buffered aqueous solution of antibody B7H3 antibody 1F9DS (0.05 M PBS-buffered aqueous solution with pH=6.5; 10.0 mg/ml, 0.89 mL, 60.14 nmol) at 37° C. The reaction solution was placed in a water bath shaker, and shaked at 37° C. for 3 hours before stopping the reaction. The reaction solution was cooled to 25° C. in a water bath.

Compound 20 (1.0 mg, 967 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-26 of formula FADC-26 (1.61 mg/mL, 4.0 mL), which was stored at 4° C.

The average value calculated by UV-Vis: n=6.15.

Example 47 ADC-27

FADC-25

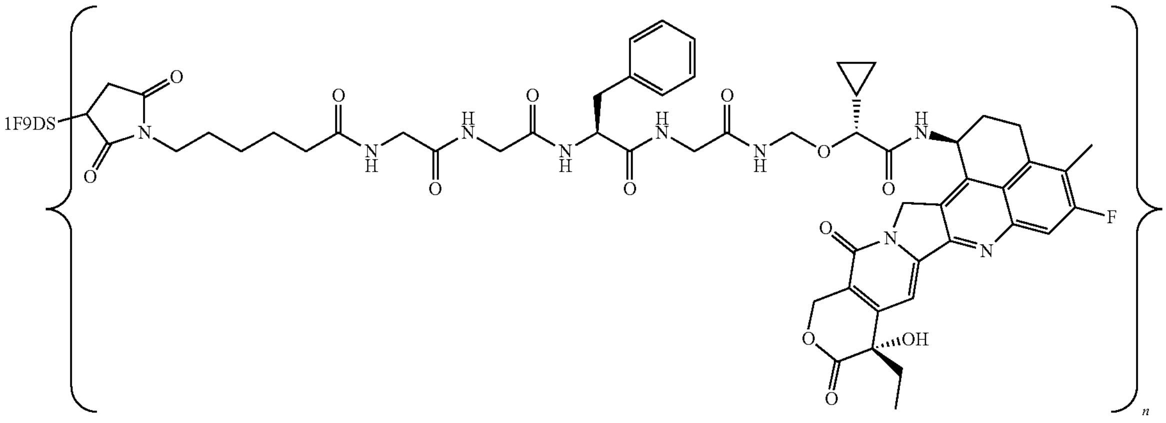

A formulated aqueous solution of tris(2-carboxyethyl) phosphine (TCEP) (10 mM, 30.1 μL, 300 nmol) was added to a PBS-buffered aqueous solution of antibody B7H3 antibody 1F9DS (0.05 M PBS-buffered aqueous solution with pH=6.5; 10.0 mg/ml, 0.89 mL, 60.14 nmol) at 37° C. The reaction solution was placed in a water bath shaker, and shaked at 37° C. for 3 hours before stopping the reaction. The reaction solution was cooled to 25° C. in a water bath.

Compound 9-having shorter retention time, the compound 9-A (1.02 mg, 950 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-27 of formula FADC-25 (1.94 mg/mL, 3.5 mL), which was stored at 4° C.

The average value calculated by UV-Vis: n=6.11.

Example 48 ADC-28 (Reference Example)

FADC-26

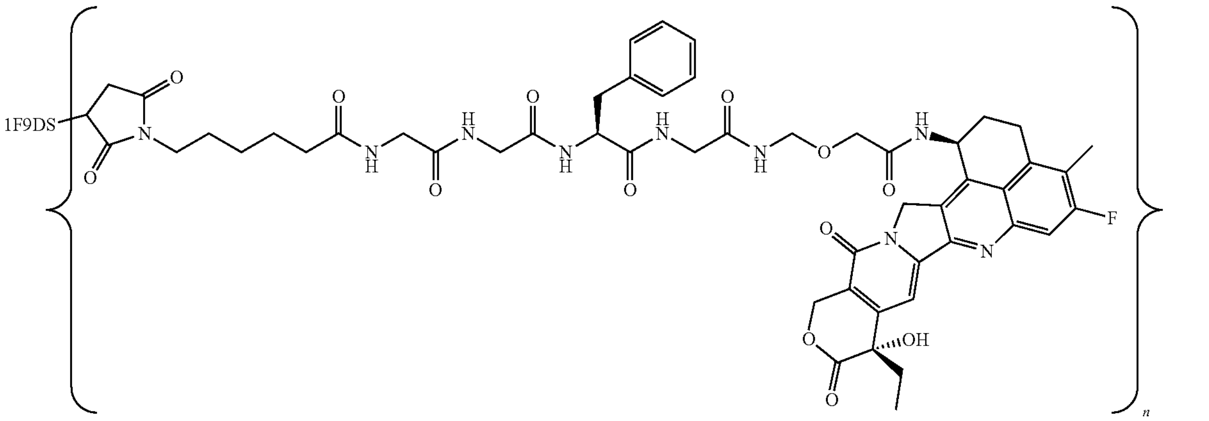

A formulated aqueous solution of tris(2-carboxyethyl) phosphine (TCEP) (10 mM, 81.3 μL, 810 nmol) was added to a PBS-buffered aqueous solution of antibody B7H3 antibody 1F9DS (0.05 M PBS-buffered aqueous solution with pH=6.5; 10.0 mg/ml, 2.36 mL, 159.47 nmol) at 37° C. The reaction solution was placed in a water bath shaker, and shaked at 37° C. for 3 hours before stopping the reaction. The reaction solution was cooled to 25° C. in a water bath.

Compound 20 (3.0 mg, 2901 nmol) was dissolved in 150 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-28 of formula FADC-26 (1.29 mg/mL, 13.0 mL), which was stored at 4° C.

The average value calculated by UV-Vis: n=7.46.

Example 49 ADC-29

FADC-25

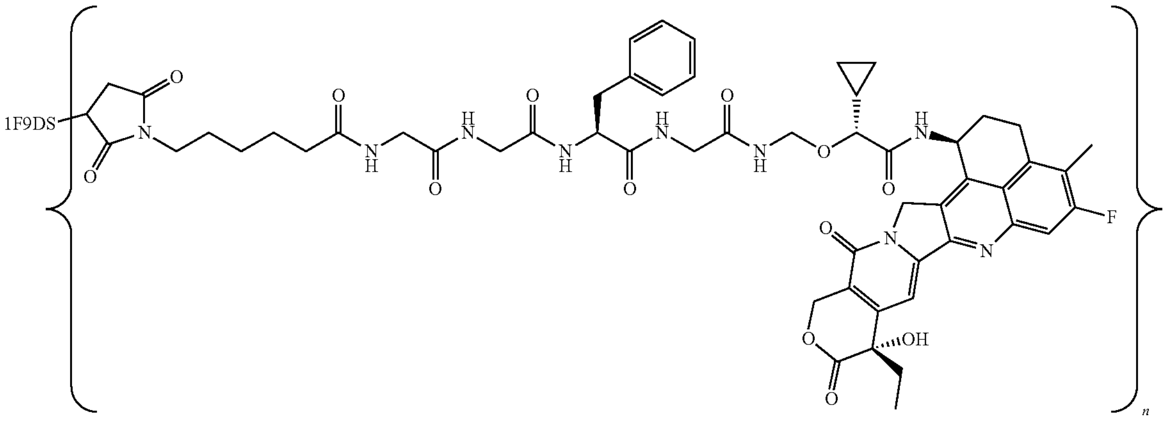

A formulated aqueous solution of tris(2-carboxyethyl) phosphine (TCEP) (10 mM, 28.6 μL, 290 nmol) was added to a PBS-buffered aqueous solution of antibody B7H3 antibody 1F9DS (0.05 M PBS-buffered aqueous solution with pH=6.5; 10.0 mg/ml, 0.80 mL, 50.06 nmol) at 37° C. The reaction solution was placed in a water bath shaker, and shaked at 37° C. for 3 hours before stopping the reaction. The reaction solution was cooled to 25° C. in a water bath.

Compound 9-having shorter retention time, the compound 9-A (1.29 mg, 1201 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-29 of formula FADC-25 (2.63 mg/mL, 2.4 mL), which was stored at 4° C.

The average value calculated by UV-Vis: n=7.24.

Example 50 ADC-30 (Reference Example)

FADC-26

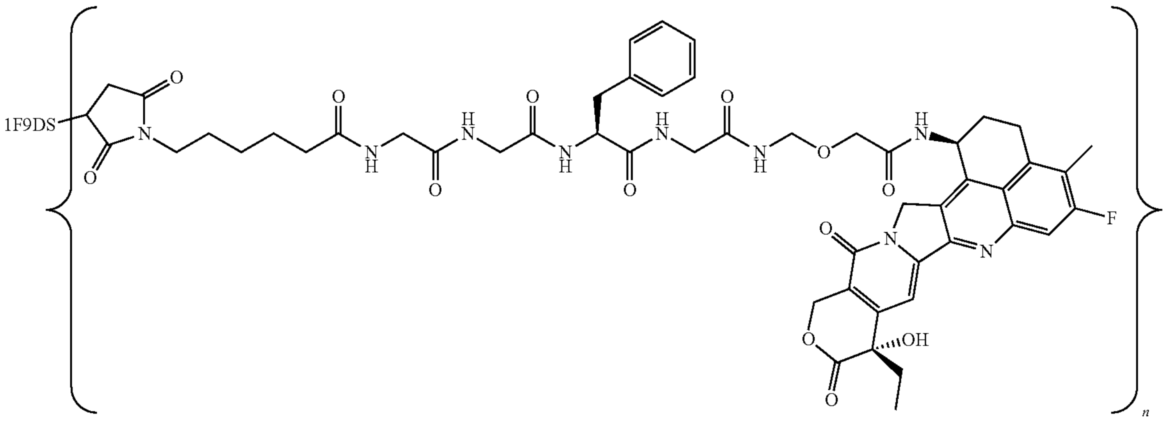

A formulated aqueous solution of tris(2-carboxyethyl) phosphine (TCEP) (10 mM, 29.1 μL, 290 nmol) was added to a PBS-buffered aqueous solution of antibody B7H3 antibody 1F9DS (0.05 M PBS-buffered aqueous solution with pH=6.5; 10.0 mg/ml, 0.86 mL, 58.4 nmol) at 37° C. The reaction solution was placed in a water bath shaker, and shaked at 37° C. for 3 hours before stopping the reaction. The reaction solution was cooled to 25° C. in a water bath.

Compound 20 (1.0 mg, 967 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-30 of formula FADC-26 (1.61 mg/mL, 4.0 mL), which was stored at 4° C.

The average value calculated by UV-Vis: n=6.15.

Example 51 ADC-31

FADC-31

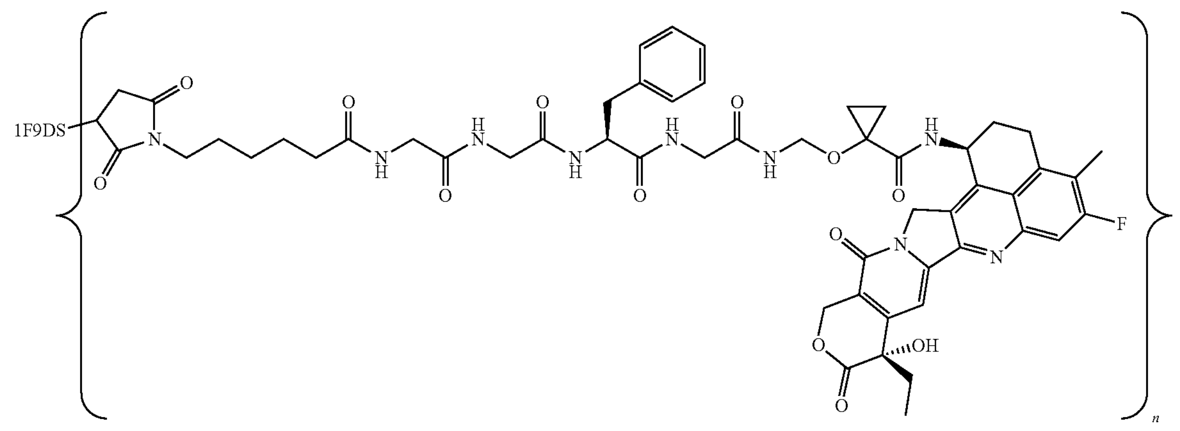

A formulated aqueous solution of tris(2-carboxyethyl) phosphine (TCEP) (10 mM, 30.1 μL, 300 nmol) was added to a PBS-buffered aqueous solution of antibody B7H3 antibody 1F9DS (0.05 M PBS-buffered aqueous solution with pH=6.5; 10.0 mg/ml, 0.89 mL, 60.14 nmol) at 37° C. The reaction solution was placed in a water bath shaker, and shaked at 37° C. for 3 hours before stopping the reaction. The reaction solution was cooled to 25° C. in a water bath.

Compound 8 (1.0 mg, 943 nmol) was dissolved in 100 μl of DMSO, and then added to the above reaction solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-31 of formula FADC-31 (1.47 mg/mL, 4.5 mL), which was stored at 4° C.

The average value calculated by UV-Vis: n=6.33.

Analysis of Drug Loading of ADC Stock Solution

Experimental Purpose and Principle

ADC stock solution is a kind of antibody conjugate drug. Its mechanism for treating disease is to deliver toxin molecules into cells by antibody targeting, thereby killing the cells. The drug loading plays a decisive role in the efficacy of the drug. The drug loading of ADC stock solution was determined by ultraviolet method.

Experimental Method

A cuvette containing sodium succinate buffer was placed in the reference absorption cell and the sample measuring absorption cell, respectively. After deducting the solvent blank, a cuvette containing the test solution was placed in the sample measuring absorption cell, and the absorbance at 280 nm and 370 nm was measured.

Calculation of results: The drug loading of ADC stock solution was determined by ultraviolet spectrophotometry (instrument: Thermo nanodrop2000 ultraviolet spectrophotometer). Its principle is that the total absorbance of the ADC stock solution at a certain wavelength is equal to the sum of the absorbance of the cytotoxic drug and the absorbance of the monoclonal antibody at that wavelength, i.e.:

$$A_{280nm}=\varepsilon_{mab\text{-}280}bC_{mab}+\varepsilon_{Drug\text{-}280}bC_{Drug} \quad (1)$$

$\varepsilon_{Drug\text{-}280}$: the average value of the molar aborsorption coefficientof the drug at 280 nm is 5100;

$C_{Drug}$: concentration of the drug;

$\varepsilon_{mab\text{-}280}$: the average value of the molar aborsorption coefficient of trastuzumab stock solution or pertuzumab stock solution at 280 nm is 214600;

$C_{mab}$: concentration of trastuzumab stock solution or pertuzumab stock solution;

b: the optical path length is 1 cm.

In the same way, the total absorbance equation of the sample at 370 nm can be obtained:

$$A_{370nm}=\varepsilon_{mab\text{-}370}bC_{mab}+\varepsilon_{Drug\text{-}370}bC_{Drug} \quad (2)$$

$\varepsilon_{Drug}$-370: the average value of the molar aborsorption coefficient of the drug at 370 nm is 19000;

$C_{Drug}$: concentration of the drug;

$\varepsilon_{mab\text{-}370}$: the average value of the molar aborsorption coefficient of trastuzumab stock solution or pertuzumab stock solution at 370 nm is 0;

$C_{mab}$: concentration of trastuzumab stock solution;

b: the optical path length is 1 cm.

The drug loading can be calculated by the two equations (1) and (2) in combination with the extinction coefficient and concentration data of the monoclonal antibody and the drug at the two detection wavelengths.

Drug loading=$C_{Drug}/C_{mab}$.

Biological Assay

Test Example 1: In Vitro Test of the Inhibition of Compound of Formula (D) on Tumor Cell Proliferation I. Test Purpose The purpose of this test is to test the in vitro inhibition effect of the drug compound of formula (D) of the present invention on the proliferation of U87MG cells (Chinese Academy of Sciences cell bank, Catalog # TCHu138) and SK-BR-3 tumor cells (human breast cancer cells, ATCC, article number HTB-30). The cells were treated with different concentrations of the compound in vitro. After 6 days of cultivation, the cell proliferation was determined by CTG reagent (CellTiter-Glo® Luminescent Cell Viability Assay, Promega, article number: G7573), and the in vitro activity of the compound was evaluated according to the $IC_{50}$ value.

II. Test Method

The test method for in vitro proliferation inhibition test of the present compounds on tumor cells is described below by taking in vitro proliferation inhibition test method onU87MG cells as an example. This method is also applicable to, but not limited to, the in vitro proliferation inhibition tests on other tumor cells.

1. Cell cultivation: U87MG cells and SK-BR-3 cells were cultured in EMEM medium containing 10% FBS (GE, article number SH30024.01) and McCoy's 5A medium containing 10% FBS (Gibco, article number 16600-108), respectively.

2. Cell preparation: U87MG cells and SK-BR-3 cells in logarithmic growth phase were washed with PBS (phosphate buffer, Shanghai Basal Media Technologies Co., Ltd.) once, and then added with 2-3 ml of trypsin (0.25% Trypsin-EDTA (1×), Gibico, Life Technologies) to digest for 2-3 min. 10-15 ml of cell culture medium was added after the cells were completely digested. The digested cells were eluted, and centrifuged at 1000 rpm for 5 min. The supernatant was discarded, and 10-20 ml of cell culture medium was added to resuspend the cells to obtain a single-cell suspension.

3. Cell plating: the U87MG and SK-BR-3 single-cell suspensions were mixed well, and the cell densities were adjusted to $2.75\times10^3$ cells/ml and $8.25\times10^3$ cells/ml with the cell culture medium respectively. The density-adjusted cell suspension was mixed well, and added to a 96-well cell culture plate at 180 µl/well. 200 µl of culture medium was added to the peripheral wells of the 96-well plate. The plate was incubated in an incubator for 24 hours (37° C., 5% $CO_2$).

4. Compound formulation: the compound was dissolved with DMSO (dimethylsulfoxide, Shanghai Titan Technology Co., Ltd.) to obtain a stock solution with an initial concentration of 10 mM.

The initial concentration of the small molecule compound was 500 nM, and the formulating method is as follows.

30 µl of different test samples were respectively added into the first column of the 96-well U-shaped bottom formulating plate with a sample concentration of 100 µM. 20 µl of DMSO was added to each well from the second column to the $11^{th}$ column. 10 µl of the sample from the first column was added to the 20 µl of DMSO in the second column and mixed well, from which 10 µl was taken and added to the third column, and so on to the 10th column. 5 µl of drug from each well of the formulating plate was added to 95 µl of EMEM culture medium, and mixed well for later use.

The initial concentration of ADC was 10 nM or 500 nM, and the formulating method is as follows.

100 µl of different test samples were respectively added into the first column of the 96-well plate with a sample concentration of 100 nM or 5 µM. 100 µl of PBS was added to each well from the second column to the $11^{th}$ column. 50 µl of the sample from the first column was added to the 100 µl of PBS in the second column and mixed well, from which 50 µl was taken and added to the third column, and so on to the 10th column with a 3-fold dilution.

5. Sample loading: 20 µl of the formulated test samples of different concentrations was added to the culture plate, each sample was tested in duplicate. The plate was incubated in an incubator for 6 days (37° C., 5% $CO_2$).

6. Coloring operation: the 96-well cell culture plate was taken out, and 90 µl of CTG solution was added to each well and incubated at room temperature for 10 minutes.

7. Plate reading: the 96-well cell culture plate was taken out and placed in a microplate reader (BMG labtech, PHERAstar FS) to measure the chemiluminiscence.

III. Data Analysis

Data was analyzed with Microsoft Excel and Graphpad Prism 5. The results are shown in the following table.

TABLE 1

$IC_{50}$ value of in vitro inhibition of the small molecule fragments of the present disclosure on the proliferation of SK-BR-3 cells and U87 cells

| | $IC_{50}$ (nM) | |
|---|---|---|
| Compound No. | SK-BR-3 | U87 |
| 1 | 0.12 | 0.23 |
| 2-shorter retention time 2-B | 0.33 | 0.86 |
| 2-longer retention time 2-A | 8.11 | 2.31 |
| 3-shorter retention time | 0.36 | 0.83 |
| 3-longer retention time | 1.67 | 2.98 |
| 4 | 1.9 | / |
| 5 | / | 4.81 |
| 6 | / | 1.83 |
| 7 | / | 1.95 |

Conclusion: The small molecule fragment of the present disclosure has obvious inhibitory activity on the proliferation of SK-BR-3 cells and U87 cells, and the chiral center has certain affection on the inhibitory activity of the compound.

Test Example 2: In Vitro Test of the Inhibition of the Present HER2-Targeted Antibody-Drug Conjugate on the Tumor Cell Proliferation The purpose of this test is to test the in vitro inhibition effect of the present HER2-targeted antibody-drug conjugate on the proliferation of SK-BR-3 cells (human breast cancer cells, ATCC, article number HTB-30) and MDA-MB-468 cells (human breast cancer cells, ATCC, article number HTB-132). The cells were treated with different concentrations of the compounds in vitro. After 6 days of cultivation, the cell proliferation was determined by CTG reagent, and the in vitro activity of the compounds was evaluated according to the $IC_{50}$ value.

According to the test method of Test Example 1, the test cells were SK-BR-3 cells and MDA-MB-468 cells, and the cell culture medium were McCoy's 5A medium containing 10% FBS (Gibco, article number 16600-108), EMEM medium containing 10% FBS (GE, article number SH30024.01) and L-15 medium containing 10% FBS (ThermoFisher, article number 11415-114). The viable cell densities of the three cell lines were adjusted to $8.33\times10^3$ cells/ml, $8.33\times10^3$ cells/ml and $1.39\times10^4$ cells/ml with the cell culture medium respectively. The density-adjusted cell suspension was mixed well, and added to a 96-well cell culture plate at 180 µl/well. Related compounds were tested, and the results are shown in the table below.

TABLE 2

$IC_{50}$ value of in vitro inhibition of the present HER2-targeted antibody-drug conjugate on the tumor cell proliferation

| | $IC_{50}$ (nM) | |
|---|---|---|
| Compound No | SK-BR-3 | MDA-MB-468 |
| ADC-3 | 0.43 | >50 |
| ADC-4 | 0.30 | >50 |
| ADC-6 | 0.48 | >50 |
| ADC-7 | 0.14 | >50 |
| ADC-9 | 0.95 | >50 |
| ADC-10 | 1.36 | >50 |
| ADC-11 | 0.73 | >50 |
| ADC-12 | 0.82 | >50 |
| ADC-13 | 0.47 | >50 |
| ADC-14 | 0.53 | >50 |
| ADC-15 | 0.38 | >50 |
| ADC-16 | 0.49 | >50 |
| ADC-17 | 0.37 | >50 |

Conclusion: the HER2-targeted antibody-drug conjugate of the present disclosure has obvious inhibitory activity on the proliferation of HER2-positive cell SK-BR-3. Meanwhile, it has poor inhibitory activity on the proliferation of HER2-negative cell MDA-MB-468. Therefore, it has good selectivity.

Test Example 3: Her2-ADC Plasma Stability Test

ADC-19 sample, ADC-18 sample, ADC-20 sample, human plasma, monkey plasma (Shanghai Medicilon Inc.) and 1% BSA (Sigma) PBS solution (Sangon Biotech (Shanghai) Co., Ltd.) were respectively filtered through a 0.22 µm filter for sterilization. ADC-19, ADC-18 and ADC-20 were added to the above sterile plasma or 1% BSA PBS solution at a final concentration of 200 µg/ml, respectively, which was then incubated in a cell incubator at 37° C., and the starting day of incubation was recorded as Day 0. Samples were collected at Day 7, Day 14 and Day 21 for free toxin detection.

25 µl of sample was added to a 96-well plate. 50 µL of internal standard working solution (100 ng/mL camptothecin in acetonitrile) and 150 µl of acetonitrile were added. The solution was vortexed for 5 minutes, and centrifuged for 10 minutes (4000 rpm). 5 µl of the solution was taken out for LC/MS/MS (Applied Biosystems, Inc., USA) analysis.

The results show that ADC-19 is quite stable in human plasma, monkey plasma and 1% BSA PBS solution. The release rate of free toxin did not exceed 2.1%, and became stable on Day 14. The results are shown in FIG. 1A.

Figure 1B:
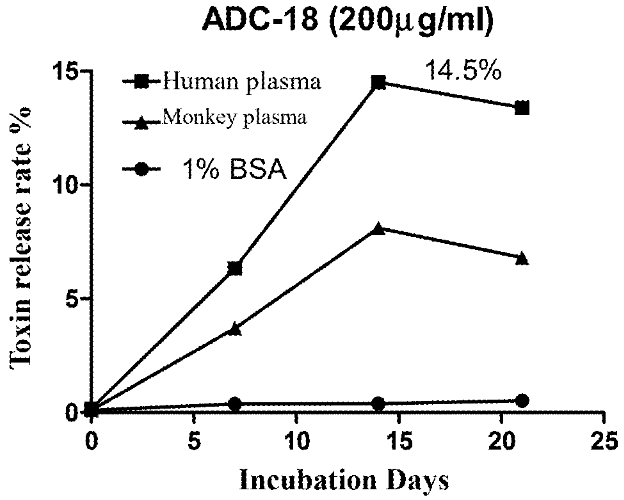
FIG. 1B: Plasma stability test results of ADC-18 of the present disclosure.

ADC-18 has poor stability in human plasma and monkey plasma, and the highest release rate of free toxin were 14.5% and 8.10% respectively. It is stable in 1% BSA PBS solution. The results are shown in FIG. 1B.

Figure 1C:
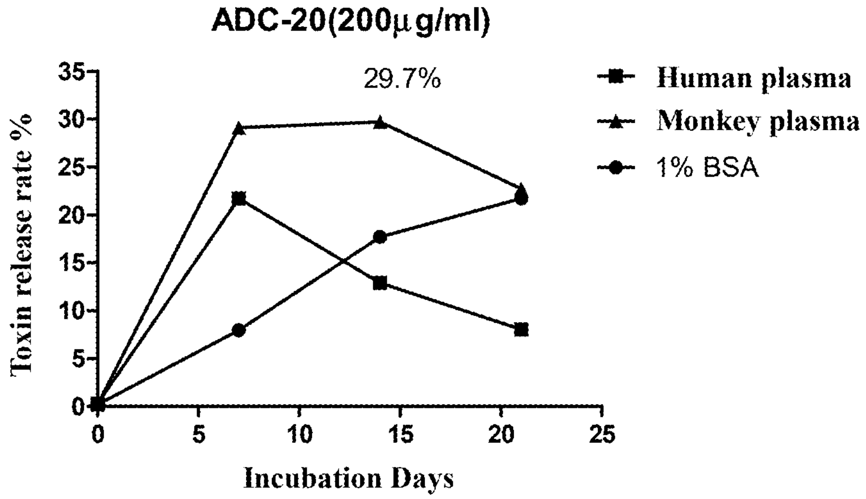
FIG. 1C: Plasma stability test results of ADC-20 of the present disclosure.

ADC-20 has poor stability in human plasma, monkey plasma and 1% BSA PBS solution, and the highest release rate of free toxin were 21.7%, 29.7% and 21.7% respectively. It was always in a degradation state in 1% BSA PBS solution. The results are shown in FIG. 1C.

Test Example 4: Efficacy Evaluation in JIMT-1 Tumor-Bearing Mice

I. Test Purpose

Nunu nude mice were used as the test animal to evaluate the efficacy of Her2-ADC antibody T-DM1, ADC-21 and ADC-24 on trastuzumab (Herceptin) resistant human breast cancer cell strain JIMT-1 transplanted tumor nude mice after intraperitoneal injection.

II. Test Drugs and Materials

1. Test drugs

T-DM1 (prepared with reference to the patent application US20050169933)

ADC-21: 3 mg/kg

ADC-21: 10 mg/kg

ADC-24: 3 mg/kg

ADC-24: 10 mg/kg

Blank: PBS

2. Formulation method: the drugs were all diluted and formulated with PBS.

3. Test animals

Nunu nude mice, purchased from Beijing Vital River Laboratory Animal Technology Co., Ltd.

III. Test Method

JIMT-1 cells (Nanjing Cobioer Biosciences Co., Ltd.) ($5\times10^6$ cells/mouse, having 50% matrigel) were inoculated subcutaneously in the right rib of mouse. After the tumor grew for 8 days and reached 203.09±11.94 $mm^3$, the animals were randomly grouped into 6 groups with 8 animals per group (dl).

The drugs were administered by intraperitoneal injection for a total of 2 times. The tumor volume and body weight were measured twice a week, and the data were recorded.

Excel 2003 statistical software was used for data statistics: mean value was calculated as avg; SD value was calculated as STDEV; SEM value was calculated as STDEV/SQRT; P value between different groups was calculated as TTEST.

Tumor volume (V) was calculated as: $V=\frac{1}{2}\times L_{length}\times L_{short}^2$ $$\text{Relative volume (RTV)}=V_T/V_0$$

$$\text{Tumor inhibition rate (\%)}=(C_{RTV}-T_{RTV})/C_{RTV}(\%),$$

wherein $V_0$ and $V_T$ represent the tumor volume at the beginning of the test and at the end of the test, respectively. $C_{RTV}$ and $T_{RTV}$ represent the relative tumor volume of the blank control group (Vehicle, PBS) and the test group at the end of the test, respectively.

IV. Test Results

Figure 2:
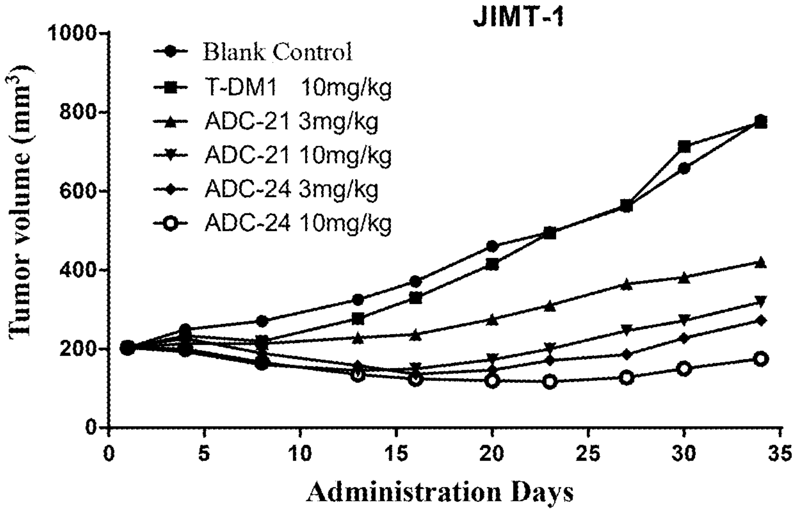
FIG. 2: Evaluation of the efficacy of ADC-21 and ADC-24 of the present disclosure on JIMT-1 tumor-bearing mice.

The test results are shown in FIG. 2. The drugs were administered by intraperitoneal injection for 2 times, and the test ended at Day 34 of observation. T-DM1 (10 mg/kg) shows no inhibition effect on tumor; ADC-21 (3 mg/kg) shows a tumor inhibition rate of 46.22% (P<0.01); ADC-21 (10 mg/kg) shows a tumor inhibition rate of 56.77% (P<0.001); ADC-24 (3 mg/kg) shows a tumor inhibition rate of 62.77% (P<0.001); and ADC-24 (10 mg/kg) shows a tumor inhibition rate of 76.32% (P<0.001). Under the same dose, the tumor inhibition effect of ADC-24 is significantly better than that of ADC-21.

Test Example 5: Efficacy evaluation in SK-BR-3 tumor-bearing mice

I. Test Purpose

Nunu nude mice were used as the test animal to evaluate the efficacy of Her2-ADC antibody ADC-21 and ADC-22 on human breast cancer cell strain SK-BR-3 transplanted tumor nude mice after intraperitoneal injection.

II. Test Drugs and Materials

1. Test drugs

ADC-21: 1 mg/kg

ADC-21: 6 mg/kg

ADC-22: 1 mg/kg

ADC-22: 6 mg/kg

Blank: PBS

2. Formulation method: the drugs were all diluted and formulated with PBS.

3. Test animals

Nunu nude mice, purchased from Beijing Vital River Laboratory Animal Technology Co., Ltd.

III. Test Method

SK-BR-3 cells (ATCC) ($5\times10^6$ cells/mouse, having 50% matrigel) were inoculated subcutaneously in the right rib of mouse. After the tumor grew for 20 days and reached $153.34\pm11.73$ $mm^3$, the animals were randomly grouped into 5 groups with 8 animals per group (d0).

The drugs were administered by intraperitoneal injection once. The tumor volume and body weight were measured twice a week, and the data were recorded.

Excel 2003 statistical software was used for data statistics: mean value was calculated as avg; SD value was calculated as STDEV; SEM value was calculated as STDEV/SQRT; P value between different groups was calculated as TTEST.

Tumor volume (V) was calculated as: $V=\frac{1}{2}\times L_{length}\times L_{short}^2$ $$\text{Relative volume (RTV)}=V_T/V_0$$

$$\text{Tumor inhibition rate (\%)}=(C_{RTV}-T_{RTV})/C_{RTV}(\%),$$

wherein $V_0$ and $V_T$ represent the tumor volume at the beginning of the test and at the end of the test, respectively. $C_{RTV}$ and $T_{RTV}$ represent the relative tumor volume of the blank control group and the test group at the end of the experiment, respectively.

IV. Test Results

Figure 3:
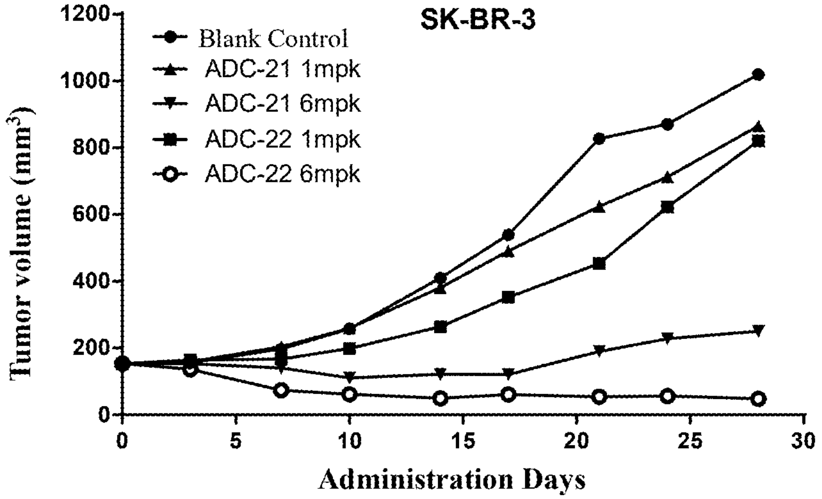
FIG. 3: Evaluation of the efficacy of ADC of the present disclosure on human breast cancer cell SK-BR-3 xenograft tumor in nude mice.

The test results are shown in FIG. 3. The drugs were administered by intraperitoneal injection once, and the test ended at Day 28 of observation. ADC-21 (1 mg/kg) shows a tumor inhibition rate of 15.01%; and ADC-21 (6 mg/kg) shows a tumor inhibition rate of 77.4%, which differs significantly from that of the blank control (P<0.001). ADC-22 (1 mg/kg) shows a tumor inhibition rate of 19.82%; and ADC-22 (6 mg/kg) shows a tumor inhibition rate of 98.38% (P<0.001). Under the same dose of 6 mg/kg, the tumor inhibition effect of ADC-22 is significantly better than that of ADC-21.

Test Example 6: Plasma Stability Test

ADC-25 sample was mixed well with human plasma, monkey plasma and 1% BSA PBS solution respectively at a final concentration of 100 μg/ml, and filtered for sterilization. The mixture was incubated in a water bath at 37° C., and the starting day of incubation was recorded as Day 0. Samples were collected at Day 7, Day 14 and Day 21 for free toxin detection.

Samples collected at different time points were cooled to room temperature, and mixed well by vortex. 25 μl of sample was added to a 96-well plate. 50 μL of internal standard working solution (100 ng/mL camptothecin in acetonitrile) and 150 μl of acetonitrile were added. The solution was vortexed for 5 minutes, and centrifuged for 10 minutes (4000 rpm). 5 μl of the solution was taken out for LC/MS/MS analysis.

Figure 4:
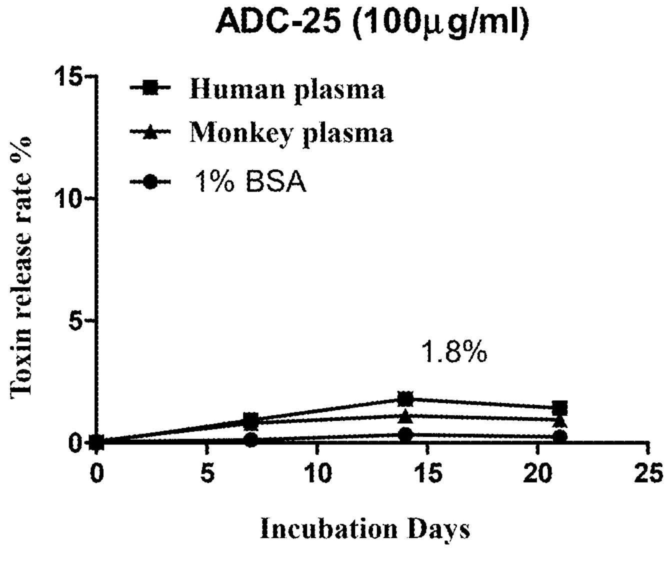
FIG. 4: Plasma stability test results of ADC-25 of the present disclosure.

The results are shown in FIG. 4. ADC-25 is quite stable in human plasma, monkey plasma and 1% BSA PBS solution. The release rate of free toxin did not exceed 2%, and became stable on Day 14.

Test Example 7: Efficacy Evaluation of ADC on Human Brain Astroblastoma U87MG Xenograft Tumor in Nude Mice I. Test Purpose BALB/cA-nude nude mice were used as the test animal to evaluate the efficacy of the ADC compound of the present disclosure on human brain astroblastoma U87MG xenograft tumor in nude mice.

II. Test Drugs and Materials

1. Test drugs

ADC-27 (3 mg/kg)

ADC-26 (3 mg/kg)

Blank: PBS buffer solution (pH 7.4)

2. Formulation method: PBS buffer solution (pH 7.4).

3. Test animals

BALB/cA-nude nude mice, purchased from Shanghai JieSiJie Laboratory Animal Co., Ltd.

III. Test Method

BALB/cA-nude nude mice (female, 6 to 7 weeks old) were used in the test. Human brain astroblastoma U87MG cells (human brain astroblastoma, Chinese Academy of Sciences cell bank, Catalog # TCHu138) were inoculated subcutaneously. On Day 10 after the inoculation, the animals were randomly grouped 8 animals per group (D0), and the drugs were administered by intraperitoneal injection once a week for 3 times. The tumor volume and body weight were measured 2 to 3 times a week, and the data were recorded. The calculation formula of tumor volume (V) is as follows:

$$V=\frac{1}{2}\times a\times b^2$$

wherein a and b represent length and width respectively.

$$\text{Relative volume (RTV)}=V_T/V_0$$

$$\text{Tumor inhibition rate (\%)}=(C_{RTV}-T_{RTV})/C_{RTV}(\%)$$

wherein $V_0$ and $V_T$ represent the tumor volume at the beginning of the test and at the end of the test, respectively. $C_{RTV}$ and $T_{RTV}$ represent the relative tumor volume of the control group (blank) and the test group at the end of the test, respectively.

IV. Test Results

Intraperitoneal injection (i.p.) administration was carried out once a week for 3 times. On Day 22 of the observation, the tumor inhibition rate of ADC-27 (3 mg/kg) reached 63.3% (P<0.0001); and the tumor inhibition rate of ADC-26 (3 mg/kg) reached 49.1%. ADC-27 shows stronger anti-tumor efficacy than ADC-26.

Figure 5:
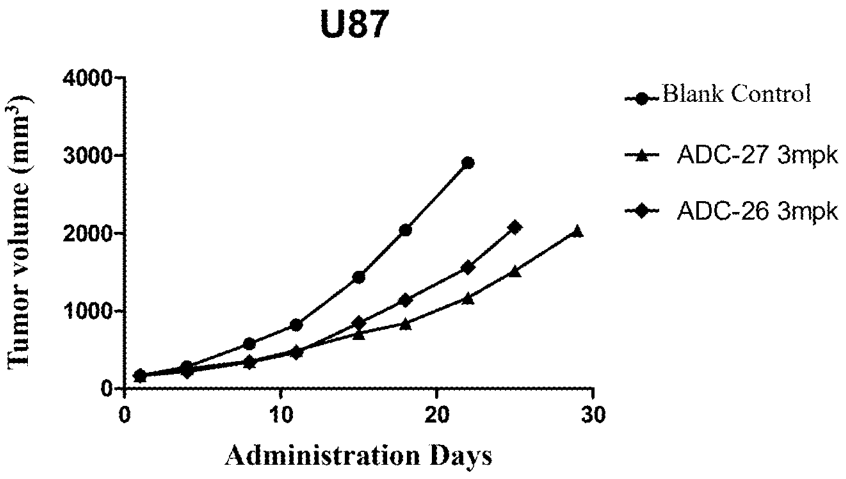
FIG. 5: Efficacy of ADC of the present disclosure on human brain astroblastoma U87MG xenograft tumor in nude mice.

During the administration, the animals in each group show normal body weights, suggesting that the ADC has no obvious side effects. The test results are shown in Table 3 and FIG. 5. The tested antibodies can effectively inhibit the growth of U87MG xenograft tumor in tumor-bearing nude mice, and show a dose-dependent manner.

TABLE 3

Efficacy of the administered antibody on human brain astroblastoma U87MG xenograft tumor in nude mice (D22)

| | Averange tumor volume (mm$^3$) | | | | Relative tumor volume | | Tumor inhibition rate (%) |
|---|---|---|---|---|---|---|---|
| Group | Day 0 | SEM | Day 22 | SEM | Day 22 | SEM | Day 22 |
| Blank control | 167.06 | 17.74 | 2906.96 | 327.6 | 17.76 | 1.63 | — |
| ADC-27 3mpk | 167.07 | 16.06 | 1172.48 | 80.27 | 7.55 | 0.95 | 63.3*** |
| ADC-26 3mpk | 167.73 | 17.63 | 1561.03 | 303.37 | 8.83 | 1.17 | 49.1*** |

Test Example 8: Efficacy Evaluation of ADC on Human Pharyngeal Carcinoma Pleural Fluid Metastatic Cell Detroit 562 Xenograft Tumor in Nude Mice I. Test Purpose BALB/cA-nude nude mice were used as the test animal to evaluate the efficacy of the ADC compound of the present disclosure on human pharyngeal carcinoma pleural fluid metastatic cell Detroit 562 xenograft tumor in nude mice.

II. Test Drugs and Materials

1. Test drugs

ADC-29 (3 mg/kg)

ADC-28 (3 mg/kg)

Negative control ADC (3 mg/kg): ligand-toxin conjugate formed by coupling of non-B7H3 target with compound 20.

2. Formulation method: the drugs were all diluted and formulated with PBS.

3. Test animals

BALB/cA-nude nude mice, purchased from Changzhou Cavens Laboratory Animal Co., Ltd.

III. Test Method

BALB/cA-nude nude mice (female, 6 to 7 weeks old) were used in the test. Human pharyngeal carcinoma pleural fluid metastatic cell Detroit 562 cells (ATCC, Catalog #ATCC® CCL-138™) were inoculated subcutaneously. On Day 10 after the inoculation, the animals were randomly grouped 8 animals per group (D0), and the drugs were administered by intraperitoneal injection once a week for 3 times. The tumor volume and body weight were measured 2 to 3 times a week, and the data were recorded. The calculation formula of tumor volume (V) is as follows:

$$V=\frac{1}{2}\times a\times b^2$$

wherein a and b represent length and width respectively.

$$\text{Relative volume (RTV)}=V_T/V_0$$

$$\text{Tumor inhibition rate (\%)}=(C_{RTV}-T_{RTV})/C_{RTV}(\%)$$

wherein $V_0$ and $V_T$ represent the tumor volume at the beginning of the test and at the end of the test, respectively. $C_{RTV}$ and $T_{RTV}$ represent the relative tumor volume of the control group (negative control) and the test group at the end of the test, respectively.

IV. Test Results

Intraperitoneal injection administration was carried out once a week for 3 times. On Day 28 of the observation, the tumor inhibition rate of ADC-29 (3 mg/kg, 3 mpk) reached 72.27% (P<0.001); and the tumor inhibition rate of ADC-28 (3 mg/kg, 3 mpk) reached 56.2% (P<0.001). ADC-29 shows stronger anti-tumor efficacy than ADC-28.

Figure 6:
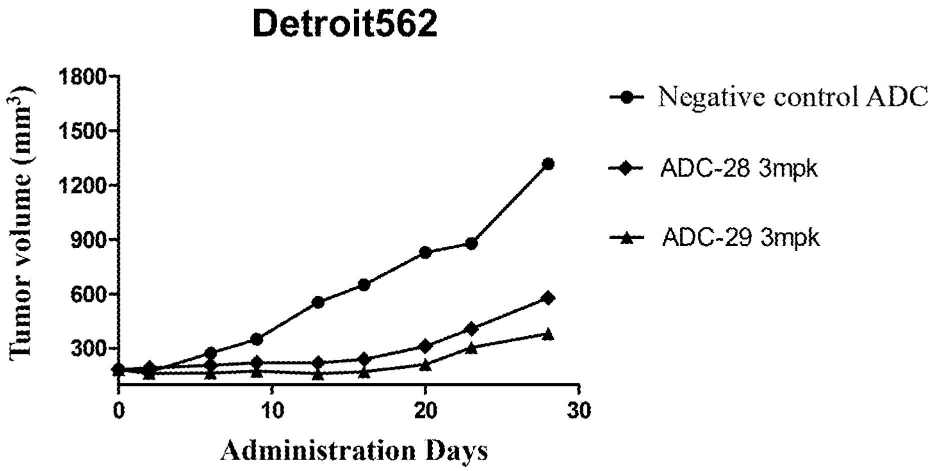
FIG. 6: Efficacy of ADC of the present disclosure on human pharyngeal carcinoma pleural fluid metastatic cell Detroit 562 xenograft tumor in nude mice.

During the administration, the animals in each group showed normal body weights, suggesting that the ADC has no obvious side effects. The test results are shown in Table 4 and FIG. 6. The tested antibodies can effectively inhibit the growth of Detroit 562 xenograft tumor in tumor-bearing nude mice, and show a dose-dependent manner.

TABLE 4

Efficacy of the administered antibody on Detroit 562 xenograft tumor in tumor-bearing nude mice (D28)

| | Averange tumor volume (mm$^3$) | | Averange tumor volume (mm$^3$) | | Relative tumor volume | | Tumor inhibition rate (%) |
|---|---|---|---|---|---|---|---|
| Group | Day 0 | SEM | Day 28 | SEM | Day 28 | SEM | on Day 28 |
| Negative control | 182.70 | 6.79 | 1317.99 | 223.20 | 7.47 | 1.46 | — |
| ADC-29 3mpk | 182.59 | 6.50 | 381.48 | 105.76 | 2.07 | 0.58 | 72.27*** |
| ADC-28 3mpk | 182.57 | 6.92 | 578.07 | 160.13 | 3.43 | 1.09 | 56.2*** |

Test Example 9: Efficacy Evaluation in U87-MG Tumor-Bearing Mice

I. Test Purpose

BALB/c nude mice were used as the test animal to evaluate the efficacy of B7H3-antibody-drug conjugate administered by intraperitoneal injection in human glioma cell U87MG xenograft tumor model.

II. Test Drugs and Materials

1. Test drugs

ADC-30 1 mg/kg

ADC-30 3 mg/kg

ADC-31 1 mg/kg

ADC-31 3 mg/kg

Blank: PBS

2. Formulation method: the drugs were all diluted and formulated with PBS.

3. Test animals

BALB/cA-nude nude mice, purchased from Shanghai Slac Laboratory Animal Co. Ltd.

III. Test Method

U87MG cells (human brain astroblastoma, Chinese Academy of Sciences cell bank, Catalog # TCHu138) ($2.5\times10^6$ cells/mouse) were inoculated subcutaneously in the right rib of mouse. After the tumor grew for 14 days and reached 167.49 $mm^3$, the animals were randomly grouped into 5 groups with 8 animals per group (dl).

The drugs were administered by intraperitoneal injection once per week for a total of 3 times. The tumor volume and body weight were measured twice a week, and the data were recorded.

Excel 2003 statistical software was used for data statistics: mean value was calculated as avg; SD value was calculated as STDEV; SEM value was calculated as STDEV/SQRT; P value between different groups was calculated as TTEST.

Tumor volume (V) was calculated as: $V=\frac{1}{2}\times L_{length}\times L_{short}^2$ $$\text{Relative volume (RTV)}=V_T/V_0$$

$$\text{Tumor inhibition rate (\%)}=(C_{RTV}-T_{RTV})/C_{RTV}(\%)$$

wherein $V_0$ and $V_T$ represent the tumor volume at the beginning of the test and at the end of the test, respectively. $C_{RTV}$ and $T_{RTV}$ represent the relative tumor volume of the blank control group (Vehicle) and the test group at the end of the test, respectively.

IV. Test Results

The test results are shown in FIG. 7. Intraperitoneal injection administration was carried out once a week for a total of 3 times. On Day 18 of the observation, the tumor inhibition rate of ADC-30 (1 mg/kg) reached 0.31%; the tumor inhibition rate of ADC-30 (3 mg/kg) reached 45.23% (P<0.0001); the tumor inhibition rate of ADC-31 (1 mg/kg) reached 39.22% (P<0.01); and the tumor inhibition rate of ADC-31 (3 mg/kg) reached 80.24% (P<0.0001). Under the same dose, the tumor inhibition effect of ADC-31 is significantly better than that of ADC-30.

What is claimed is:

1. A ligand-drug conjugate or a pharmaceutically acceptable salt or solvate thereof, being a ligand-drug conjugate of formula (Pc-L-Y-Dr) or a pharmaceutically acceptable salt or solvate thereof:

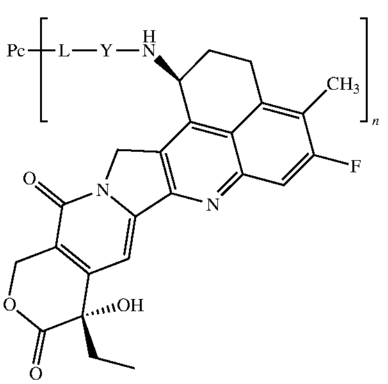

(Pc-L-Y-Dr)

wherein:

Y is —O—$(CR^aR^b)_m$—$CR^1R^2$—C(O)—;

$R^a$ and $R^b$ are identical or different and are each independently selected from the group consisting of hydrogen atom, deuterium atom, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$ together with the carbon atom to which they are attached form a cycloalkyl or heterocyclyl;

$R^1$ is selected from the group consisting of halogen, haloalkyl, cycloalkyl, cycloalkylalkyl, alkoxyalkyl, heterocyclyl, aryl and heteroaryl;

$R^2$ is selected from the group consisting of hydrogen atom, halogen, haloalkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

or, $R^a$ and $R^2$ together with the carbon atom to which they are attached form a cycloalkyl or heterocyclyl;

m is an integer from 0 to 4;

n is 1 to 10, which can be an integer or a decimal;

Pc is an antibody; and L is a linker unit.

2. The ligand-drug conjugate or the pharmaceutically acceptable salt or solvate thereof according to claim 1, wherein n is 2 to 8, which can be an integer or a decimal.

3. The ligand-drug conjugate or the pharmaceutically acceptable salt or solvate thereof according to claim 1, wherein the linker unit -L- is $$-L^1-L^2-L^3-L^4-,$$

$L^1$ is selected from the group consisting of -(succinimide-3-yl-N)—W—C(O)—, —$CH_2$—C(O)—$NR^3$—W—C(O)-and-C(O)—W—C(O)—, wherein W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue composed of 2 to 7 amino acids, wherein the amino acids are optionally further substituted by one or more substituent(s) selected from the group consisting of halogen, hydroxy, cyano, amino, alkyl, chloroalkyl, deuterated alkyl, alkoxy and cycloalkyl;

$L^4$ is selected from the group consisting of —$NR^5(CR^6R^7)_t$—, —$C(O)NR^5$, —$C(O)NR^5(CH_2)_t$— and a chemical bond, wherein t is an integer from 1 to 6;

$R^3$, $R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl.

4. The ligand-drug conjugate or the pharmaceutically acceptable salt or solvate thereof according to claim 3, wherein the linker unit $$-L^1-L^2-L^3-L^4-,$$

$L^1$ is

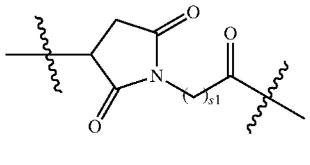
, and $s^1$ is an integer from 2 to 8;

$L^2$ is a chemical bond;

$L^3$ is a tetrapeptide residue;

$L^4$ is —$NR^5$ $(CR^6R^7)_t$—, $R^5$ is selected from the group consisting of hydrogen atom and alkyl, $R^6$ and $R^7$ are identical or different and are each independently selected from the group consisting of hydrogen atom and alkyl, and t is 1 or 2.

5. The ligand-drug conjugate or the pharmaceutically acceptable salt or solvate thereof according to claim 3, wherein the $L^1$ terminal of the linker unit -L- is connected to the ligand, and the $L^4$ terminal of the linker unit -L- is connected to Y.

6. The ligand-drug conjugate or the pharmaceutically acceptable salt or solvate thereof according to claim 1, being a ligand-drug conjugate of formula (Pc-$L_a$-Y-Dr) or a pharmaceutically acceptable salt or solvate thereof:

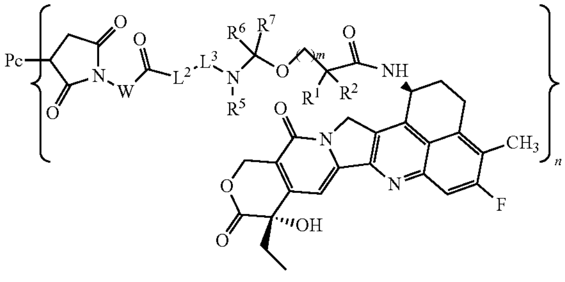

(Pc-$L_a$-Y-Dr)

wherein:

W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue composed of 2 to 7 amino acids, wherein the amino acids are optionally further substituted by one or more substituent(s) selected from the group consisting of halogen, hydroxy, cyano, amino, alkyl, chloroalkyl, deuterated alkyl, alkoxy and cycloalkyl;

$R^1$ is selected from the group consisting of halogen, cycloalkylalkyl, cycloalkyl, heterocyclyl, aryl and heteroaryl;

$R^2$ is selected from the group consisting of hydrogen atom, halogen, haloalkyl, cycloalkyl, heterocyclyl, aryl and heteroaryl;

or, $R^1$ and $R^2$ together with the carbon atom to which they are attached form a cycloalkyl or heterocyclyl;

$R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

m is an integer from 0 to 4;

n is 1 to 10, which can be an integer or a decimal;

Pc is an antibody.

7. The ligand-drug conjugate or the pharmaceutically acceptable salt or solvate thereof according to claim 6, being a ligand-drug conjugate of formula (PC-$L_b$-Y-Dr) or a pharmaceutically acceptable salt or solvate thereof:

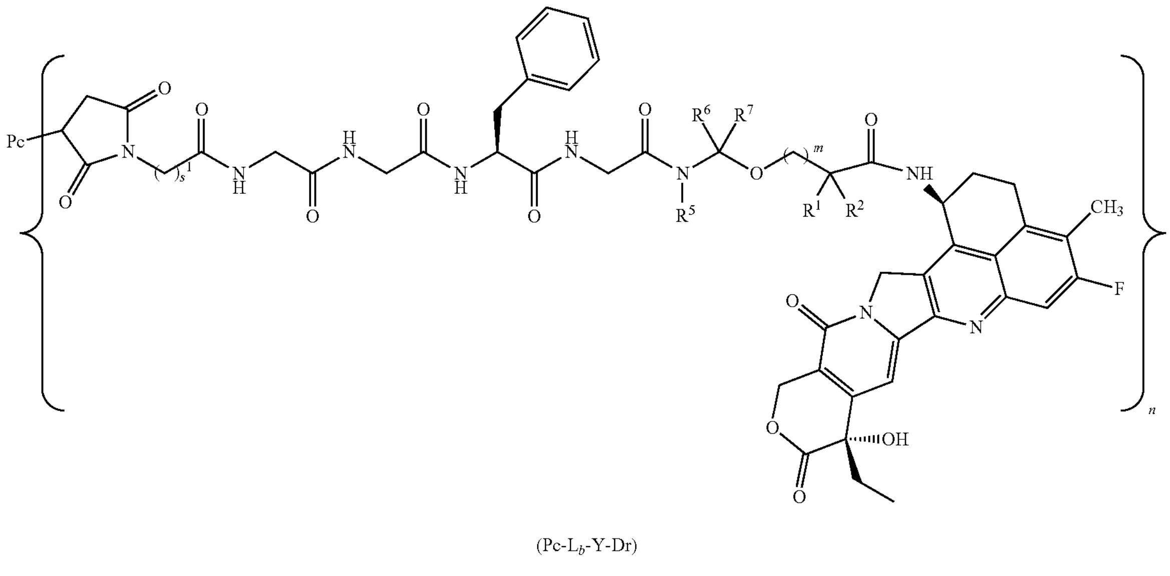

(Pc-$L_b$-Y-Dr)

wherein:
$s^1$ is an integer from 2 to 8;
Pc, $R^1$, $R^2$, and $R^5$~$R^7$ are as defined in claim 6;
m is an integer from 0 to 4; and
n is 1 to 10, which can be an integer or a decimal.
8. The ligand-drug conjugate or the pharmaceutically acceptable salt or solvate thereof according to claim 1, selected from the group consisting of:
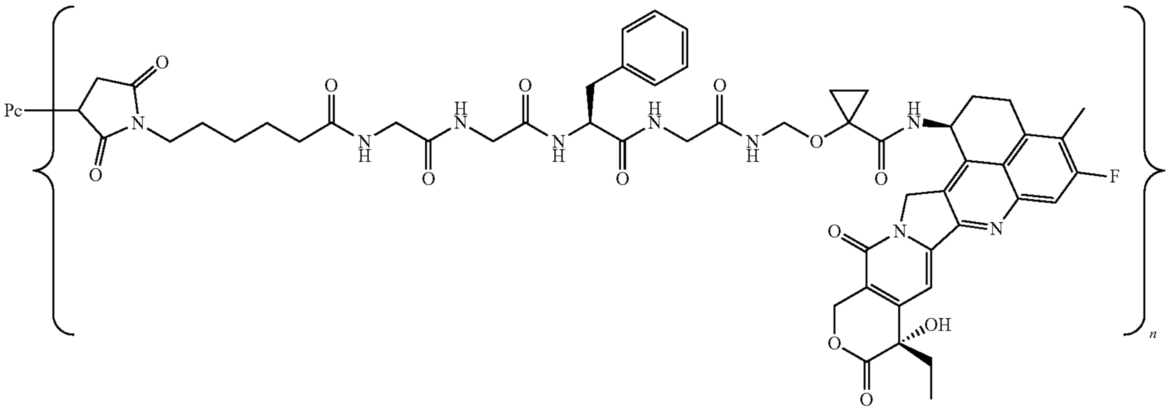
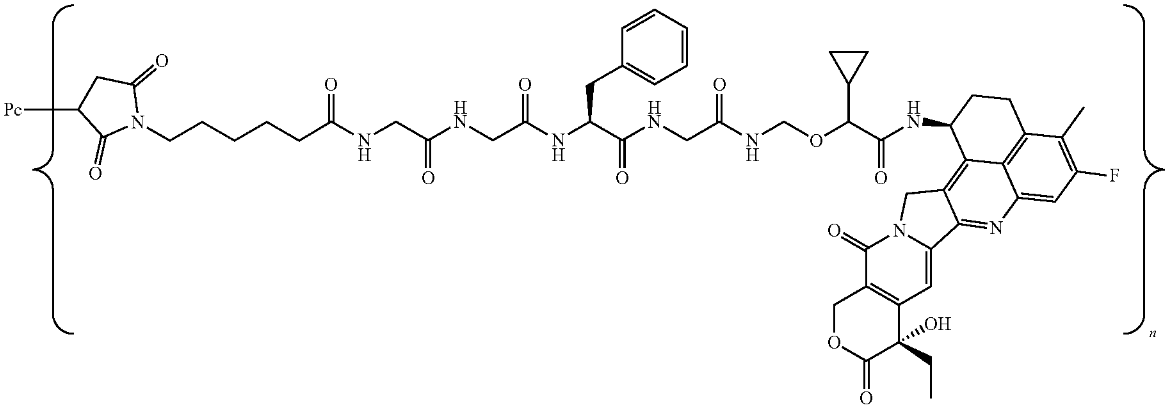
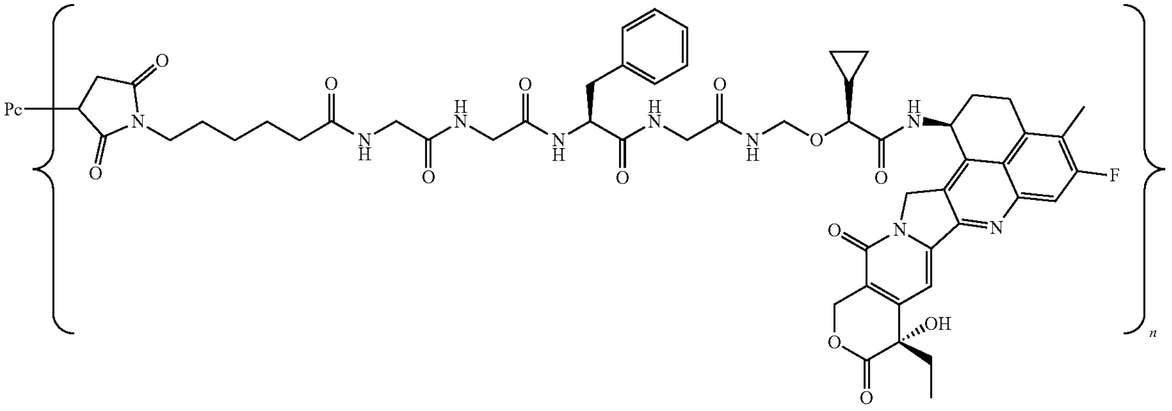

-continued
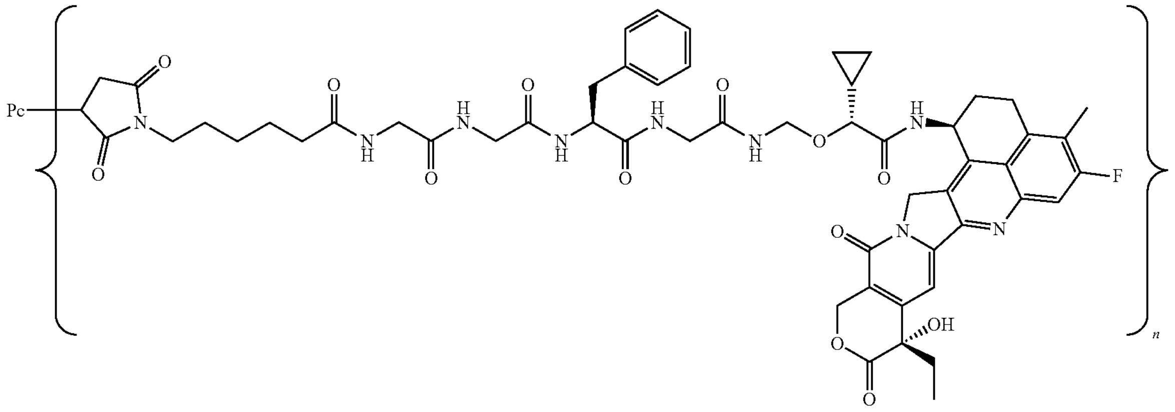
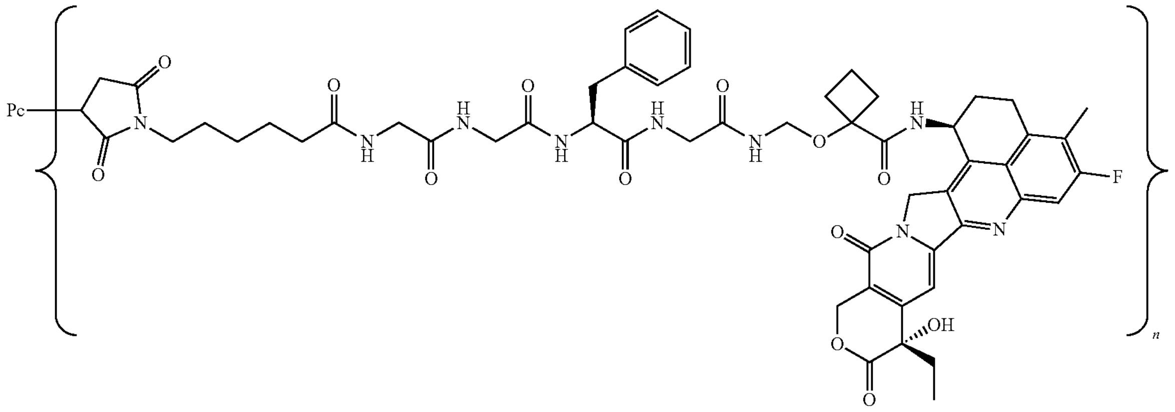
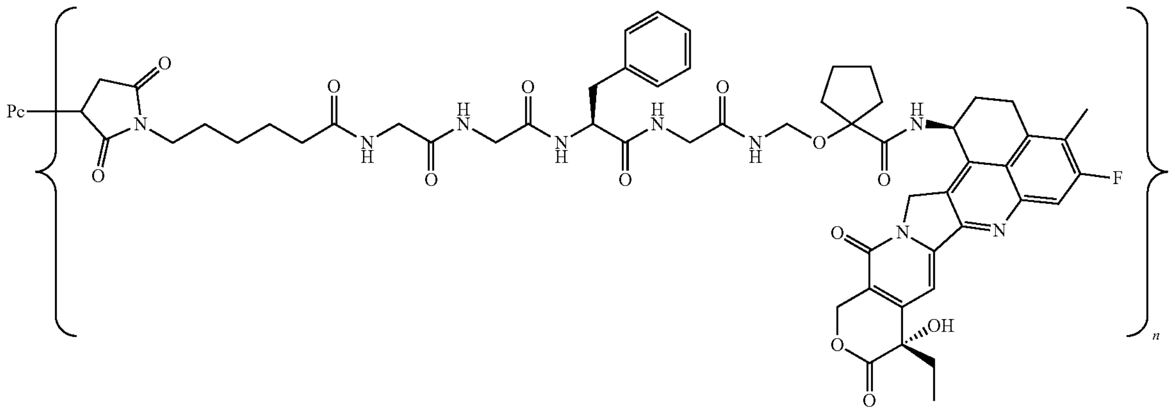
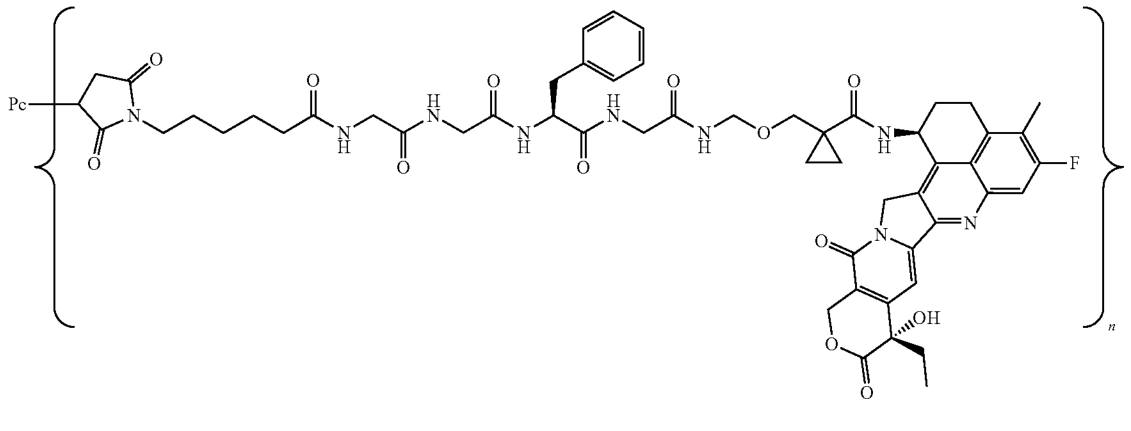

-continued
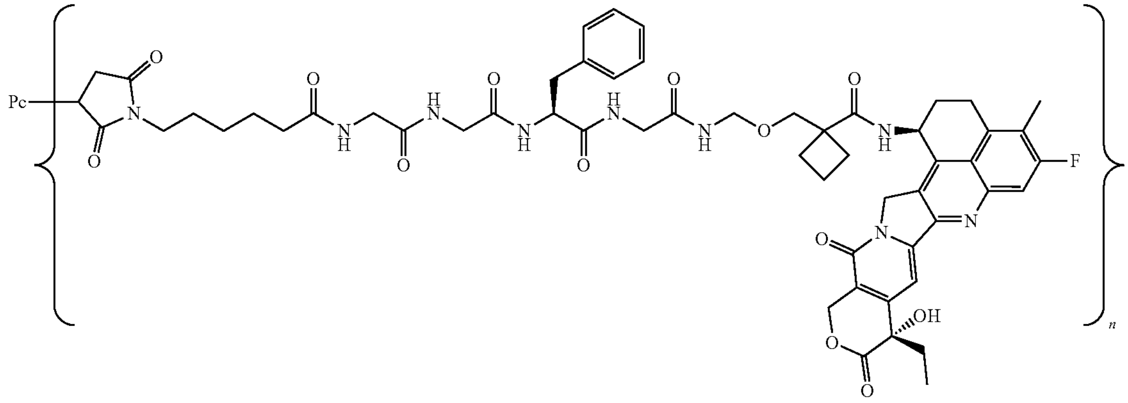
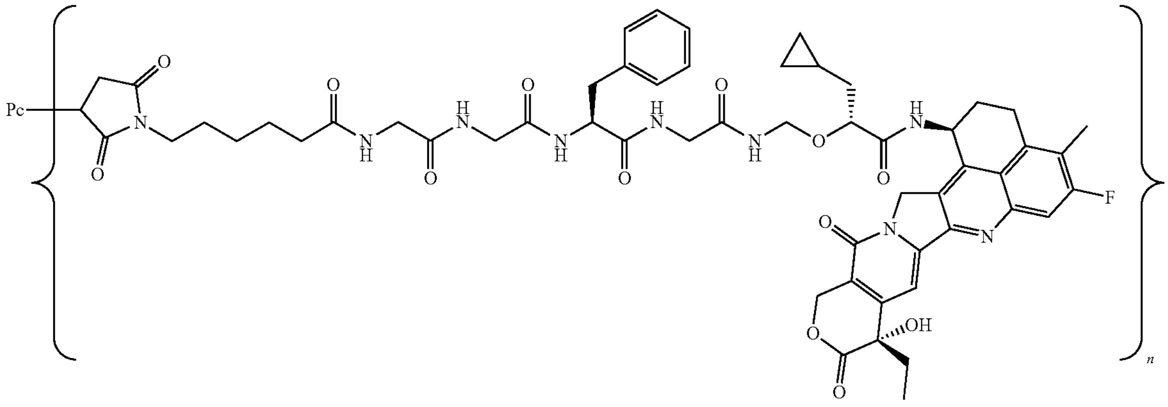
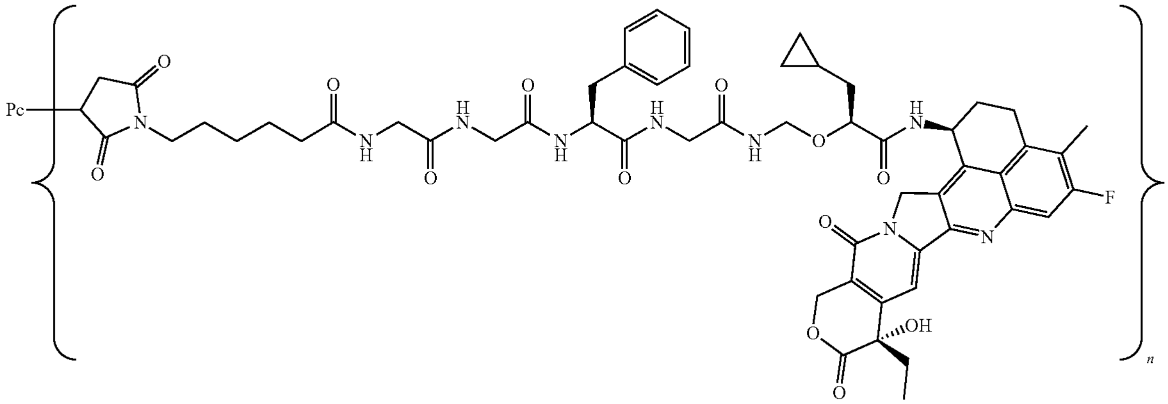
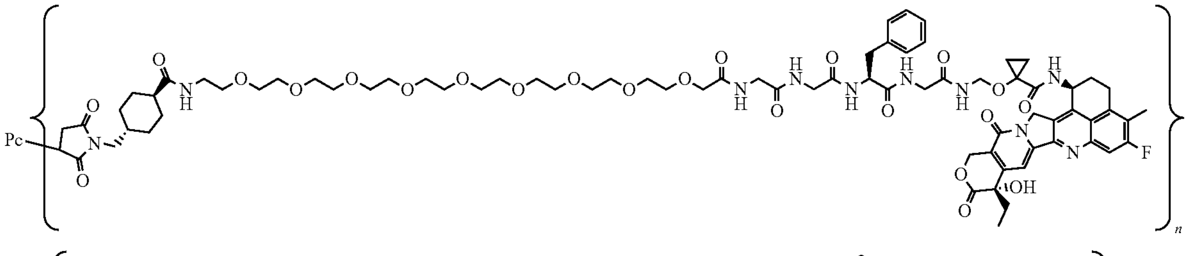
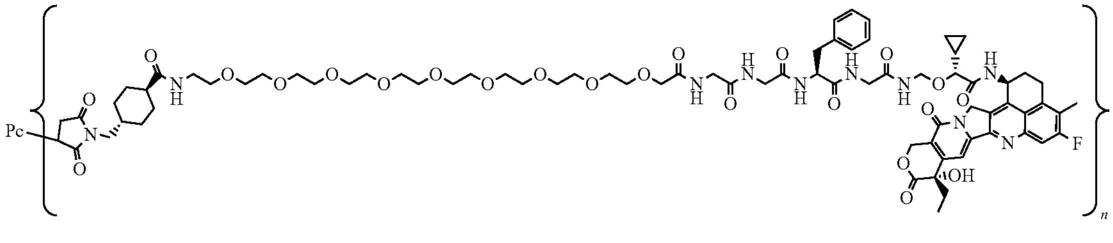
and

-continued

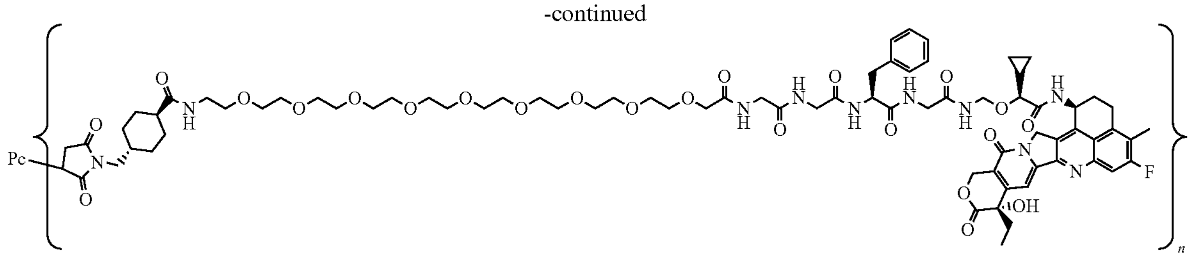

wherein:

n is 1 to 10, which can be an integer or a decimal;

Pc is an antibody.

9. The ligand-drug conjugate or the pharmaceutically acceptable salt or solvate thereof according to claim 1, wherein Pc is an antibody or an antigen-binding fragment thereof, and the antibody is selected from the group consisting of chimeric antibody, humanized antibody and fully humanized antibody.

10. The ligand-drug conjugate or the pharmaceutically acceptable salt or solvate thereof according to claim 9, wherein the antibody or antigen-binding fragment thereof is selected from the group consisting of anti-HER2 (ErbB2) antibody, anti-EGFR antibody, anti-c-Met antibody, anti-HER3 (ErbB3) antibody, anti-HER4 (ErbB4) antibody, anti-CD20 antibody, anti-CD22 antibody, anti-CD30 antibody, anti-CD33 antibody, anti-CD44 antibody, anti-CD56 antibody, anti-CD70 antibody, anti-CD73 antibody, anti-CD105 antibody, anti-CEA antibody, anti-A33 antibody, anti-Cripto antibody, anti-EphA2 antibody, anti-G250 antibody, anti-MUCI antibody, anti-Lewis Y antibody, anti-VEGFR antibody, anti-GPNMB antibody, anti-Integrin antibody, anti-PSMA antibody, anti-Tenascin-C antibody, anti-SLC44A4 antibody, anti-Mesothelin antibody and antigen-binding fragments thereof.

11. The ligand-drug conjugate or the pharmaceutically acceptable salt or solvate thereof according to claim 9, wherein the antibody or antigen-binding fragment thereof is selected from the group consisting of Trastuzumab, Pertuzumab, Nimotuzumab, Enoblituzumab, Emibetuzumab, Inotuzumab, Pinatuzumab, Brentuximab, Gemtuzumab, Bivatuzumab, Lorvotuzumab, cBR96 and Glematumamab, or antigen-binding fragments thereof.

12. The ligand-drug conjugate or the pharmaceutically acceptable salt or solvate thereof according to claim 1, selected from the group consisting of:

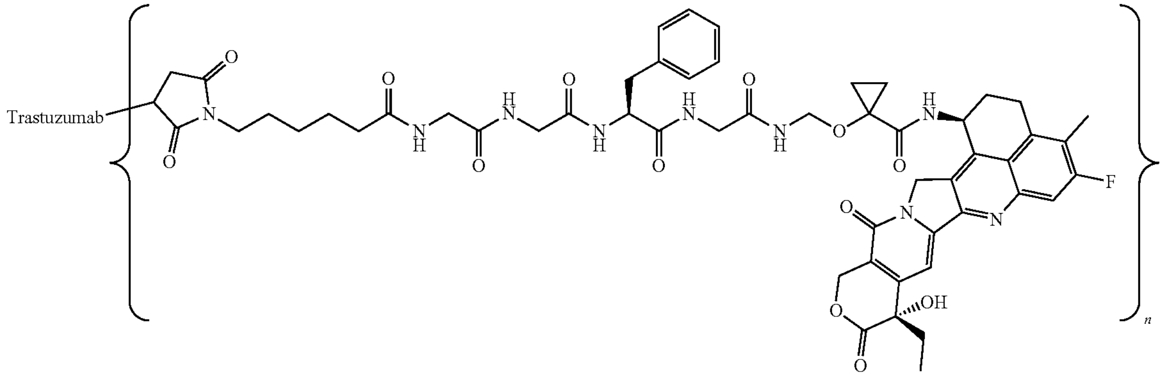

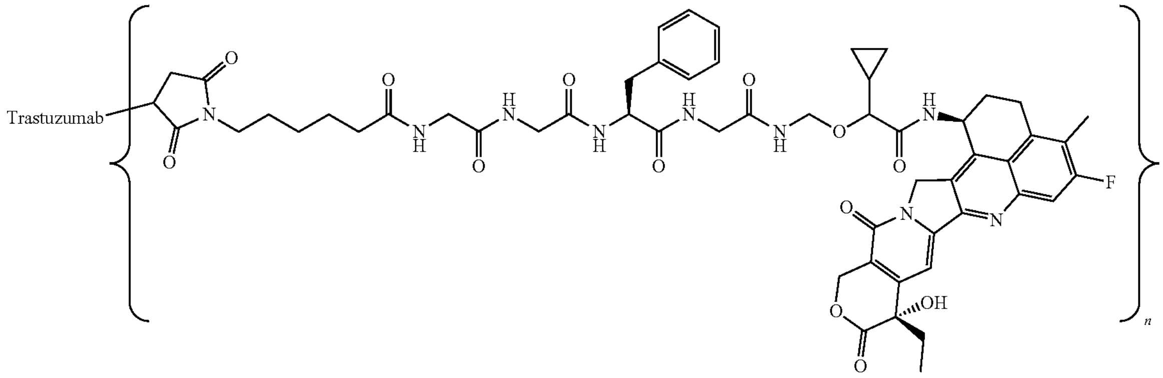

-continued
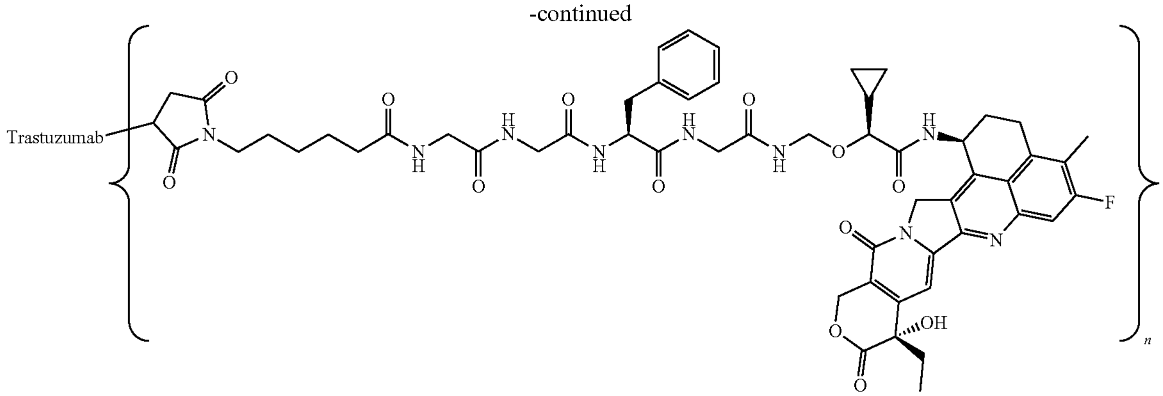
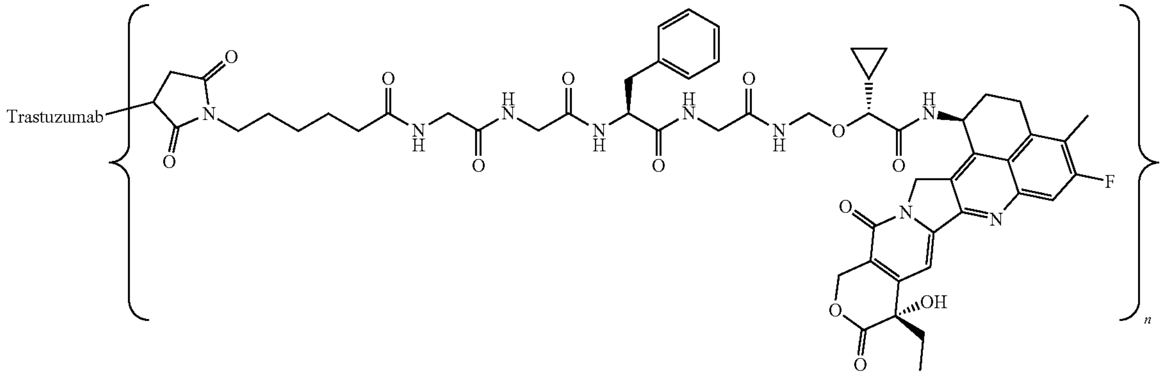
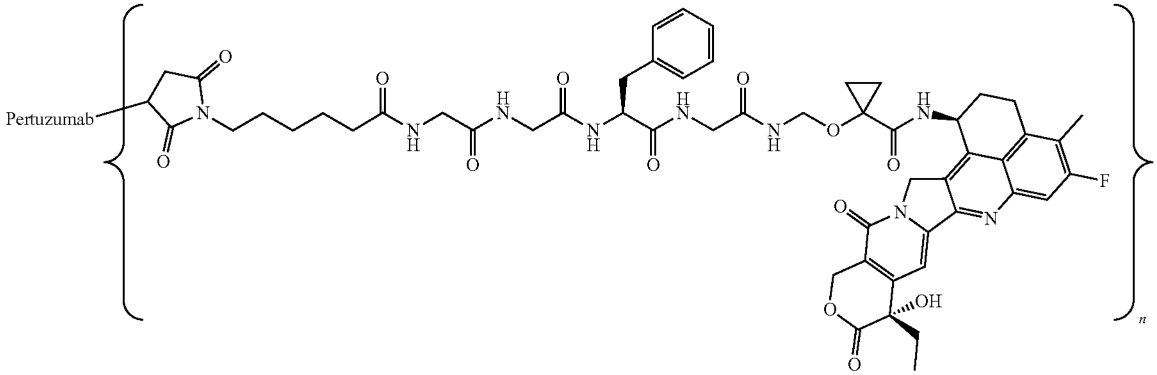
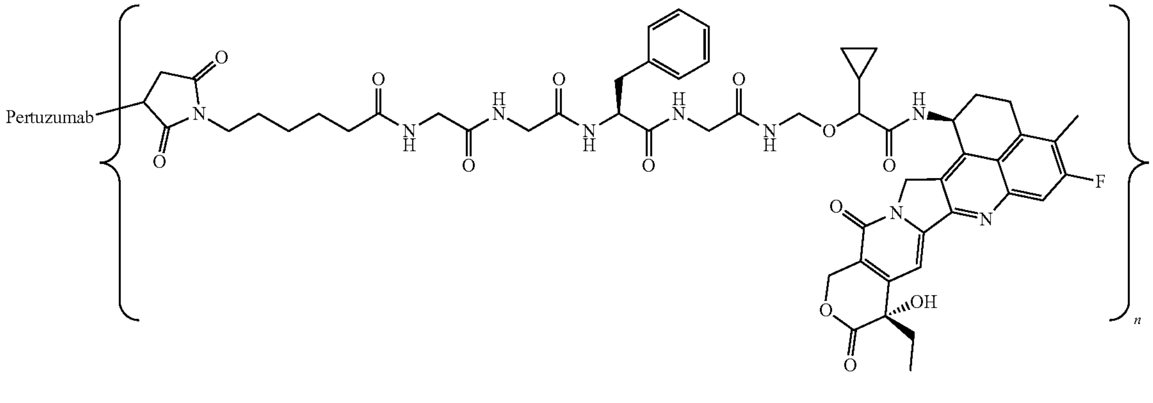

-continued
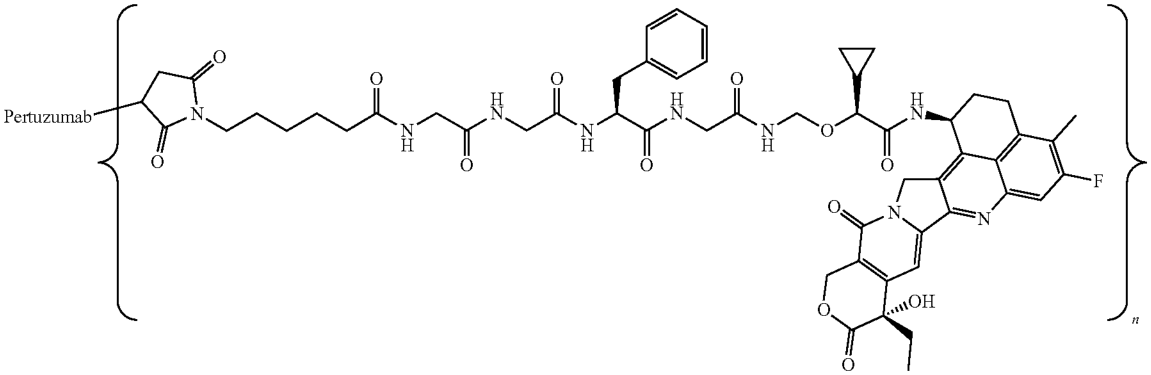
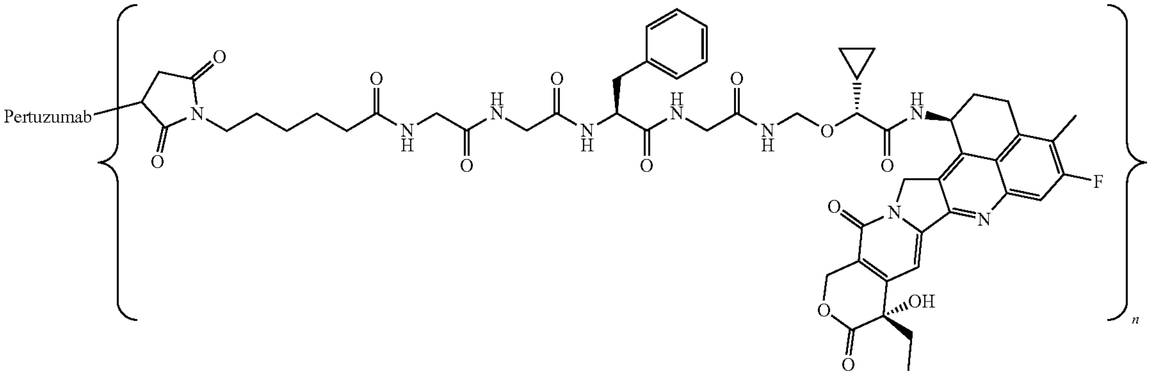
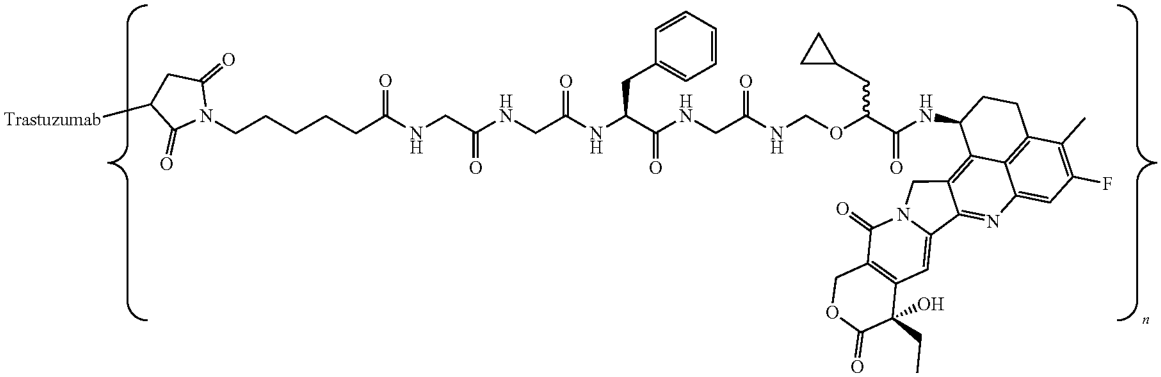
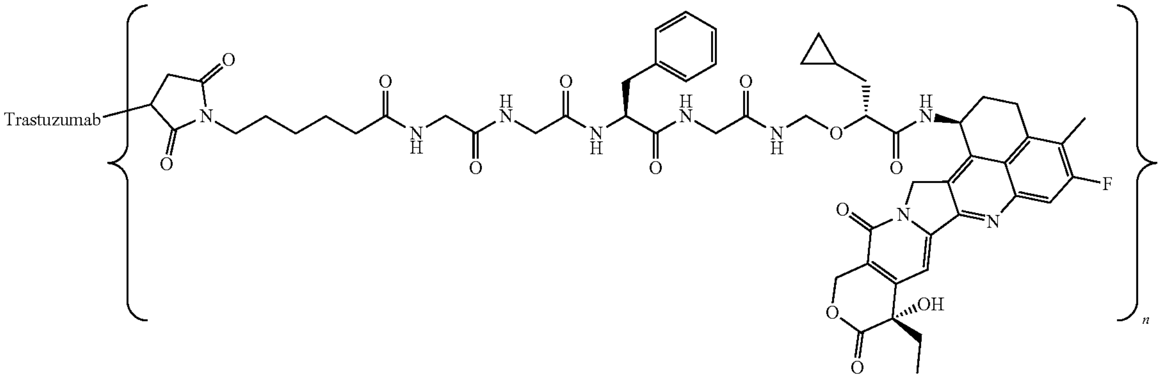

-continued
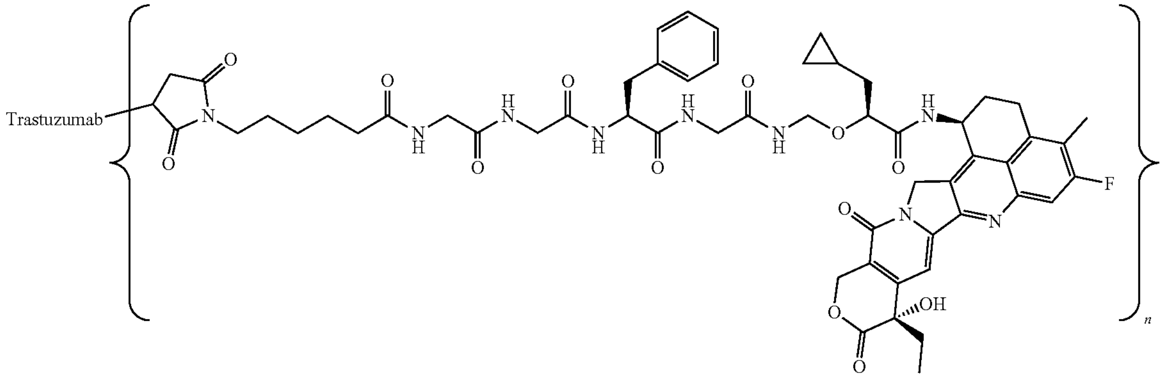
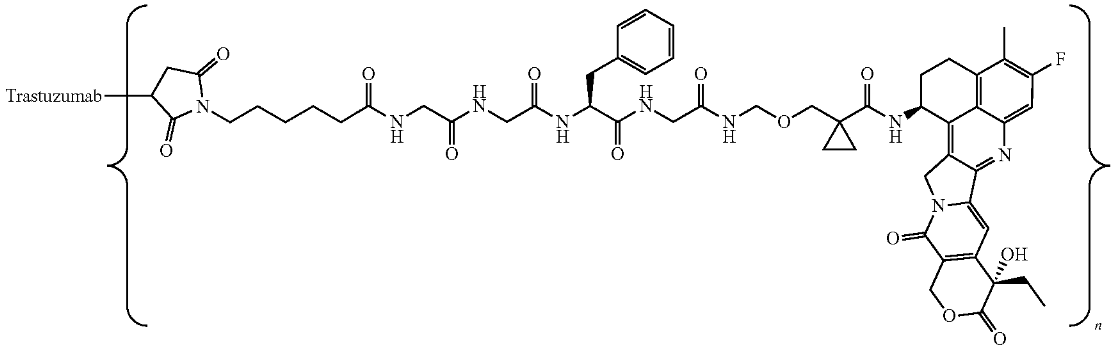
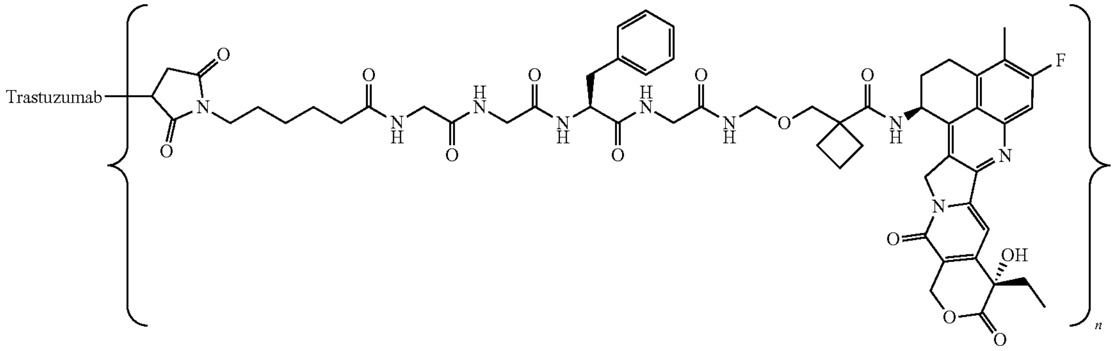
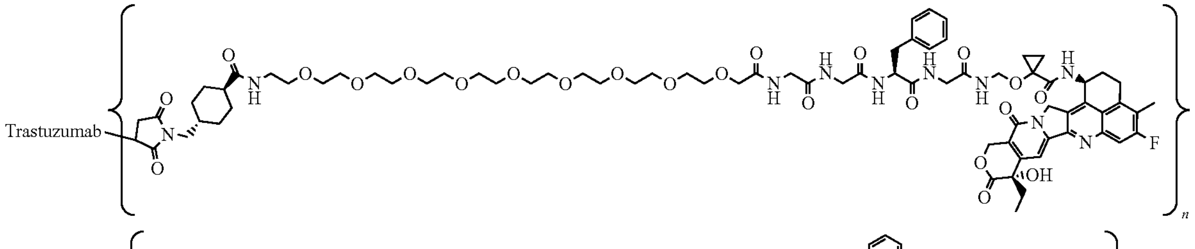
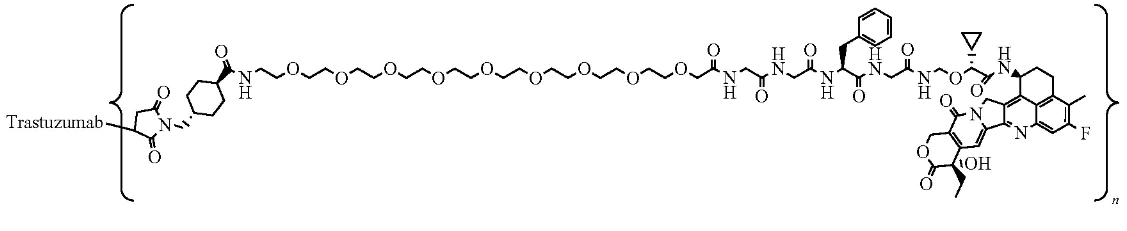
and

-continued

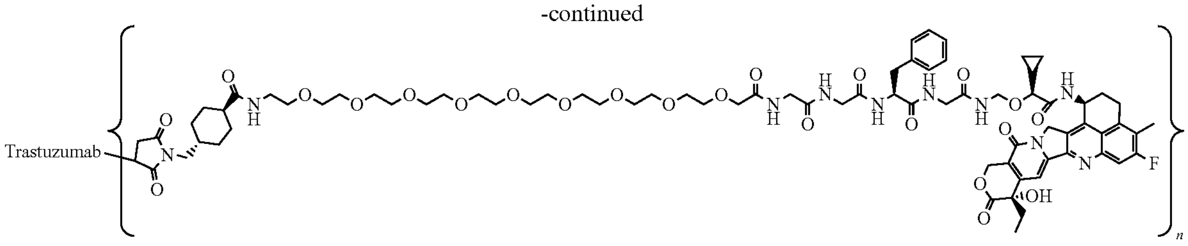

wherein n is 1 to 10, which can be an integer or a decimal.

13. A pharmaceutical composition, comprising a therapeutically effective amount of the ligand-drug conjugate or the pharmaceutically acceptable salt or solvate thereof according to claim 1, and pharmaceutically acceptable carrier(s), diluent(s), or excipient(s).

14. A method of treating or preventing a tumor, the method comprising administering to a subject in need thereof a ligand-drug conjugate according to claim 1.

15. The ligand-drug conjugate or the pharmaceutically acceptable salt or solvate thereof according to claim 1,

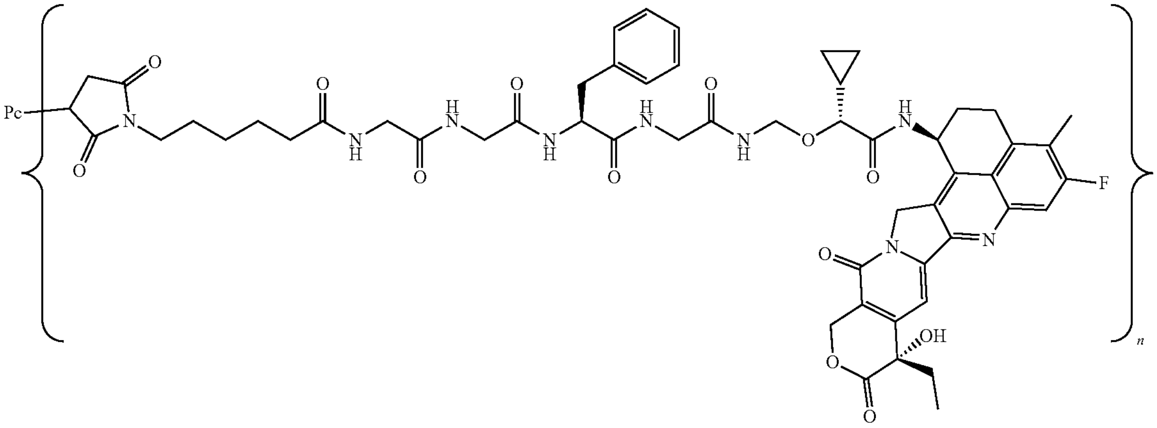

wherein:

n is 1 to 10, which can be an integer or a decimal;

Pc is an antibody.

16. A ligand-drug conjugate or a pharmaceutically acceptable salt or solvate thereof:

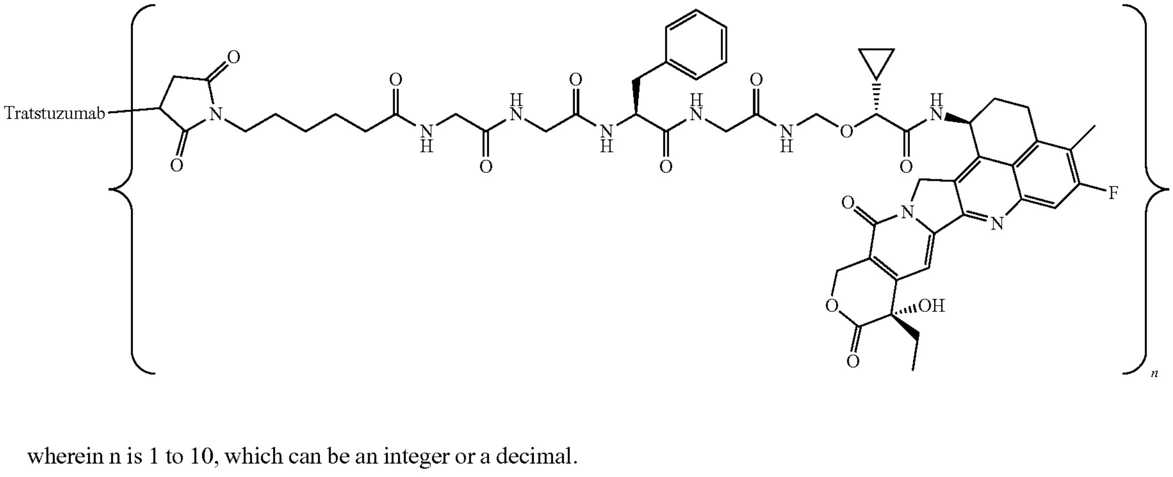

wherein n is 1 to 10, which can be an integer or a decimal.

17. The ligand-drug conjugate or the pharmaceutically acceptable salt or solvate thereof according to claim 1, wherein:

Y is —O—$(CR^aR^b)$m-$CR^1R^2$—C(O)—;

$R^a$ and $R^b$ are identical or different and are each independently selected from the group consisting of hydrogen atom, deuterium atom, halogen, and alkyl;

$R^1$ is a $C_{3-6}$ cycloalkylalkyl or $C_{3-6}$ cycloalkyl;

$R^2$ is selected from the group consisting of hydrogen atom, haloalkyl and $C_{3-6}$ cycloalkyl;

or, $R^1$ and $R^2$ together with the carbon atom to which they are attached form a $C_{3-6}$ cycloalkyl;

m is 0 or 1.

18. The ligand-drug conjugate or the pharmaceutically acceptable salt or solvate thereof according to claim 1, wherein Y is selected from the group consisting of:

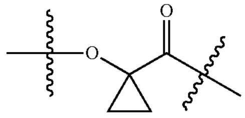,
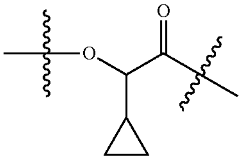,
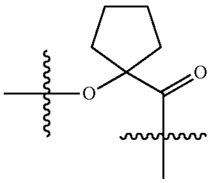,
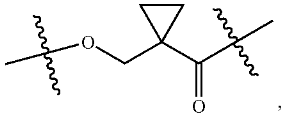,
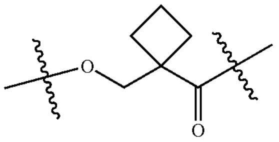
and
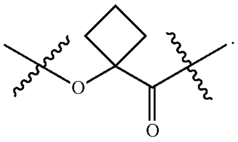.

19. The ligand-drug conjugate or the pharmaceutically acceptable salt or solvate thereof according to claim 1, being a ligand-drug conjugate of formula (Pc-L-D1) or a pharmaceutically acceptable salt or solvate thereof:

(Pc-L-$D_1$)

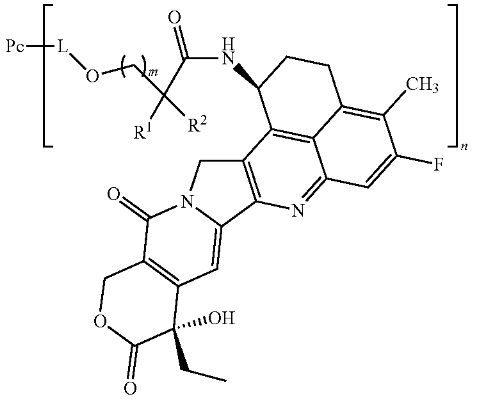

wherein:

$R^1$ is a $C_{3-6}$ cycloalkylalkyl or $C_{3-6}$ cycloalkyl;

$R^2$ is selected from the group consisting of hydrogen atom, haloalkyl and $C_{3-6}$ cycloalkyl;

or, $R^1$ and $R^2$ together with the carbon atom to which they are attached form a $C_{3-6}$ cycloalkyl;

m is 0 or 1;

n is 1 to 10, which can be an integer or a decimal;

Pc is an antibody; and Lis a linker unit.

20. A compound of formula ($L_a$-Y-Dr):

($L_a$-Y-Dr)

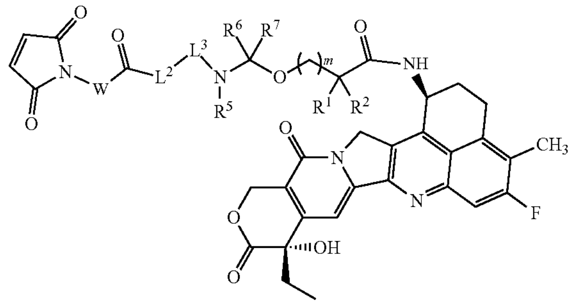

or a tautomer, mesomer, racemate, enantiomer, diastereomer thereof, or mixture thereof, or a pharmaceutically acceptable salt thereof, wherein:

W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4$($CH_2CH_2O$) $p^1CH_2CH_2C(O)$—, —$NR^4$($CH_2CH_2O$) $p^1CH_2C(O)$—, —$S(CH_2)p^1C(O)$— and a chemical bond, wherein $p^1$ is an integer from 1 to 20;

$L^3$ is a peptide residue composed of 2 to 7 amino acids, wherein the amino acids are optionally further substituted by one or more substituent(s) selected from the group consisting of halogen, hydroxy, cyano, amino, alkyl, chloroalkyl, deuterated alkyl, alkoxy and cycloalkyl;

$R^1$ is selected from the group consisting of halogen, cycloalkyl, cycloalkylalkyl, alkoxyalkyl, heterocyclyl, aryl and heteroaryl;

$R^2$ is selected from the group consisting of hydrogen atom, halogen, haloalkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

$R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

m is an integer from 0 to 4.

21. The compound of formula (La-Y-Dr) according to claim 20, being a compound of formula ($L_b$-Y-Dr):

($L_b$-Y-Dr)

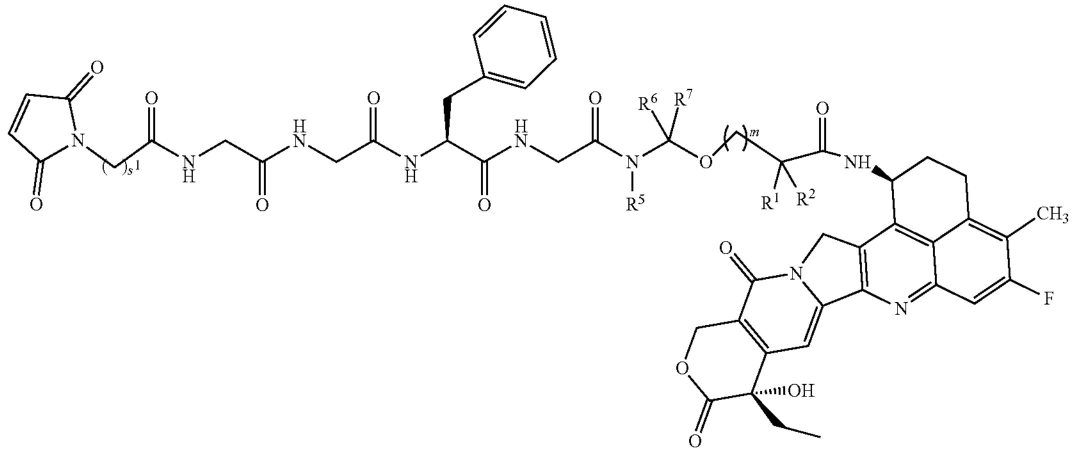

or a tautomer, mesomer, racemate, enantiomer, diastereomer thereof, or mixture thereof, or a pharmaceutically acceptable salt thereof, wherein $R^1$ is selected from the group consisting of halogen, cycloalkyl, cycloalkylalkyl, alkoxyalkyl, heterocyclyl, aryl and heteroaryl;

$R^2$ is selected from the group consisting of hydrogen atom, halogen, haloalkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

$R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

$s^1$ is an integer from 2 to 8; m is an integer from 0 to 4.

22. The compound of formula (La-Y-Dr) according to claim 20, selected from the group consisting of:

8

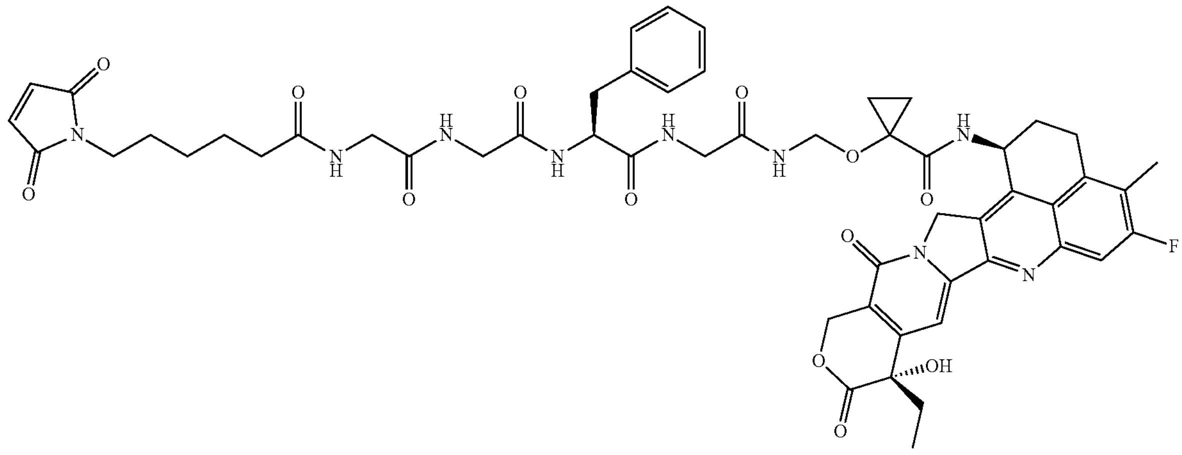

-continued
9
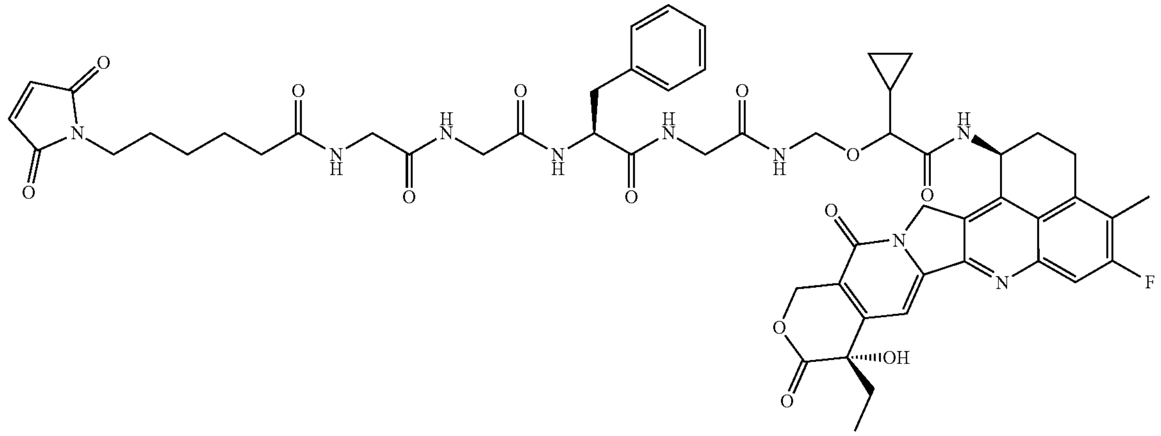
9-A
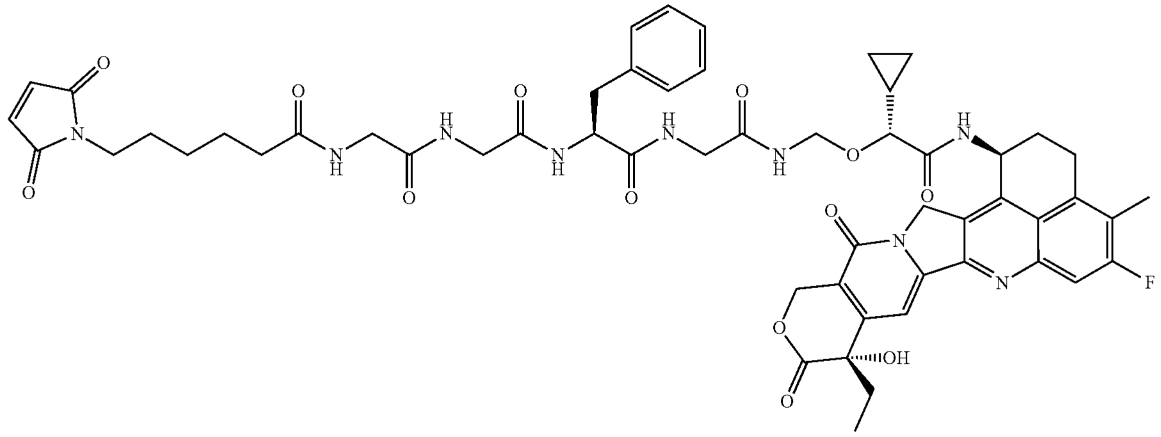
9-B
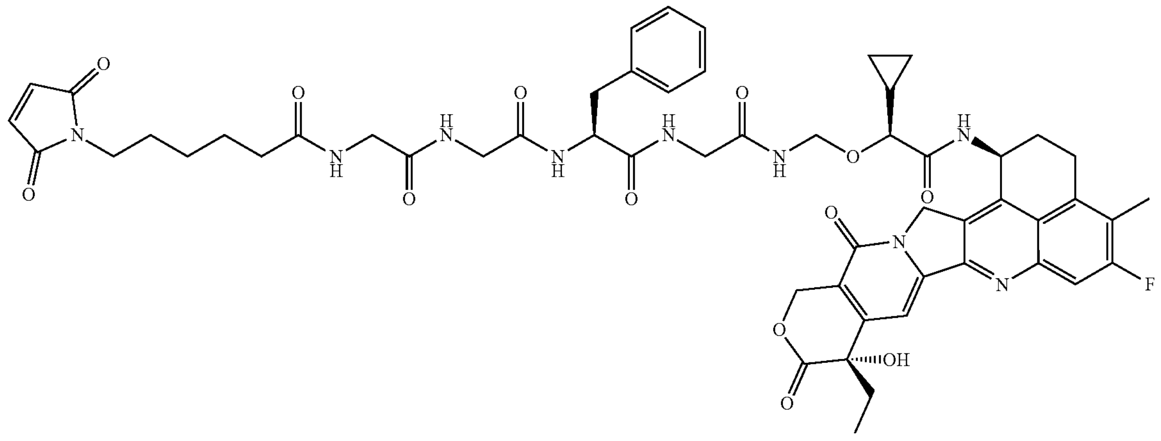

-continued
11
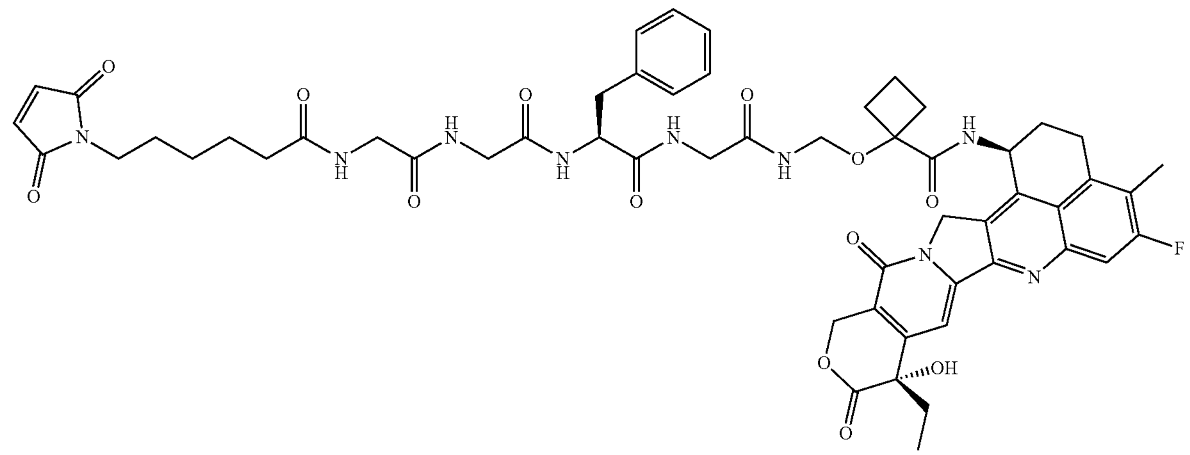
14-A
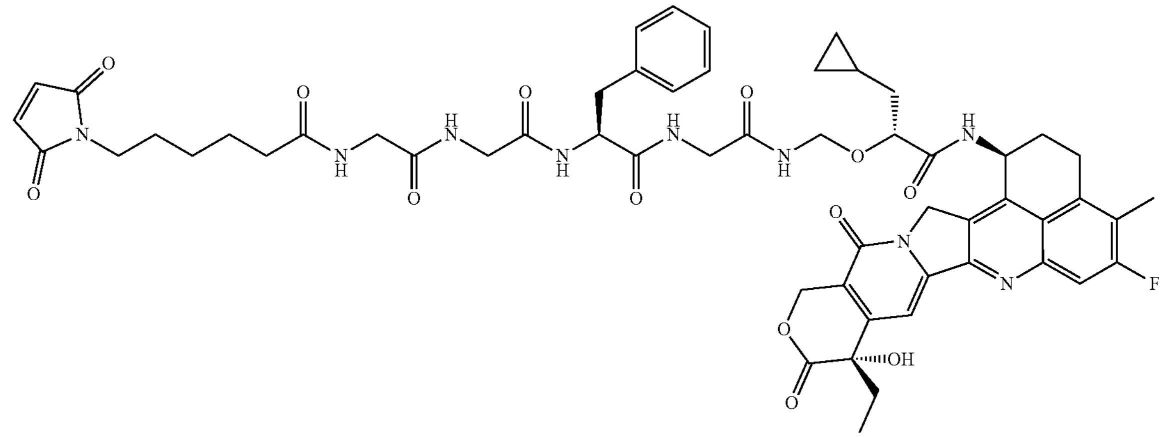
14-B
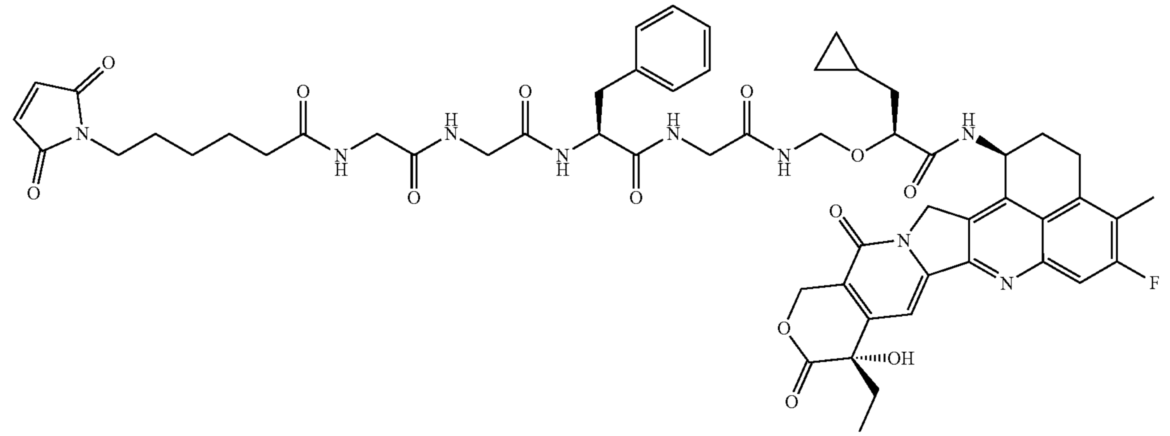

-continued
15
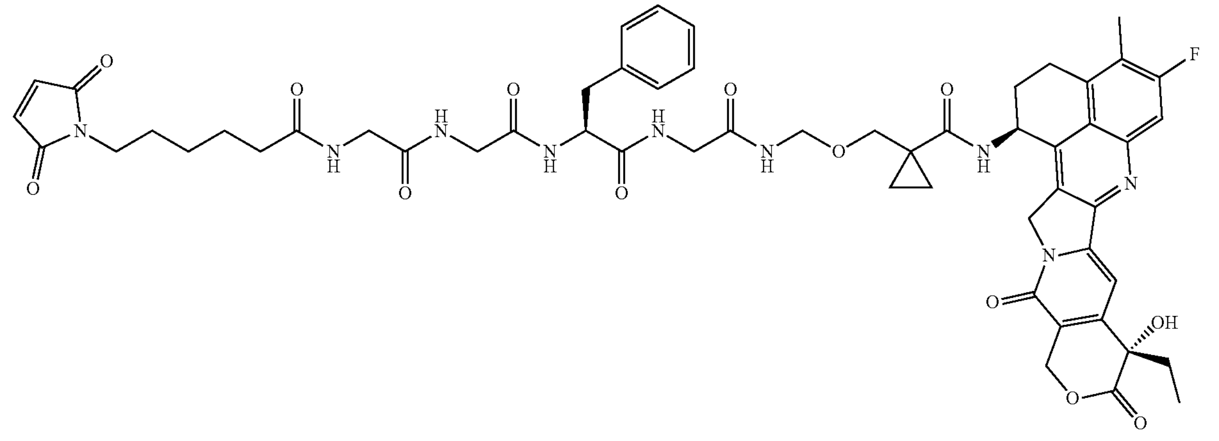
16
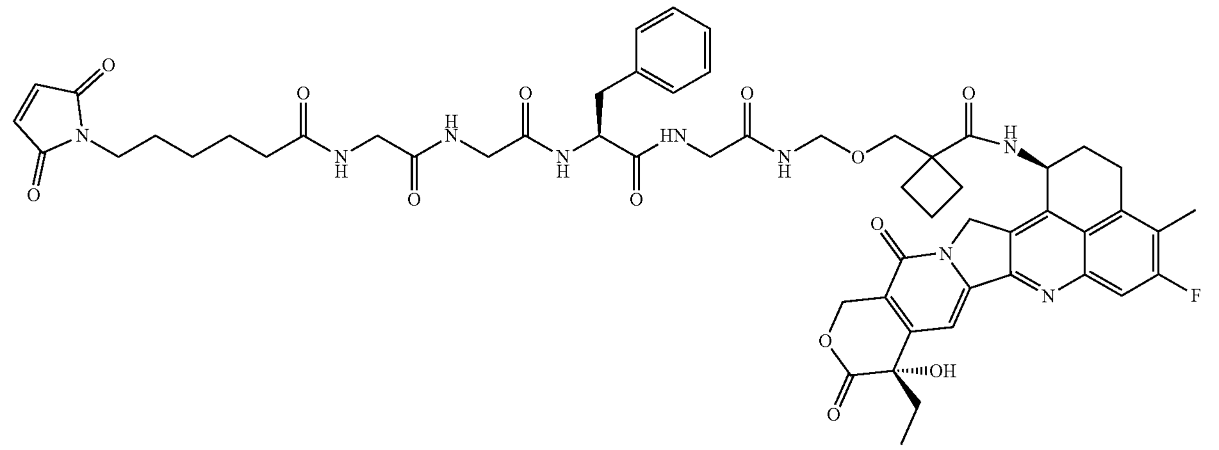
17
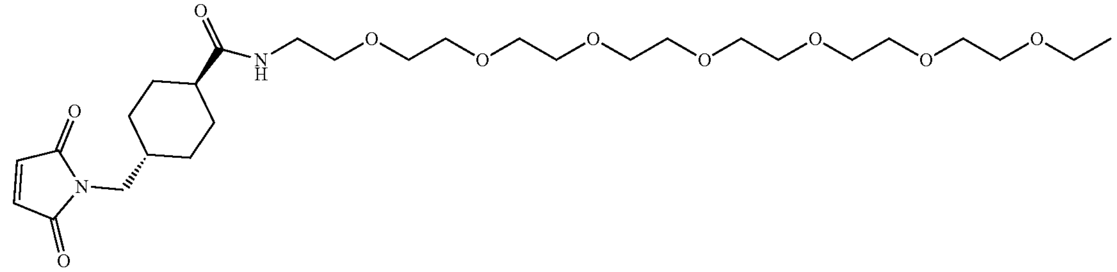
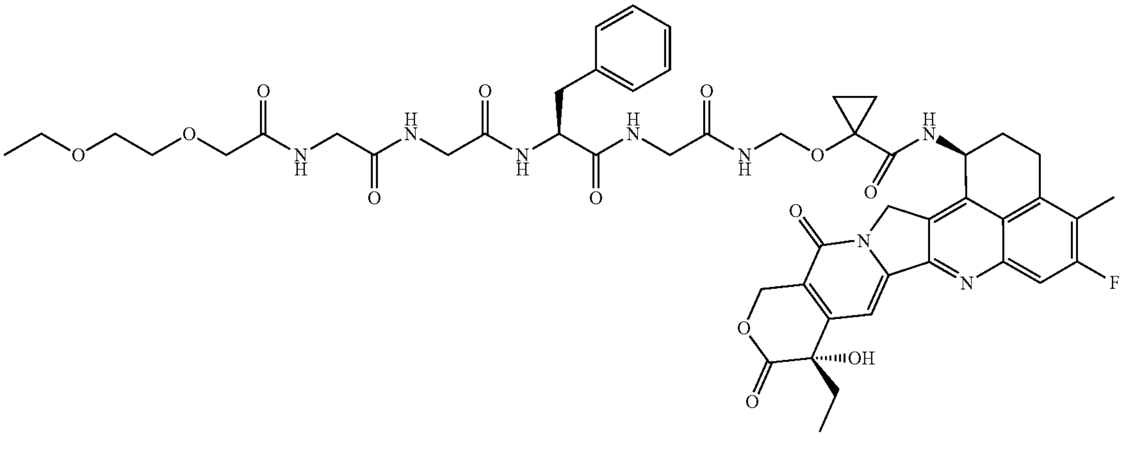

-continued
18
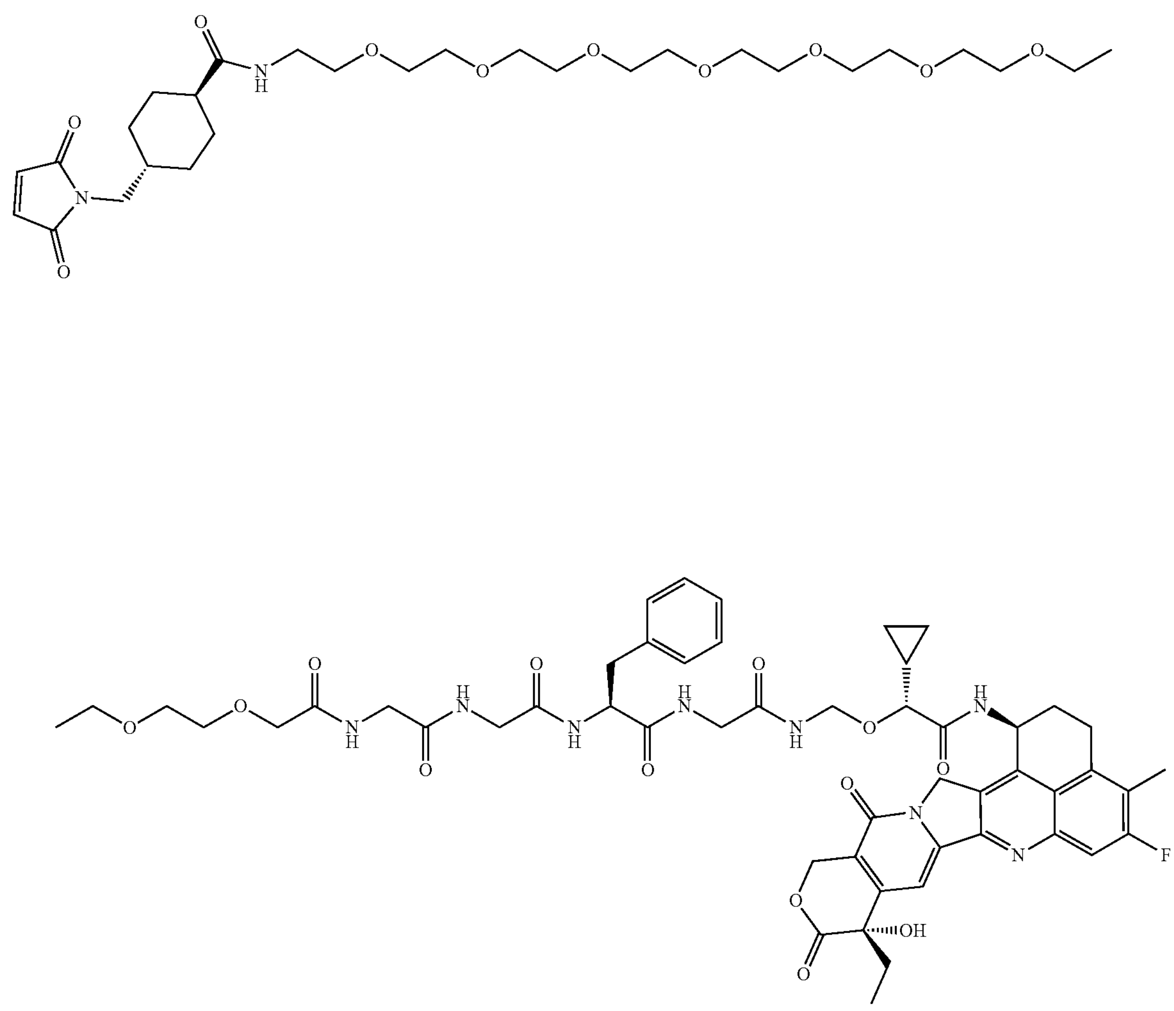
and
19
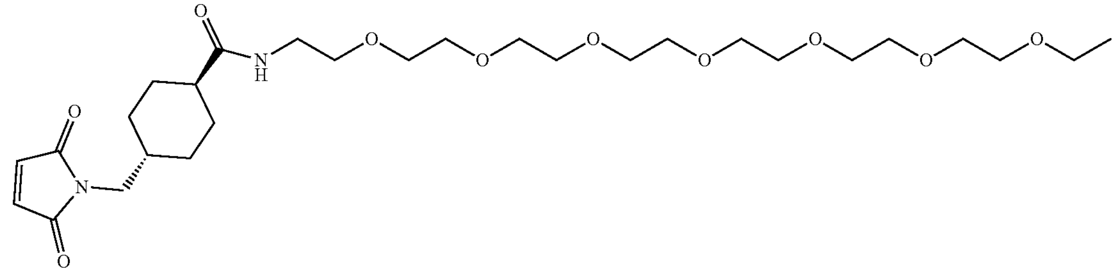

-continued
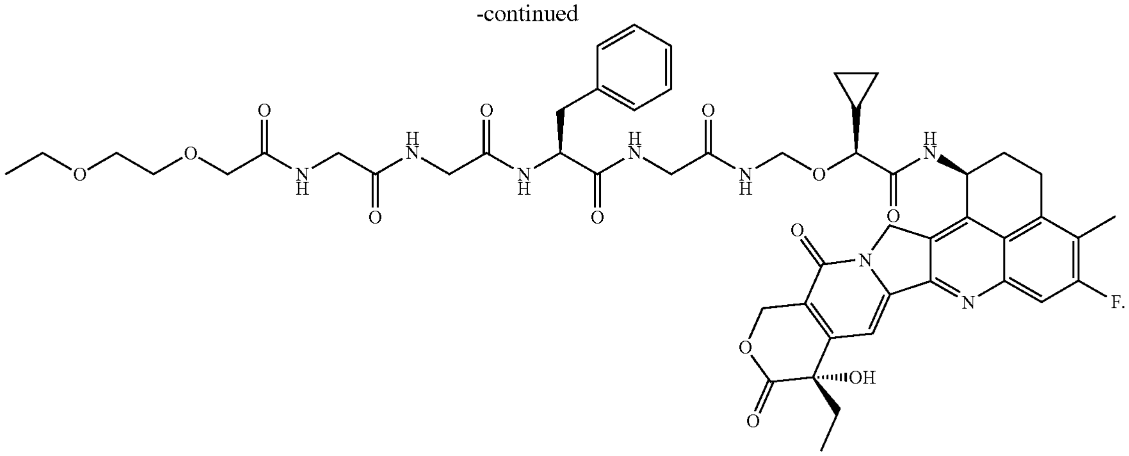
* * * * *

SEQUENCE LISTING

```
<160> NUMBER OF SEQ ID NOS: 6

<210> SEQ ID NO 1
<211> LENGTH: 214
<212> TYPE: PRT
<213> ORGANISM: Artificial Sequence
<220> FEATURE:
<223> OTHER INFORMATION: Synthetic Sequence_Trastuzumab Light Chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 2
<211> LENGTH: 450
<212> TYPE: PRT
<213> ORGANISM: Artificial Sequence
<220> FEATURE:
<223> OTHER INFORMATION: Synthetic Sequence_Trastuzumab Light Chain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

-continued

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 3
<211> LENGTH: 214
<212> TYPE: PRT
<213> ORGANISM: Artificial Sequence
<220> FEATURE:
<223> OTHER INFORMATION: Synthetic Sequence_Pertuzumab Light Chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 4
<211> LENGTH: 449
<212> TYPE: PRT
<213> ORGANISM: Artificial Sequence
<220> FEATURE:
<223> OTHER INFORMATION: Synthetic Sequence_Pertuzumab Heavy Chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 5
<211> LENGTH: 215
<212> TYPE: PRT
<213> ORGANISM: Artificial Sequence
<220> FEATURE:
<223> OTHER INFORMATION: Synthetic Sequence_7H3antibody1F9DS Light Chain

<400> SEQUENCE: 5

Asp Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 6
<211> LENGTH: 449
<212> TYPE: PRT
<213> ORGANISM: Artificial Sequence
<220> FEATURE:
<223> OTHER INFORMATION: Synthetic Sequence_B7H3antibody1F9DS Heavy -continued Chain

<400> SEQUENCE: 6

```
Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```